United States Patent
Ritchey et al.

(10) Patent No.: US 9,451,899 B2
(45) Date of Patent: Sep. 27, 2016

(54) MOBILE USER BORNE BRAIN ACTIVITY DATA AND SURROUNDING ENVIRONMENT DATA CORRELATION SYSTEM

(71) Applicants: Kurtis John Ritchey, Leavenworth, KS (US); Kenneth Ira Ritchey, Leavenworth, KS (US)

(72) Inventors: Kurtis John Ritchey, Leavenworth, KS (US); Kenneth Ira Ritchey, Leavenworth, KS (US)

(*) Notice: Subject to any disclaimer, the term of this patent is extended or adjusted under 35 U.S.C. 154(b) by 1 day.

(21) Appl. No.: 14/788,437

(22) Filed: Jun. 30, 2015

(65) Prior Publication Data

US 2015/0324692 A1 Nov. 12, 2015

Related U.S. Application Data

(63) Continuation of application No. 13/507,190, filed on Jun. 11, 2012, now Pat. No. 9,101,279, and a continuation of application No. 13/294,986, filed on Nov. 11, 2011, now Pat. No. 9,344,612, and a continuation of application No. 12/266,308, filed on Nov. 6, 2008, now abandoned.

(51) Int. Cl.
*G06F 13/00* (2006.01)
*A61B 5/0476* (2006.01)
(Continued)

(52) U.S. Cl.
CPC ........... *A61B 5/0476* (2013.01); *A61B 5/0022* (2013.01); *A61B 5/04008* (2013.01); *A61B 5/055* (2013.01); *A61B 5/1114* (2013.01); *A61B 5/6803* (2013.01); *A61B 5/686* (2013.01); *G03B 37/00* (2013.01); *G06F 1/1626* (2013.01); *G06F 1/1686* (2013.01); *G06F 3/013* (2013.01); *G06F 3/015* (2013.01); *G06F 3/038* (2013.01); *G06F 15/18* (2013.01); *G06F 19/3406* (2013.01);
*H04N 5/2259* (2013.01); *H04N 5/335* (2013.01); *H04N 7/18* (2013.01); *A61B 5/0024* (2013.01); *A61B 5/745* (2013.01);
(Continued)

(58) Field of Classification Search
CPC ........... H04N 5/23238; H04N 5/2628; H04N 5/2259; H04N 7/18; H04N 5/335; G06T 3/4038; A61B 5/0476; A61B 5/745; A61B 5/686; A61B 5/0022; A61B 5/0024; A61B 5/04008; A61B 5/055; A61B 5/1114; A61B 5/6803; A61B 2560/0242; G02B 13/06; G02B 15/10; G06F 3/038; G06F 15/18; G06F 19/3406; G06F 1/1626; G06F 1/1686; G06F 3/013; G06F 3/015; G06F 2203/0381; G03B 37/00; G01R 33/4806
USPC ......................................................... 348/36
See application file for complete search history.

(56) References Cited

U.S. PATENT DOCUMENTS

| 6,171,239 B1 * | 1/2001 | Humphrey | A61B 5/0482 600/372 |
| 2003/0093129 A1 * | 5/2003 | Nicolelis | A61B 5/0478 607/45 |

(Continued)

*Primary Examiner* — Robert B Harrell
(74) *Attorney, Agent, or Firm* — Hovey Williams LLP

(57) ABSTRACT

A mobile user borne brain activity data and surrounding environment data correlation system comprising a brain activity sensing subsystem, a recording subsystem, a measurement computer subsystem, a user sensing subsystem, a surrounding environment sensing subsystem, a correlation subsystem, a user portable electronic device, a non-transitory computer readable medium, and a computer processing device. The mobile user borne system collects and records brain activity data and surrounding environment data and statistically correlates and processes the data for communicating the data into a recipient biological, mechanical, or bio-mechanical system.

32 Claims, 50 Drawing Sheets

(51) Int. Cl.
  *H04N 7/18*    (2006.01)
  *G06F 3/038*   (2013.01)
  *H04N 5/335*   (2011.01)
  *G06F 15/18*   (2006.01)
  *G03B 37/00*   (2006.01)
  *H04N 5/225*   (2006.01)
  *A61B 5/04*    (2006.01)
  *A61B 5/055*   (2006.01)
  *A61B 5/11*    (2006.01)
  *G06F 19/00*   (2011.01)
  *G06F 1/16*    (2006.01)
  *G06F 3/01*    (2006.01)
  *G02B 13/06*   (2006.01)
  *G02B 15/10*   (2006.01)
  *A61B 5/00*    (2006.01)
  *G01R 33/48*   (2006.01)

(52) U.S. Cl.
  CPC .. *A61B 2560/0242* (2013.01); *G01R 33/4806* (2013.01); *G02B 13/06* (2013.01); *G02B 15/10* (2013.01); *G06F 2203/0381* (2013.01)

(56) References Cited

U.S. PATENT DOCUMENTS

2004/0092809 A1*  5/2004  DeCharms ......... G01R 33/4806
                                                600/410
2004/0131998 A1*  7/2004  Marom ............. A61N 1/36021
                                                434/236
2004/0267320 A1*  12/2004 Taylor ................ A61F 2/72
                                                607/2

* cited by examiner

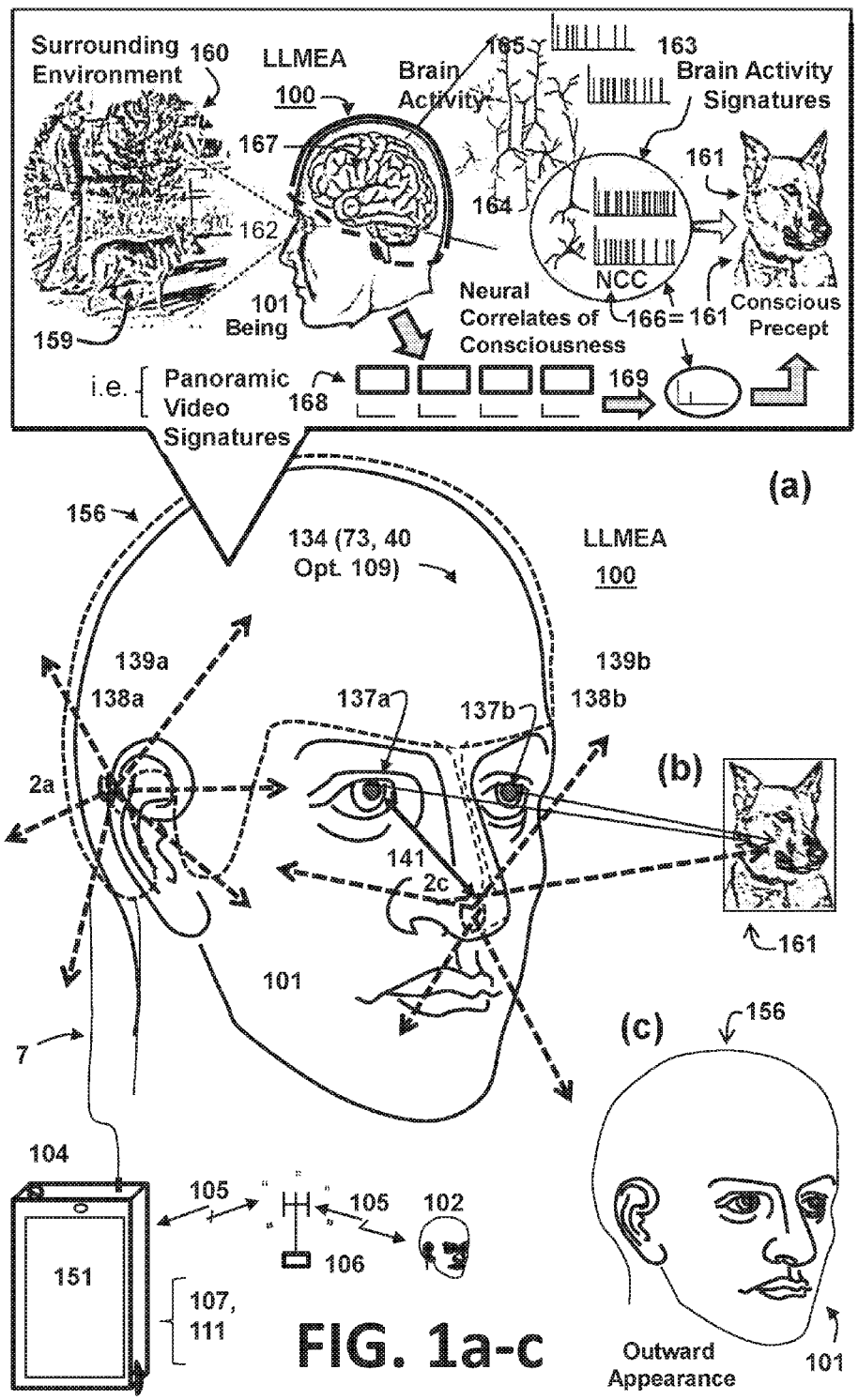
FIG. 1a-c

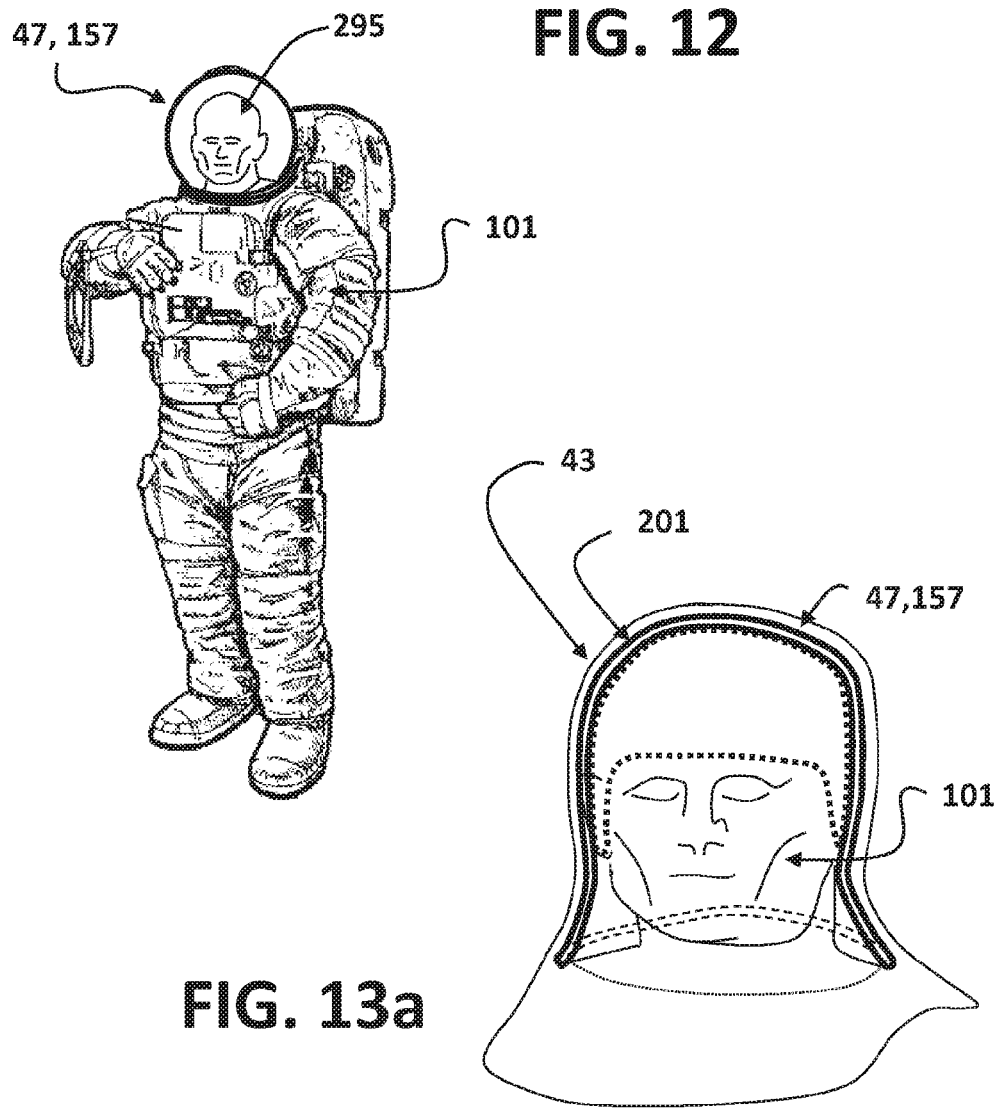
FIG. 12
FIG. 13a
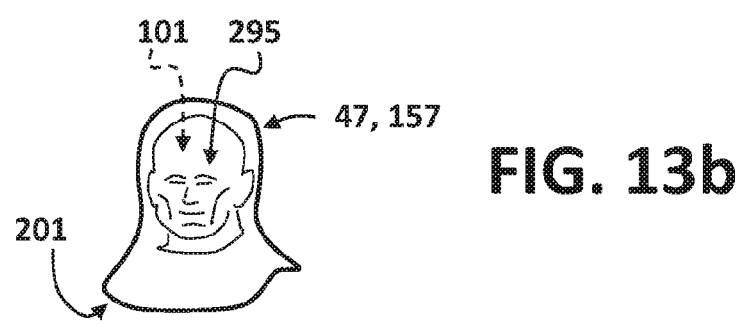
FIG. 13b

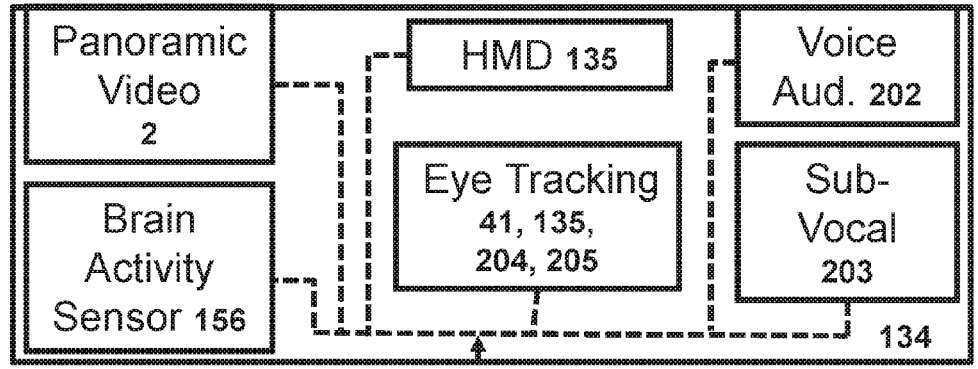
FIG. 14b
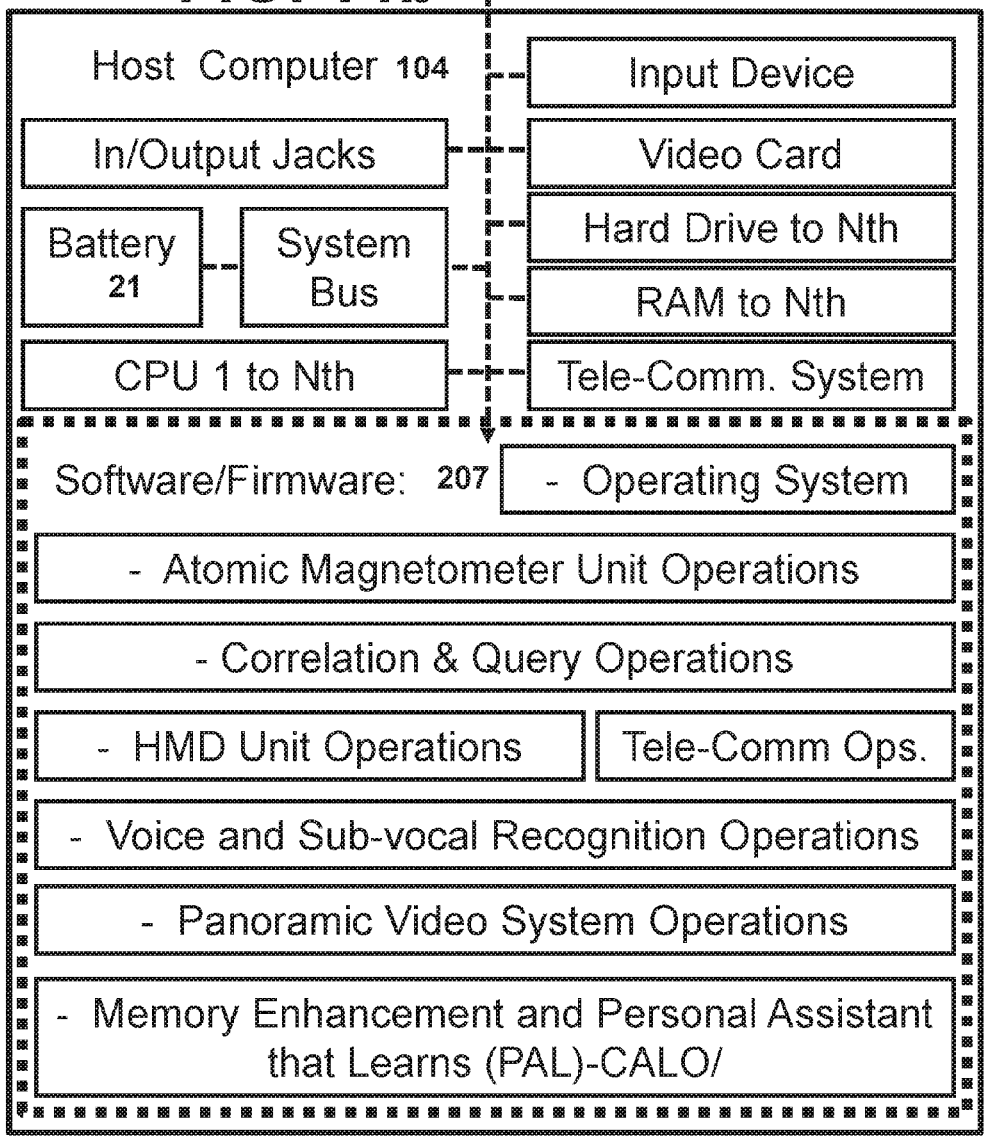

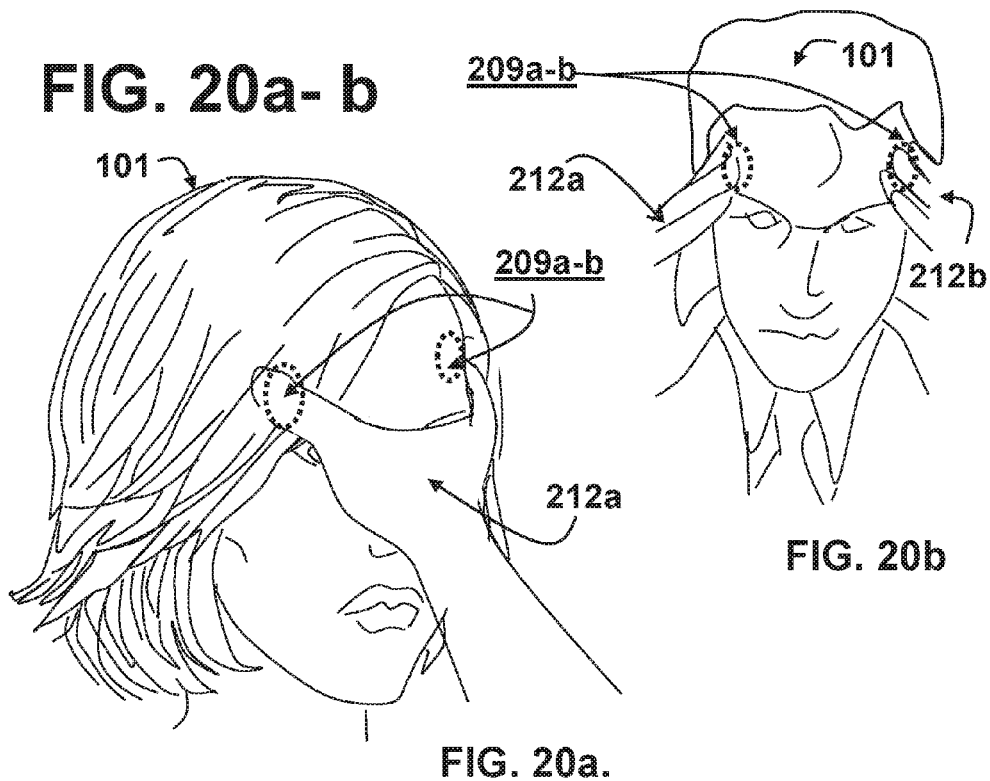
FIG. 20a-b
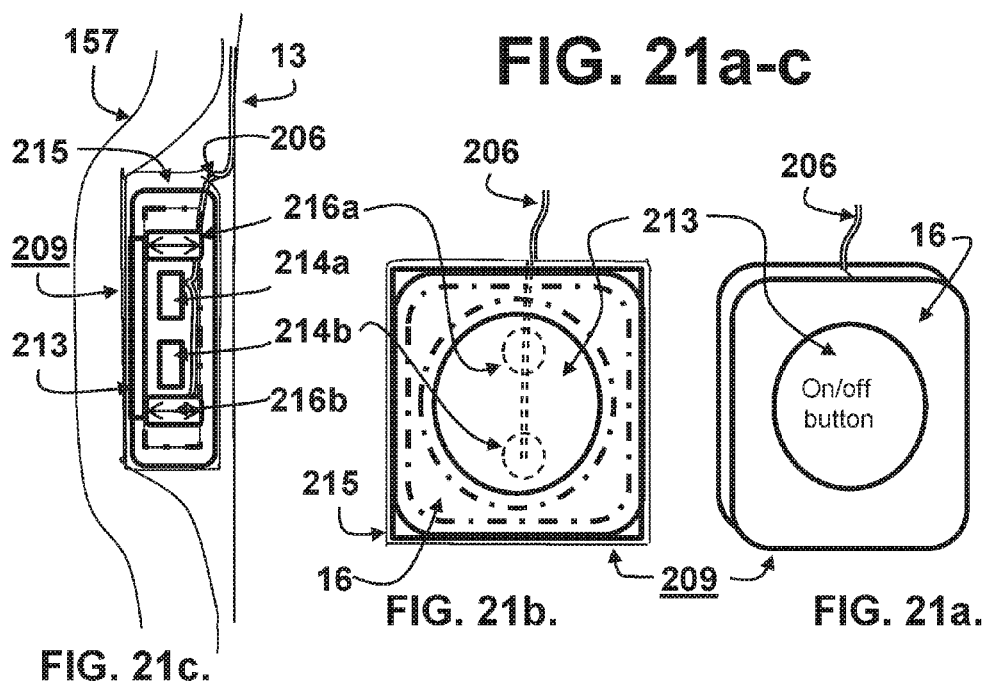
FIG. 21a-c

FIG. 23a-f

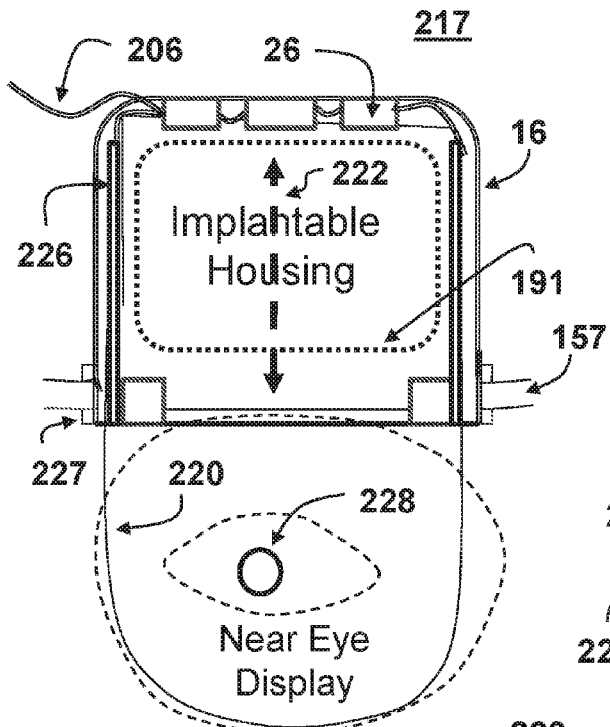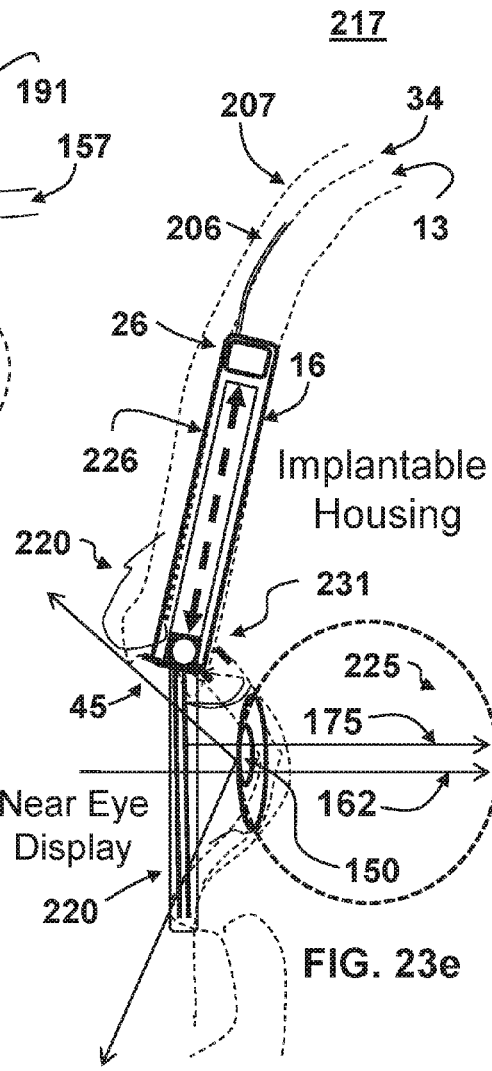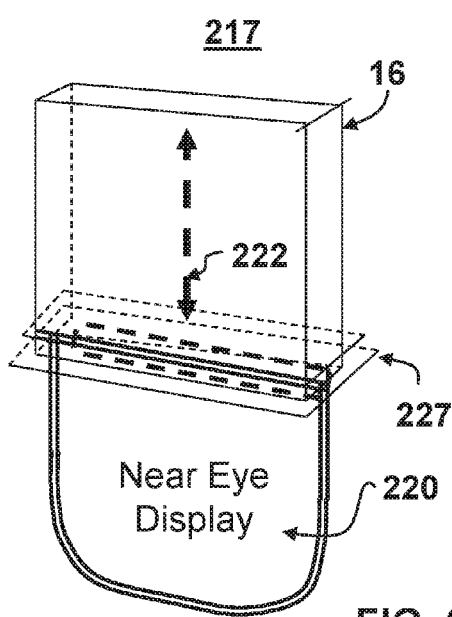
FIG. 23a-f
FIG. 23d
FIG. 23e
FIG. 23f

FIG. 24a-f

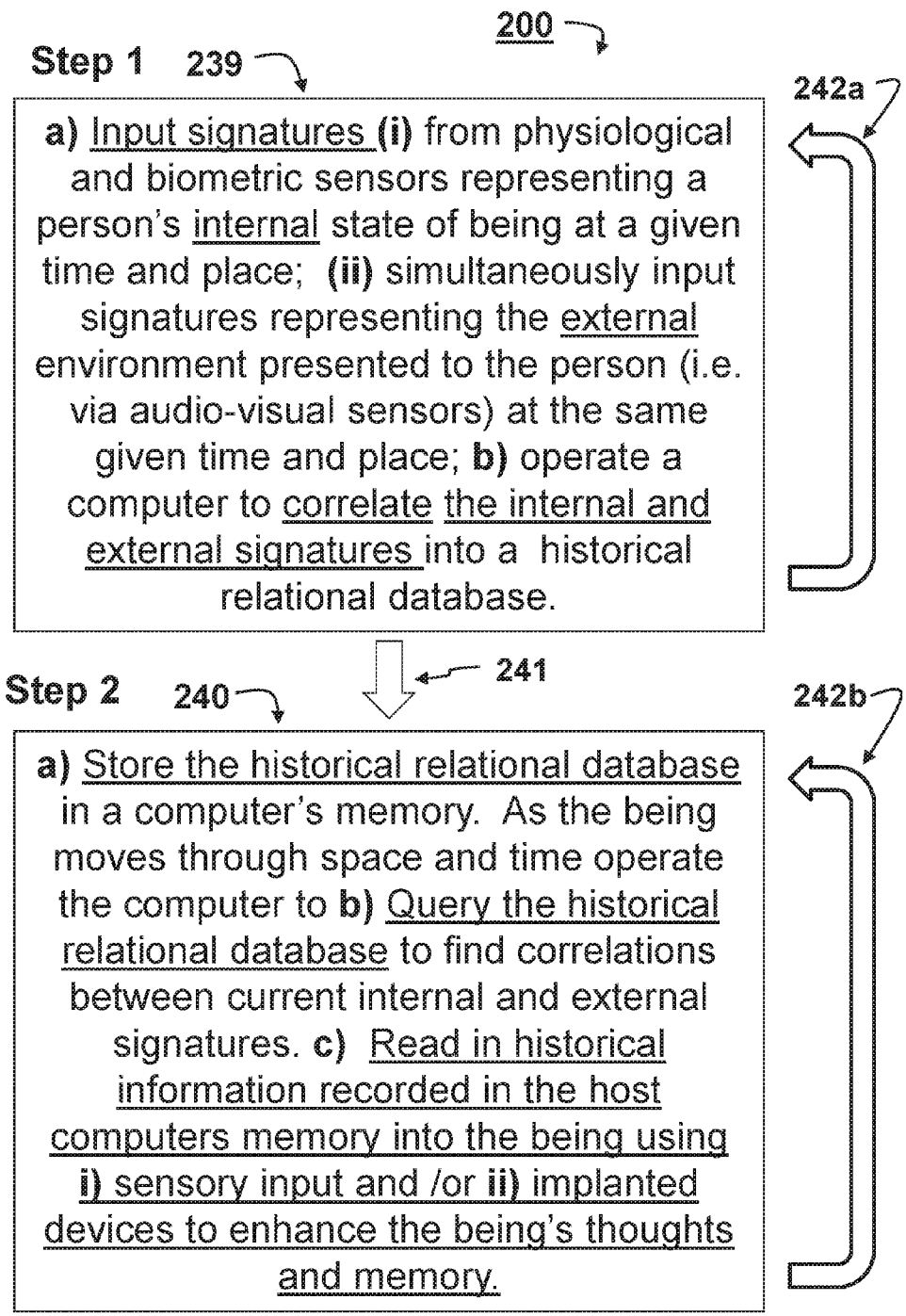

FIG. 27

Step 1, Phase 1 — 239

- Operator activates the AMR, system to record a brain activity image. ⇔ Operator activates the host visual environment visual image logging system

Step 1, Phase 2 — 241, 242a

- AMR system polarizes nuclear spin in user specimen in a magnetic field;
- 241 → AMR sensors detect and transmit NMR signatures to host computer (HC)
- The brain image info. derived from the AMR NMR signals is stored into the memory of a HC.

- Objective lens group receives and projects the visual scene to a sensor
- Sensor receives the scene and converts it into an image signal
- Image signal is communicated to the host computer (HC)
- The image info. is stored into the memory of the HC

Step 1, Phase 3 — 241

- Neural correlations to video imagery and other sensors are searched for, and neural correlations found above threshold are logged and recorded in the historical database. ⇔ Video correlations to brain imagery and to other sensors are searched for, and neural correlations found above threshold are logged and recorded in the historical database.

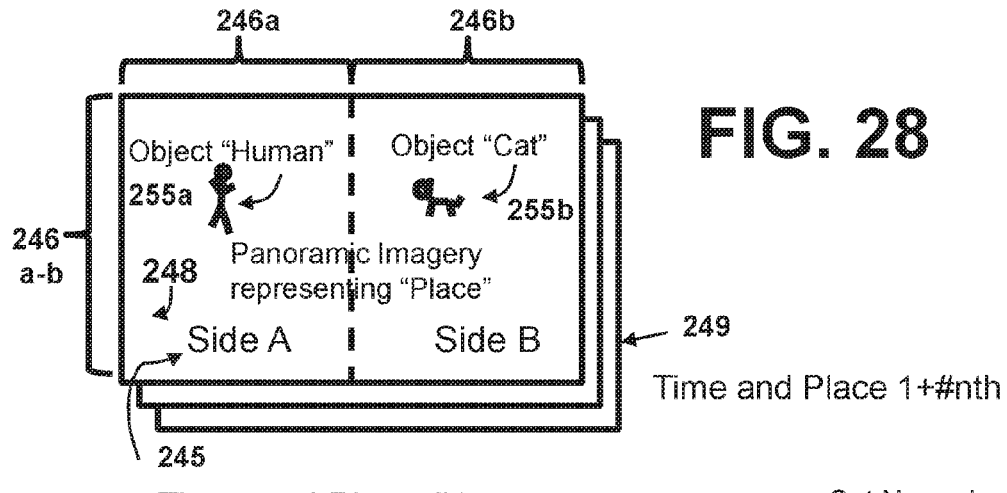
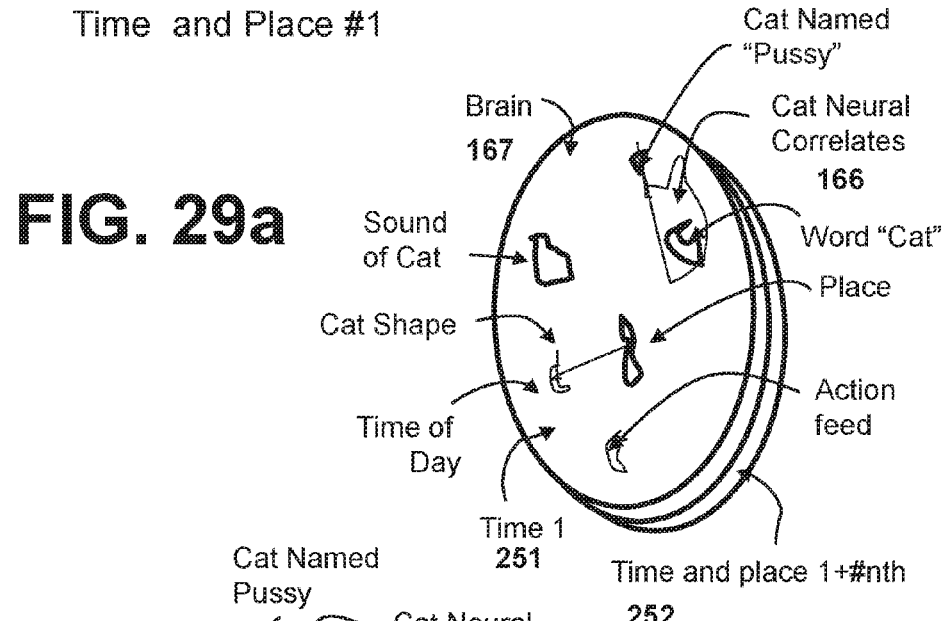
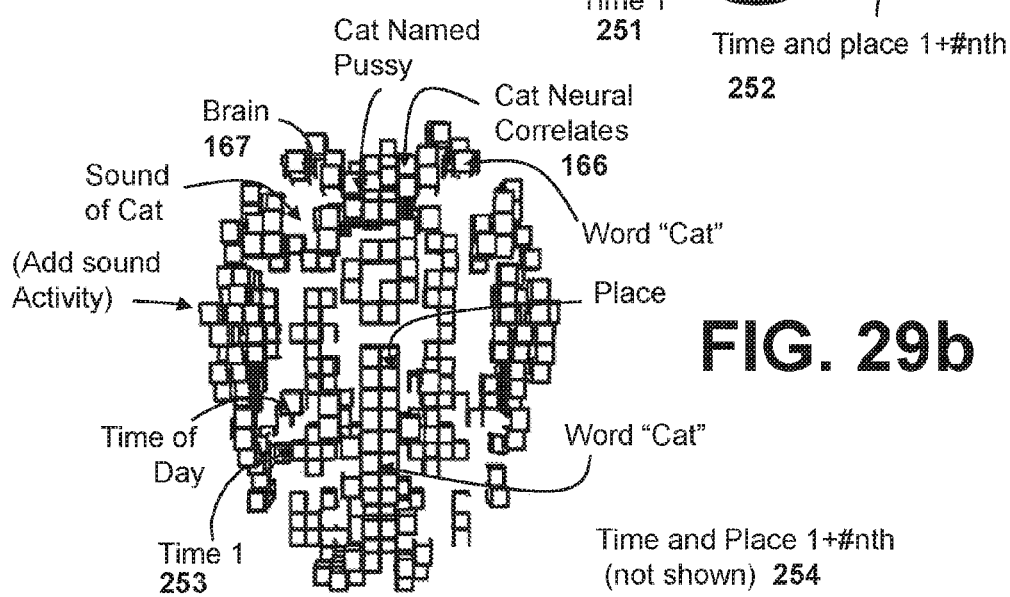

FIG. 30

Person 1: Brain Activity Images

Time & Place 1 251

Time & Place 1+#nth 252

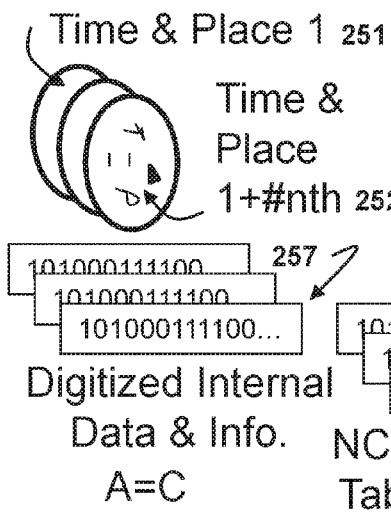

101000111100... 257

Digitized Internal Data & Info. A=C

Person 1: Surrounding Scene Images

Time & Place 1 255

Time & Place 1+#nth 256

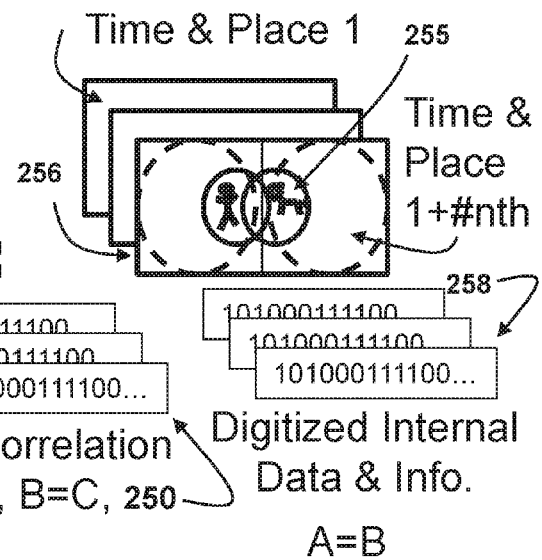

101000111100... 258

Digitized Internal Data & Info. A=B

101000111100... NCC Correlation Tables, B=C, 250

FIG. 31

Person 1: Brain Activity Image 101a, 251a

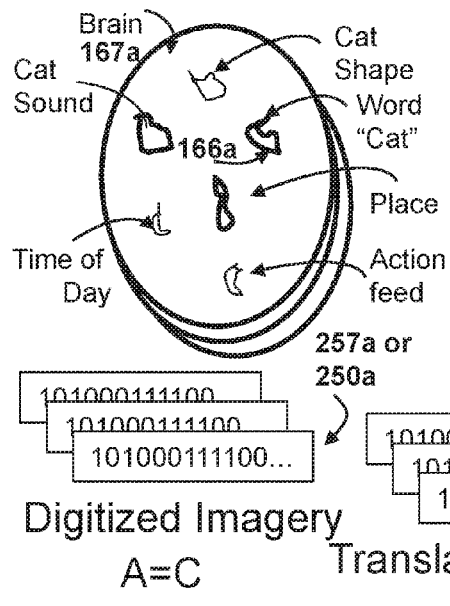

Brain 167a, Cat Sound, 166a, Cat Shape, Word "Cat", Place, Time of Day, Action feed 101000111100... 257a or 250a Digitized Imagery A=C Person 2: Brain Activity Image 101b, 251b

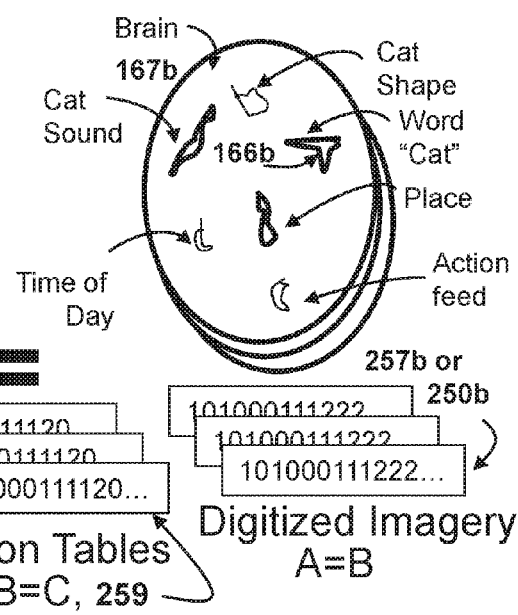

Brain 167b, Cat Sound, 166b, Cat Shape, Word "Cat", Place, Time of Day, Action feed 101000111222... 257b or 250b Digitized Imagery A=B 101000111120... Translation Tables B=C, 259

FIG. 32

Step 2, Phase 1  240

The user activates the host computer (HC) and memory correlation databases.

↓ ← 241

Step 2, Phase 2

A stimulus in the environment, thought or action generated by the user stimulates the mind and causes a brain activity.

↓ ← 241

Step 2, Phase 3

The HC receives the live brain activity and queries the correlated databases for matches between the live brain activity and the historical brain pattern database pre-associated with historical information.

↓ ← 241

Step 2, Phase 4

The matches are presented to the user.

↓ ← 241

Step 2, Phase 5

The operator chooses which matches to activate/select and act upon.

↓ ← 241

Step 2, Phase 6

The operators brain is stimulated with the matched information.

242b

| Time 1 fMRI Unit 401, 421 | Time 1 Panoramic Video Camera 422 Unit | Time 1 Sub-vocalization 423 Unit | Time 1 Target Desig. & Tracking 224 Unit GPS |  |
|---|---|---|---|---|
| Brain Signature Readout 402 | Panoramic Imagery Readout | Spatial Audio Readout | EEG Audio Signature Readout | Eye and Head coordinate data, Geospatial Data Readout |
| Record the Brain Activity to HC of a 403 "Cat". | Record the Imagery to HC "Cat". | Record the Audio to HC "Cat". | Record the EEG signature to HC "Cat". | Record coordinates, time, & places associated with each spatial sensor to HC "Cat". |
| Computer firmware processes neural activity patterns of imagery signatures from Time1 to Time n when user sees, hears, smells, or touches, a "Cat". 404 | Computer pattern recognition firmware processes image patterns, shapes, and colors when the user sees a "Cat". | Computer pattern recognition firmware processes sound signature when the user hears a "Cat". | Computer sub-vocal firmware processes sub-vocal EEG signatures when the user sees, hears, smells, or touches a "Cat". | Computer geospatial firmware records geospatial data associated with the place and location of where the user sees, hears, smells, or touches a "Cat".<br><br>FIG. 33a<br>247a |
| The HC Computer AI/or AI-like System Correlates Relationships of the above signatures relevant to User based on Time, Space, Location, Subject Matter, and Activity that defines the subject as 405 what the user calls a "Cat". ||||| 
| Log Brain Activity NCC relationship with other signatures. | Log Imagery relationship with other signatures. 406 | Log Audio relationship with other signatures. | Log EEG relationship with other signatures. | Log Target ID & GPS relationship with other signatures. |
| Store Information in Computer Memory as a Relational Database 407 (DB) (Comprising a Historical DB which includes an NCC DB |||||

| Time 2 fMRI Unit 408, 421 | Time 2 Panoramic Video Camera Unit 422 | Time 2 New Sub-vocalization 423 Unit | Time 2 New Target Designation & ROI Tracking 224 Unit w/GPS |
|---|---|---|---|
| Brain Signature 409 | Panor- amic Imagery | Spatial Audio | Sub-Vocal Signature | Eye and Head coordinate data, Geospatial Data |
| Computer software identifies new neural activity signatures in real time & identifies sounds, smells, images, sounds, etc. representi -ing a "Cat". 410 | Computer pattern recogni- tion software identifies new image patterns, shapes, and colors when the users sees a "Cat". | Computer pattern recogni- tion software identifies new certain sound signature when the users hears a "Cat". | Computer sub-vocal software identifies certain new sub-vocal EEG signature when the user sub- vocalizes seeing, hearing, smelling, or touching a "Cat". | Computer target designation & geospatial software identifies new geospatial data associated with where the user sees, hears, smells, or touches a "Cat". |

The HC Computer AI System Searches the Relational Database for historical signatures that are similar to new signatures as they are recorded and input into the host computer. If significant relationships are found between the old and new signatures then the user is notified or an action is automatically taken based on prior rules set up by the user. (i.e. The signature of a "Cat" prompts the computer to post a message on the users display and/or a voice synthesized audio message that the user may wish to take his allergy medicine before experiencing an allergic reaction to the "Cat" in the surrounding environment.) Additionally, new significant sensor signatures are noted and the relational database (s) are update
411

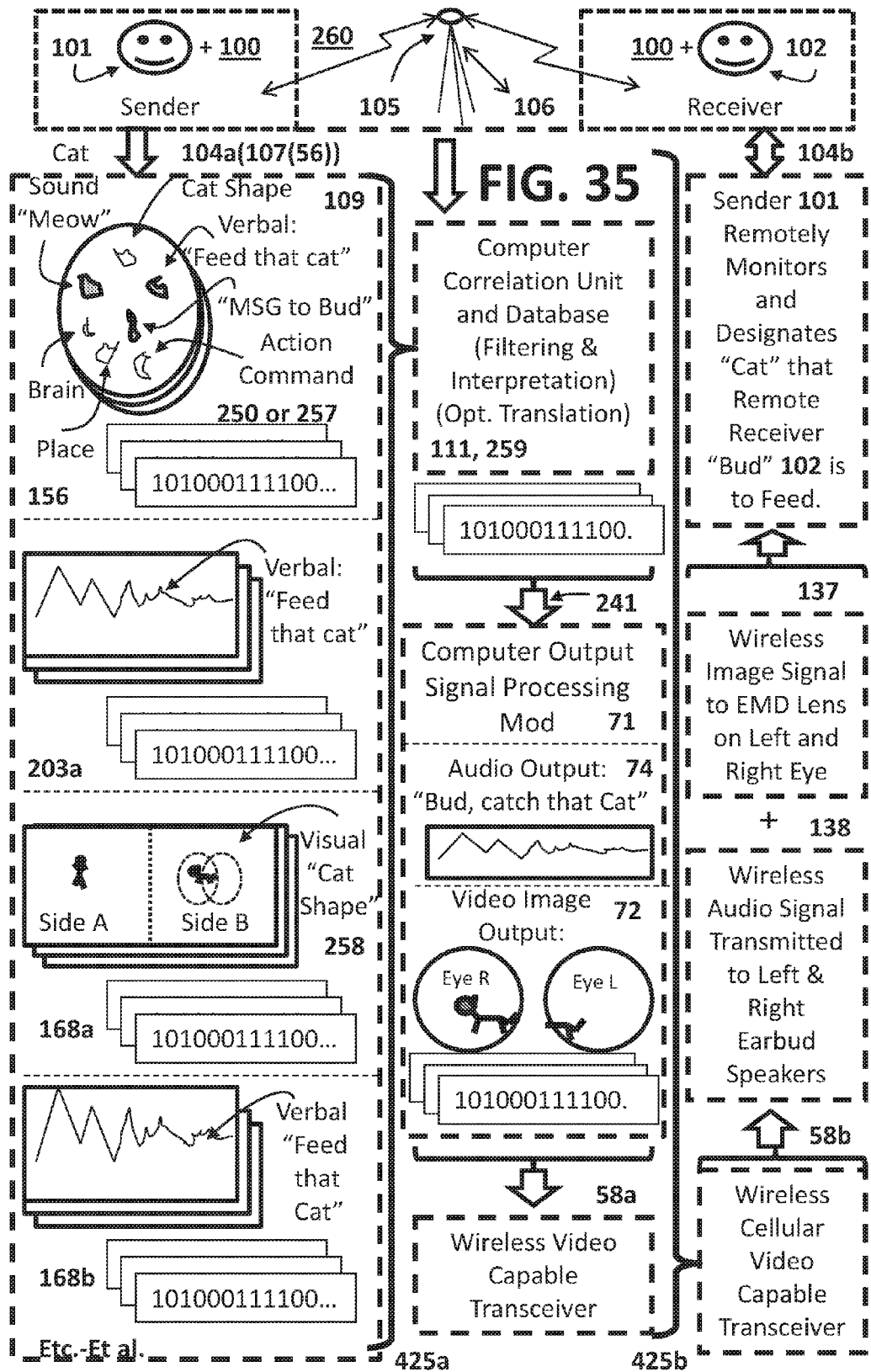

FIG. 36a-b

Internal and External Data Recording and Transmission, (i.e. Panoramic Audio-Visual Camera, Brain Imaging, and Sub-vocalization Data Transmission to the Host Computer Processor).

Internal and External Correlation and Translation Processing, (i.e. Panoramic Audio-Visual Camera, Brain Imaging, and Sub-vocalization Computer Processing and Presentation).

FIG. 37a-c

Pan, Zoom, Rotate 360 degree Spherical FOV Scene

Multiple ROI of a Windowing 360 degrees/ spherical FOV Scene

MindShare Home Profile Friends Inbox      Settings

John Curtis   - For Me (Select One)   ences      Type, Think, or Say:
            - For My Friends
            - For Unknown Visitors

[Portrait labeled 101]

Live Feed    available now Click to View   10010111...

Previous Experiences

Left Eye and Ear   Right Eye & Ear 2011
2012
2013
2014

[My Cat]   [My Cat]

Bud this is what you are currently video logging with AR brain correlation notes.

MindShare with jc@gmail.com (click here)

Primary Selections    (Select any)
- Video Login   [On]
- Memory Enhancement   [On]

User Display Device: (Select one)
--- Contact Lenses Display
--- HMD
--- VideoRoom

Presentation Type: (Select one)
--- Monoscopic Video Feed
--- Biocular Video Feed
--- Stereoscopic Video Feed
--- Spherical Video Feed

- Through My Eyes (Select one)
- Look All Around Me

What I am thinking:
- My Focus
- By Areas in my Brain
-- Prefrontal Lobe
-- Frontal Lobe
-- Temporal Lobe
-- Rear Lobe
-- Place Cells
-- Facial ID Cells
-- Shape Cells
-- (more)

My Senses (Select any)
- Visual
- Audio
- Smell
- Taste
- Touch
- Spatial Orientation

| MindShare  Home  Profile  Friends  Inbox | | Settings  Logout |
|---|---|---|
| John Curtis | - For Me (Select One)<br>- For My Friends<br>- For Unknown Visitors | Type, Think, or Say: |

Live 2-Way Feed is ON

MindShare with: jc@gmail.com
(stop feed)

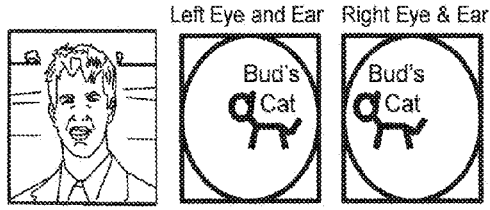

Left Eye and Ear    Right Eye & Ear

JC, this is what you are sending Mark.
(What you are currently seeing with AR
brain correlation notes).

MindShare with:
- Mark.Livston@Hightechier.edu
(stop feed)

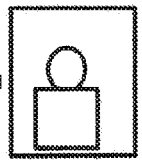 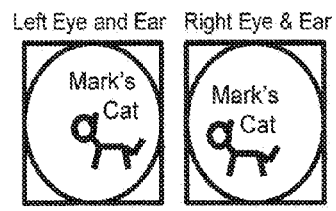

Left Eye and Ear    Right Eye & Ear

JC, this is what Mark is sending you.
(What is currently seeing with
AR brain correlation notes.)

Recent History:

Friend online: Live Feed On
 - Mark.Livston@Hightechier.edu

Friend visited: KU Graduation 2015
 - Blake.Adams@gmail.com

Visitor visited earlier: Whitewater Kayaking
 - Don.Won@yahoo.com  $1.00 paid
  for your experience. Left e-mail.

Primary Selections
- Video Logging:  On
- Memory Enhancement:  On

Other Selections
- In Simulation Gaming: Off
- Surrogate Robot:  Off

FIG. 39e 189, 278

MindShare Home Profile Friends Inbox      Settings Login

John Curtis   - For Me (Select One)      Type, Think, or Say:
          - For My Friends
          - For Unknown Visitors Search Engine: 11Nov2011Churc
--- By Time or Timeframe
--- By Location
--- By Subject
--- By Activity

10010111...

Left Eye and Ear    Right Eye & Ear

Pastor Vern          Say or Think Yes to View

MindShare with jc@gmail.com (click here)

Primary Selections (Select any)
- Video Logging   [On]
- Memory Enhancement   [On]

Safeguards:
--- Auto-Correlation (Select any)
    - Strength of "Hit"
      Threshold level.   [90%]
--- Prompt User before
    taking action.    Yes

Personal Assistant Databases:
--- My Life Experience Database
--- My Dad's Data
--- My Mom's Data
--- Mark.Livston@Hightechier.(
--- Bud Richie's Data
--- Pastor Vern's Data
--- YouTube Data
--- Google Data
--- Wikipedia Data
--- US PTO Database

1 RESULT:
CJ's Database 11Nov2011
11AM @ Church Sermon on
"Creation and/or Evolution".
---Selections Available:
    -- Stereoscopic Panoramic
Video
      - Imagery
      - Audio
     -- AR Brain Correlation Notes.

User Interfaces: (Select any)
--- AMR Brain Activity
--- Stereoscopic Video
--- Panoramic Video
     - Imagery (Target recog. & track)
     - Audio (Voice and sound recog.)
--- Sub-vocalization
--- Touch Sensitive HC on/off button
--- Keyboard and Mouse Other:   -Simulations     -Robotics

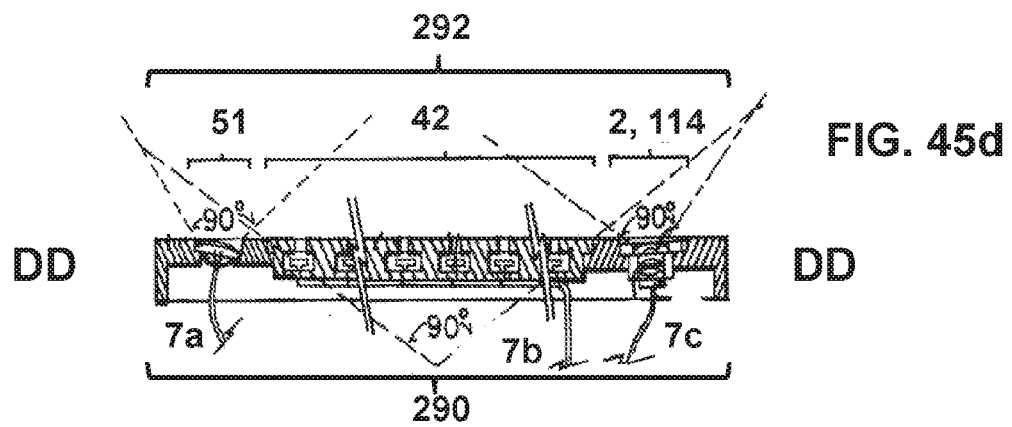
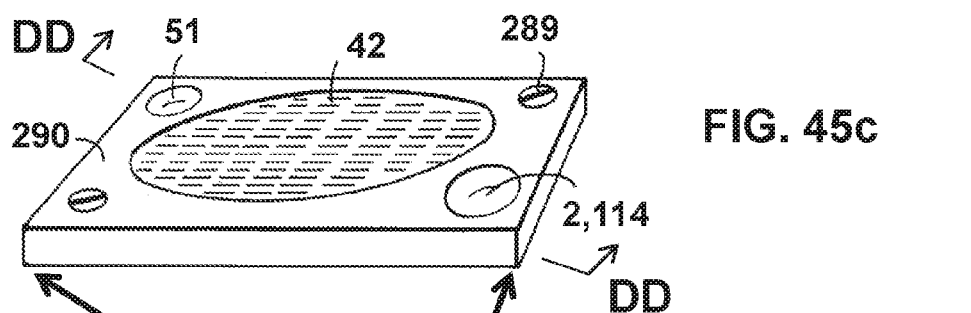
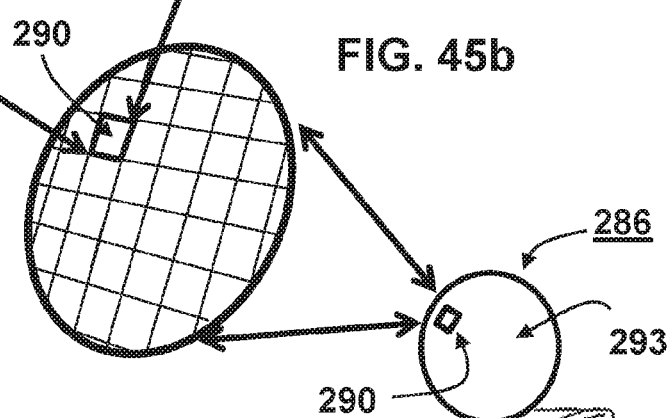
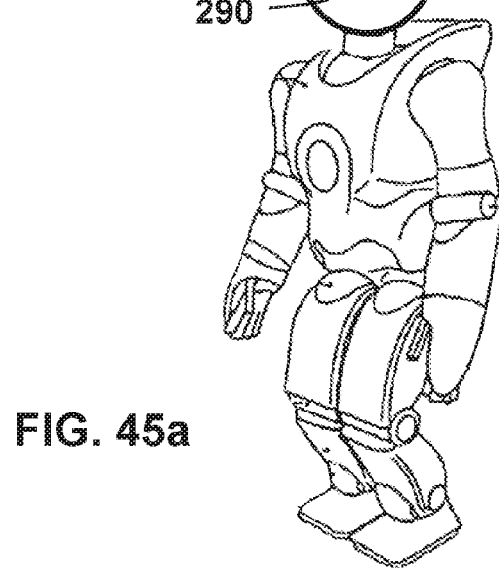
FIG. 45a-d

MOBILE USER BORNE BRAIN ACTIVITY DATA AND SURROUNDING ENVIRONMENT DATA CORRELATION SYSTEM

CROSS-REFERENCE TO RELATED APPLICATIONS

This continuation application is related to and claims the benefit of application Ser. No. 12/266,308 filed on 6 Nov. 2008 entitled "Panoramic Adapter System and Method with Spherical Field-of-View Coverage" (abandoned); application Ser. No. 13/294,986 filed on 11 Nov. 2011 entitled "Non-Interference" Field-of-View Support Apparatus for a Panoramic Facial Sensor"; and application Ser. No. 13/507,190 filed on 11 Jun. 2012 entitled "Mobile User Borne Brain Activity Data And Surrounding Environment Data Correlation System". The above applications are hereby incorporated by reference in their entireties into the present application.

INTRODUCTION

This invention relates to data logging of neural correlates of consciousness derived from host internal physiological and external panoramic and positional sensors operated upon via computer processing to provide information for memory enhancement. The fields of neurology, biology, biometric sensor engineering, prosthetic devices, implants, augmented cognition, whole brain emulation, computer science, statistical analysis, fast fusion computer processing, panoramic imaging, surround audio, sub-vocalization, computer simulation, geospatial information, telecommunications, internet search engines and social media, robotics, body modification, body worn, surgically implanted, and body mounted devices are relevant to and embodied within the present invention.

BACKGROUND OF THE INVENTION

A fundamental endeavor of mankind is to overcome natural and manmade limitations through the use of invention and design; with two innate goals being to live a contented life and in due course overcome mortality. The present invention is especially aimed at furthering these goals by the disclosure and use of a data logging and memory enhancement system and method. While humans have the natural ability to pass on physical attributes via genetics directly through reproduction, humans do not naturally have the ability to pass memory and thought processes through reproduction. And only very recently in human history has mankind had the ability to not just evolve but to determine how they evolve. Traditionally, environment caused changes in man's evolution, often taking many generations and thousands to millions of years for significant changes to naturally occur. But increasingly humans can use modern procedures and technological advances to instantly change their make-up. Increasingly modern technology is being offered that goes beyond traditional maintenance of the human faculties we are born with and is providing systems and methods to substitute, replace, or enhance what humans are provided with naturally at birth. The artificial heart, the Dobelle Eye, growing artificial body parts, using stem cells to differentiate into host cells, and genetic engineering are just a few examples. This invention is aimed at providing "designed evolutionary" systems and methods that accomplish this type of utility. Part of being a sentient being is being self-aware and realizing that there is a past, present, and future consequences of one's actions. It is therefore conceived as part of this invention that the user of the data logging and memory enhancement system, when coupled with problem solving, mobility, and available resources, will perform maintenance that will allow himself, herself, or itself to continue to exist in some fashion indefinitely.

The brain is the center of all human thought and memory. The sentientness of a being ends up encompassing what the being processed and retained in the beings central nervous system. The being is constantly perceiving the environment that surrounds in order to update his or her thought and memory. With this in mind a central objective of present invention is developing a human internal to external correlation of conscious percepts relative to a particular being realized in a system and method for personnel data logging and memory enhancement. For purposes of the present invention, the concept of "Neural Correlates of Consciousness" (NCC) and "Conscious Percept" (CP) are discussed and defined in publications and presentations by, for example, Christof Koch in "The Quest for Consciousness: A Neurobiological Approach" dated 2010 and as depicted in a diagram by Dlende entitled "Neural Correlates of Consciousness" dated 2008. Neural Correlates of Consciousness (NCC) can be defined as "the minimal neuronal mechanisms jointly sufficient for any one conscious percept" of a self-aware being, the being also aware of the surrounding environment, and other conscious contents to which that being is relating at a given time. A "conscious percept" may be defined as a subject's focus of attention as a being, machine, or bio-mechanical system in a particular surrounding environment at a given time. A surrounding environment may also be referred to as "place", which may for example be defined by imagery, audio, brain activity, or geospatial information. Achieving this objective can be done by recording and measuring internal and external activity and relating the activity in the mind to the activity and subjects that the person is thinking about in the surrounding environment. Studies have taught us that various senses can stimulate the central nervous center. Examples focused on in the present invention are those which yield the most utility for learning. Approximately 78% of all information taken in is through our eyes, 12% through our ears, 5% through touch, 2.5% through smell, and 2.5% through taste. It is an objective of the present invention and it will be understood to those skilled in the art that various internal and external types of sensor systems (i.e. audio, imagery, video camera, geospatial, position, orientation, brain activity, and biometric systems) may be used to record sensory data and that this data may be processed in a computer to build a correlation, transcription, and translation system for human to machine interaction. Statistical correlations are useful in the present invention because they can indicate a predictive relationship that can be exploited in practice. A computer can operate upon recorded sensory data using adaptive filters (i.e. Kalaman and/or Bloom filter algorithms implemented in computer language) to determine the correlation between the internal and external representations to determine the strength of the statistical relationship between internal and external representations. Threshold's for retaining, disregarding, or acting upon the data may be based on the statistical relationships and used to determine targeted data output. In the present invention translation is the communication of the meaning of a source-language, be it human or machine. It is an objective of the present invention to incorporate machine translation (MT) as a process wherein computer program(s) analyze inter-related raw and preprocessed sensor data and produce target output data (i.e. human understandable GUI text, video or synthesized voice audio output into human interactive input devices of a human user) with little or no human intervention. In the context of the current invention computer-assisted translation (CAT), also called "computer-aided translation," "machine-aided human translation" (MAHT), and "interactive translation," is a form of translation wherein a machine translation system uses machine language to create a target language, be it human or machine, correlated with text, sub-vocalization, brain activity, and sensory signatures of subjects and activities in the surrounding environment with the assistance of computer program(s). It is an objective of the present invention to use the above translations to form the basis of a relational database which may be drawn upon by a user to perform various functions using a mobile computing device such as a smartphone or the like as described in the present invention.

Spherical field-of-view sensing and logging about the user is preferable when it comes to recording how the mind works because the mind constantly perceives the space one finds himself or herself occupying. In an academic paper entitled "Intelligent Systems in the Context of Surrounding Environment" Joseph Wakeling and Per Bak of the Department of Mathematics, London, UK, dated 29 Jun. 2001, describe a biological learning pattern based on "Darwinian selection" that suggests that intelligence can only be measured in the context of the surrounding environment of the organism studied: i.e. "We must always consider the embodiment of any intelligent system. The preferred embodiment reflects that the mind and its surrounding environment (including the physical body of the individual) are inseparable and that intelligence only exists in the context of its surrounding environment." Studies by O'Keefe, J. and Nadel, L. (1978) entitled The Hippocampus as a Cognitive Map. Clarendon Press: Oxford and Rotenberg, A., Mayford, M., Hawkins, R. D., Kandel, E. R., and Muller, R. U. (1996) and classic studies of John O'Keefe and John Dostrovsky (1998), point to strong evidence why a video logging machine needs to provide a panoramic FOV about a user in order to get a true representation or reproduction of their consciousness. In 1971 it was discovered that the pyramidal cells of the hippocampus—the cells one examines artificially using electrical stimuli to the Schaffer collateral pathway while studying LTP—are "place cells"; they actually encode extra-personal space in real life. A given pyramidal cell will fire only when the head of a user is in a certain part of an enclosed space: the cell's place field. Thus, when a person walks borne with the present invention in a given space, a particular subset of pyramidal cells in the hippocampus becomes active. When the user is in different space, different sets of pyramidal cells become active. Cells of the hippocampus form an internal neural representation, or "cognitive map" of the space surrounding the user. This holistic neural representation permits the user to solve spatial problems efficiently. And when placed in a new environment, a person forms an internal representation of the new space (the coordinated firing of a population of place cells) within minutes, and once this representation is formed it is normally stable for at least several days. The same cell will have the same firing field each time the person is reintroduced to that environment. When now placed in a second environment, a new map is formed—again in minutes—in part from some of the cells that made up the map of the first environment and in part from pyramidal cells that had been silent previously. These place cells and spatial memory can be studied by recording brain pattern activation using MRI, and various other brain activity systems such as AMR, fMRI, fNRI, EEG, PET, or DECI to record brain activity from individual pyramidal cells in the hippocampus (ref. Kandel and Squire, 1998). Studies show that regions of the brain that have place cells that are active when one is in a familiar place versus when one is not in a familiar place. Activity is especially noticeable in these cells when a person is navigating a space in the dark. Human memory works to recall and visualize what was there in the daylight to help a user of the present invention navigate a dark space.

Neurological research has identified specific locations, processes, and interactions down to the human neuron and molecular level for thinking and memory. Research has shown that human neurons and synapse both are actively involved in thought and memory, and that brain imaging technology such as Magnetic Resonance Imaging (MRI), Nuclear Magnetic Resonance Imaging, or Magnetic Resonance Tomography (MRT) can be used to observe this brain activity at the molecular level. Recently atomic magnetometers have begun development of cheap and portable MRI instruments without large magnets used in traditional MRI machines to image parts of the human anatomy, including the brain. There are over 100 billion brain cells/neurons in the brain, each of which has synapses that are involved in memory and learning, which can also be observed by brain imaging techniques. It has also been proven that new brain cells are created whenever one learns something new. Whenever stimuli in the environment or through thought make a significant enough impact on the beings brain new neurons are formed. During this process synapses carry on electrochemical activities that reflect activity related to both memory and thought. Important for purposes of the present invention is that using modern technological devices, such as an Atomic Magnetometer, this activity in the brain at the molecular level can be detected, measured, stored, and operated upon using computers according to the present invention as these processes are taking place in the brain. Research has also shown that even though there are important similarities in the brain activity of different people each person has a unique brain "fingerprint". This fingerprint of the brain is unique to each person's thought processes and how and where they store their memories in their brain. It is an objective of the present invention to facilitate recording and translating the uniqueness of a subject's brain and the subjects corresponding brain activity. Yet additionally, to design a universal brain translation system and method that facilitates communication between different beings, machines, or a combination thereof.

In September 2006 Stefan Posse and his colleagues at the University of New Mexico used MRI techniques to observe brain activity correlated with the thought of a single word. And they recently recorded longer imaging sequences and decomposed the thought processes into individual thoughts. When images of Marilyn Monroe were shown a specific neuron fired, when images of another actor was shown a neuron specific to that actor fired. Likewise, Francis Krick and Christof Koch in the periodical Nature Neuroscience, Vol. 6, number 2, dated February 2003, in an article entitled "A Framework for Consciousness" along with their more recent findings demonstrate that certain neurons fire selectively to certain visual stimuli. Koch argues for including the neural correlates for conscious precepts as any part of understanding how human beings are consciously aware. Koch research has shown that neural correlates of both basal arousal and activity in the inferior temporal cortex are necessary for a human being to be consciously aware. And that brain decoding techniques can be translated into images based on reading a patients mind. In a study 20-30 specific neurons were listened to too infer what the patient was conscious of. Research by Koch has also shown that physical input (i.e. A person actually looking at an object.) and imagined input (i.e. A person closing their eyes and imagining an object in their mind.) stimulated the same neurons. It is an object of the present invention to correlate repeated recordings and loggings of user physiological activity (i.e. user brain activity, sub-vocal imitations, etc.) with recordings and loggings of the surrounding environmental activity (i.e. panoramic video images of gaze of the user upon a subject, etc.) to build an esemplastic patterned language using the present invention. The computerized logging and assistance system that forms the present invention thus yielding a representation of the consciousness and understanding of the world from the given point-of-view of the being whose information is operated upon. And the computerized logging and assistance system that forms the present invention thus providing an informational system that may be operated upon to assist a user being, machine, or combination thereof in negotiating the world in which he, she, or it respectively lives or operates.

An example of a brain activity sensing system providing enabling technology incorporated into the present invention is a portable Magnetic Resonance Imaging devices such as the Atomic Magnetometer Sensor Array Magnetic Resonance (AMR) Imaging Systems and Methods. Recently portable Atomic MR systems such as those described in U.S. Patent 2009/0149736, dated 11 Jun. 2009 by Skidmore et al and U.S. Patent 2010/0090697, dated 15 Apr. 2010 by Savukov have been disclosed that are of a type compatible and enabling of the present invention. Further, John Kitching, a physicist at the National Institute of Standards and Technology in Boulder, Colo. has developed a tiny (grain of rice size) atomic magnetic sensors of a type compatible for use in the present invention. Specifically, systems and devices disclosed in the Skidmore patent and Kitching presents a wearable portable array, of reduced size, low power consumption, reducible to a wafer-level, has rapid signal transfer, and with decreased magnetic field that facilitates lower cost and easy mounting on and/or inside a person, animal, or inanimate object. U.S. Patent Application 20100016752, by Jeffery M. Sieracki dated 21 Jan. 2010 entitled System and Method for Neurological Activity Signature Determination, Discrimination, and Detection discloses a system for automatically correlating neurological activity to a predetermined physiological response comprising: at least one sensor operable to sense signals indicative of the neurological activity; a processing engine coupled to said sensor, said processing engine being operable in a first system mode to execute a simultaneous sparse approximation jointly upon a group of signals sensed by said sensor to generate signature information corresponding to the predetermined physiological response; and, a detector coupled to said sensors, said detector being operable in a second system mode to monitor the sensed signals and generate upon selective detection according to said signature information a control signal for actuating a control action according to the predetermined physiological response.

Still alternatively, U.S. Patent Application 2010/0042011, dated 18 Feb. 2010, by Doidge et al entitled "Three-dimensional Localization, Display, Recording, and Analysis of Electrical Activity in the Cerebral Cortex" discloses a computerized Dynamic Electro-cortical Imaging (DECI) method and apparatus for measuring EEG signatures of the brain in real time. The DECI system and method is portable and can be worn by the user to generate dynamic three-dimensional (voxel) information of the electrical activity occurring in the cerebral cortex of the brain. The DECI system is of a type that may be incorporated in the present invention to provide brain activity information according to the present invention. U.S. Patent Application 2010/0041962, dated 18 Feb. 2010 by Causevic et al., entitled "Flexible Headset for Sensing Electrical Activity" discloses a headset worn on the outside of the head for sensing brain activity.

Additionally, scientific studies show that images we recall in our imagination are not always as detailed as a photographic image. In 1999, researchers led by Yang Dan at University of California, Berkeley decoded neuronal firings to reproduce images seen by laboratory animals. The team used an array of electrodes embedded in the thalamus (which integrates all of the brain's sensory input) of animals. Researchers targeted 177 brain cells in the thalamus lateral *geniculate* nucleus area, which decodes signals from the retina. The animals were shown eight short movies, and their neuron firings were recorded. Using mathematical filters, the researchers decoded the signals to generate movies of what the animals saw and were able to reconstruct recognizable scenes and moving objects. An object of the present invention is to provide imagery and audio of the subject of the CP and surrounding environment that is correlated to brain activity which can be queried by a user of the invention from logged information recorded by the invention which is more complete and accurate than what the brain remembers. To derive this utility from the above mentioned brain activity systems, like the AMR system, the resulting brain activity signatures are related to a thoughts and memories as associated with things in the surrounding environment with respect to the individual using the AMR system. A monocular or binocular camera system may be incorporated into the present invention. But preferably a camera system with stereoscopic capability is incorporated. U.S. Patent Application 20070124292 A1, by Kirshenbaum et al, dated 31 May 2007, entitled Autobiographical and Other Data Collection System describes a system for collecting/recording, storing, retrieving, and transmitting video information that may be incorporated into the present invention. Stereoscopic cameras that approximate human vision are preferable because they reflect how humans naturally see and experience the world, and provide depth clues to the brain. Panoramic stereoscopic cameras are also more preferable because they provide more measurable data, added spatial awareness like that what persons experience, and allow the replay of the total surrounding environment is more attune to what is actually stimulating the user's senses, memories, and resulting thoughts in the real world. Portable head-mounted panoramic video cameras of a type that may be used in the present invention include U.S. Pat. No. 6,552,744 B2 by Chen, dated Apr. 22, 2003, entitled Virtual Reality Camera which presents a camera which records discrete still or video images that can be stitched together to create a panoramic scene that incorporates computer processing so that the user may pan and zoom around the panoramic scene; U.S. Patent Application 2001/00105555 and U.S. Pat. No. 6,539,547, by Driscoll, dated Aug. 2, 2001, discloses a Method and Apparatus for electronically recording, storing, and distributing panoramic images from a panoptic camera system to a remote location using the internet; U.S. Patent Publication 2005/0157166 by Peleg, dated Jul. 21, 2005 entitled Digitally Enhanced Depth Image which discloses a camera method to simultaneously record, store, and process panoramic stereoscopic imagery; U.S. Pat. No. 5,023,725, by McCutchen, dated Jun. 11, 1991, FIG. 21, which discloses a cap with a plurality of high resolution video cameras that record a plurality of imagery that may be stitched together to form a hemispherical scene; U.S. Patent 20020015047 Okada, Hiroshi" et al, dated Feb. 7, 2002 entitled "Image cut-away/display system" that describes a panoramic camera, processing, display system in which the images are combined for forming a single wide-area view image for use as a virtual environment, telepresence environment, texture mapped three-dimensional simulated environment, or an augmented reality environment consistent for use in the present invention; U.S. Patent Application Publication 2005/0128286 dated 16 Jun. 2005 by Angus Richards that discloses a panoramic camera mounted helmet that also includes a head-mounted display (HMD) with telecommunication capabilities; U.S. Pat. Nos. 5,130,794, and 5,495,576, and grandparent, parent, and pending related applications by Ritchey and Ritchey et al; and U.S. Patent Applications 2005/0128286 dated 16 Jun. 2006 and 2006/0082643 dated 20 Apr. 2006 that disclose HMD systems of a type compatible for incorporation in the present invention. All of the camera systems cited in this paragraph are of a type that may be incorporated as a component of the present invention.

Still alternatively, eye-in and eye-on contact lenses may include cameras for recording and displaying imagery according to the present invention. For example a camera device that is mounted on and/or inside the eye is disclosed in US Patent 20090189974 A1, by Michael F. Deering, dated 30 Jul. 2009, entitled Systems Using Eye Mounted Displays (EMD). Deering describes a still and/or video camera could be placed directly on the eye mounted display worn on or in the user's eye(s). Such a camera in essence automatically tracks the motions of the user's eye(s) because it is effectively part of the user's eye(s). The eye mounted camera is folded within the EMD using some of the same optical folding techniques used in folding the display optics of the EMD. The processing of the image is handled on the contact lens, an electronics package on the user's body, or by a remote processing center. A remote user can pan and tilt the camera to point in the same direction as the user's eyes, using the direction information from the eye tracking subsystem. Such a camera greatly reduces the time and physical grabbing of an external camera when taking a picture; as an example a particularly gorgeous sunset can be photographed with something as simple as a quick glance and a double eye blink. The camera can be located in one or both eyes. A plurality of camera systems, like EMD and panoramic camera systems, may be integrated in the present invention to attain the required FOV coverage and overall system functionality. An EMD system of this type may provide capture and/or display for the present invention, and may transmit to and from the smartphone when incorporated according to the present invention. Additionally, another EMD design consists of a contact lens that harvests radio waves to power an LED that displays information beamed to the contact lens from mobile devices, like a smartphone. The EMD system was invented by Babak Parviz and is currently in prototype at the University of Washington (Ref. New Scientist, 12 Nov. 2009 by Vijaysree Venkatraman). The above systems are of a type compatible with and are incorporated into the present invention.

A smartphone is a portable electronic device (PED) that combines the functions of a personal digital assistant (PDA) with a mobile phone. Smartphones typically have computer and computer processing hardware, firmware, and software built in to the unit. An example of a smartphone is the iPhone 4S and 5, sold by Apple Inc. Later models added the functionality of portable media players, low-end compact digital cameras, pocket video cameras, and global positioning system (GPS) navigation units to form one multi-use device. Modern smartphones also include high-resolution touch screens and web browsers that display standard web pages as well as mobile-optimized sites. High-speed data access is provided by Wi-Fi and Mobile Broadband. The most common mobile operating systems (OS) used by modern smartphones include Google's Android, Apple's iOS, Nokia's Symbian, RIM's BlackBerry OS, Samsung's Bada, Microsoft's Windows Phone, Hewlett-Packard's webOS, and embedded Linux distributions such as Maemo and MeeGo. Such operating systems can be installed on many different phone models, and typically each device can receive multiple OS software updates over its lifetime.

It is also known in the art that small independent pill capsules may be used to capture imagery. A very small wireless video camera and lens, transceiver, data processor and power system and components that may be integrated and adapted to form the panoramic capable wireless communication terminals/units is disclosed by Dr. David Cumming of Glasgow University and by Dr. Blair Lewis of Mt Sinai Hospital in New York. It is known as the "Given Diagnostic Imaging System" and administered orally as a pill/capsule that can pass through the body and is used for diagnostic purposes. U.S. Pat. No. 7,662,093, by Gilad et al, dated 16 Feb. 2010, entitled Reduced Size Imaging Device describes a swallowable imaging capsule that includes an imager, processing, and wireless transmission system that may be incorporated and is compatible with the present invention. Others similarly include U.S. Pat. No. 7,664,174 and U.S. Patent Application 20080033274 and 20080030573. Small pen cameras, tie cameras, and so on used in the spy and surveillance may also be incorporated into forming camera components of the present invention. Objective micro-lenses suitable for taking lenses in the present invention, especially the panoramic taking assembly, are manufactured and of a type by AEI North America, of Skaneateles, N.Y., that provide alternative small and compact visual inspection systems. AEI sales micro-lenses for use in borescopes, fiberscopes, and endoscopes. AEI manufacture objective lens systems (including the objective lens and relay lens group) from 4-14 millimeters in diameter, and 4-14 millimeters in length, with circular FOV coverage from 20 to approximately 180 degrees. Of specific note is that AEI can provide an objective lens with over 180 FOV coverage required for some embodiments of the panoramic sensor assembly like that incorporated in the present invention required in order to achieve overlapping adjacent hemispherical FOV coverage of two back-to-back fisheye lenses or stereoscopic panoramic coverage when four lenses are incorporated at 90 degree intervals. The above cameras, transmitters, and lenses may be incorporated into the above video logging system or other portion of the panoramic capable wireless communication terminals/units to form the present invention. Camera systems may be operated by powered and controlled via wire clad, fiber-optics, or over a radio frequency signal. Camera signals may be processed and transmitted separately or multiplexed by any manner familiar to those in the art in the present invention. Both EMD and pill camera technology are enabling and are incorporated in the present invention to record and transmit imagery of the user and the scene surrounding the user in the present invention.

As stated above, deriving utility from the above mentioned brain activity systems includes relating the brain activity to a subject(s) in the surrounding environment at the time that the focus was on the subject observed. User born position orientation, geospatial position and orientation systems, target designators, and eye tracking systems may be incorporated in the present invention to accomplish the task of recording what the attention of the user is focused upon. Pointing devices may be any user-operated pointing device including, but not limited to, a joystick, a trackball, a touch-sensitive pad or screen, a set of directional "arrow" cursor control keys, a helmet-mounted sight, or an eye-tracking system. Many navigation systems, surveillance systems and weapon systems provide a user with a video image of a region of interest (ROI) from which the user may designate an object or feature for tracking. In a typical tracker, the user selects the desired target and from that point onward the target is tracked automatically. Known techniques for video-based target designation employ a use operated pointing device (e.g., joystick, trackball, helmet-mounted sight, eye-tracking system. etc.) to either move a cursor/marker or move a gimbal on which the camera is mounted so that a marker (e.g. a crosshair) is located on the desired target on the live video display. Then, by pushing a button, the user finally locks the tracker on the current target. A video scalar and rangefinder may be incorporated as part of the target tracking system. A tracking module is then actuated and attempts to reliably acquire a trackable target at the designated position within the image for subsequent automated tracking. Target tracking systems may be integrated with eye tracking systems to determine what the eyes of a person is focused upon. Tracking and pointing devices may be manually operated, or automatically operated by a computer given a rule set. Eye tracking systems are known in prior art that monitor the position of a user's eye within its socket in order to determine the user's line of gaze, for example to enable the user to control a device, such as a weapon, by eye movements or to determine whether the user is watching a predetermined location, such as a location on a television screen, or simply to determine the state of wakefulness of the user.

Furthermore a number of different methods have been proposed for monitoring the position of the user's eye associated with gaze and focus on a subject in the users field-of-view (FOV), including the so-called corneal reflection (CR) method in which a point light source is used to produce a bright image on the anterior surface of the cornea, and a tracking system monitors the position of the image. A differential CR/pupil tracking method has been developed in which the relative positions of the pupil and a corneal reflection are monitored by a suitable camera and a wave-length-sensitive beam splitter being used to ensure that the user's view is not obstructed by the light source and camera. This method is less sensitive to sensor movements. Generally the eye is illuminated by a near infrared source (or multiple sources) and a solid state video camera captures an image of the eye. In so-called bright pupil imaging the light source produces a light beam which is coaxial with the camera axis, and light reflected back from the retina making the pupil appear to be a bright circle, the apparent brightness increasing roughly with the fourth power of pupil diameter. In so-called dark pupil imaging the light source produces a light beam which is off axis relative to the camera axis, and a dark pupil image is produced. Real time image analysis is used to identify the pupil and corneal reflections and to find their centers. Portable target tracking and pointing devices of a type that can be incorporated in the present invention to associate the image observed in the surrounding environment with specific subjects there-in and brain activity to facilitate recording correlate designation include the eye tracking system generally described above and specifically described in U.S. Patent Application 20040196433, by Durnell, dated 7 Oct. 2004, titled Eye Tracking System, and in U.S. Patent Application 20080205700, by Nir, dated 28 Aug. 2008 titled Apparatus and Method for Assisted Target Designation which includes video designation and tracking via imagery and/or directional audio. The above systems referenced in this paragraph produced information that can be digitally stored and processed by a computer. The eye tracking, gaze, and directional FOV, and GPS derived from systems described in this paragraph can be correlated with recorded and stored AMR, and camera data of objects and scenes according to the present invention. The Ultra-Vis, Leader, system developed by ARA, which includes the subsidiary companies MWD, Vertek, and KAD, Lockheed Martin, and Microvision Incorporated is a type of target designation and tracking system that may be integrated into the present invention. The portable iLeader system includes a HMD system with a micro-laser range finder system for target designation, see through eyewear, head and eye tracking system, waveguide display goggles, video cameras for recording the view the user is seeing directly ahead of where he is looking, helmet electronics, eye tracking and target designation system, voice mics and earbuds, and an associated electronics unit to control the HMD, telecommunications network and GPS interface, iGlove, battery power and sensor feed, and a soldier augmented reality (AR) system. In the planning and patrol mode view the users see-through HMD of the iLeader system is operated by the user to designate and record targets in the surrounding environment and overlay information on a see-through display. The overlaid information displayed to the user may be from associated sensors the user is wearing, sensors other users are wearing, or from other information on networked devices that is wirelessly transmitted from a remote location that is part of the telecommunication system and network that includes the iLeader system. Technology of a type disclosed in the iLeader system is consistent with and may be incorporated into the present invention.

As mentioned above audio input systems provide a significant portion of human sensory input. A microphone system is incorporated to record audio from and about the user as part of the video logging system described in the present invention. Microphones are faced inward to record audio from the user and outward to record audio about the user. Typically microphones are located on the user as a device worn or carried by the user. Small microphones are known to those in the art and are commonly used in the hand-free cell phone operation and known as throat mics that fit around the ear or as lapel mics worn by those in the television industry and security industry and are of a type that is compatible with and incorporated into the present invention. The microphone can be part of an audio recording or communication system common on cellular telephones and in the cellular telephone industry. Alternatively, a three-dimensional surround sound ambisonic audio recording system exist to capture using a tetrahedrally arranged quartet of cardioid pattern microphone capsules connected to some simple circuitry to convert the outputs to a standard B-format signal. B-format signals represent a 3D sound-field with four signals; X, Y and Z representing three orthogonal figure of eight patterns and an omni-directional W reference signal. Audio from ambisonic microphones may be spatially encoded using surround sound encoders to output spatial audio may be played back in a user's earphones or earbuds. Ambisonic microphones may be distributed in an outward facing manner according to the present invention.

Ambisonic hardware known as TetraMic Spheround with associated software of a type applicable to the present invention is manufactured by Core Sound of Teaneck, N.J., USA.

Vocal representations of the user or from a remote user, be they words spoken aloud or sub-vocalized, may be sensed and provide data input according to the present invention. Audio can be used for correlation purposes or for command and control of the logging and enhancement system according to the present invention. Speech recognition (also known as automatic speech recognition or computer speech recognition) converts spoken words to text. The term "voice recognition" is sometimes used to refer to recognition systems that must be trained to a particular speaker—as is the case for most desktop recognition software. Recognizing the speaker can simplify the task of translating speech. In the present invention a microphone is a user interface for recording audio signatures of the user and surrounding environment for input in to an associated computer in order to facilitate hands-free computing. Conventional voice-command systems that use conventional voice recognition systems of a type that may be used in the present invention include the Kurzweil Applied Intelligence (KAI) Speech Recognition System for commercial use. The large-vocabulary present invention a microphone is a user interface for recording audio signatures of the user and surrounding environment for input in to an associated computer in order to facilitate hands-free computing.

An embodiment and sensor input component of the present invention includes a sub-vocalization system. Sub-vocalization is the tendency of a user to silently say individual words to themselves as they read or think. Sub-vocal recognition (SVR) is the process of taking sub-vocalization and converting the detected results to a digital text-based or text-synthesized voice audio output. It is similar to voice recognition except it is silent sub-vocalization being detected. A sub-vocalization system of a type that may be incorporated into the present invention as a component disclosed in U.S. Pat. No. 6,272,466, dated 7 Aug. 2001, byt Harada, et al., entitled "Speech detection apparatus using specularly reflected light" and that described in the ongoing NASA Sub-vocal Recognition (SVR) program began in 1999, and later renamed the Extension of Human Senses program. In the NASA program muscles of the vocal tract (e.g. electromyographic or EMG) signatures are sensed by contact sensors placed on the throat (either internally or externally to the body). The signatures are read out as electrical signals which are translated by a computer into patterns recognized by classifiers as word or word components. Another sensor input system that may be integrated with the present logging and memory enhancement system and method include infrared and LIDAR systems. LIDAR (Light Detection and Ranging) is an optical remote sensing technology that measures properties of scattered light to find range and/or other information of a distant target. LIDAR systems can see through fog and darkness to record the shape and motion of objects in their FOV, overcoming the limitation of visible spectrum cameras. LIDAR systems and methods of a type that may be integrated into and is compatible with the present invention are those found in U.S. Patent Application 2003/0154010 and 6,859,705, by Rae et al, dated 14 Aug. 2003 and 22 Feb. 2005, entitled "Method for Operating a pre-crash sensing system in a vehicle having a countermeasure system" using a radar and camera; U.S. Patent 2007/0001822 by Karsten Haug, dated 4 Jan. 2004, entitled "Method for improving vision in a motor vehicle"; and that mentioned in U.S. patent application Ser. No. 11/432,568 entitled "Volumetric Panoramic Sensor Systems" filed May 11, 2006 and LIDAR systems cited in related patent applications by the present inventor. An objective of the present invention is to provide and embodiment to the present invention which includes a LIDAR system for logging the surrounding environment: and man portable systems described in U.S Patent Application Publication 2011/0273451, dated 10 Nov. 2011, by Salemann; and a publication entitled "An approach for collection of geo-specific 3D features from terrestrial LIDAR, by Dr. David Optiz et al., of Overwatch Geospatial Incorporated, of Missoula, Mont., dated 28 Apr. 2008, at the ASPRS Conference.

Turning now to user feedback systems of a type incorporated into the present invention. Feedback to the user can be through any of the user's senses. Portable audio-visual devices of a type that may be incorporated in the present invention to provide visual and audio information to the user include information appliances like cellular phones, head-mounted displays, laptops, and speaker headphones. Additionally, separate eye and audio capture and presentation devices may be worn by the user. The separate devices may be connected via radio-frequency, infrared, wire, fiber-optic communications network on or off the user. Processing of the audio and visual signature information may be at the site of the sensor or downstream in the body, or outside the body on a system mounted on, carried by, or at a remote server in communication with the user's video logging and enhancement/assistance system.

According to many users, a current limitation of panoramic head mounted display (HMD) systems integrated with panoramic camera systems is that they are too heavy and bulky. The additions of wider field-of-view displays and viewing optics, microphones, speakers, cameras, global positioning systems, head and eye tracking systems, telecommunication, associated power and processing capabilities, along with helmet padding can add additional weight and bulkiness. These problems contribute to the majority of head mounted displays being too large and not being portable. Correspondingly, a limitation is that putting-on, adjusting, and taking-off the HMD is a difficult task. Finally, another limitation is that good head mounted displays are expensive. Head-mounted display (HMD) devices of a type that are compatible with the present invention are described in the present inventors previous disclosed prior art. HMD design well known to those skilled in the art and that may be used in the present invention is described in the following papers: Head-Worn Displays, The Future Through New Eyes, by Jannick Rolland and Ozan Cakmakci, published by the Optical Society of America, April 2009; Head-Worn Displays: A review by Jannick Rolland and Ozan Cakmakci, published IEEE in the Journal of Display Technology, Vol. 2, No. 3, September 2006. Specifically, a type of system applicable to the present invention is a low profile writeable holographic head worn display (HWD) that has see-through capabilities that facilitate augmented reality. U.S. Patent Application 20100149073, by David Chaum et al, dated 17 Jun. 2010, entitled "Near to Eye Display System and Appliance" is such a holographic type of display compatible with and that is incorporated into the present invention. Such a system compatible with and integrated by reference into the present invention manufactured by Microvision of Redmond, Wash., includes the small portable Integrated Photonics Module (IPM) only a couple of centimeters square that is mounted on a HMD device. The IPM uses integrated electronics to control a laser and bi-axial MEMS scanner to project an image through optics onto and including eyeglasses a user is wearing. Furthermore, U.S. Patent 2005/0083248, by Biocca, Frank and Rolland, Jannick et al., dated 21 Apr. 2005, entitled "Mobile face capture and image processing system and method" disclose a camera system that looks inward to capture a user's face and not outward such that a continuous panoramic view of the remaining surrounding scene can be recorded and interacted with, which is critical for 2-way teleconferencing and for establishing neural correlates of consciousness with surrounding environment. A further limitation of Biocca is that the cameras facing inward block the users peripheral FOV.

Flexible electronic displays of a type integrated in the present invention are of a type shown in U.S Patent Application Publication 2010/0045705, dated 25 Feb. 2010, Vertegaal et al., entitled "Interaction Techniques For Flexible Displays" that incorporate what is referred to as "e-paper" in the display industry; and display screens and associated computerized image processing systems to drive flexible thin, light-weight, either of soft or semi-rigid material, energy saving, and irregular shaped and curved LED display systems of a type integrated into the present invention are manufactured by Beijing Brilliant Technology Co, LTD, China, under the trade name "flexible display". It is known that non-see-through and see-through LED and OLED systems are manufactured. See-through LED and OLED are frequently used in augmented reality HMD applications. Systems referenced in this paragraph are of a type that may be integrated, retrofitted, and in some cases improved upon to realize the present invention.

Providing electrical power to the smartphone, portable brain activity sensing system, surround video logging system, correlation system, and sub-components are an enabling technology to the operation of the present invention. A conventional battery charger may be operated to recharge the battery carried by the user, typically in the smartphone. Landline transfer of energy, especially for recharging of portable systems is well known to those skilled in the art and may be used in some embodiments of the system that comprises the current invention. However, while less common, wireless energy transfer or wireless power transmission for recharging electrical devices is preferable because it facilitates ease of use in some embodiments described in the present invention. Wireless energy transfer or wireless power transmission is the process that takes place in any system where energy transfer or wireless power transmission. An induction charging system of a type that may be used to recharge devices external to the body of the user or implanted in the user is of a type put forth in the Provisional Application by Ritchey et al; U.S. patent Ser. No. 13/222,2011 dated 31 Aug. 2011 by Parker et al and as US Patent Application Publication No 2012/0053657 on 1 Mar. 2011 entitled "Implant Recharging"; and in U.S. Pat. No. 5,638,832, issued 17 Jun. 1997, by Singer et al., entitled "Programmable Subcutaneous Visible Implant". Another method of providing electrical power incorporated in the present invention is by kinetic energy replacement. Where electrical power is generated by movement and used to power electrical devices. Energy can also be harvested to power small autonomous sensors such as those developed using Micro-electromechanical Systems (MEMS) technology. These systems are often very small and require little power and whose applications are limited by the reliance on battery power. Scavenging energy from ambient vibrations, wind, heat or light enables smart computers and sensors in the present invention to function indefinitely. Energy can be stored in a capacitor, super capacitor, or battery. In small applications (wearable and implanted electronics), the power follows the following circuit: after being transformed (by e.g. AC/DC-to-DC/DC-inverter) and stored in an energy buffer (e.g., a battery, condenser, capacitor, etc.), the power travels through a microprocessor (fitted with optional sensors) and then transmits out the gathered sensor data (usually wirelessly) over a transceiver. Biomechanical energy harvesters have been created and are incorporated into the present invention. One current model is the biomechanical energy harvester of Max Donelan which straps around the knee. Devices as this allow the generation of 2.5 watts of power per knee. This is enough to power some five cell phones. Incorporation of the above mentioned electrical power and battery technologies is incorporated and anticipated in realizing the present invention.

Correlation processing of information from the portable brain activity sensing system, surround video logging system and other sensing systems is a key part of the present invention. Post processing of sensor data includes noise filtering of brain activity data transmitted from the brain activity sensor system, such as an AMR or other internal biometric or physiological sensor system. And also includes post processing of external data representing the surrounding environment recorded by devices such as panoramic video. A key part of the correlation is target identification and tracking which involves performing target recognition and filtering out false targets. Computer software and firmware of a type that is incorporated into the present invention to filter data and make correlations between brain pattern data and video is disclosed in U.S. Patent 2009/0196493, dated 6 Aug. 2009, by Widrow et al entitled Cognitive Method and Auto-Associative Neural Network Based Search Engine for Computer and Network Located Images and Photographs. Hierarchical tree and relational databases familiar to those in the computer industry and discipline are incorporated in the present invention to organize and retrieve information in the computer. Widrow teaches storing input data, images, or patterns, and quickly retrieving them as part of a computer system when cognitive memory is prompted by a query pattern that is related to the sought stored pattern. Widrow teaches search, filtering techniques, pre-processing of sensor data, post processing of sensor data, comparator operations done on data, storage of data, and keying techniques incorporated into the present invention. Widrow also teaches that the computer may be part of a computer or information appliance and that the system may be remotely connected to the global information grid (GIG)/internet and the processes distributed. U.S. Patent Application 20070124292 A1, by Kirshenbaum et al, dated 31 May 2007, entitled "Autobiographical and Other Data Collection System" teaches a stereoscopic video logging system with recall. However, neither Widrow or Kirshenbaum teach a portable device for brain pattern correlation with video logging and memory enhancement as does the present invention. And neither Widrow nor Kirshenbaum teach spherical recording with brain correlation. Compact computer processing systems, including the latest 3G, 4G, and 5G communication telecommunication systems and follow-on devices like smartphone phones (i.e. Apple iPhone 4S and 5, Samsung Epic 4G; Blackberry 4G smartphones's; chips, PCB's, DSP's FPGA's; Quantum 3D Inc., San Jose, Calif., powerful compact portable computer processing and imaging generator modules (i.e. IDX 7000, ExpeditionDI, and Thermite 4110); Mini & Small PC's by Stealth Computer Inc.; the Pixel Edge Center 3770 HTPC with Dual Core i7 or dual chip Xeon processors; U.S. Pat. No. 7,646,367, dated Jan. 9, 2006, by Hajime Kimura entitled Semiconductor device, display device and electronic apparatus; and associated telecommunications systems and methods disclosed in U.S. Pat. No. 7,720,488, by Kamilo Feher, dated Jun. 21, 2007, entitled "RFID wireless 2G, 3G, 4G, 5G internet systems including Wi-Fi, Wi-Max, and OFDM" and the like compatible and of a type incorporated into the present invention.

Dynamic user/host command and control of the present invention through interactive machine assist systems is a major feature of the above invention. Interactive computer machine assist and learning systems are incorporated in the present invention to assist the host in command and control of the logging and memory system. Once neural correlates are identified using technologies specifically described in the preceding paragraph the information is referenced by artificial intelligent (AI) and AI like systems to form an enduring cognitive assistant for the user or another client in the present invention. An AI computer hardware and software of a type that may be integrated with the present invention is the Cognitive Agent that Learns and Organizes (CALO), developed by SRI between 2003 and 2008. CALO is a PC based cognitive software system that can reason, learn from experience, be told what to do, explain what they are doing, reflect on their experience, and respond robustly to a client's specific commands or based on a client's repeated actions when using the CALO system. The SIRI system is a software application on the I-Phone 4S and 5, a portable electronic device, manufactured by Apple Corporation Inc, CA. The SIRI application is a personal assistant that learns (PAL) application that is run on the I-Phone 4S and 5. The SIRI system includes a speech recognition and speech synthesis application that may be integrated with the smartphone of the present invention to interact with on-board and off-system devices and software applications that comprise the entire system of the current invention. It is an object of the present invention to integrate AI and AI-like CALO and SIRI software, Widrow's 2009/0196493 art, and Kirshenbaum's logging and database software and hardware into a single integrated computer architecture to achieve the objectives of the present invention.

Microprocessor speed and memory capacity have increased along a number of dimensions which enable the present invention. Computers get twice as powerful relative to price every eighteen months, or in other words, increase by about an order of magnitude every five years. Additionally, decreases in size and volume of mobile computing and communication devices continue to make them even more portable. Bandwidth is also increasing dramatically. Therefore, new uses for such powerful machines, programs, and bandwidth may be developed, as evidenced by the present invention. Particularly, as computing speed and memory capacity drop in price, personal use systems become more powerful and more available. Personal communication systems, like smartphones with video cell capability, may be in part or in whole in the present invention to process, display, transmit and receive data in accordance with the present invention. One valuable use for powerful computing processes is multimedia, surveillance, and personal data collection. There is known in the art individual devices which already employ microprocessors and application specific integrated circuits for recording specific types of data; e.g., video (with sound track capability) and video cameras for recording the local surroundings (including day-date imprints), pen-size digital dictation devices for sound recording, space satellite connected global positioning systems (GPS) for providing instantaneous position, movement tracking, date and time information, smartphone downloadable note taking and other computing activities, biofeedback devices, e.g., portable cardio-vascular monitors, for medical patients and sports enthusiast, and the like. Additionally, remotely located servers may be incorporated into the present invention to receive and transmit data to and from users of the data logging and communication system comprising the present invention.

An additional feature of the command and control portion of the present invention, typically conducted by the user operating a host computer, is an integral part of the present invention. In the present invention the U.S. Patent Application 2009113298, by Edward Jung et al, dated 30 Apr., 2009, entitled "Method of selecting a second content based on a user's reaction to a first content" provides a method of a type compatible with and incorporated into the present invention. Accordingly, data sensed or recorded by the logging and video enhancement system of the present invention may be operated upon in response to other data sensed or recorded to include at least one a person's gaze, attention, gaze dwell time, facial movements, eye movements, pupil dilation, physiological parameters (heart rate, respiration rate, etc.), stance, sub-vocalization (and other non-word audio), P-300 response, brain waves, brain patterns, or other detectable aspects. In another embodiment, data indicative of a response may include data indicative of at least one of a user's physiological, behavioral, emotional, voluntary, or involuntary response sensed by the system of the present invention.

User activation and authentication is important in the present invention because inadvertent input might cause confusion in a host beings brain or malfunctioning in a host and remote server machines processing. Surreptitious activation by a hostile being or machine, either locally or remotely, could introduce unwanted input and control of the host being or machine. Thus, at least standard intrusion detection and information security systems and methods are incorporated into the present invention (i.e. firewalls and virus protection software). Preferably, the present system incorporates an identification and an authentication system for activating and deactivating the system due to the critical nature to the user which access the present invention allows. It is an object to integrate and combine both standard and new novel identification (ID) and authentication systems into the present invention.

In some instances it may be preferable to locate at least some processing and database storage of the present invention at a remote location. This may be preferable in order to reduce weight and because of limited space considerations. Additionally, locating processing at a remote location may be important for safety and security reasons.

Size, location, unobtrusiveness, concealment, and support of components borne by the user, whether external or internal to the body of the user, are important parts of the present invention. These requirements vary and dictate the various embodiments of this invention. Traditional support assemblies include securing components onto the clothing of the user. Backpacks and belt-packs are one such conventional example. Distribution of some components in the present invention is a technique used to decrease the weight and volume of the present invention.

Improved and novel systems and methods of positioning and securing devices to or in the host user are an important contribution and objective of the present invention. These systems and methods of dividing up and securing the components overcome many of the limitations mentioned above with HMD's. Alternatives include using invasive and/or noninvasive techniques. The present invention includes various systems and methods that lesson or disguise the visual impact of people wearing data logging and memory enhancement systems. U.S. Pat. No. 4,809,690, dated 7 Mar. 1989, by Jean-Francois Bouyssi et al, entitled "Protective skull cap for the skull" is compatible and of a type that may be integrated into the present invention. Additionally, data derived from the present invention may be transmitted for presentation by a programmable subcutaneous visual implant as described in U.S. Pat. No. 5,638,832 by Singer in order to hide or communicate with others in the surrounding environment in a non-verbal manner compatible with the present invention. Concealing implants by the use of a hair-piece, wig, fall, synthetic skin, prosthetics, optical film, skin colored and tattoo sleeves, sticky material, material coverings that blend into and with the exterior body and extremities and is an objective of the present invention. For instance, skull caps may be used to hide or conceal components of the present invention that are mounted in and on the head of the user according to the present invention. It is a further objective is to integrate a covering a covering that conceals the camera optics comprised of a one-way film used in the optical industry on contact lenses and eye glasses. These concealment devices are well known to those in the medical, optical, and cosmetic industry. However, the use of these concealment devices as described in the present invention is not known in prior art.

In the present invention miniaturization allows sensor, input, processing, storage, and display devices to be positioned on the exterior of the user by means of conventional double sided adhesive based techniques commonly used in the medical industry to mount heart and brain monitoring sensors to a patient. Body piercings known to people in the body art industry are used in the present invention to support components of the present invention. Specifically, industrial, snug, forward helix, conch, and lobe piercings of the skin may support components. In medicine, fistula are unnatural connections or passageway between two organs or areas that do not connect naturally. While, fistula may be surgically created for therapeutic reasons, in the present invention fistula are created to facilitate passageways for components that facilitate and form the present invention. Fistula used in the present invention include: blind-with only one end open; complete-with both external and internal openings; and incomplete-a fistula with an external skin opening, which does not connect to any internal organ. While most fistula are in the form of a tube, some can also have multiple branches, various shapes and sizes. In medicine, a canula is a tube that can be inserted in the body, often for the delivery or removal of fluid. Cannula may be inserted by puncturing of the skin. Alternatively, cannula may be placed into the skull by drilling or cutting a portion of the skull away and replacing it with an appropriate material or device. In the present invention fistula and cannula are used to house, support, connect, and conceal components of the present invention.

Subdermal and transdermal implants are known in the body modification industry and medical profession and adapted to the present invention to hold components of the invention in place. Subdermal implants are the implantation of an object that resides entirely below the dermis, including (i.e. horn implants for body art: a pacemaker placed beneath the skin for medical purposes; or a magnet implant beneath the skin to assist a user in mounting or picking up devices above the skin.) In contrast, transdermal implants are placed under the skin, but also protrude out of it. Binding and healing of the skin around and over implants and piercings is an import part and objective of the present invention. Aftercare of implants is known in the body modification industry and medical profession and is also a part of the present invention. (Ref. Shannon Larratt (Mar. 18, 2002). ModCon: The Secret World Of Extreme Body Modification. BMEbooks. ISBN 0973008008); (Ref. Various Medical Atlas's of Plastic Sugery, ENT Surgery, and Neuro Surgery).

Surgical methods used to implant components in the present invention are described in various surgical atlas known to those in the medical field. Making holes in the skin and skull of living animals and insuring their survival is done routinely in the medical and vetinary profession. For instance, a paper by Laflin and Gnad, DVM, entitled "Rumen Cannulation: Procedure and Use of a Cannulated Bovine" in 2008 by Kansas State University and an article by Hodges and Simpson, DVM, in 2005 entitled "Bovine Surgery for Fistulation of the Rumen and Cannula Placement" describe surgical techniques for making large holes between the outer skin and stomach of cattle. These techniques demonstrate surgical methods and the survivability of animals when large cannula and fistula are placed in animals. In the present invention these techniques are used to make passage ways for communication between implanted electronic components using cannula and fistula into and on the body of users consistent with the present invention.

It is known in medicine that specialty implants are used in plastic surgery to achieve aesthetic surgery. Common implants include chin, calf, pectorial, nasal, carving, and check bone implants. Additionally, it is known in medicine that implants are used in the body art industry to create bumps as body art. A manufacturer of such implants is Spectrum Designs Medical, of Carpinteria, Calif. These implants may be filed with silicone, foam, or teflon are typically placed just beneath the skin. In the present system implants are filled with electronic components. The components may be connected to the interior and exterior of the body via fistula and cannula. Furthermore, Craig Sanders et al demonstrate in an article entitled "Force Requirements for Artificial Muscle to Create and Eyelid Blink With Eyelid Sling" dated 19 Jan. 2010, in the ARCH Facial Plastic Surg/Vol 12, No 1, January/February 2010 and in an article entitled "Artificial muscles restore ability to blink, save eyesight", by U.C. Davis Health System, dated 11 Feb. 2010 describes an implanted artificial muscle system to restore a person's eyelid blinks. The eyelid blinking system demonstrates the surgical implantation techniques and method of small electrical processing, battery, servos, and planted wiring beneath the skin surgical of a type used in and enabling certain aspects of the present invention.

With respect to implants, it is known by neurosurgeons in the medical profession that artificial plastic skull plates may replace the skull; ref. "Applications of Rapid Prototyping in Cranio-Maxilofacial Surgery Procedures, Igor Drstvensek et al, International Journal of Biology and biomedical Engineering, Issue 1, Volume 2, 2008. And it is known in the electronics industry that plastic is the base material on which many printed circuit boards are built. Printed circuit boards are traditionally flat, however, curved printed circuit boards have recently been produced. It is an objective of the present invention to incorporate PCB technology into irregular and cranial skull plate implants to facilitate some embodiments of the present invention. Development of curved printed circuit boards of a type that enable and are compatible with the present invention include those developed at the Center for Rapid Product Development, Creative Research Engineering Institute, Auckland University of Technology, New Zealand in 2009 under their Curved Layer Rapid Prototyping, Conductive 3D Printing, and Rapid Prototyping and Design Methodology Programs. It is therefore an objective of the present invention to enable implantation of specially designed curved and irregularly shaped printed circuit boards as a substitute for removed sections of the skull to enable the present invention.

Additionally, it is an objective to use optical concealment and cloaking systems and methods in the present invention to conceal worn devices and implants mounted over, on top of, into, and under the skin. Systems and methods for cloaking integrated into and compatible with the present invention include those described in: U.S. Patent 2002/0090131, by Alden, dated 11 Jul. 2002, entitled "Multi-perspective background simulation cloaking process and apparatus"; U.S. Patent Application Publication 2002/0117605, by Alden et al, dated 29 Aug. 2002, entitled "Three-Dimensional Receiving and Displaying Process and Apparatus with Military Application".

It is an object to input data and information derived by the present invention into a simulation system Hosts simulations of a type consistent with the present invention include U.S. Pat. No. 5,495,576, by Ritchey, dated 27 Feb. 1996 entitled "Panoramic image based virtual reality/telepresence audio-visual system and method". Other enabling simulation technology of a type compatible with and that may be integrated into the present invention includes U.S. Patent Application 2004/0032649 by Kondo et al, dated 19 Feb. 2004, entitled "Method and Apparatus for Taking an image, method and apparatus for processing and image, and program and storage medium"; U.S. Patent Application 2004/0247173, by Frank Nielson et al, dated 9 Dec. 2004, entitled "Non-flat image processing apparatus, in-processing method, recording medium, and computer program"; U.S. Patent Application 20100030578, by Siddique et al, dated 4 Feb. 2010, entitled "System and Method for collaborative shopping, business, and entertainment; U.S. Patent Application 20100045670, by O'Brien et al, dated 25 Feb. 2010, entitled "Systems and Methods for RenderingThree-Dimensional Objects"; U.S. Patent Application 20090237564, by Kikinis et al, dated 24 Sep. 2009, entitled "Interactive Immersive Virtual Reality and Simulation"; U.S. Patent Application 201000115579 by Jerry Schlabach, dated 21 Jan. 2010, entitled "Cognitive Amplification for Contextural Game-Theoretic Analysis of Courses of Action Addressing Physical Engagements"; U.S. Patent Application 2005/0083248 A1, by Frank Biocca, Jannick P. Roland et al., dated 21 Apr. 2005, entitled "Mobile Face Capture and Image Processing System and Method"; U.S. Patent Application 20040104935, by Williamson et al, dated 20040104935, entitled "Virtual reality immersion system"; and U.S. Patent Application 2005/0128286.

Host computer servers for storing and retrieving data and information derived by the present inventions data logging system and other social network and search engine systems operated by a user via a wireless telecommunication system of a type consistent with the present invention include those in U.S. Patent Application 20070182812, specifically FIGS. 47-51, and those above mentioned in U.S. Patent Application 20070124292 A1, by Kirshenbaum et al and in U.S. Patent Application 2009/0196493 by Widrow et al. For instance, Google Earth™ and video chat like technologies and graphics may be adapted as a platform for geospatial referencing and video teleconferencing in which users of the present invention interact with one another. It is an objective of the present invention to describe a social telecommunication network that allows users to interactively share their thoughts and a view of themselves and their surrounding environments using the present invention. Telecommunications systems that are integrated with the internet of a type that may be incorporated into the present invention to accomplish video communications within the scope of the present invention are described in U.S. Patent Application Publication 2007/0182812 A1 dated Aug. 9, 2007 by Ritchey entitled Panoramic Image-based Virtual Reality/Telepresence Audio-Visual System and Method and are incorporated by reference.

Robotic and cybertronic systems of a type that may be populated with data derived by a data logging system of a type compatible with the present invention include those discussed at the: Proceedings of the 18th Joint International Conference on Artificial Intelligence, Aug. 9-15, 2003, Acapulco, Mexico in the article "Non-Invasive Brain-Actuated Control of a Mobile Robot", by José del R. Millán et al; the ongoing NASA Robonaut 2 Program; in the scientific paper A Brain-Actuated Wheelchair: Asynchronous and Non-Invasive Brain-Computer Interfaces for Continuous Control of Robots by F. Gal'an et al from the IDIAP Research Institute, Martigny, Switzerland, dated 2007; U.S. Patent Application 20040104702 by Nakadai, Kazuhiro; et al., dated Jun. 3, 2004, entitled Robot audiovisual system; U.S. Patent Application 20040236467, by Sano, Shigeo, entitled Remote control device of bipedal mobile robot, dated Nov. 25, 2004; and United States Patent Application 20060241808 by Nakadai; Kazuhiro; et al, dated Oct. 26, 2006, entitled Robotics Visual and Auditory System. It is known by those skilled in the art that robotic devices may be remotely piloted or operate autonomously. It is also known that robots can be programmed to replicate characteristics of a being by translating information derived from data logged about a given being and converting that data into computer code based on those characteristics of the living being consistent with some embodiments is the present invention.

Video logging and memory enhancement devices that form the present invention carried on and in a being can add additional weight. Exoskeletal systems compatible with and of a type that may be incorporated to support the additional weight of the system disclosed in the present invention includes U.S. Patent Application Publication 2997/0123997, by Herr et al, dated 31 May 2007, entitled "Exoskeletons for running and walking". Passive and active exoskeletal systems known to those skilled in the art may be incorporated into the present invention. An exoskeleton like that disclosed in U.S. 2003/0223844, by Schile et al, dated 4 Dec. 2003 entitled "Exoskeleton for the Human Particular for Space Applications" which may be used for remotely control of robots may be integrated into the present invention. Astronaut suites, scuba gear, other life support garb and equipment, protective garments, backpacks, helmets and so forth may be supported. Garb integrated with and supported by a user in the present invention may incorporate various displays, microphones, cameras, communication devices like cell phones, body armor, power sources, or computers and associated devices. In one embodiment of the data logging and memory enhancement system of the present invention the helmet design and backpack is supported by an exoskeletal system in order reduce the weight on the being carrying the portion of the invention born by a being. Alternatively, the helmet design can be supported by the weightlessness of outer space or by underwater buoyancy compensation apparatus in some situations. Still alternatively, an opaque helmet design embodiment that captures imagery from camera systems and displays the imagery on the interior and exterior of the helmet is disclosed in the present invention. Recently developed thin form flat, curved, flexible, opaque and see-through display devices known in the industry are integrated into the novel helmet design enabled various embodiment of the present invention.

Direct sensing and stimulation of existing brain cells to drive the data logging and memory enhancement system is an objective of the present invention. Direct sensing and stimulation system and methods of a type compatible and incorporated into the present invention includes: U.S. Patent 2008/0097496, 24 Apr. 2008, by Chang et al, entitled "System and Method for Securing an Implantable Interface to a Mammal"; U.S. Patent Application Publication 2009/0105605, dated 23 Apr. 2009, by Marcio Abreu, entitled "Apparatus and Method for Measuring Biological Parameters"; U.S. Patent Application Publication US 2009/0163982 and 2009/0306741, by Christopher deCharms, dated 25 Jun. 2009 and 10 Dec. 2009, entitled "Applications of the Stimulation of Neural Tissue Using Light"; U.S. Patent Application Publication, by Hogle et al, dated 10 Dec. 2009, entitled Systems and Methods for Altering Brain and Body Functions and For Treating Conditions and Diseases of the Same"; U.S. Patent Application 20090062825, 5 Mar. 2009, by Scott Pool et al, entitled "Adjustable Implant and Method of Use"; U.S. Patent 20090108974 by Michael Deering (cited earlier); U.S. Patent Application 20020082665, by Markus Haller et al, dated 27 Jun. 2002, entitled "System and method of communicating between an implantable medical device and a remote computer system or health care professional"; U.S. Patent Application 20050084513, by Liping Tang, dated 21 Apr. 2005, entitled "Nanocoating for improving biocompatibility of medical implants"; U.S. Patent Application 20050209687, dated 22 Sep. 2005, by James Sitzmann et al, entitled "Artificial vessel scaffold and artificial organs therefrom"; U.S. Patent Application 20070045902, dated 1 Mar. 2007, entitled "Analyte Sensor"; U.S. Patent 20090306741, Hogle et al, dated 10 Dec. 2009, entitled Systems and Methods for Altering Brain and Body Functions and for Treating Conditions and Diseases of the Same"; atlases and articles on Surgical Implants; and Neurosurgical Atlases familiar to those in the medical profession. Biological material grown in vitro or ex vitro containing data and/or information derived from operating the present invention may be implanted in the same or a different recipient. Additionally, logged data derived according to the present invention may be incorporated into a genetically modified organism (GMO) or genetically engineered organism (GEO) is an organism whose genetic material has been altered using genetic engineering techniques. These techniques, generally known as recombinant DNA technology, use DNA molecules from different sources, which are combined into one molecule to create a new set of genes. This DNA is then transferred into an organism, giving it modified or novel genes. Transgenic organisms, a subset of GMOs, are organisms which have inserted DNA that originated in a different species. In such an instance, additional and enhanced sensor systems, embedded communication devices, disease resistance, hostile environment survival capabilities, and superior brain and muscle strength may be engineered into the DNA such that humans with unique and enhanced-human capabilities develop from birth with data logged according to the present invention recorded by a user of previous generations. Still further, it is an objective of the present invention that a cloned beings may be stimulated with historical data derived from the data logging system in an immersive manner such that the brain of the cloned being is stimulated similar to that of the original being from which the data was logged.

A related objective to that described in the two preceding paragraphs is loading and monitoring of implanted stem cells with data logged and data evoked by logged data according to the present invention. Adult neurogenesis (the creation of new brain cells in adult brains) was first discovered in 1965, but only recently has it been accepted as a general phenomenon that occurs in many species, including humans (1998). Like stem cells, progenitor cells have a capacity to differentiate into a specific type of cell. In contrast to stem cells, however, they are already far more specific: they are pushed to differentiate into their "target" cell. The most important difference between stem cells and progenitor cells is that stem cells can replicate indefinitely, whereas progenitor cells can only divide a limited number of times. Systems and methods of a type applicable to the present invention include: Those discussed in the International Review of Cytology, Volume 228, 2003, Pages 1-30, by Kiminobu Sugaya, University of Illinois at Chicago, entitled "Potential Use of Stem Cells in Neuro-replacement Therapies for Neurodegenerative Diseases"; in Stem Cell Research & Therapy 2010 1:17, by Jackson et al, entitled "Homing of stem cells to sites of inflammatory brain injury after intracerebral and intravenous administration: a longitudinal imaging study"; U.S. Patent Application Publication 2008/0255163, by Kiminobu Sugaya et al, dated 16 Oct. 2008, entitled "Use of Modified Pyrimidine Compounds to Promote Stem Cell Migration and Proliferation"; PHYSorg.com. 31 Oct. 2007. Entitled "Stem cells can improve memory after brain injury"; and in *Molecules* 2010, 15, 6743-6758; doi:10.3390/molecules 15106743, Yong-Ping Wu et al, entitled "Stem Cells for the Treatment of Neurodegenerative Diseases".

Nanobots may be also be introduced into the brain of a recipient with data and/or information derived from operating the present invention. The data and/or information may introduced in order to reintroduced lost memory to a prior user or add a new memory to a new user. A recipients implanted data and/or information may be derived from another user. Incorporating programmable nanobots and computer electronic interfaces with brain tissue are additional methods of sensing brain activity and introduce information derived from queries in the present invention into the brain is a further objective of the present invention. It is there for an objective of the present invention to record and incorporated information that has been logged or derived from data logged using the present invention such that it may be placed in storage and then loaded into nanobots and the nanobots targeted to replace neurons in the brain. Additionally, nanobots may be introduced into the brain to block neural connections to inhibit or allow information formulated by the video logging and memory enhancement system according to the present invention. Nanobot technologies of a type compatible with and integrated into the present invention include those described in the internet video entitled "Nanobot Replacing Neurons 3D Animation" by info@cg4tv.com dated Jun. 6, 2011. The host computer or a server may be used to transmit electronic signatures thru electrodes or light fibers into the brain of the user. The stimulants may represent feedback responses to information queries conducted by the user of the present. Machine interfaces to brain tissue that are of a type compatible with and integrated into the present invention include: U.S Patent Application Publication 2003/0032946 A1, dated 13 Feb. 2003 by Fisherman et al. entitled "Artificial Synapse Chip Interface for Electronic Prosthetic Retina". It is also an object of the present invention to disclose sensor methods and systems according to the present invention that may be interfaced with audio, electro-optical, and other sensors directly with body tissues according to the Fisherman '946 Patent.

The data logged by individuals may be operated upon for programming nanobots that may be introduced into the brain to restore memory or introduce information into the neural network of the brain. Additionally, data logged by the present invention may be incorporated in bio-engineering human systems that carry memories forward through encoding those memories in human DNA and RNA. U.S. Patent Publication 2005/0053968, by Bharadwaj et al, dated 10 Mar. 2005, and techniques disclosed in the UCD, Dublin, year 2012, publication Bioinformatics article entitled, "DNA Data Embedding Benchmark", by David Haughton, that describes a system and method for embedding information in the DNA string while still preserving the biological meaning of the string; is incorporated in full as a system and method of a type which is integrated with the present invention to encode and decode raw or correlated information derived from the present invention into human DNA. The logged information could may include a test file, image file, or audio file that in which large sequences are divided into multiple segments and placed in DNA introduced to the user human or other organism. It is therefore an object to provide an invention that logs a beings life experience such that a least some portions of the logged data may be codified and stored into DNA and RNA and passed to a later generations, as stored information in a living organism, a cadaver, or transfer to another living being though reproduction.

Finally, in accordance with the present invention, historical data from brain activity sensing systems, like AMR recordings, along with other physiological and biometric data is read into life support systems to assist in keeping a user on life support alive. Using historical biometric data and information from a given user derived by the present invention that is consistent with the users homeostasis, when the user is a patient, can assist in making the settings of a life support system(s) compatible to the specific patient. It is conceived that historical logged and derived from the system 100 will be used in brain, head, body or other transplants to achieve this objective. Alternatively, robotic, prosthetic, cybortronic, and robotic systems may also be adapted and hooked to the life support system in order to receive and operate on the the logged data derived from system 100. Brain and head transplant methods and techniques applicable to the present invention are disclosed by: Browne, Malcolm W. (May 5, 1998), "Essay; From Science Fiction to Science; The Whole Body Transplant" in the New York Times; by White, Robert J.; as "Head Transplants" in Scientific American; and in U.S. Pat. No. 4,666,425, entitled "Device for perfusing an animal head".

The above mentioned references and the information all of which are distinctly different from current invention are incorporated by reference as enabling the present invention.

SUMMARY

An integrated human and machine portable data logging and memory enhancement method and system are provided for interactive input/output, storage, processing, and display. More specifically, a device for the input of human signatures from physiological and biometric sensors representing a person's internal state of being while simultaneously inputting signatures representing the external environment around the same human at a given time and place are correlated into a historical relational database. The device includes real-time query means of the stored historical relational database for identifying correlations between current internal and external signatures of the human as the human moves through space and time. Body integrated panoramic sensor, processing, and display devices are provided to accomplish a statistically valid "correlation of consciousness" say for example, to pyramidal cells as an internal neural representation, or "cognitive map" of place and spatial cells related within the brain to externally derived geo-spatial information and sensory representations surrounding the user. Methods and systems are disclosed for using the resultant data from the data logging system as an input into a simulation, stimulation, relational database, internet social network and search engine, telecommunications network, or emulation system within a biological, mechanical, and bio-mechanical system.

OBJECT OF THE INVENTION

It is therefore an objective of the present invention to overcome the limitations of the above referenced and any non-referenced prior art in the related classes and subclasses. Scientific studies show that images a person recalls in his or her imagination is not always as detailed or nearly as accurate as a photographic image. It is an objective of the present invention to provide a higher resolution and more complete record of a beings thoughts and their environment than the mind of a typical person remembers by providing a human portable physiological (internal body) and surrounding world (external to the body) life logging correlation, recall, and query system. It is therefore an objective to allow the logged information to be operated upon by the person recording the information, another person, or a machine. It is also an objective to optionally provide at least one remote computer to carry out some of the computer processing operations and memory storage of information logged and derived over a telecommunications system in communication with said user borne system of the said invention.

It is also an objective to provide a computer memory storage device which periodically achieves at least some instance of the information captured or derived from said user born system that comprises the present invention for utilization in recipient being, machine, or combination thereof at a later time. And it is an objective of the system to provide a user born system that generates a database comprising at least some portion of the information captured and derived from the user born system, which may include a neural correlates of consciousness (NCC) database and Conscious Precept (CP) derived by the user born system or a remote computer.

In the present invention low resolution images generated from electrodes that are part of a brain activity sensing system may be correlated to subjects the user focuses upon in the surrounding environment that are higher resolution recorded by the surround video system. Then when the user recalls the subject matter at a later date the higher resolution images logged in and correlated are retrieved from system memory of the host computer to assists the user in remembering the subject in greater detail than he can remember in his mind. It is therefore an objective of the present invention to provide a clearer more detailed method and system to call up detailed images based upon brain activity. For instance, images recorded in the daytime by the panoramic camera in the present invention and overlay them over a darkened space using augmented reality (AR) may be used to help the user navigate a space in the dark. Or alternatively, to help the user remember the audio and imagery of his or her Mom who died when the user was a young person. Still alternatively, an Alzheimer's patient may use the historical audio and imagery to remember or restore their memory. Or still alternatively, to simply provide a system where a person can review their history by operating the present invention to search for an item they lost, such as their car keys or keys to their house.

It is an objective to provide a method which operates upon at least some portion of said data and information logged and derived by said logging and memory enhancement system, hereby referred to as the "present invention", "said invention" or "said logging system". It is an objective of said logging system to facilitate a method of communication between humans and/or machines by using computers to translate data derived from said logging system. It is an objective of said logging system to provide a method wherein said user activates a host computer (i.e. smartphone) to turn on a brain activity sensing system, surround sensing system, and correlation system; brain activity sensing system and surround sensing system activated to transmit respective signatures to correlation system; and correlation system operated to identify neural correlates of consciousness in the form of conscious precepts. It is an objective of said logging system to operate upon signatures from a physiological and biometric sensor system (i.e. brain activity sensor) representing a user's internal state of being at a given time and place are input to a correlation system; while simultaneously signatures representing the external environment presented to a person (i.e. via an audio-visual sensor system) are also input to the correlation system; wherein the correlation system operates to receive internal and external signatures and determines relationships between said internal and external signatures to define NCC and CPs from said signatures which form a historical database which is stored as a relational database; and at time two query said historical relational database to find correlations between current internal and external signatures; and read in said historical information from resulting from the query into said host computers memory (i.e. smartphone) via at least one user input device (i.e. SIRI voice response to a user query) to enhance a user's thoughts and memory based on at least one occasion that took place at a given historical instance at a given place and time.

It is also an objective of said invention to provide a method wherein said user activates the host computer (i.e. smartphone) and memory correlation databases such that a stimulus in the environment or thought in the mind of the user causes brain activity; the host computer queries said historical database for matches between the live brain activity and the historical brain signature database to identify similar brain activity patterns; the matches are presented via user input devices; the user chooses which matches to activate and act upon; and the users brain is stimulated with the matched information.

It is also an objective of said invention to provide a system and method to provide a system wherein signatures of at least one the surrounding environment or the individuals brain activity are input into a computer simulation system; and an objective to provide a system wherein a user wears an input device and takes the form of an avatar to interact within the computer simulated environment; and an objective to provide a system wherein at least one subject in the simulation operates upon an artificial intelligence software application; and an objective to provide a system wherein a robot or cyborg is loaded with at data derived from at least one user brain activity sensing system, a surround sensing system, or correlation system; and an objective to provide a system wherein a being or machine is loaded with data derived from at least one user brain activity sensing system, a surround sensing system, or correlation system; and an objective to provide a system wherein and an objective to provide a system wherein a being is kept alive by mechanical life support systems by using historical data derived from at least one user brain activity sensing system, a surround sensing system, or correlation system; and an objective to provide a system wherein a being is implanted with growth stem cells in at least one area of memory loss; historical data derived from the surround sensing system is introduced to the user in the form of an immersive simulation; and said stem cells are monitored said system to determine if similar neural percepts are regenerated; and an objective to provide a system wherein data derived from at least the surround sensing system or correlation system is replayed to at least restore a beings memory or experience the memory of another being; and an objective to provide a system wherein brain cells stimulated in one being using immersive simulation derived from date using at least one the brain activity sensing system, a surround sensing system, or correlation system are implanted in a second being.

It is an objective of the present invention to provide a system and method that incorporate high resolution brain activity sensing, video, and correlation systems to facilitate the detailed reconstruction of physiological activity, surrounding environments for historical purposes, such as recreating a video log of historical moments in a beings life. It is an object of the present invention to record memories and thought processes and provides several methods for passing memory and thought processes to beings and machines. It is also an objective of the present invention to enable synthesizing thoughts formed and memories from a plurality of beings or machines that may be placed together to form the collective memory for a being or machine, or a combination thereof in the form of a computerized database. For instance the thoughts, thought processes, and/or memories of all noble prize winners may be collectively gathered and joined using the present invention. The present invention enables near perfect recall. It is also an objective to extend the mortality of humans, machines, or a combination thereof, by extending their consciousness and memory beyond their natural body or machine lifespan via mind, body, and machine replication, implantation, substitution. It is an objective to make human survival less about reproduction and age and more about maintaining and growing of the information of an existing being, machine, or biomechanical being.

It is also an object of the present invention to provide a system and method for incorporating computer processing to identify the above mentioned brain activity, identifying brain cells with related neural activity, identifying and relating the focus of the users attention to brain cells and brain activity patterns, the formation of new brain cells when new brain cells are formed relative to a given time and location, given the overall physiology of the user. An objective of the present invention is to not only log information, but to also operate on the information to provide user feedback, memory enhancement, and subsequent replication of a recipient user. It is also the objective of the present invention to provide a system include a person to person conscious precept translation system and method; and a person to machine or machine person to conscious precept translation module. It is an objective to provide a user identification and authentication system.

It is an objective of the present invention to provide a system for logging life experiences comprising a personal portable computer, a brain activity sensing system, a surround sensing system, and a correlation system. It is a further objective that the personal portable computer, like a smartphone iPhone S4 or S5, that has learning and communication capability, with applications like SIRI, CALO, iLeader, PAL, A.I., or A.I. like functionality. It is an objective to provide a user a user artificial intelligence (A.I.) system (i.e. PAL, CALO, or SIRI), or the like, that learns and communicates with at least one a user, remote user, the smartphone, or a remote computer server. For instance, the iLeader system does not incorporate the elements comprising a neural activity sensor and correlation system which is an objective of the present invention. Additionally, the iLeader system does not incorporate panoramic recording capability. An objective of this invention is to overcome these limitations.

A fundamental object of the present invention is also to provide a system and method of user controls for operating the present invention. It is also an objective of the present invention be primarily interactive, portable, and hands-free. It is also objective that the present invention be compatible and optionally include voice synthesis, wake-up features, sub-vocal recognition, neural activity sensing, panoramic audio-visual sensing, stereoscopic capability, multiple ROI processing and readout, on chip processing, infrared sensors, target tracking, eye tracking, gaze tracking, and touch sensing and various interactive sensory feedback hardware with computer software/firmware applications for input, display, processing, and feedback. It is also an objective of the present invention that the smartphone comprises user interactive input and presentation system for controlling the brain activity sensing system, a surround sensing system, and a correlation system; wherein the smartphone includes a software application that comprises an internet search engine that communicates over a telecommunication system and network over which in information derived by the invention may be processed and shared among users of the search engine; and wherein the smartphone includes a software application that is part of a social network on the internet over which at least brain activity information, surround sensing, or correlated data derived from the invention may be processed and shared among users of the social network.

It is an objective of the present invention to provide body worn devices systems and methods that sense and present information of the surrounding environment. It is also an objective of the present invention that the brain activity sensing system comprises a sensor system that senses and records neural activity signatures by location in the brain at a given time to enable the identification of CP's that are the basis for an NCC database. It is also an objective of the present invention that the surround sensing system comprises a substantially spherical field-of-regard sensing system that at least includes one of a image, audio, touch, gesture recognition, taste recording record, processing, input, and output system; and the invention includes integrated camera and display system made of thin flexible e-paper/material that can be shaped around a being, machine, or a combination thereof; wherein the flexible display includes an auto-stereoscopic display; and the camera of the system have the stereoscopic image capture capability; and wherein the display and associated components may be integrated into the visual appearance of the users skin, hair, eyeglasses, body form, clothing, jewelry, or surrounding environment. For instance it is an objective to provide a surround sensing system comprising a pierced ear-ring that includes a panoramic video capture system that works in concert with a plurality video camera modules to create a composite scene of the environment surrounding; and an objective to track at least one of the users eyes in order for an eye tracking and gaze system to calculate the subject a user is observing in the surrounding environment for correlation with a conscious precept derived from a brain activity sensing system. It is also a objective to provide devices and methods to surgically implant at least some portion of the personal portable computer, a brain activity sensing system, a surround sensing system, and a correlation system inside the body of the user in order to conceal and facilitate portability of the invention; and a system where at least some portion of the personal portable computer, a brain activity sensing system, a surround sensing system, and a correlation system borne by the user is mounted on or about the exterior of the body of the user; such as the smartphone, a skull-cap, an integrated camera with display OLED thumb or noise prophetic device, or a skin colored or tattoo sleeve whose outer covering conceals a data link or electrical power link sandwiched between a top and bottom layer of see-through, skin colored, or tattoo looking material. It is therefore an further objective of the present invention to concealing the present invention borne by the user via an implant, clothing, jewelry, earbuds, EMD, skull cap, hairpiece, wig, fall, synthetic skin, prosthetics, optical film, skin colored and tattoo sleeves, sticky material, material coverings and so forth that blend into and with the exterior body and extremities and is an objective of the present invention so that the user of the invention fits into the population without being self-conscious and uncomfortable around the population not bearing the present invention.

It is an object to provide a portable computer driven integrated image capture system and method that comprises at least one three-dimensional Very Large Scale Integrated Circuit (VLSIC) with at least one Region-of-Interest (ROI) image sensor that receives at least one image transmitted through at least one unexcited transparent portion of the addressable OLED display through the objective lens system to the light sensitive surface of the ROI image, where the OLED is located along the outer surface of the panoramic sensor; and where the remaining active portion of the OLED that is displaying an image blocks the remaining portion of the panoramic scene from reaching the ROI sensor. It is also an object to provide a portable computer driven integrated capture and display system and method responsive to the external and internal context of a being comprising a wearable image capture system with adjacent field-of-view coverage about the user that is concealed by an active integrated display system; said display system responsive to a biometric and physiological sensor system born by the user that monitors at least the users brain; and a support housing to hold said integrated capture and display system born worn by said user. It is an object to provide a portable computer driven integrated capture and display system where the capture system includes a support armature extending from the users head; at least one panoramic sensor head with optics for recording all, a portion, or portions of the continuous panorama comprising the users face and surrounding scene; an ear bud to allow the user to receive an audio signal; at least one microphone for simultaneously recording at least the users voice or surrounding audio; electrical means for driving said image sensor; transmission means for receiving and communicating at least some portion of said signal; control means; support means on the users head to hold said integrated logging system born by the user. It is an object to provide a portable computer driven integrated capture and display system includes a user born display device. (i.e. HMD or electronic contact lenses.)

It is an object of the present invention to provide a system and method that incorporates various spatial audio sensing and presentation systems such as ambisonic microphones that are spatially encoded using surround sound encoders to output spatial audio may be played back in a user's earphones or earbuds. Ambisonic microphones may be distributed in an outward facing manner according to the present invention. Ambisonic hardware known as TetraMic Spheround with associated software of a type applicable to the present invention is manufactured by Core Sound of Teaneck, N.J., USA.

It is also an objective of the present invention to provide a system and method that incorporates conventional voice-command systems that use conventional voice recognition and voice syntheses systems like those found on the iPhone 4S and 5 and the SIRI systems, and to integrate the above voice command, recognition, and voice synthesis system into various head gear consistent and disclosed within the present invention.

It is an objective of the present invention to provide a system and method that incorporates the sub-vocalization signatures of the user as an additional sensor input system in helping determine "neural correlates of consciousness" to the surrounding environment and as a command and control device to drive the memory enhancement portion of the present invention.

It is an object of the present system to provide a system and method that integrates AI and AI-like that of the CALO and SIRI software, Widrow's 2009/0196493, and Kirshenbaum's logging and database software and hardware into a single integrated computer system architecture to achieve the objectives of the present invention. An object of the present invention is to integrate these devices as components into the present invention in a novel manner to accomplish the present invention and overcome the limitations of prior art.

It is an object of the present invention to operate on the entire NCC database (i.e. including the raw data, processed data, and specifically the NCC's of the being) derived by the present invention to form a basis of a relational database which may be drawn upon by a user to perform various functions using a smartphone or the like as described in the present invention. It is an objective of the present invention to include hardware and software that facilitates recording and translating the uniqueness of a subject's brain and the subjects corresponding brain activity. And additionally, to design a universal brain translation system and method that facilitates communication between different beings, machines, or a combination thereof which use different languages to communicate with one another. Wherein at least some portion of said information logged and derived (i.e. the NCC database) from said invention is translated between natural and machine language to facilitate communication between humans or machines much like a "Rosetta Stone" for communication between beings, machines, or a combination thereof.

It is an object of the present invention to provide a system and method that integrates into a self contained life support system like an astronaut suite, scuba gear, fireman, or combat soldier wears in a hazardous environment. An objective of the present invention is to incorporate an integrated camera and display system which can be operated to mask the wearer and yet still communicate a chosen appearance to an onlooker.

It is an object of the present invention to provide a user system and method wherein at least some portion of said information logged and derived by said system is introduced to stimulate existing cells or stem cells that have been implanted into a target being. It is also an objective of the present invention is to implant electronic devices such as microchips and nanobots to sense, stimulate, and test existing brain activity before, during, and after information derived from the present invention is introduced to a recipient user.

It is an object of the present invention to provide a system and method of presenting at least some portion of said information logged and derived from said system to a surrogate or cloned being in order to create a being similar to the user from which the information was derived.

It is an object of the present invention to provide a system and method that consists of downloading at least some portion of said information logged and derived from said system into a second system that is a robot in order to create a second system with similar attributes as the being or machine the from which the information was derived.

It is an object to provide a system and method of introducing data and information derived from the sensing systems of the present invention for input into DNA and RNA. Besides augmented cognition applications highlighted in the present invention, a final concluding objective is to enable beings to transfer more than just biological information forward during reproduction to a user's heirs and the rest of mankind. DNA with encoded information derived from the present invention is implanted into a fertile egg or sperm of a human, embryo, or fetes, to transfer the information genetically using medical procedures familiar to those skilled in the art. For instance an image of a being's ancestors could be carried forward in the DNA of the being so that the being could access the image in order to see the being they evolved from. In this manner a human may transcend or pass on to his experience in the form of his memories and the lessons he or she learns throughout life. Much of the information that comprises the individual essence of a person's consciousness, including thinking process, experiences, and memory, is lost because of human mortality. The present invention may be used to help overcome that limitation by recording, storing, and reloading logged data into a post predecessor specimen. In the past what a person begins life with informationally is a body with its genetic code or a robot with whatever data it has been loaded with. And in the past what a person ends life with informationally is a body with whatever memories and DNA or a robot with whatever additional new stored data has been accumulated. It therefore conceived in the present invention that nanobots may be programmed with data logged into and derived from the present video logging and enhancement system. It is also conceived in the present invention data logged into and derived from the present video logging and enhancement system may be coded into genetic DNA or RNA which may be passed via reproduction into offspring or implanted into other individuals. A person's experiences being is the memories and connections beings construct as beings journey through life. This invention allows mankind to carry forth that journey with decreased loss of information and consciousness.

Another objective is to provide a system and method comprising a life support system which operates upon physiological, sensory data, and other information derived from the present invention to assist in the recovery or regeneration of a being that is injured or has an illness.

A final objective of the present invention is to provide a system and method for overcoming the limitations of mankind's not being able to put their thinking presence into created and manmade hostile environments. Examples of manmade hostile environments are burning houses, forest fires, and radioactive environments. Examples of naturally hostile environments are the earth's oceans and outer space. And to introduce the NCC of a being into a recipient being, machine, or bio-mechanical system in order to extend the scientiousness of that being well beyond the normal consciousness of that beings natural life.

BRIEF DESCRIPTION OF THE DRAWINGS

FIG. 1a diagrammatically illustrates a first embodiment of a system and method to derive Neural Correlate of Consciousness (NCC) of a user according the present invention;

FIG. 1b is a diagrammatic perspective of a user worn headgear comprising a brain activity sensor system, surround audio-visual sensor system, and host computer required to achieve the invention in FIG. 1a;

FIG. 1c is an exterior perspective pointing out the natural looking appearance of the user wearing the system diagramed in FIG. 1b;

FIG. 8a diagrammatically illustrates another embodiment of a system and method to derive Neural Correlate of Consciousness (NCC) of a user according the present invention;

FIG. 8b is a diagrammatic perspective of another embodiment of a user worn headgear comprising a brain activity sensor system, surround audio-visual sensor system, and host computer required to achieve the invention in FIG. 8a;

FIG. 8c is an exterior perspective pointing out the natural looking appearance of the user wearing the system diagramed in FIG. 8b;

FIG. 12 is an exterior perspective of an astronaut suite which incorporates a video logging and memory enhancement method and system with integrated micro-bead array capture and display as illustrated in FIG. 11;

FIG. 13a is a sectional cutaway diagram of a head covering worn by the user according to the present invention;

FIG. 13b is an exterior perspective of the head covering shown in FIG. 13a;

FIG. 14b is a block diagram that names principal system components described in FIG. 14a;

FIG. 20*a* is a perspective diagram illustrating the one-hand activation/deactivate and authentication sensor module of the invention operated by the user pressing their skin to activate an under-the-skin sensor shown in FIGS. 18-19 and FIGS. 21*a-c;*

FIG. 20*b* is a perspective diagram illustrating a two-handed activation/deactivate and authentication arrangement which incorporates a plurality of sensor modules shown in FIGS. 18-19 and FIGS. 21*a-c;*

FIG. 21*a* is a perspective diagram illustrating a user implantable under-the-skin activation/deactivate and authentication sensor modules in FIGS. 20*a-b;*

FIG. 21*b* is a plan diagram illustrating a user implantable under-the-skin activation/deactivate and authentication sensor modules in FIGS. 20*a-b;*

FIG. 21*c* is a side sectional diagram illustrating a user implantable under-the-skin activation/deactivate and authentication sensor modules in FIGS. 20*a-b;*

FIG. 23*d* is a front sectional view showing the components that comprise the implantable retractable electronics display module consistent with FIGS. 18*a* and 23*a;*

FIG. 23*e* is a front sectional view showing the components that comprise the implantable retractable electronics display module. The module may be connected by electrical cable or wirelessly to an electronics module consistent with FIGS. 18*a* and 23*a;*

FIG. 23*f* is a diagrammatic see-through axonometric schematic with arrows indicating the motion of the retractable near eye holographic or OLED display consistent with FIGS. 18*a* and 23*a;*

FIG. 26*a* is a block diagram that describes the two basic Steps 1 and 2 of operation of the portable user interactive data logging and memory enhancement system of the present invention;

FIG. 27 is a block diagram describing Step 1, Phases 1-3 of the operation of the portable data logging portion of the present invention;

FIG. 28 provides a diagrammatic representation of the front view of a composite frame of undistorted panoramic imagery taken at Time 1 at a given location by the panoramic spherical field-of-view (FOV) surround video camera system of subject matter that corresponds to neural activity related to a conscious precept in the brain shown in FIGS. 29*a-b;*

FIG. 29*a* is a diagrammatic representation of brain imagery representing subject matter that may be logged into the host computer system that correlates with panoramic imagery shown in FIG. 28;

FIG. 29*b* is a diagrammatic representation of voxel brain imagery representing subject matter that may be logged into the host computer system that correlates with panoramic imagery shown in FIG. 28;

FIG. 30 is a diagram illustrating the method of constructing a computer database of neural correlation tables derived from internal and external sensor data recorded from and about a being, machine, or bio-mechanical system in the present invention by operating a computerized correlation system;

FIG. 31 is a diagram illustrating computer normalization of common relationships of brain activity sensor, CP, and NCC data derived from two different beings in order to construct a translation table that form a computer database to facilitate communication between two different beings, machines, or bio-mechanical systems;

FIG. 32 is a block diagram describing Step 2, Phases 1-6 of the operation of the interactive portable memory enhancement method of the invention;

FIG. 33*a* is a table that illustrates a more detailed description of the major component systems, their functions, and corresponding processes that make up the data logging and memory enhancement system described in the present example;

FIG. 33b is a continuation of the table in FIG. 33a that illustrates a more detailed description of the major component systems, their functions, and corresponding processes that make up the data logging and memory enhancement system described in the present example;

FIG. 35 is diagrammatic representation of a two-way telecommunication embodiment of the invention in which a message is transmitted between a sender and receiver which may comprise beings, machines, or bio-mechanical systems based upon a computing arrangement of the video logging and memory enhancement system in which a sending being with a first portable host computer (i.e. a first smartphone with portable brain activity sensor system and surround video system), a correlation, database, and query system transmits to a receiving recipient (i.e. a second smartphone with portable brain activity sensor system and surround video system);

FIG. 37c illustrates a resulting frame processed for viewing by the user in which three images are sampled out of the images shown in FIG. 36a-b and FIG. 37a;

FIGS. 39a-39e illustrate a series of alternate graphic user interface (GUI) menus displayed on a host computer operated by a user to command and interact over the internet using a social media and/or search engine of the present invention;

FIG. 39a is a is a graphic representation of the GUI menu displayed on the host computer the user operates to command the host computer of the social media network embodiment of the present invention in which users can share life experiences logged by operating the internal and external sensor systems, correlation system, and host computer system that comprises the present invention;

FIG. 39b is a graphic representation of the GUI menu displayed of the host computer the user operates to command the host computer to select and record, process, store/log, and display information derived from the brain and surround sensor systems borne by the user of the social network;

FIG. 39c is a graphic representation of the GUI menu displayed on the host computer the user operates to designate logged selections he shares with others on the social network;

FIG. 39d is a graphic representation of the GUI menu displayed on the host computer the user operates to designate selections required to conduct a live video teleconference with friends logged onto the social network;

FIG. 39e is a graphic representation of the GUI menu displayed on the host computer the user operates to conduct a search for information using the memory enhancement and query capabilities of the invention borne by the user;

FIG. 45a-d are a series of illustrations showing the present invention integrated into a robot with a sensor array that includes a visual system that comprises a camera, a three-dimensional digitizing system comprising a small conventional radar, and an acoustical system including a microphone used for sensing and guidance consistent with FIG. 41 and FIG. 44, Option C, of the present invention;

DETAILED DESCRIPTION

Figure 2A:
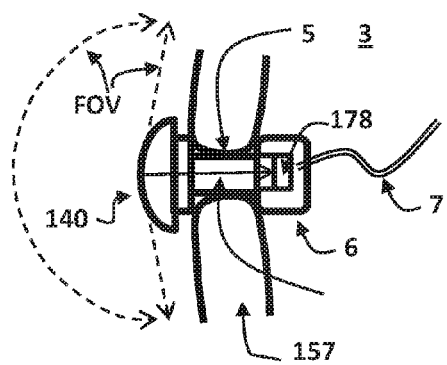
FIG. 2a is a side sectional view of a pierced earring arrangement for capturing exterior and peripheral video logging according to the present invention.

Given the above listed enabling technologies the following detailed description is provided to demonstrate the unique, unobvious, and novel incorporation of these technologies into a design for a portable user integrated interactive Life-Logging and Memory Enhancement Assistant (LLMEA) system and method 100 for use by a being, machine, or combination thereof. Art cited in the "Background of Invention" are incorporated in full as enabling art of the present invention. Art disclosed in the "Brief Description of the Drawings" and "FIGS. 1-49" are also incorporated in full as enabling of the present invention.

Various embodiments of the present invention will now be described more fully with reference to the accompanying drawings, in which some, but not all embodiments of the invention are shown. Indeed, this invention may be embodied in many different forms and should not be construed as limited to the embodiments set forth herein. Rather, these embodiments are provided so that this disclosure will satisfy applicable legal requirements. When the words "may," "can," "might" "optional", "alternative", or the like are used, they mean that the associated feature or description is not a necessary, critical or required aspect of the broadest disclosed inventions, even though they may be desirable or preferred in certain instances. Also please note that within the context of the specification the "User" wearing the portable portion of system 104 comprising the invention may be referred interchangeably as a being, specimen, person, machine, bio-mechanical system, or recipient in various context of the present invention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. Those having skill in the art will recognize that the state of the art has progressed to the point where there is little distinction left between hardware, software, and/or firmware implementations of aspects of systems; the use of hardware, software, and/or firmware is generally a design choice representing cost versus efficiency tradeoffs. Those having skill in the art will appreciate that there are various logging and memory enhancement embodiments of the present invention by which processes and/or systems and/or other technologies described herein can be implemented (e.g., hardware, software, and/or firmware), and that the preferred vehicle will vary with the context in which the processes and/or systems and/or other technologies incorporated. Those skilled in the art will recognize that optical aspects of implementations may employ optically-oriented hardware, software, and or firmware solution to manipulate an image within the invention (i.e. removal of image distortion). Hence, many different types of wide angle and panoramic camera systems, sensor packages, brain activity sensor and physiological sensing systems, wireless communication devices, correlation systems, storage systems, force feedback, and graphic user interfaces may be incorporated without departing from the scope of the invention. There are several possible embodiments of the logging and memory enhancement system of the present invention by which the processes and/or devices and/or other technologies described herein may be effected, none of which is inherently superior to the other in that any logging and memory enhancement system to be utilized is a choice dependent upon the context in which the logging and memory enhancement system will be deployed and the specific concerns (e.g. portability, flexibility, or predictability) of the implementer, any of which may vary. Additionally, it will be apparent to those skilled in the art that various components and arrangements may be exercised in part or in whole to some extent without departing from the spirit of the invention.

In some implementations described herein, logic and similar implementations may include software or other control structures suitable to operation. Electronic circuitry, for example, may manifest one or more paths of electrical current constructed and arranged to implement various logic functions as described herein. Electronics within the invention may be in the form of an IC, LSIC, VLSIC, PCB, or motherboard. Components of the logging and memory enhancement system may communicate directly (i.e. over wire or fiber optics) or via wireless technologies (i.e. radio-frequency, using WIFI and Bluetooth technology) known in the art, and may be supported outside or inside the human body, machine, or a combination thereof. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. For instance, in the present invention personal electronic devices (PEDs), like smartphones, are a derivation of a host computer, and are referred to interchangeably depending on the context of the discussion. Specifications or other implementations may be transmitted by one or more instances of tangible transmission media as described herein, optionally by packet transmission or otherwise by passing through distributed media at various times. Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings. In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program. In the embodiments host, being, user, person, recipient, subject or machine may be used interchangeably and refers to a thing or object on or into which the portable interactive data logging and memory enhancement system is situated or connected.

While line drawings are predominantly shown in the present invention to illustrate its workings and design, it should be noted that images of hardware, software, and firmware in the real world and the actual components comprising system 100 may be substituted without changing the scope of the invention. For instance, horizontal sectional line drawings representing latitudinal cross sections of the human brain are shown that graphically represent an fMRI, AMR scan, regions, neurons, connections in the brain. And for instance, it will be understood by those skilled in the art that related subject matter external and internal to the body that represents a given subject may be illustrated in the drawings as line as photos, line drawings, or numbers representing the same subject to help describe the invention. It will be understood well known to those skilled in the art that two-dimensional images (i.e. spectrum image, voxel based brain image, brain network image, etc.) or three-dimensional perspective images (i.e. spectrum image, voxel based brain image, brain network image, etc.) may be substituted to represent the same subject as a line drawing without deviating from the spirit of the invention. And line drawings representing subjects such as people and things can be replaced with images and photos of the actual subject without changing the disclosure of the present invention and without changing the scope and spirit of the invention.

Implementations of some embodiments of the present invention require special medical procedures and devices that should only be implemented by a trained physician using proper medical facilities, equipment, and care. Additionally international, federal, and state laws may bear on and should be adhered to when considering performing an implementing some of the embodiments of the present invention.

Furthermore, all graphic representations used as examples herein are purely coincidental, fictitious, and any resemblance to actual people or places is unintentional and incidental and solely meant to illustrate the workings of the present invention. And any prior art, names of individuals, companies, logos, trademarks referenced in the present invention are meant to be used solely for a teaching tool, and are solely owned by their agent and not claimed in any way by the present inventor, as they are being used solely for educational and demonstrational purposes.

The "Detailed Description" and corresponding "Drawings" are divided into three interrelated sections to facilitate understanding and for organizational purposes. Sheets 1-22 (FIGS. 1-24*f*) describe the hardware, firmware, and software enabling the invention. Sheets 23-35 (FIGS. 25-37*c*) describe the processes and methods enabling the invention. And sheets 36-50 (FIGS. 38-49) illustrate embodiments/applications of the invention that may be derived from the Life-Logging and Memory Enhancement Assistant (LLMEA) 100 system.

Figure 25:
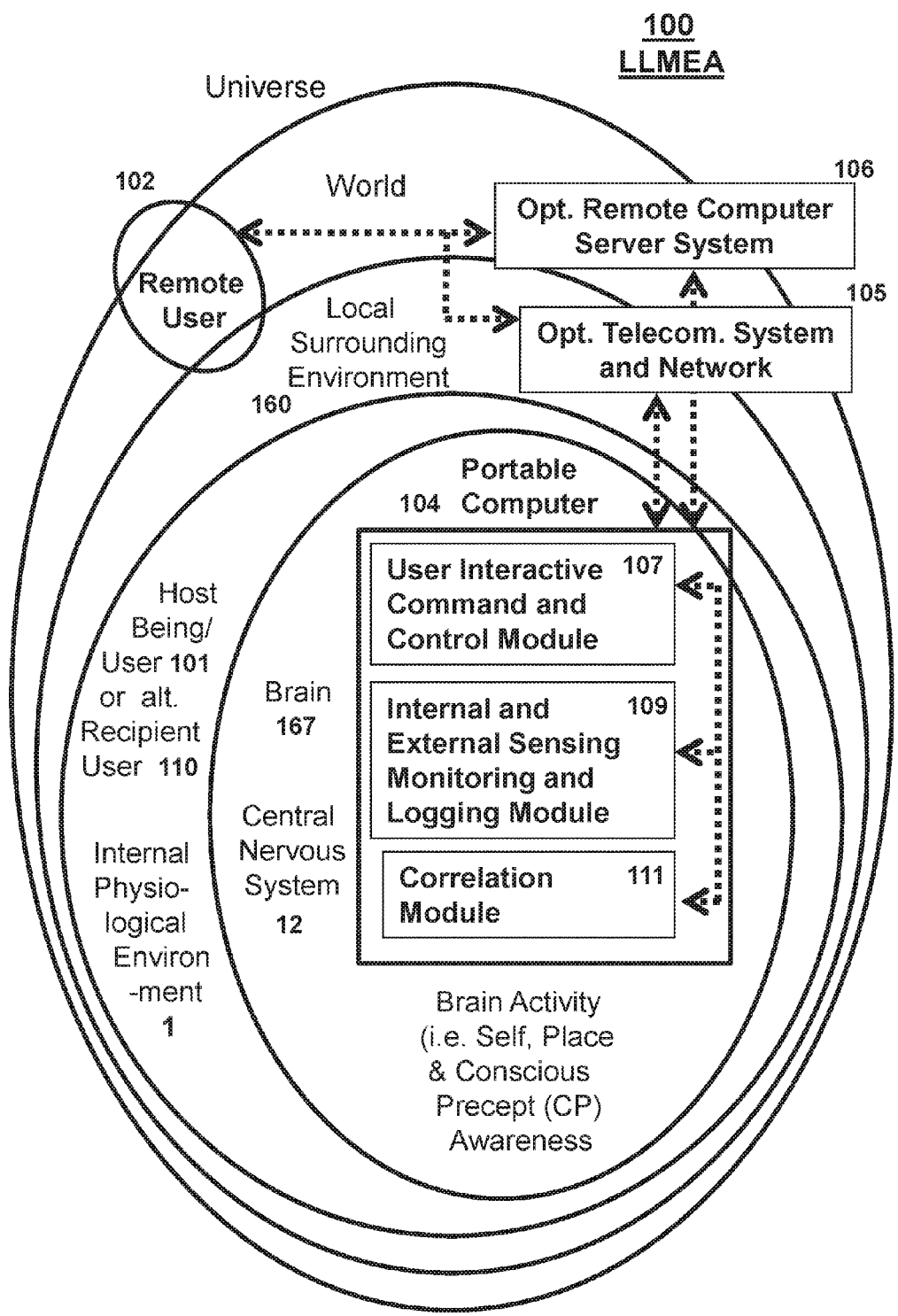
FIG. 25 is a block diagram of the portable interactive data logging and memory enhancement system that describes the overall concept and major components of the invention.

FIG. 25 illustrates a schematic diagram of system 100 which comprises the invention. The system 100 includes a portable host computer system 104 that consist of a user interface that includes an interactive command and control module 107, internal and external sensing module monitoring and logging module 109, and a correlation module 111. Module 107 processes the host being 101 (i.e. also referred as a user) commands that control the portable computer 104 that controls module 109 and module 111. Command and control module 107 is operated to specify which data, information, and/or media content that the system 104 acts upon. Internal and external sensor data and information is transmitted to the internal and external sensing monitoring and logging module 109. Module 109 includes physiologic activity, periphery, and surrounding environment sensor units. Correlation module 111 includes a feature, quality, and/or a media content identification unit commanded by control module 107. Module 109 operates to command and control the transmission of data and information to and from the correlation module 111 along with other stored or incoming data which may be transmitted to system 104 over a telecommunications system and network 105. User commands and logged information are operated upon to draw relationships utilizing correlation module 111. The device 104 is borne by the user 101 and may interact over the telecommunications system and network 105 with another user 102 or a remote computer server system 106.

The telecommunication network 105 may include at least one remote server 106 that communicates with and shares functionality with other servers, networks, and portable computers. Portions of system 100 may be comprised of separate connected components to realize portable computer 104. And virtually any kind of computing device may be used to implement the internal and external sensor system monitoring and logging module 109 and correlation module 111. The system 100 may comprise various components, to include a networked computer, a server, a collection of servers and/or databases, a virtual machine running inside a computing device, a mobile computing device, a PDA, cell phone, smartphone, a tablet PC, a robot, or man-machine integrated system. For example, computer processing of sensor signatures gathered by module 109 and processed by correlation module 111 may be accomplished on one or more remote computer server 106 systems in the world or universe or computer 104 systems in the local surrounding environment 160.

Alternatively, the portable host computer 104 system may operate in a standalone mode. In such an instance, host computer 104 includes modules 107, 109, 111 and other associated computer functions that are integrated into a single device, such as a headgear. Optionally, in the standalone mode, portions of host computer 104 may be distributed about the body of the user.

Data and information derived from system 100 may be operated upon by computer system 104 and 106 to perform user 101 queries for information or for social interaction. The internal sensing portion of sensing module 109 includes a brain 167 activity sensing unit that records data from which self, place, and the conscious precept (CP) and the neural correlates of consciousness (NCC) of the user 101 may be derived. The CP and NCC information is derived by commanding the correlation module 111 to perform operations which determine the relationship to the other internal and external sensor signatures derived by the logging module 109 of system 104. Data and information to operate and derived by system 100 may be stored on any suitable memory storage device. Memory storage devices for use with system 104 and 106 are well known to those in the computer industry. Additionally, data and information derived by a being 101 wearing system 104 may be input into a recipient user 110 or archived for later use.

For example, in operation the system 100 layout described above in FIG. 25 may be implemented in a computer hardware and firmware configuration shown in FIG. 1a-c. FIG. 1a-c is a diagrammatic perspective of a first embodiment of the present invention 100. FIG. 1a illustrates the system and method that the present invention 100 employs to identify the Neural Correlates of Consciousness (NCC) 166 in this instance, the conscious precept (CP) 161 in the mind of the user 101 in the local surrounding environment 160. In this example the subject of the user's CP is a "dog" 159, located in the user's field-of-view 162 in the surrounding environment. The user 101 brain 167 activity 165 causes neurons 164 to fire and the neural network activity is detected by the brain activity sensing unit 156 of system 100 which generates electronic signatures 163 that are digitized and processed by system 104. The brain activity 165 is correlated with panoramic video 168 imagery and audio signatures 169 also captured by system 100 that are the focus of attention of the user 101. Correlation of the brain activity and video signatures is then derived by performing computer operations comparing the signatures in order to deduce the conscious precept 161 and identify the neural correlates of consciousness 166 of the being 101 at a given time and place during the life of the being.

FIG. 1b is a diagrammatic perspective of a first embodiment of the present invention 100. In this embodiment host computer system 104 comprises a smartphone 151 and a headgear 73. The smartphone and headgear are in a communicating relationship. The headgear 73 includes at least the sensing and readout portion of the internal and external sensing module monitoring and logging module 109 that includes a brain activity sensing unit 112. The sensing and readout portion of the internal and external sensing module monitoring and logging module 109 includes a video camera unit 2a-2d. Video camera unit 2a-d includes small cameras with microphones on the ears and nose of the user. Camera unit 2a is mounted on the right ear of the user, and camera unit 2c is mounted on the right side of the user's nose. Not visible in the drawing is camera unit 2b mounted on the left ear of the user, and camera unit 2d mounted on the left side of the user's nose. Additionally and preferably, at least one left ear and/or right audio amplifier 138a and 138b (138b is not shown) are mounted on or in the corresponding right and left ears of the user. The amplifier 138a and 138b may comprise an earbud with a speaker. EMDs, audio amplifiers/ earbuds, and microphones are in communicating relationship to modules 107, 109, and 111 of host computer 104 by wires, fiber optics, wireless RF transceiver system, or other conventional communications methods. In the FIG. 1b the host computer 104 consists of a smartphone 151 carried by the user 101. Host computer 104 includes an input means and output means that allow the user to interactively input commands into the control module 107. In the present example the display means is a component part of a mobile presentation unit that may alternatively comprise a smartphone display and/or a wearable display, like a HMD or EMD 137a and 137b. In the present embodiment, at least one right eye EMD 137a and/or left eye EMD 137b is mounted on the corresponding eyes of the user. The source of electrical power to the EMD and HMD may be by battery, solar cells, or via electrical induction means, depending on the specific design of the HMD or EMD unit.

Headgear 73 and smartphone 151 share portions of the internal and external sensor monitoring and logging module 109. Brain activity sensing is accomplished by sensors in the headgear. Sensor readings are read out from the headgear and transmitted to the smartphone for processing and storage. In FIG. 1b sensor module 109 includes a brain activity sensing unit 73 that is comprised of at least one of the following: a near-infrared imaging (fNIR) unit, functional magnetic resonance imaging (fMRI) unit, magneto encephalography (MED) unit, electroencephalography (EEG) unit, and/or positron emission topography (PET) unit, and other similar type of unit that senses brain activity. The brain activity sensing unit and sensor module is configured to look at regions, neurons, and/or activity patterns of the brain in order to derive data to enable identification of Neural Correlates of Consciousness (NCC) and conscious precepts. Emotional association, attention association, and/or cognition associations may also be deduced from the analysis of the brain activity of the system 100. The brain activity sensing unit transmits electronic signatures 165 of the brain activity to the correlation module 111 located in the smartphone 151. Module 111 performs measurements on the brain signatures and then stores information about the brain activity signatures that meets certain predetermined thresholds and rule sets stored in the computer memory of the smartphone. The exterior looking portion of the sensor system includes at least one video camera unit 2 that faces outward, inward, or both to record the environment surrounding the user and the periphery of the user's body. The video camera unit comprises a plurality of video recording devices that record image and audio signatures representing the surrounding environment 160. Module 111 stores the video in the memory of the smartphone. Alternatively, module 111 transmits video to another computer or server 106 that stores the video in memory which may be recalled at a later date by the user 101 or another user 102. Recall of stored information may be part of a cloud computing application and service of the network 105. Video is stored in nonvolatile or volatile memory depending on the application specified by the user. Module 111 includes a content identification section that performs computer operations that analyze the stored brain activity information and video signatures to identify neural correlates of consciousness (NCC) 166 that relate to and identify the conscious precept (CP) 161. As illustrated in our present example, the Life-Logging and Memory Enhancement Assistant (LLMEA) system 100 identifies a "dog" as the conscious precept 161 that the mind of the user is focused upon in the surrounding environment 160.

Because data logging is a memory intensive system 151 may be programmed to delete old recordings after a given period of elapsed time in order to save memory or recover memory for newer recordings (i.e. ref. Looxcie™ wearable camera system). Additionally, smartphone 151 may include an automatic reaction capability that is initiated in response to brain activity sensed by the monitoring portion of module 109. For instance the system 100 may react in a predetermined manner to perform various operations, based upon input brain activity or video imagery, when certain NCCs are activated or CPs are observed. Portable host computer system 104 correlation module 109 may include an eye-tracking unit, including an iris response unit, gaze tracking unit, touch feedback unit, and/or voice response unit that the user may control and command to drive system 100.

FIG. 1c illustrates the outward appearance of a non-invasive assembly the user 101 wears to support the headgear 73 of system 100. In the present example, a flesh colored skull cap with brain activity sensing unit 156 worn by the user. The skull cap covers the head in a manner that blends the headgear 73 with the normal appearance of the user. Alternatively, other non-invasive headgear 73 of a type compatible with the present invention may comprise a hairpiece, hood, cap, hat, helmet, or eyeglasses.

FIGS. 2a-f are side sectional views of various alternative support assemblies and methods that are alternatively incorporated to hold the portable data logging and memory enhancement method and system of the present invention to the user. Assemblies supported according to the present invention include sensors, such as a small camera, microphone, vibration, touch, pressure, and/or brain activity sensors, and/or a micro-chip, VLSIC's and/or a computer, and the like. The example support assemblies can also be incorporated to hold head mounted display systems consistent with the present invention. Assemblies may be connected to one another by wire or wirelessly. And non-invasive support assemblies may be mounted onto the exterior skin or gear worn by the user. Invasive assemblies are implanted into or under the skin 157 or into or beneath the skull 13 of the user.

FIG. 2a is a side sectional view of a body pierced support assembly 3 that captures and reads out video images into system 100. System 100 comprises a plurality of panoramic camera units 2 that record video. In the present example the optical system has a greater than 180 degree field-of-view (FOV) that is indicated by dashed lines that designate the FOV. Each camera module faces outward to provide adjacent FOV coverage with adjacent camera 2a-d. As shown in FIG. 1b the camera unit 2c and 2d record imagery of which includes the face of the user. Facial imagery is processed to track the direction of focus of the eyes of the user necessary to help the system 100 determine the subject CP in the surrounding environment the users attention is focused upon. The camera unit 2a-d includes an optical system that focuses an image of a portion of the environment toward which it is directed on the image sensor 178. The image sensor reads out a video signal to the host computer 104 for processing. As shown in FIG. 2a the camera is held in place by a post 5 that penetrates through the skin 157 of the user's ear which is held by a back 6 or clutch. In the present embodiment imagery from the objective lens system 140 is held in place by the housing that comprises the hollow post 5. Imagery is projected from the objective lens system through the post 5 to the image sensor 178 located in the back 6. The back is threaded and screws onto the post. Electrical power for the camera and electronic communication to and from the camera is transmitted through a wired or fiber optic cable 7 that transverses from the back to the body worn camera unit 2 to the skull cap 156. Alternatively, the earring can include a battery for power that is located in the back 6. And alternatively, the electronic communication between the camera unit and host computer is transmitted using radio frequency communication, in which case the transceiver is located in the back 6.

Figure 2B:
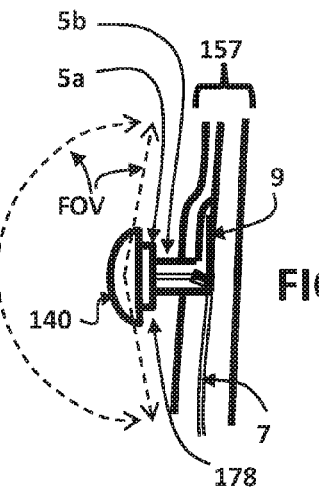
FIG. 2b is a side sectional diagram with a sensor assembly that incorporates a sub-dermal implant to hold a stud into the body of a user in accordance with the present invention.

FIG. 2b is a side sectional diagram with a sensor assembly that incorporates a sub-dermal implant assembly 8 to hold a stud or locking bar 9 into the user's body that forms a portion of the back 6 of the implant. The locking bar 9 holds a rear post 5b which penetrates the skin in place. Standard surgical procedures are used to place the base of the implanted stud under the skin 157. The outward end of the post 5b screws into the post 5a that holds the objective lens system 140 of the camera 2. The objective lens faces outward from the user. A rigid housing holds all components of the implant 8 in place. The housing holds the objective lens system 140 that focuses the image onto an image sensor 178 of post 5a. The end of the cable 7 that penetrates the back of the sub-dermal implant has electrical contacts that connect to the image sensor 178 when posts 5a and 5b are screwed together in the operation position. Alternatively, the sub-dermal implant 8 may include a battery to power the module. And alternatively, the electronic communication between the camera unit 2 and host computer 104 may comprise a radio frequency communication system. In such an instance a transceiver is located within the housing of the sub-dermal implant 8 and a host computer system 104 in a communicating relationship. Video images are transmitted to image processing portion of the video logging and memory enhancement and awareness system of the invention for additional processing and or storage.

Figure 2C:
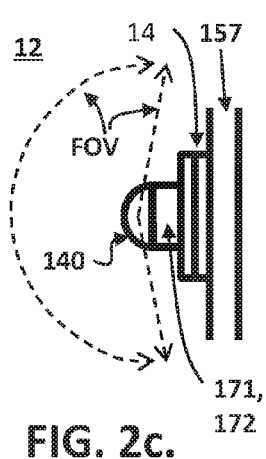
FIG. 2c is a side sectional diagram of a body worn sensor held in place by a double sided adhesive pad in accordance with the present invention.

FIG. 2c is a side sectional view of an adhesively mounted sensor assembly 12 comprising a double-sided adhesive pad 14 adhered to an image capture device 171 with transceiver 172 for capturing exterior video for logging into the system 100. Double sided adhesive stick pads with a foam center are readily available at most hardware stores. Typically, the adhesive is of a type that may be removed by pealing it off of the user. Pads of this type are used widely in the medical field to mount EKG sensors on human skin 157. Alternatively, the sensor unit 12 may be faced outward from user and adhered to the skin or apparel worn by the user.

Figure 2D:
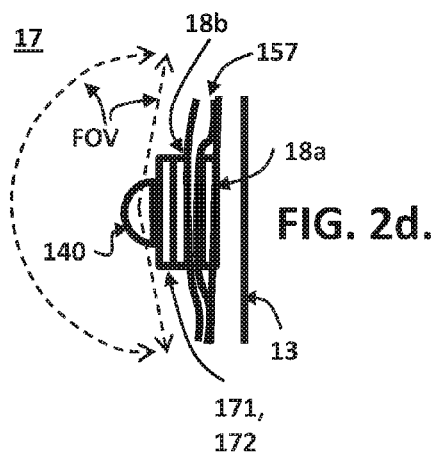
FIG. 2d is a side sectional view of a magnetic implant device and arrangement for supporting an assembly located over the outer skin of the user in accordance with the present invention.

FIG. 2d side sectional diagram with a magnetic implant assembly 17 mounted to the body comprising a magnet 18a implanted beneath the skin 157 in the form of a sub-dermal implant. An attracting metal or magnet 18b is placed on the exterior of the user that is attached to a sensor in place on the exterior of the body of the user. Implants in the present invention, such as the magnetic implant arrangement 17, are implanted using surgical techniques well known within the medical community.

Figure 2E:
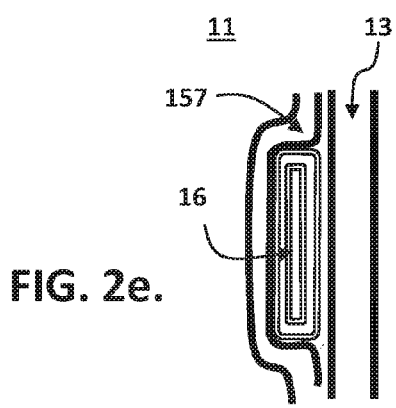
FIG. 2e is a side sectional diagram of a cannular or fistular implant to hold components in place in the body of the user according to the present invention.

FIG. 2e is a side sectional view of an implanted modular assembly 11. The modular assembly is used to house and support various head and body borne components of the present invention. In FIG. 2e, assembly 11 may comprise a cannular or fistular implant housing 16. The assembly 11 is located next to the skull 13 and beneath the skin 157 of the user. The implanted cannula or fistula is placed within a hermetically sealed and sterilized outer membrane of the housing 16. The cannular or fistular implant may include an access opening through the skin. The access opening may be used as a port to perform various maintenance functions, such as for electrically recharging a battery, removing memory chips, and the like. Alternatively, the implant can be recharged remotely using induction charging. The cannula and fistula are implanted using surgical techniques well known within the medical community.

Figure 2F:
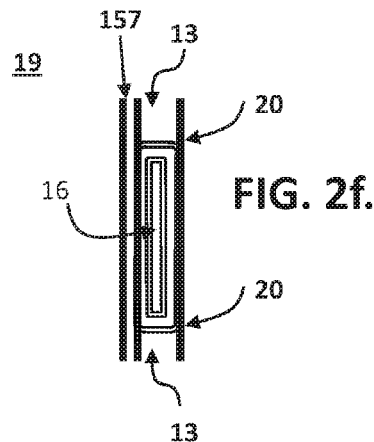
FIG. 2f is a side sectional view of a skull implant device and arrangement for supporting an assembly in accordance with the present invention.

FIG. 2f is a side sectional view of a skull implant support assembly 19. The implant housing 16 is embedded as a part of the human skull 13 lying beneath the skin 157 of the user. The portion of the skull the implant replaces is surgically removed. The implant is implanted using surgical techniques well known in the medical profession. The implant in this embodiment of the invention is a printed circuit board constructed within a hermetically sealed and sterilized outer membrane of the housing 16. The electronics are shielded within the implant the outer membrane will typically be made of a hard plastic. The implant 19 is held by a fastening means 20 to the adjacent portion of the skull 13. The fastening means may be fasten clips, screws, adhesive, or other well-known techniques known and practiced in neurosurgery. If the implant includes a battery it may be recharged remotely by using induction charging methods known to the medical profession, or alternatively by a kinetic or wired charging system.

Figure 3:
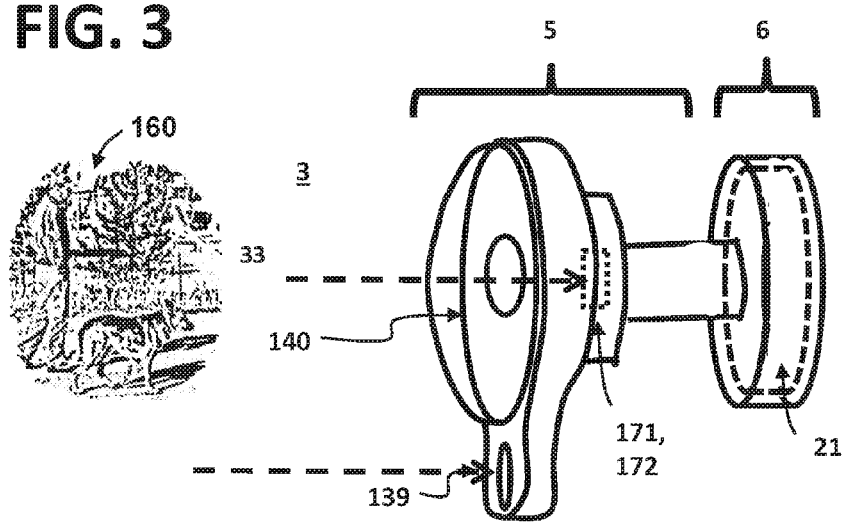
FIG. 3 is a exterior perspective drawing of a pierced earring with a fisheye lens and microphone according to the present invention like that which may be worn on the ears and/or nose in FIG. 1.

FIG. 3 is a perspective drawing of an embodiment of the pierced earring with a panoramic video camera unit 2a, including a microphone 139, like that worn by the user in FIG. 1b. However, in FIG. 3 the earring wirelessly transmits a video feed to the electronics module like that detailed in FIGS. 15-17 and FIG. 19. Dashed lines with arrows indicate the direction of the on-center image path the objective lens and the audio attends to arrive at the image sensor and microphone respectively. The front post 5 of the earring includes an objective lens system 140, image capture device 171 with transceiver 172, and microphone 139. The front post 5 screws into the back 6 of the earring. The back 6 includes a battery 21 which connects to and powers the electronic components in the front post 5. The battery may be replaced by opening a compartment on the earring back or optionally recharged using induction charging. The FOV of each objective lens system 140 is from greater than 180 up to 220 degrees FOV. This wide FOV coverage yields a composite adjacent spherical FOV coverage by the two objective lenses when the hemispherical images from camera unit 2b are stitched together. The edges of the two hemispherical images from a plurality of pierced earring or nose video cameras may be stitched together by the computer 104 to form a spherical FOV panoramic scene using computer processing. Images are sampled in the panoramic scene for display on the HMD or eye mounted display (EMD) of the user.

Similarly, a body pierced support assembly 3, 8, 12, or 17 shown in FIG. 2a-c, with a video camera may be mounted on the user to capture other portions of the surrounding scene. And the surrounding scene may include the periphery of the body of the user such as his or her eyes. For instance, in FIG. 1b, nose mounted camera systems 2c and 2d and prosthetic camera systems shown in FIGS. 5a and 5b have a FOV coverage that images the eyes of the user, including the pupils. The image from the cameras may be sampled and processed by system 100 to determine the gaze and focus of the user 101. Because the scene forward of the user is also in the FOV of the nose earring the subject in the FOV that user is gazing or focused upon is also imaged in the same image. Preferably a Region of Interest (ROI) image sensor is incorporated into the nose camera pierced earring that is programmed to sample the eye and the focus of the eye of the user. Each eye may be imaged in the same manner, and a stereoscopic image may be displayed. Referring again to FIG. 3, preferably camera assembly may include a very small microphone 139 with hemispherical coverage that faces outward from the side of the users head. Audio from the two microphones mounted on the ears of the user may be recorded achieve stereophonic sound. Still alternatively microphones may be positioned about the users head and body to record an ambisonic spatial audio file using computer processing. Audio may be replayed for a user by the user wearing left and a right earbud audio speakers. The earbuds may be integrated into the design of the pierced earring 3. Hemispherical audio is also put together to form spherical field-of-regard audio coverage. Optionally, electrical power and data connection from the pierced earrings in FIG. 3 is via cable running to the smartphone. Alternatively a battery for electrical power and transceiver for data exchange with the smartphone may be provided for wireless connectivity. Additionally, the earring may be integrated with the skull cap worn by the user. The skull cap 156 may include an integrated camera and display system like that described in FIGS. 1a-c, 8a-c, 12, 13a-b, 18, 19, 20, or 22. The skull cap may include all components of the smartphone, surround video, brain activity, and correlation system referred in wholes as system 1. And include and connect to pierced and non-pierced support assemblies of a type shown in FIGS. 2a-f. And may include the fisheye lenses in FIG. 3-5a, and in the LED system in FIG. 5b.

Figure 4:
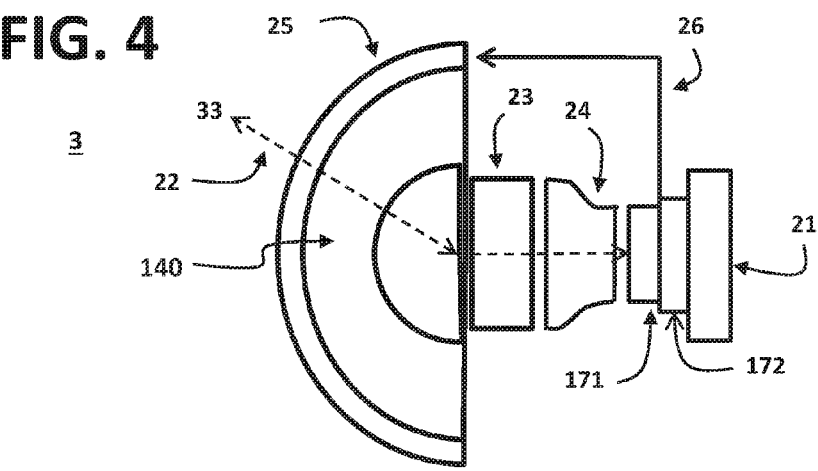
FIG. 4 is a side sectional diagram of an alternative fisheye lens arrangement for use according to the present invention like that which may be worn on the ears and/or nose in FIG. 1.

FIG. 4 is a detailed side sectional diagram of another embodiment of a body pierced support assembly 3 comprising a wireless panoramic video camera unit 2 that transmits images to the smartphone according to the present invention. The objective lens 140 of the camera faces outward from the ear of the user. The objective lens system of the camera is a fisheye lens. All components are held in place by a rigid opaque housing (not shown). The image sensor is located behind the objective lens to receive the image. A hollow cylindrical post behind the objective lens is placed through the earlobe and is inserted through the earlobe into another fastener or screw mount to hold the front and back part of the earring together and securely to the ear of the user. The very back of the earring is constructed to hold a wireless transceiver 172 which is used to transmit video signals and receive commands from host computer 104. The back portion of the earring holds additional image and audio processing firmware that operates upon the incoming image. Image processing may include image and audio noise reduction, image stabilization, brightness control, barrel distortion removal, image translation, and ROI sampling processing electronics. The image sensor 171 may comprise a VLSIC that accomplish at least some of these functions. The image sensor will typically be a CCD, CID, or CMOS (APS) sensor. Distortion removal optics 24, like Fibreye™ or panamorphic lens elements, may be incorporated to assist in removal of the barrel distortion from captured image before it reaches the sensor. Still optionally, fisheye lenses adjacent to one another may incorporate fiber optic image conduits to optically translate the image into a continuous scene between the exit and entrance end of the conduit such that a continuous and correctly oriented panoramic scene for viewing results at the sensor end of the conduit. Still optionally, electro-optical shutter means 25 such as beam-splitter or micro-mirror with SLM, LCD, or an LED shutter 179 assembly is incorporated along the optical path to block or allow images to be projected onto the image sensor as described in additional detail in the "Related Applications" by the present inventor. Electronic circuitry 26 extends to the shutter control means from the image sensor processing portion of the camera 171 and transceiver 172 in order to transmit command and control signal to the shutter 179. Still alternatively, barrel distortion of the image may be removed by pre-processing of the raw image by firmware that is incorporated into the image sensor chip, or later the electronics module or at the remote server. The entire image projected to the sensor from the objective lens system may be imaged on the sensor and relayed to the electronics module. Or alternatively, pre-processing may include ROI sampling and readout of a portion or portions of the entire image to the electronics module. The back of the earring post includes an image sensor with processing to facilitate readout of the video signal. The post also includes a small battery that provides electrical power electrical components of the earring. The unit also includes electrical power in the form of a battery unit. The earring may be designed to have a replaceable or rechargeable battery. If the battery is rechargeable it may be designed to be able to be recharged by an induction recharging method, such as a induction charging pad (i.e. pierced-earring camera, skull cap, thumb display/camera, nose display/camera, etc.). The same is true with charging any removable electronic devices described in the present invention. Video audio and imagery signals are transmitted from the earring to a transceiver in the electronics module of the video logging and memory enhancement system of the invention for additional processing and or storage. The pierced earring camera may include a microphone for audio pickup like that shown in the perspective shown of an example earring shown in FIG. 3. In this manner a very low profile and commonly worn piece of body art or jewelry facilitates panoramic video recording for the video logging and enhancement system according to the present invention.

Figure 5A:
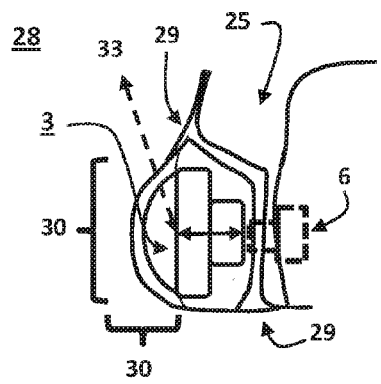
FIG. 5a is a side sectional diagram of a prosthetic integrated camera sensor which may alternatively incorporate technology like that shown in FIG. 3 or 4 like that which may be worn on the ears and/or nose in FIG. 1.
Figure 5B:
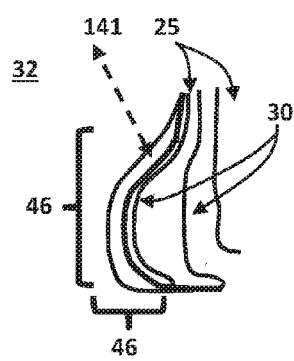
FIG. 5b is a side sectional diagram of an implantable integrated camera and display sensor which may alternatively incorporate technology like that shown in FIG. 10 or 11 like that which may be worn on the ears and/or nose in FIG. 1.

FIGS. 5a and 5b illustrate a prosthetic and implanted video camera and display system consistent and enabling the present invention. The camera and display optics supported by the user may be concealed by a transparent or semi-transparent covering material 30 tinted material, a micro-screen means, or LED and OLED display means. Such covering material is at most frequently made of rubber, plastic, or glass material commonly used in the manufacturing of sunglasses, contact lenses, and electronic display screens. The prosthetic shown in FIG. and the implant shown in FIG. 5a be concealed by any of the methods just mentioned.

FIG. 5a illustrates a integrated prosthetic camera and display assembly with transmitter and battery 28 for the nose 25 of a user similar to that shown in FIG. 4. The prosthetic may be introduced to repair an injury to the nose. Or alternatively, the flesh on the lower side of the nostril is removed surgically and replaced by the prosthetic nose assembly 28. Flesh colored mascara with adhesive 29 is then used to fill in and blend the edges of the prosthetic with the nose of the user. Alternatively, skin may be grown or grafted around the display and the assembly permanently implanted in the nose of the user. Alternatively, the noise assembly 3 may be attached by a back 6 as in FIG. 3. And optionally a microphone of less than 2 mm embedded in the display at the edge of the display, in the display, or even inside the nose on the back 6 to capture the user speaking or audio signatures near the user.

FIG. 5b illustrates an integrated camera and display prosthetic patch assembly 32 for the nose of a user. The assembly 32 comprises an array strip of electro-optical material 46 with a stick-on back that can be adhered to the nose of the user. The location of where the sticky-backed material adheres to the exterior skin of the nose is indicated by a bold solid line. The material incorporates a camera and display like that shown in FIGS. 10a and 10b. The electro-optical material may be semi-flexible and contoured to the noise such that it is inconspicuous and blends in with the natural appearance of the user. The skin color of the user may be displayed when the camera is not being operated to image the surrounding environment. The surrounding environment may include the scene surrounding the user and/or his periphery, to include image tracking his eyes to discern where he is looking and what CP he is focused upon. A transmitter and battery assembly may be designed into the assembly 32 or connected to the host computer 104 by cable, fiber optics, or a transmitter in order to receive and send data and to charge the electronic components of the assembly 32. Flesh colored mascara with adhesive 29 is then used to fill in and blend the edges of the patch assembly with the nose of the user. Alternatively, skin may be grown or grafted around the display of the patch to permanently implant the patch assembly on the nose of the user. When the display includes an integrated camera the pixel or pixels in line-of-sight 33 of the subject being captured are transparent allowing for image capture by the sensor 171.

Figure 6:
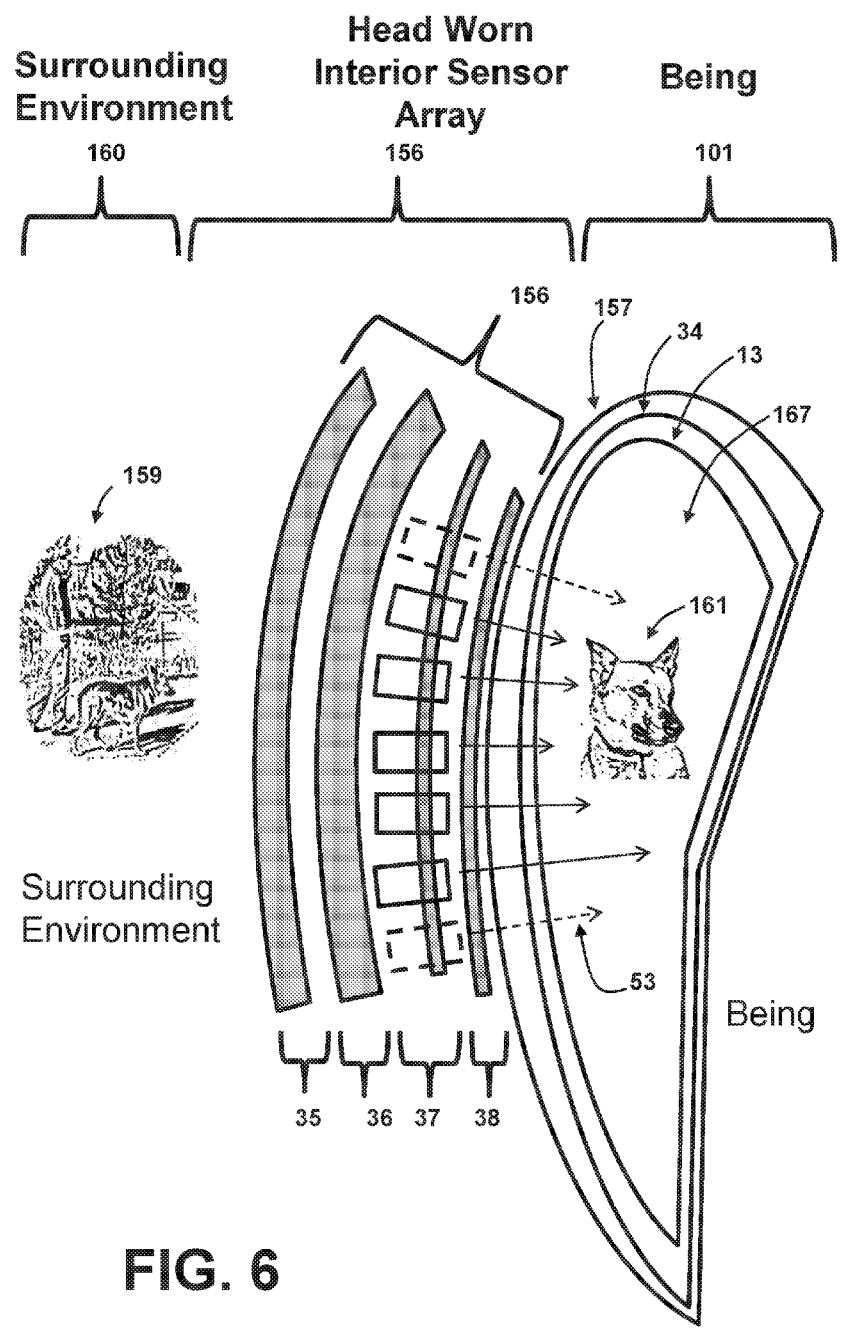
FIG. 6 is a side sectional diagrammatic illustration of an inward facing atomic magnatrometer sensor array worn as headgear by the user as illustrated in FIG. 1 according to the present invention.
Figure 7:
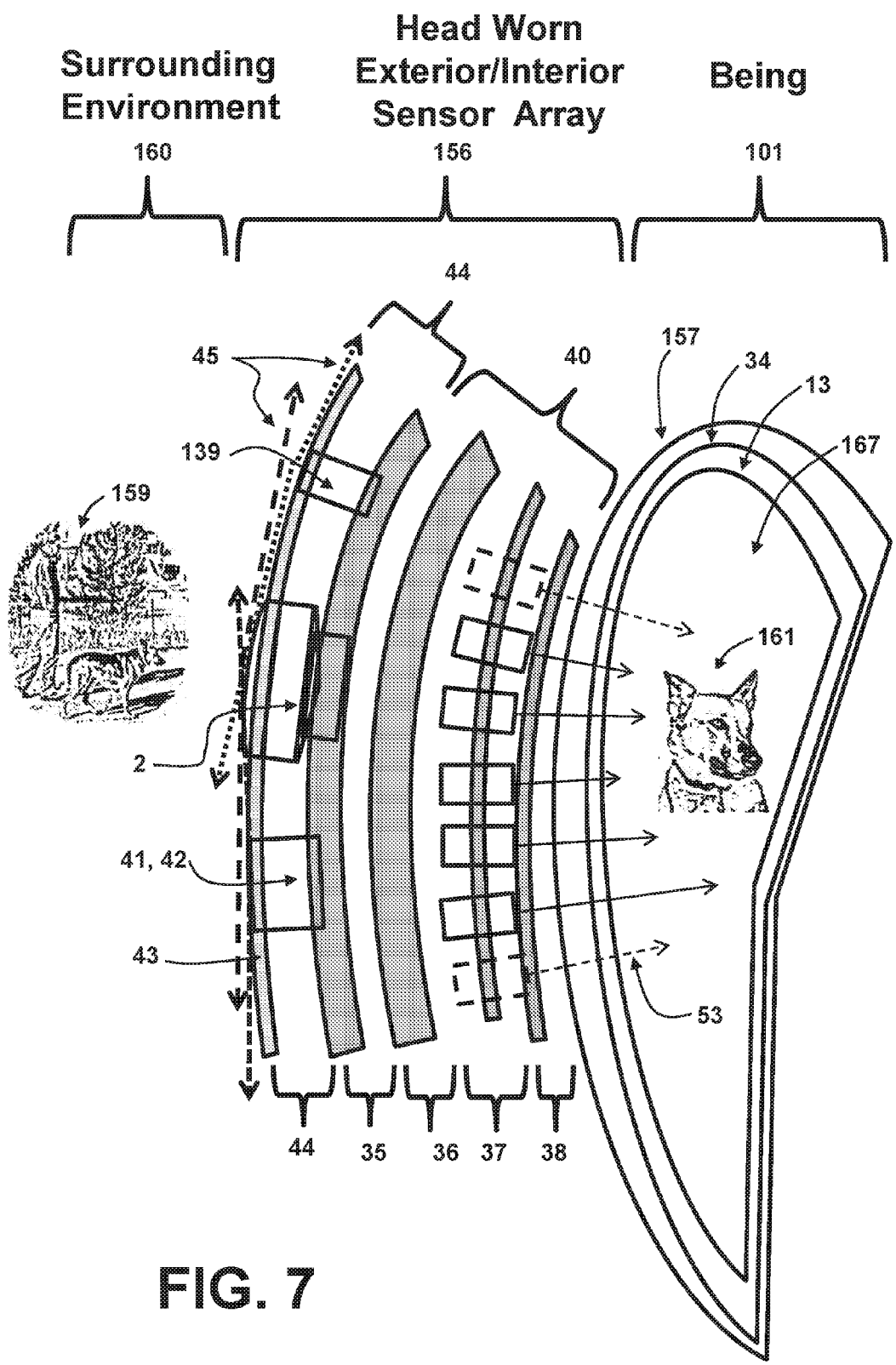
FIG. 7 is a side sectional diagrammatic illustration of an alternative head borne sensor array comprising an inward facing atomic magnatrometer sensor array and an outward facing array of integrated microphone, laser designator/rangefinder or laser-radar with video camera worn by the user as headgear according to the present invention.
Figure 9:
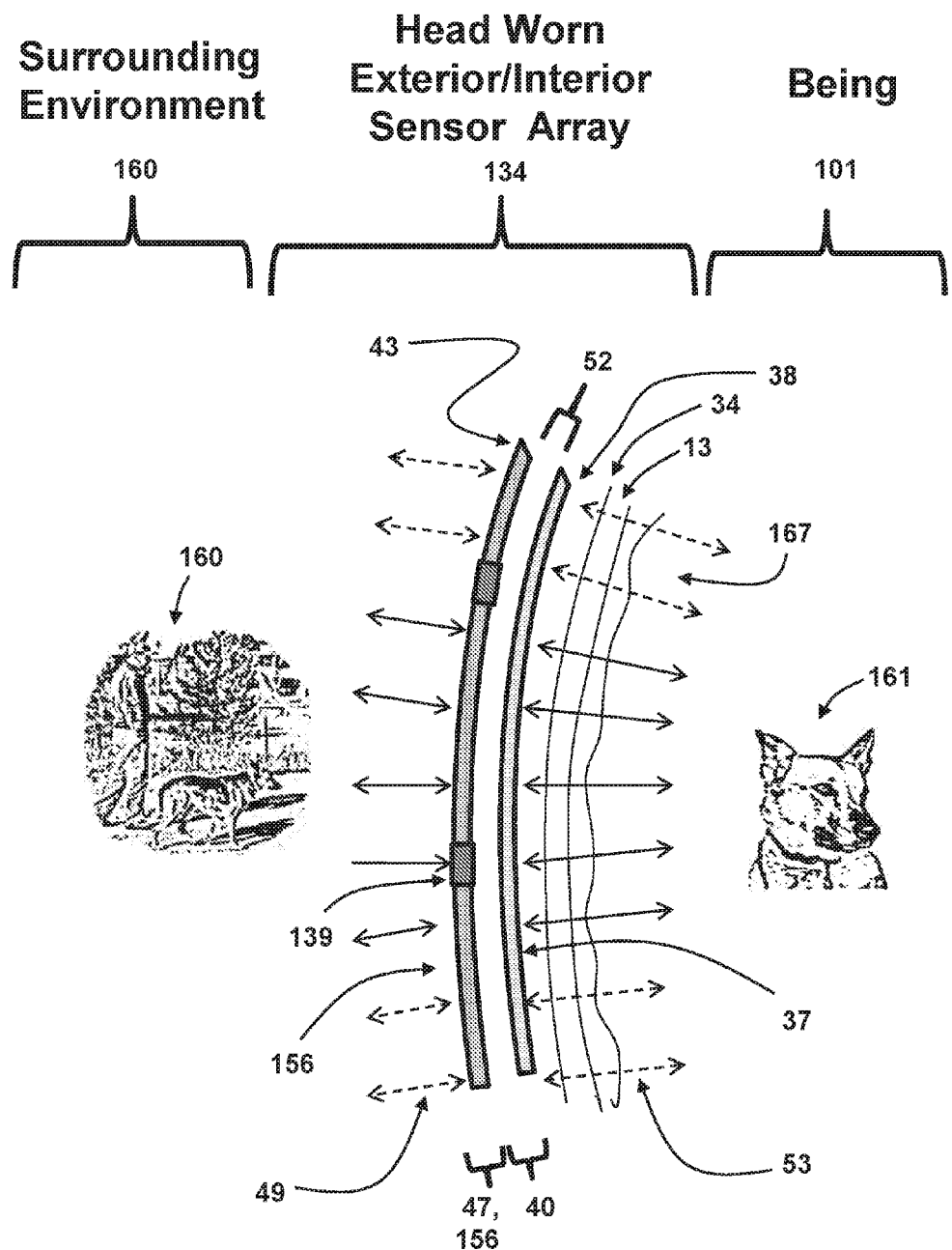
FIG. 9 is a side sectional diagram of the present invention which includes a user worn headgear comprising a brain activity sensor system and a surround audio-visual sensor system like that shown in FIG. 8b.

FIGS. 6, 7, and 9 are sectional diagrams that illustrate the brain activity sensor 40 unit that is a component of the head worn assembly 134 of the subject invention 100. FIG. 6 illustrates a user inward facing brain activity sensing unit 40 integrated into a skull cap 46 but no user outward facing video sensors or display array. FIG. 7 illustrates a user inward facing brain activity sensor unit 40 integrated into a skull cap 46 that includes outward facing image, audio, and other sensors but no display array. FIG. 9 illustrates a user inward facing brain activity sensor unit 40 integrated into a skull cap 46 that includes outward facing integrated image sensing and display array. The array shown in FIG. 9 may optionally include other integrated sensors, such as a microphones 139. FIG. 9 incorporates the outward facing video camera sensor and a displays shown in FIGS. 10a-c, with an optional design embodiment shown in FIG. 11. In our present example, the head worn assembly 134 brain activity sensor unit 40 comprises portable Atomic Magnetometer Resonance (AMR) 37 system with one or more arrays of atomic magnetometer sensors units that detect the relaxation and excitation of the magnetic field induced or not induced, respectively and correspondingly. In the present invention one or more arrays of atomic magnetometers directly detect relaxation of a magnetic field induced with subatomic precession within a target specimen. In this instance the atomic magnetometers sensors units are arranged in a conventional head worn device or helmet wherein the capacity sensors may be used in either a scalar or a vector mode. The AMR may be used to image and provide signal readout on anatomical and non-anatomical structures. In the present example the AMR is used to record the users brain activity as a wearable, portable array, with low power consumption, incorporating wafer-level fabrication, with rapid signal processing, decreased need for development of strong magnetic fields, and lower cost allowing wider availability. Multiplexing may be utilized to periodically turn on and off sensors to allow temporal dissipation of magnetic field effects. In the case of atomic magnetometers, the speed of multiplexing can be limited by the relaxation time of the gas in the detection chamber. This relaxation time is typically on the order of microseconds, and is a function of gas composition, pressure, and temperature. Therefore, there is sufficient temporal resolution for applications such as functional imaging. Additionally, shielding may or may not be interposed between specific sensors or sensor pairs to direct magnetic field lines away from adjacent sensors. As a benefit, magnetic shielding 36 (e.g., creating a window of measurability) may augment the direction sensitivity of a given sensor or sensors. Finally, signal processing may be utilized to focus in on or to remove known frequencies related to operation of sensors from measurements. It should be understood, in light of this disclosure, that many other configurations using these concepts are possible. Signal processing algorithms can be utilized to allow localization and deconvolution of distal signals within a target by subtracting more proximal signals. Alternatively (or in addition), signal processing algorithms can be used to subtract environmental noise. Deconvolution may have the effect of reconstructing a three-dimensional map of the locations and intensities of the signals generated. Because of the relatively small size of the sensors, a relatively high sensor density within a particular array of sensors may be utilized. For example, the sensors may be placed less than 3 mm from the subject's scalp 34 in a closely packed array. Altering the direction of the pump or probe laser may additionally allow increased information at the sensor for the purpose of source localization. Additionally, magnetic shielding may be interposed between the detecting magnetometer and the user specimen to constrain field detection. Shielding may in some cases comprise a disk of mu-metal or other shielding material; other configurations are possible. In some cases, shielding may be rotated to alter directional sensitivity at a given sensor. Various other dynamic shielding strategies may also be used. Various atomic magnetometers with different detection profiles are available and the specific strategy utilized may depend on magnetometer characteristics. Stacking and grouping of arrays of sensors or arrays of sensor clusters may be utilized to progressively screen signal from noise and to account for spatially uniform sources of noise, or other externally induced magnetic fields. Since atomic magnetometers or similar sensors develop magnetic fields in the course of normal operation (typically related to the direction of light propagation along the sensor), the direction of light propagation among sensors may be alternated, or a random pattern of orientation may be utilized to minimize large scale field effects. In some cases, additional magnetic shielding (such as mu-metal shielding or active shielding) may be placed around a sensor or a cluster of sensors, for the purpose of further mitigating inter-sensor interference, and/or in order to provide a further screen for environmental noise. Since sensor-related magnetic fields typically have a particular magnitude and occur at a particular frequency, signal analysis techniques may be utilized to remove the influence of inter-sensor interference from the information derived from the sensors. While imaging can be performed using a pre-pulse and detection field, other additional features may be used to improve image quality. For example, Louis-Serge Bouchard, and Vasiliki Demas of Berkeley Labs (Patent Pending, University of California/Berkley, Patent ID pending) recently disclosed utilization of pairs of rotating fields through a sample to overcomes image distortions that typically occur when applying conventional NMR detection and MR imaging methods at low fields.

Now referring to FIGS. 1, 6, 7, 8, 9, and 14 the head worn assembly 134 communicates to the host computer via cable or wireless connection. The host computer may be of a conventional portable design which is frequently implemented in portable laptops, personal digital assistants, cell phones, and the like. The host computer includes hardware and software. Components are connected by a system bus and electrical bus and include, but are not limited to, input/output jacks, a portable power system with a battery, interactive input devices, video card, hard drive for storing data, random access memory for storing volatile data, central processing systems, cooling fans, telecommunications system, and the like. Additionally, the host computer includes either software (written programs or procedures or rules and associated documentation pertaining to the operation of a computer system and that are stored in read/write memory) and/or firmware (coded instructions that are stored permanently in read-only memory). A computer system and software of a type compatible and incorporated in the present invention is that disclosed in U.S. Patent 2009/0196493, dated 6 Aug. 2009, by Widrow et al entitled Cognitive Method and Auto-Associative Neural Network Based Search Engine for Computer and Network Located Images and Photographs; Cognitive Agent that Learns and Organizes (CALO) Software, and U.S. Patent Application 20070124292 A1, by Kirshenbaum et al, dated 31 May 2007, entitled Autobiographical and Other Data Collection System, and IL, is a system compatible with and integrated by reference as art incorporated into the present invention is the Ultra-Vis, Leader, system developed by ARA, subsidiaries MWD, Vertek, and KAD, and other companies to include Lockheed Martin and Microvision Incorporated teaches a stereoscopic video logging system with querying. Thus the host computer includes an operating system (OS), atomic magnetometer system, dynamic image and brain pattern activity translator and comparator, head mounted display system (including head and eye-tracking and optionally global positioning system), voice recognition system (and optionally sub-vocalization system), panoramic video system, optional telecommunication system, and memory enhancement and personal assistant that learns software and firmware. While preferable to use a single computer language for efficiency, it will be obvious to those skilled in the electronics and computer science that a computer program that converts a program from one language to another to link software written in a different language and machines written to run on different software together is common and may be incorporated to enable the current invention if necessary. In this manner the above referenced software may be linked together to form a single system in the present invention. This translation software may be implemented at the assembly language level as a low-level programming language for computers, microprocessors, microcontrollers, and other integrated circuits; and/or as a utility program called an assembler used to translate assembly language statements into the target computer's machine code.

FIGS. 6, 7, and 9 provides an enlarged side sectional views of that illustrates the basic components and design of the head worn assembly 134 according to the present invention of system 100. The focus of the AMR system will typically and primarily be on the subject the user is focusing on in the environment at a given time. But it also includes other surrounding AMR brain activity neural signatures that comprise the surrounding environment which stimulate place, grid, spatial view cells in the hippocampal area that provide visual cues, spatial navigation, and episodic memories of particular locations that could be a general mechanism responsible for the storage and recall of information about a particular set of events which occur together at the same time. Components of the AMR portion of the head mounted device in the figure include is situated on the users head, scalp, skull, and/or brain. In the present invention the brain is referred to as one the areas of the internal environment which the system 100 monitors. Insulation 38 and a three-dimensional vector, scalar, and gradient detection array including wiring for supplying power are additional components that comprise the AMR system. Input and output signals along with electrical power are provided through wiring and circuitry embedded in the head covering. Magnetic shielding, such as metal shielding and a noise reduction array 35 is also provided in the head covering. The head covering also includes an outer shell or covering of cloth, latex, rubber, plastic, Kevlar, or other suitable material. The AMR's sensors may be arranged so that magnetic shielding is positioned between a first array of sensors and another array of sensors. An additional layer of sensors, with each sensor comprising one or more atomic magnetometers, is grouped outside of a shielded region to allow for noise reduction. One or more arrays of sensors in vector, scalar, and/or gradient mode may be utilized, depending on the application. Accordingly, the first sensor array may be utilized for signal detection, and the second sensor array may be utilized to assess the level of noise present in the signals measured by the first sensor array. More particularly, the signals measured by the first sensor array may include both magnetic fields from a target area within the patient's body (e.g., the patient's brain) and noise. However, because the second sensor array may be shielded from magnetic field's emanating from the target area, the second sensor may measure substantially only the noise adjacent the first magnetometer. Accordingly, the magnetic fields from the target area may be determined by subtracting the noise (as measured by the second array) from the signals measured by the first sensor array. As mentioned earlier in this application, an enabling technology of type compatible with the present invention are portable Atomic Magnetometer Sensor Array Magnetic Resonance (AMR) Imaging Systems and Methods devices of a type like those described in U.S. Patent 2009/0149736, dated 11 Jun. 2009 by Skidmore et al and U.S. Patent 2010/0090697, dated 15 Apr. 2010 by Savukov have been disclosed that are of a type compatible and enabling of the present invention. John Kitching, a physicist at the National Institute of Standards and Technology in Boulder, Colo. has developed a tiny (grain of rice size) atomic magnetic sensors of a type compatible for use in the present invention.

Integrated with the AMR system in FIGS. 1, 6, 7, 8, 9, and 14 is a panoramic video system. The panoramic video camera system records a panoramic scene which includes the subject of visual focus in the surrounding environment that surrounds the user. But it also includes other surrounding panoramic imagery that comprises the surrounding environment which stimulate place, grid, spatial view cells in the hippocampal area that provide visual cues, spatial navigation, and episodic memories of particular locations that could be a general mechanism responsible for the storage and recall of information about a particular set of events which occur together at the same time. A plurality of objective lenses are embedded in the outer covering of the head worn device to record adjacent or overlapping imagery. The inner space of the head mounted assembly accommodates the AMR components and back side of the lenses and image sensor, including cabling and circuitry, electrical power bus, control, and video input and output signals cabling and/or circuitry. Additionally, there is an inner spacing and lining material between the component layers of the head mounted assembly. It will be apparent to one skilled in the art that various novel arrangements may be constructed according to the present invention to accommodate the head mounted assembly to the user's head, scalp, skull, and brain.

As depicted in FIGS. 1, 6, 7, 8, 9, and 14 the head worn assembly 134 worn by the user also includes panoramic audio recording system. The system may be separate from the imaging system or integrated with of the imaging system, as is the case with most camcorder systems which record a video signal that includes both audio and imagery. The panoramic recording system may be part of simple audio system or a complex ambisonic multi-directional audio recording system. The focus of the audio system is primarily and typically on the subject the user is focusing on in the environment. But audio coverage also includes other surrounding audio signatures that comprise the surrounding environment which stimulate place, grid, spatial view cells in the hippocampal area that provide visual cues, spatial navigation, and episodic memories of particular locations that could be a general mechanism responsible for the storage and recall of information about a particular set of events which occur together at the same time. The outer shell supports the embedded microphones which includes several microphones for capturing audio of the subject of focus and the surrounding visual environment. The inner space of the HMD is designed to accommodate the AMR components and back side of the microphone, including cabling and circuitry, supplying power, control, and video input and output signals. The inner lining of the head mounted system that housing the audio sensors and associated audio components protects the users's scalp, skull, and brain on which the audio components may be situated. The audio system on the head worn device also records voice signatures of the user. But alternatively or additionally includes a throat microphone to record the user's voice. The voice signatures may be run through a voice recognition system and decoded into verbal language that is translated by the correlation system to help identify neural correlates of consciousness and multi-variant correlations with other sensor signature output (i.e. brain activity and imagery) that is logged into the database of computer.

Also as shown in FIG. 7 additional sensors that are integrated into the head worn assembly 134 may include a laser rangefinder/target designator and tracking system with image and pattern recognition. The output from the laser rangefinder/target designator and tracking system with image and pattern recognition applications software or firmware is operated upon by the host computer that assists in identifying the subject or activity the rangefinder is focused upon. Once a subject or activity is decoded then it is correlated with other sensor information to determine the strength of the relationship with other sensor data to see if the same definition is derived. If the relationship is above a set threshold then the correlation is stored and acted upon per the predetermined rule set established by the user.

Still further, sub-vocalization sensor unit 203, as depicted in FIG. 14, may be integrated into the head worn assembly 134 or may be separately located on or in the user's body and feed into the host computer. In such an instance, electrodes record a Electroencephalograph (EEG) signatures that is processed by computer into words. The output from the sub-vocalization system with sub-vocal to word recognition applications software or firmware is operated upon by the host computer that assists in identifying the subject or activity the sub-vocal signature are focused upon. Once a subject or activity is decoded then it is correlated with other sensor information to determine the strength of the relationship with other sensor data to see if the same definition is derived. If the relationship is above a set threshold then the correlation is stored and acted upon per the predetermined rule set established by the user.

Figure 8:
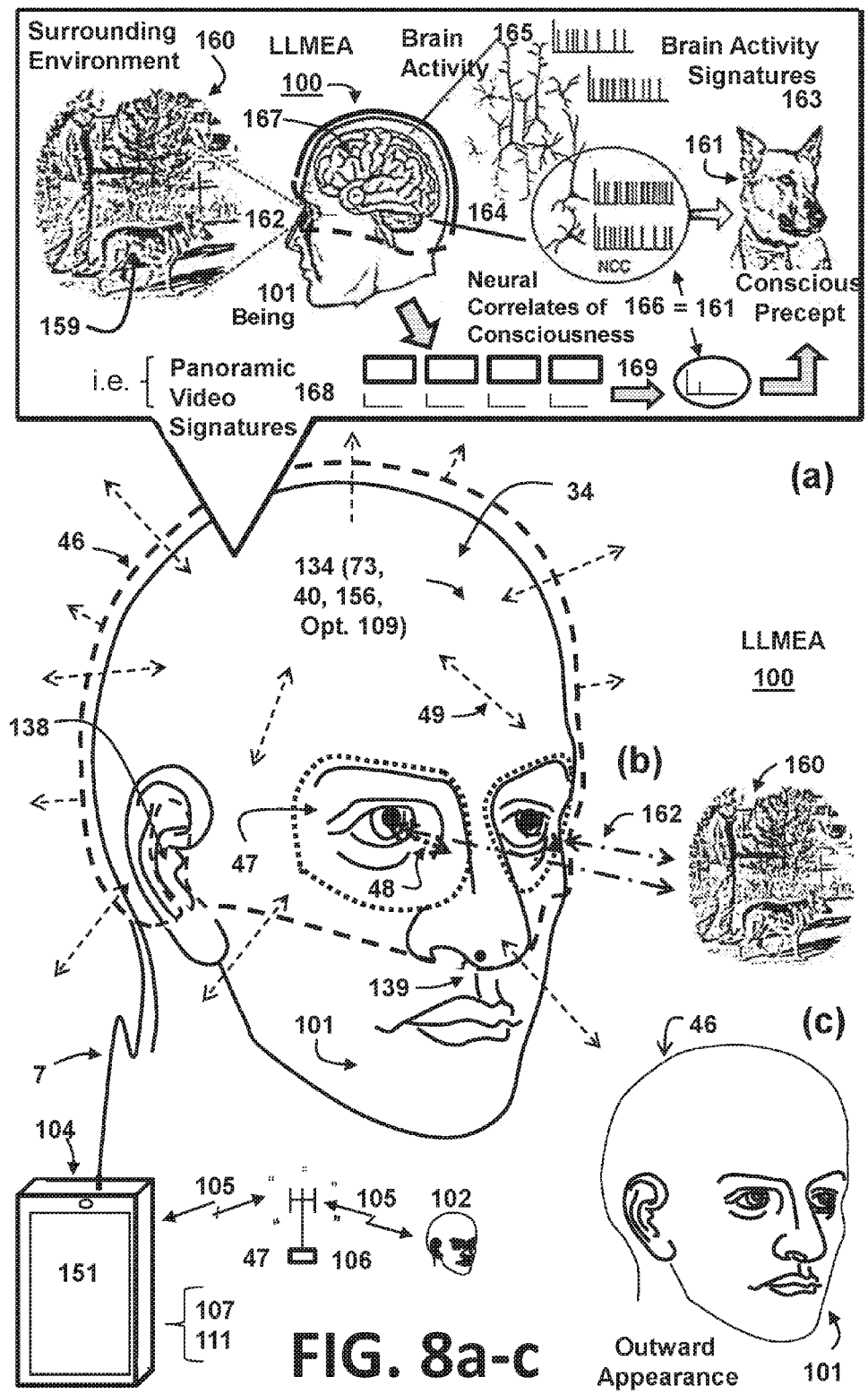
Figure 15:
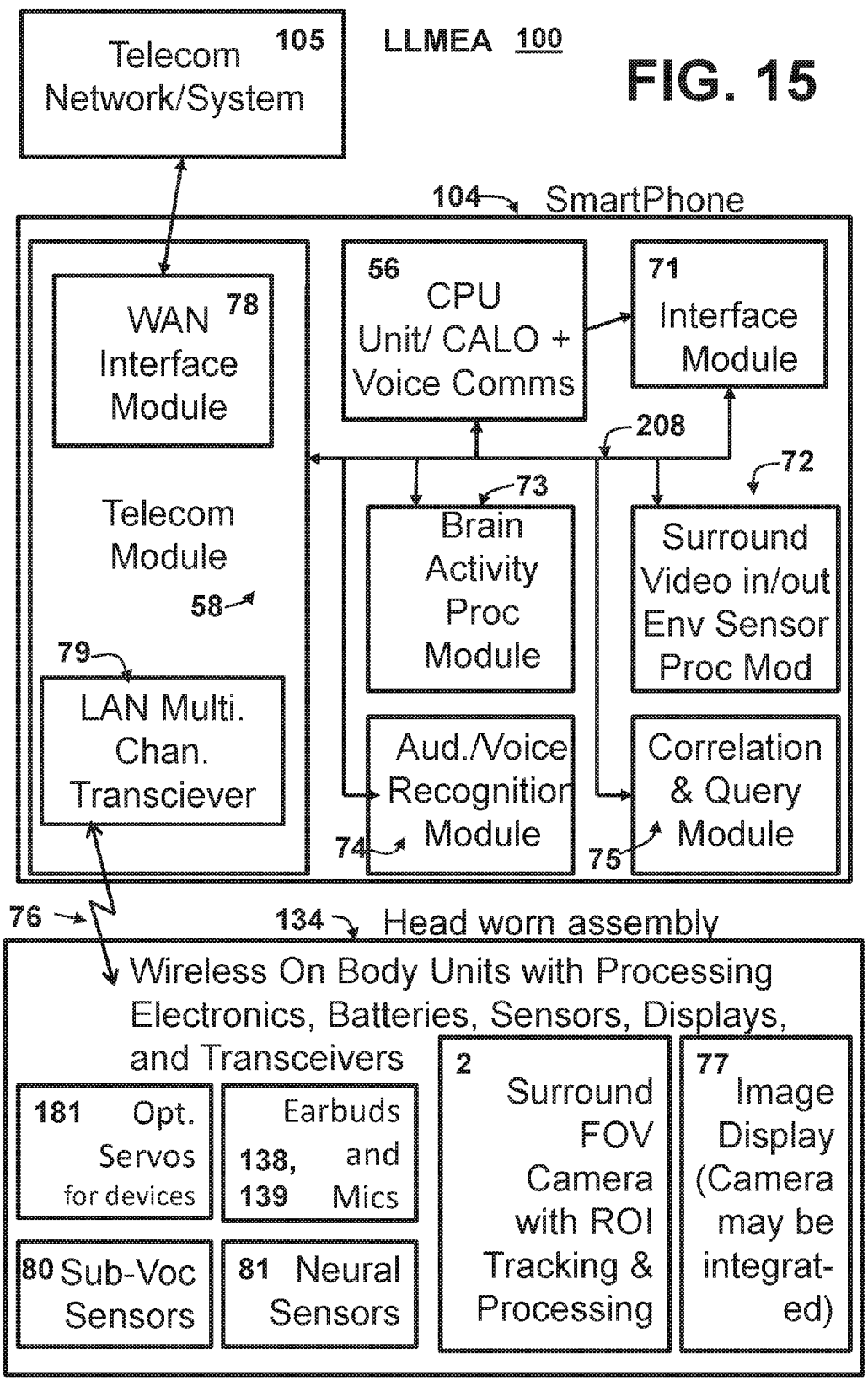
FIG. 15 is a block diagram illustrating components and interaction of an embodiment of the present invention consistent with the functional intent of FIGS. 1, 8, and 25 of the present invention.

FIG. 8a-c is a diagrammatic perspective of a second embodiment of the present invention 100 which includes a user 101 head worn assembly 134. In the present example a dog 159 in the real world surrounding environment 160 in which the user 101 is wearing system 100 senses, records, processes, and presents information. The system 100 acts on brain activity signatures 163 that equate to the Conscious Precept (CP) 161 representing the dog in the brain 167 of the user being 101. Information related to the Conscious Precept of the dog is correlated with panoramic video signatures 168 of the dog 159 to derive and define the Neural Correlates of Consciousness (NCC) 166. The NCC, data, and information from which the NCC are derived represent a computerized relational databases of information on how the user 101 perceives the dog 159 in his or her mind. The head worn assembly 134 comprises a brain activity sensor unit 40 integrated into a skull cap 46 that includes an outward facing integrated image sensing and display array 156 and see-through image sensing and display array 47. The array shown in FIG. 8 may optionally include other integrated sensors, such as a microphones 139. FIG. 8 incorporates the outward facing video camera sensor and a displays shown in FIGS. 10a-c, with an optional design embodiment shown in FIG. 11. Array display systems like that shown in FIGS. 10a-c and 11a, incorporated as display and integrated display and camera systems in FIGS. 8b-c, 9, 12, 13a-b, and 45a-d may partially or fully cover the body, depending on the specific design required for a given application. For instance, an entire suite with integrated camera and display may be designed. In such an application camera and audio inputs from the surround environment sensing system provide situational awareness to the user. The brain activity sensor is notified of any threats in the surrounding environment that that the brain activity sensing system are unaware of. The host computer system (i.e. a Smartphone with CALO and SIRI with voice command and synthesis user notification) notifies the user of any threats in the surrounding environment (i.e. a lion, tiger, or bear), and then may activate protection measures on or off the user. For instance, the full body display worn by the user may be placed in a camouflage color to hide from a threat. Or as indicated in FIG. 15, a servo 181 may activate a repellant dispenser to release shark repellant to scare of the threat (i.e. a shark around a scuba diver). Displays facing outward may display text to other people around the user and in line of sight of the user, and HMD, contacts, and the like facing inward may provide text and other graphic messages to the user in an augmented reality manner.

FIG. 9 is a diagrammatic sectional of the head worn assembly 134 with the integrated brain activity sensor unit 40 with an integrated display and panoramic camera array 156 and 47 as depicted in FIG. 8a-c. The skull cap is shaped around the ears, eyes, nose, and mouth of the user and may be folded up like a stocking cap. The head covering is constructed of molded in latex, or other flexible material to allow the skull cap to fit adjacent and firmly against the users head. Bi-directional arrows in the diagram emanating from the brain activity sensor system indicate that the brain activity sensor emits signals and collects return signals to sense brain activity. Bi-directional arrows 49 in the diagram emanating to and from the integrated display and panoramic camera system indicate illumination outward of the display and inward collection of image signatures by the panoramic camera system.

Figure 10A:
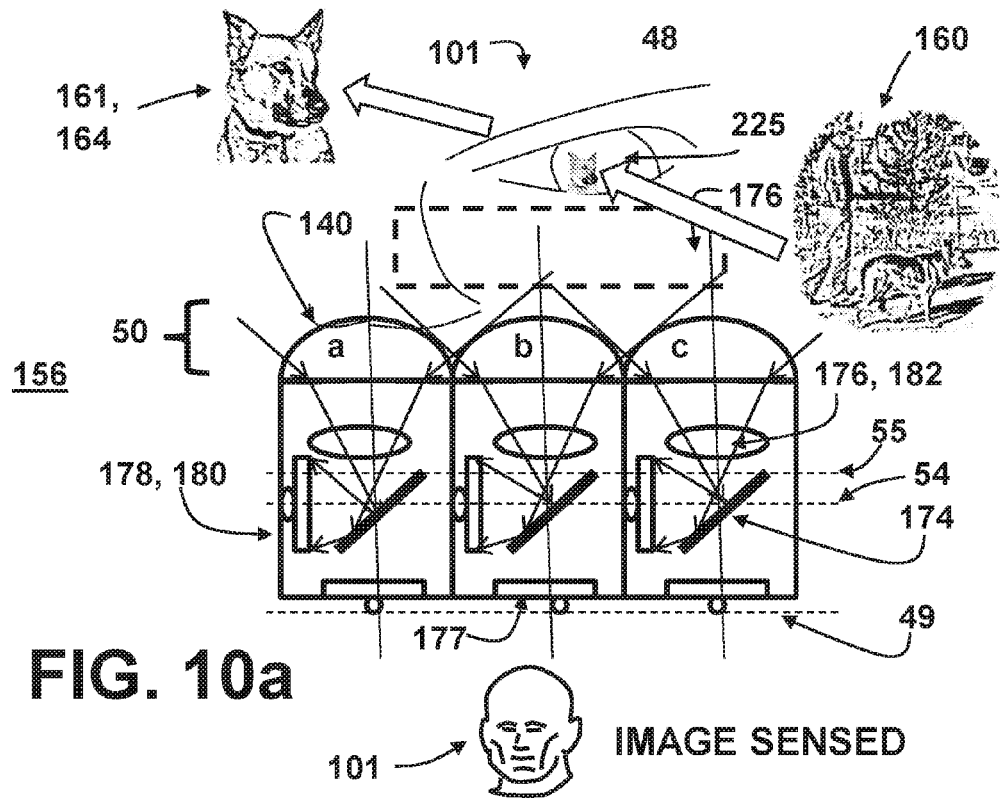
FIG. 10a is a greatly enlarged side sectional view of an integrated camera and display system showing the image capture phase of the imaging system in FIG. 8.
Figure 10B:
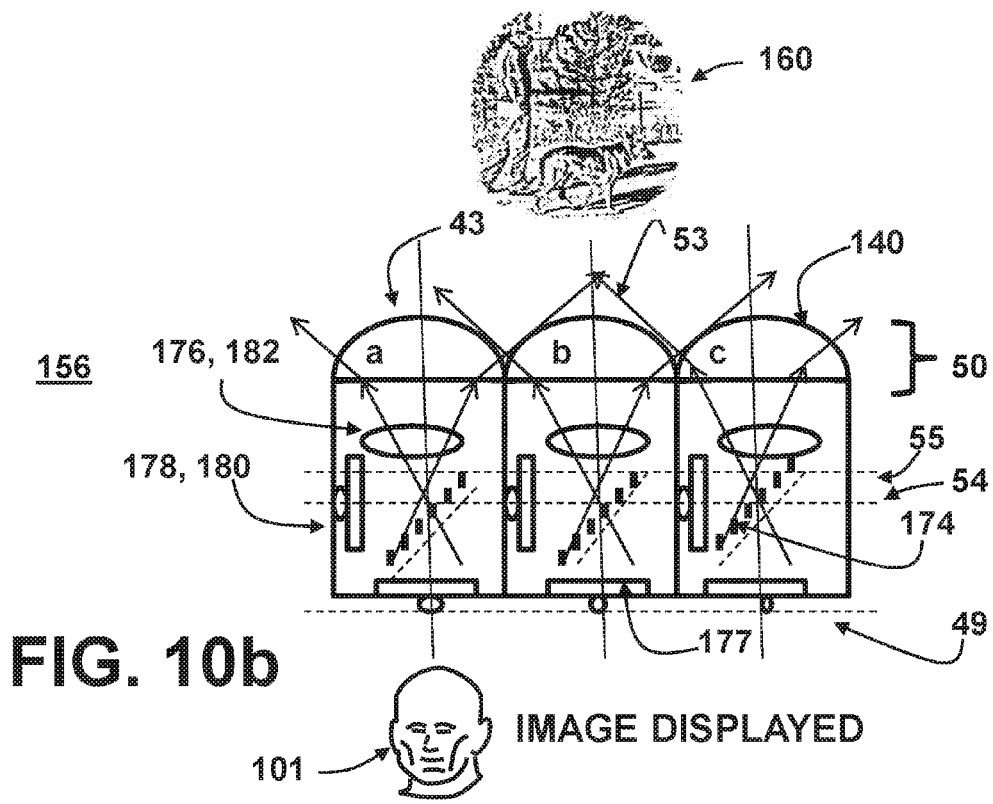
FIG. 10b is a greatly enlarged side sectional view of the embodiment shown in FIG. 10a showing the image display phase of the imaging system FIG. 8.

FIGS. 10a-b is a greatly enlarged side sectional diagram of an integrated flexible display and image sensor system according to the present invention. An addressable outward facing integrated display and panoramic camera array 156 compatible and consistent with the present invention 100. The assembly comprises a digitally driven micro-mirror device used in the present invention for projection of a type that is operated in the assembly 156 to reflect the image to the image sensor 178 or alternatively to open so that an image is displayed. The device 174 functions as a shutter and reflective device in assembly 156. A digitally driven micro-mirror 174 device used in for projection and shuttering of an image of a type that is used in the present invention is of a type manufactured by Texas Instruments as a DLSP. The sensor 178 may consist of a VLSIC 180 on-chip dynamically addressable multi-window ROI imaging sensor. A sensor 178 of a CCD or CMOS type that may be incorporated in the present invention is manufactured by JPL, Nova, Dalsa, and Photonic Vision Systems (PVS) Inc. Imaging chips manufactured by these entities include special circuitry that allows imagery recorded by an individual pixel or group of pixels within the imaging array to be read out. Once read out the image signals may be processed on-chip, sent to a processing chip on the same or an adjacent printed circuit board, or an adjacent computer for processing. Examples of such ROI chips include that found in U.S. Pat. No. 6,084,229 by Pace, and U.S. Pat. No. 5,541,654 by Roberts, U.S. Pat. Pub. 2004/0095492 by Baxter, the entirety of all being incorporated by reference. Each photo diode 177, photo sensor 178, and micro-mirror 174 reflector/shutter are addressable by a computer electronic control unit/CPU that is integrated into the VSLIC 180 or optionally electronic system 104. As shown in FIG. 10a, in operation a micro-mirror shutter 174 is closed to reflect an incoming image transmitted through an objective lens 140 and lens 178 to an image capture sensor. In the example shown in FIG. 10a the eye 225 of the user 101 is being imaged when the array 156 is in the taking mode as the user 101 views the surrounding environment 160. Or alternatively, as shown in FIG. 10b, in operation a micro-mirror shutter 174 is open to reflect an outgoing image on the display 177 through a relay optic 182 and 140 lens system to a viewer 101. In the example in FIG. 10b the face of the user 101 is being displayed to a viewer 295 by the portion of the array 156. It should be noted that the array may be operated so that some portions of the array are displaying and other portions are imaging. And that this operation may done in a user selected and/or automated manner by the user commanding the host computer which is in communication with the array. For instance, one portion of the array may be operated to image the eye of the user, while another portion of the array is imaging the surrounding scene, while still another portion of the array is displaying an image to the user or an onlooker.

As shown in FIG. 10a, in operation a micro-mirror shutter is closed to reflect an incoming image transmitted through an objective lens and 140 lens to an image capture sensor 178. In FIG. 10a light rays 48 from a subject 161 image are reflected through the micro-bead lens array 50, through open micro mirror 174 shutters, and to a photo sensor 178. Sensor 178 reads out the imagery through video drive circuitry 54 to the CPU of VLSIC 180 or host computer 104. Micro-mirror DLSP shutters are open and closed in response to commands by the VLSIC 180 or system 104. Commands to close a mirror, and capture an image are determined by VLSIC 180 or system 104. Or alternatively, as shown in FIG. 10b, in operation a micro-mirror shutter is open to reflect an outgoing image from an LED photo diode 177 through a relay optic 176 and an objective lens 140 of the micro-lens array 50 to a viewer in the surrounding environment. The host computer 104 reads out imagery to the display diode 177 through drive circuitry 49. Micro-mirror 174 DLSP shutters are open and closed in response to commands by the VLSIC or system 104 commands to reflect an image to the eye of a local user 101, onlooker 161, or a remote user 102. Interactive input devices to drive the capture and display assembly 156 include image sensor 178, target tracking, eye tracking, voice to text recognition, sub-vocal, and neural sensing systems integrated with system 100 consistent with the objectives of the present invention. The lens array 50, and for that matter the assembly 156, may be integrated into a rigid or flexible material. A plurality of lenses comprise the lens array 50 in the present view. Still referring to FIG. 10a-b, individuals skilled in the art will realize that various states of display and capture states are possible by addressing the individual photo sensors, display diodes, and micro-mirrors as depicted in FIGS. 8a and 9. Optionally, the assembly 156 may be powered by an onboard battery system, photovoltaic methods, or remote power source located on host computer system 104 in a communicating relationship to the assembly 156. And optionally, at least one microphone 139 is embedded into or along the edges of the array 50 as illustrated in FIGS. 8 and 9.

Figure 10C:
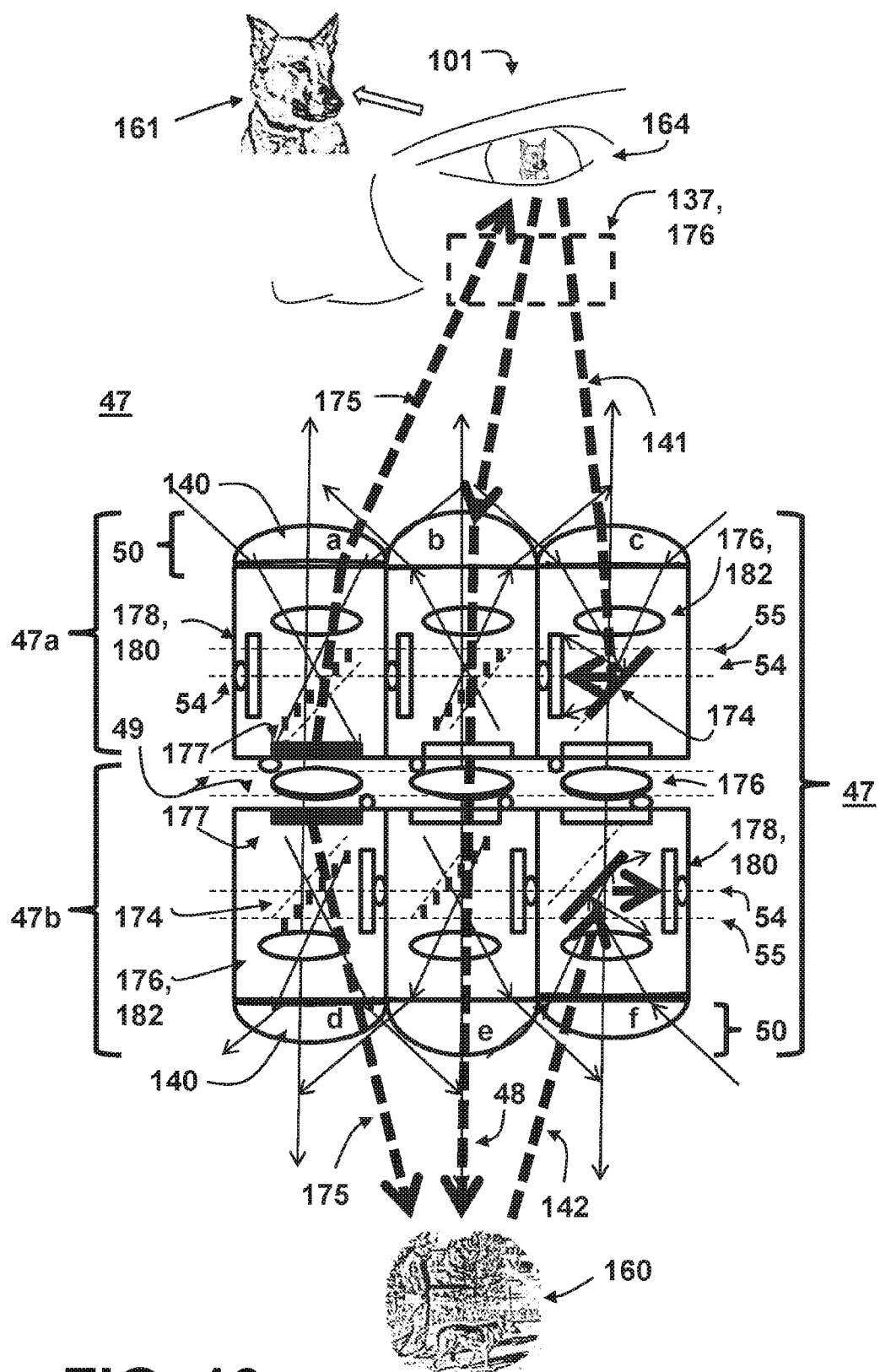
FIG. 10c is a greatly enlarged side sectional diagram of a see-through embodiment of the integrated display and image sensor system according to the present invention in FIG. 8 over the user's eyes.

FIG. 10c is a greatly enlarged side sectional diagram illustrating a user see-through sensor and display system embodiment 47 of the present invention 100. The illustration shows the user's view to the outside world 160 of the integrated display and image sensor system according to the present invention. An image of a dog depicts the user's conscious precept 159. The line of sight from the eye of the user through the LED 179 display to the outside world is shown by a dashed line 179. The integrated display and sensor system may be comprised of a flexible LED or OLED display with integrated image sensors. Micro-mirrors 174 are opened and closed to let light pass or not pass onto the see-through display diode(s) 177 or photo/image sensor(s) 178 for each individual segment of the array. Relay 180 and/or focusing lenses 176 are place in the optical path of the elements of the array to allow the user to look through the array to the outside world as dictated by the host computer as dictated by the function the user is performing. Optionally, the user may wear or relay and/or focusing lenses 176 may be placed outside the sensor system 180 in the line of sight of the outside world and users eyes to accommodate the user's vision. In the present example the user is looking through the left side of the array at a dog in the real world, while a right side of the array depicts the photo sensor on the user side of the array displaying an image to the users eye to augment the outside reality laid over the real world, and the right side of the array on the outward side records an image of the dog in the real world. Obviously, if oriented toward the user's face the photo sensor could record the user's eyes and a video target tracking system can determine the direction and gaze of the user to determine that the subject the user is focused upon is a dog. The image of the subject is then correlated with other sensory data and brain activity data to identify the subject as a dog and build a "Rosetta Stone" of the mind that corresponds and forms relationships to images, text, voice recordings, etc. Finally, an entire surrounding environment may be dynamically or selectively operated by the user control of the smartphone to record the scene surrounding the user. The image sensors of the micro-bead lens array 50 is made of flexible material that may be faced in all directions about the user to record the panoramic scene which is logged by the system 100. The LED diodes 177 are see-through when in a state not required for display. Still referring to FIG. 10c, individuals skilled in the art will realize that various states of display, capture, and see-through are possible by addressing the individual photo sensors, display diodes, and micro-mirrors as depicted in FIG. 8a.

Figure 11:
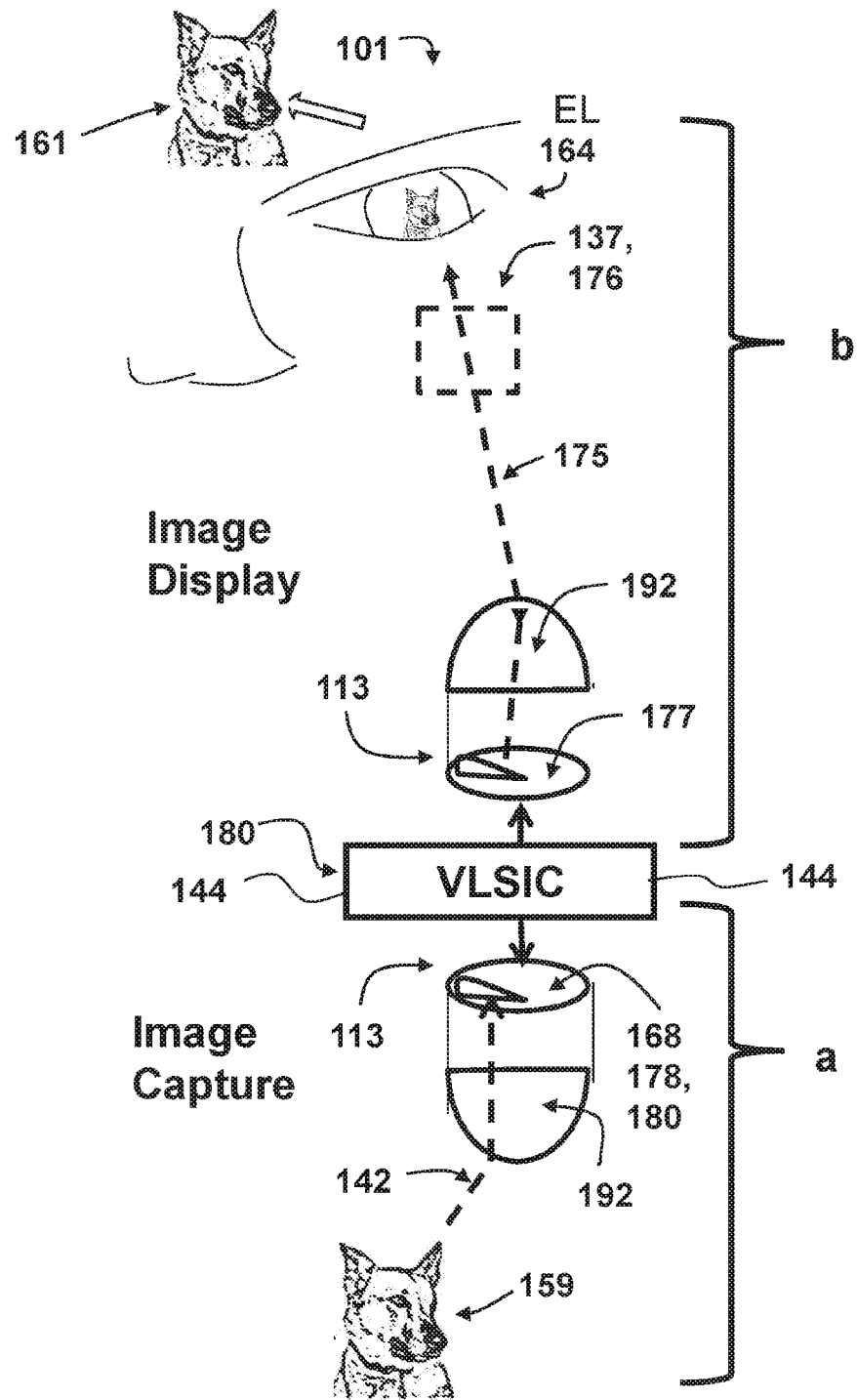
FIG. 11 is a schematic diagram illustrating an auto-stereoscopic image capture and display system and method comprising a micro-bead array with VLSIC processing that is alternatively combined into the optical and display design of the apparatus illustrated in FIGS. 10a-c to provide autostereoscopic image capture, processing, measurement, and display capability in accordance with the present invention.

FIG. 11 is a schematic diagram illustrating an auto-stereoscopic image capture and display technique and system comprising a micro-bead array with VLSIC processing. Sensors and optical elements depicted in FIG. 10a-c may be implemented in FIGS. 11a-c to achieve multi-region of interest on-chip processing for eye-tracking and subject of interest display. And the auto-stereoscopic imaging technique and system illustrated in FIG. 11 may be combined with the optical and display design of the apparatus illustrated in FIGS. 10a-c to provide auto-stereoscopic image capture, processing, and display capability in accordance with the present invention. CMOS multi-ROI tracking and imaging sensors may be incorporated in the design of the integrated capture and display system shown in FIG. 10a-c based on the functionality and design required by the user. If required, image offset processing and calculations are determined on the VLSIC CPU processor or a remote electronic device. U.S. Pat. No. 5,724,758, dated 6 May 1998, by Gulick, Jr. and U.S. Pat. No. 2,833,176, dated 21 Jul. 1953, by A. J. L. Ossoinak entitled disclose a type of optical system that is compatible and incorporated into the present invention shown in FIG. 11 for recording and displaying imagery auto-stereoscopically. The image recorded by each optical bead is project out from the display in the same orientation it was recorded from whence it was recorded. The effect seen by the user is auto-stereoscipic auto-stereoscopic viewing. Preferably, the systems and methods shown in FIGS. 10a-c or FIG. 11 are incorporated into the garbe shown in FIG. 12, 13a-b to achieve auto-stereoscopic display and viewing. Additionally and alternatively U.S. Pat. No. 7,808,540, by Cok, dated 5 Oct. 2010, entitled "Image capture and integrated display apparatus"; U.S. Pat. No. 7,714,923 entitled "Integrated display and capture apparatus; and U.S. Pat. No. 7,697,053 entitled Integrated display having multiple capture devices are of a type that may be incorporated into the present invention.

The present invention 100 may incorporate any one of a number of traditional eye tracking or head tracking systems. Examples of eye tracking and target detection systems of a type enabling and of a type for incorporation into the present invention have already been presented in the above background disclosure of the present invention and are well known to those skilled in the art. Many navigation systems, surveillance systems, weapon systems, and self protection systems provide a user with a video image of a region of interest from which the user may wish to designate an object or feature for tracking. The eye tracking system monitors the position of a user's eye within its socket in order to determine the userVs line of gaze. The present invention incorporates a video tracking system borne by the user to track the eyes of the user. For instance, in FIGS. 1b, 10a, 10c, and 11b provide examples in which a noise camera or a see-through display camera tracks the eyes of the user. And FIG. 8b provides an example where the eyes are tracked by the camera that is part of the opaque or see-through integrated camera and display systems presented in FIG. 10c and/or FIG. 11. From either of these eye-tracking methods data is provided to define the conscious precept of the user. Optionally, it should be noted that autonomous-tracking of hazardous or items of interest in the surrounding environment may be programmed into the host system 100. In this manner a self protection or situational awareness system could be realized.

FIG. 12 is a perspective of an astronaut suite which incorporates the video logging and memory enhancement system and method that comprises the present invention 100. FIG. 13a is a cutaway perspective utilizing the head covering illustrated in FIGS. 10a-c and 11. In FIG. 12 the display is integrated into an astronaut External Vehicle Activity (EVA) system worn by the user 101 of system 100. In both FIGS. 12 and 13a-b the headgear includes a display array 47 and/or 156 that forms the outer surface of the visor of the helmet. The array 47 and/or 157 facing the users face illuminates and recorded the users face. Then the VSLIC processes the image and transmits the image for display on the outward facing side of the array on the exterior of EVA helmet so that an onlooker may view the user of the EVA's face. An advantage of this helmet design is that it offers greater protection to the users head because a thicker protective material may be used between the inward and outward facing arrays of the EVA helmet, yet still allows facial communication with another person in the surrounding environment. The EVA system such as life support system may include propulsion, waste, food, and a breathing apparatus plus integration of the components that comprise the present invention 100. The headgear may be designed with hard or flexible material. And headgear and integrated system 100 may also be designed to accommodate various environmental situations and conditions, such as outer space or under water environments.

FIGS. 13a and 13b illustrate an embodiment of the present invention that comprises a system that acts as a head covering and poncho worn by the user. The headgear is preferably supported by an exoskeletal structure 201. The purpose of the exoskeletal structure is to support the weight of the helmet that holds the life logging and enhancement system. FIG. 13b is a perspective drawing illustrating exterior of the head covering 43. The exterior of the head covering may be flat or of a curved material. FIG. 13a is a cutaway perspective showing the interior of the hemispheric shaped head covering. Typically, the base, or supporting structure of the headgear is made of a rigid composite plastic, such as Kevlar. However, various substrate material may be used in constructing the helmet in order to achieve less or greater strength, protection, and weight. Besides rigid material the headgear may be constructed of a flexible material. Device drivers able to address imaging sensor and displays of irregular shaped coverings, such a circular patterns, are known in the display industry. The curved display screen preferably comprises at least an area in front of the users face in focus graphics and imagery on the display array facing inward. The users face may also be illuminated by the interior facing display. Facial actions may be sensed by monitoring brain activity or by using imaging systems that monitor facial expressions. The array image sensor may be operated to record imagery for logging and transmission. For instance, facial expressions of the user may be displayed on the outward facing surface 43 of the external display array of the visor so that the user may interact and communicate with other beings while the user is still being protected inside the helmet. Besides the user's facial features the helmet may display colors that make it blend in with the surrounding environment. The colors may blend in with the background which make the head covering especially tailored for wild game hunting. And the entire covering of the user, including the clothing and vehicle the user is using may covered with a similar exterior display. Microphones and image sensors embedded in the exterior of the display helmet or elsewhere record the images and audio of the surrounding environment. The recorded images and audio are processed by a computer for input to the user. Audio speakers embedded on or into the headgear adjacent to the left and right ear front and back of the user 101 may provide directional binaural audio to the user. Image sensors may be placed facing outward from and embedded in or on the headgear or elsewhere on the user capture video imagery that is displayed to the user. In the present system a curved display system is embedded on or into the interior side of the helmet. Optical systems that provide integrated image capture and display of a type that may be incorporated into the present invention are those described in U.S. Pat. Nos. 11,621,150, 12,375,805, 4,769,292, 4,928,301, 5,061,569, 5,194,955, 5,639,151, 5,777,665, 6,072,496, 6,454,414, 6,771,303, 6,888,562, 7,042,486, 7,474,799, 7,697,053, 7,714,923, 7,808,540, and 7,808,540. For user respiration, heating, ventilation, and air conditioning a life support system may be included for the user as part of the head covering. These systems are preferably located in a suite or backpack unit worn by the user that circulates air up into the helmet. A movable visor may optionally be constructed in the front of the users face. The visor may be raised and closed manually or mechanically by the user.

Figure 14A:
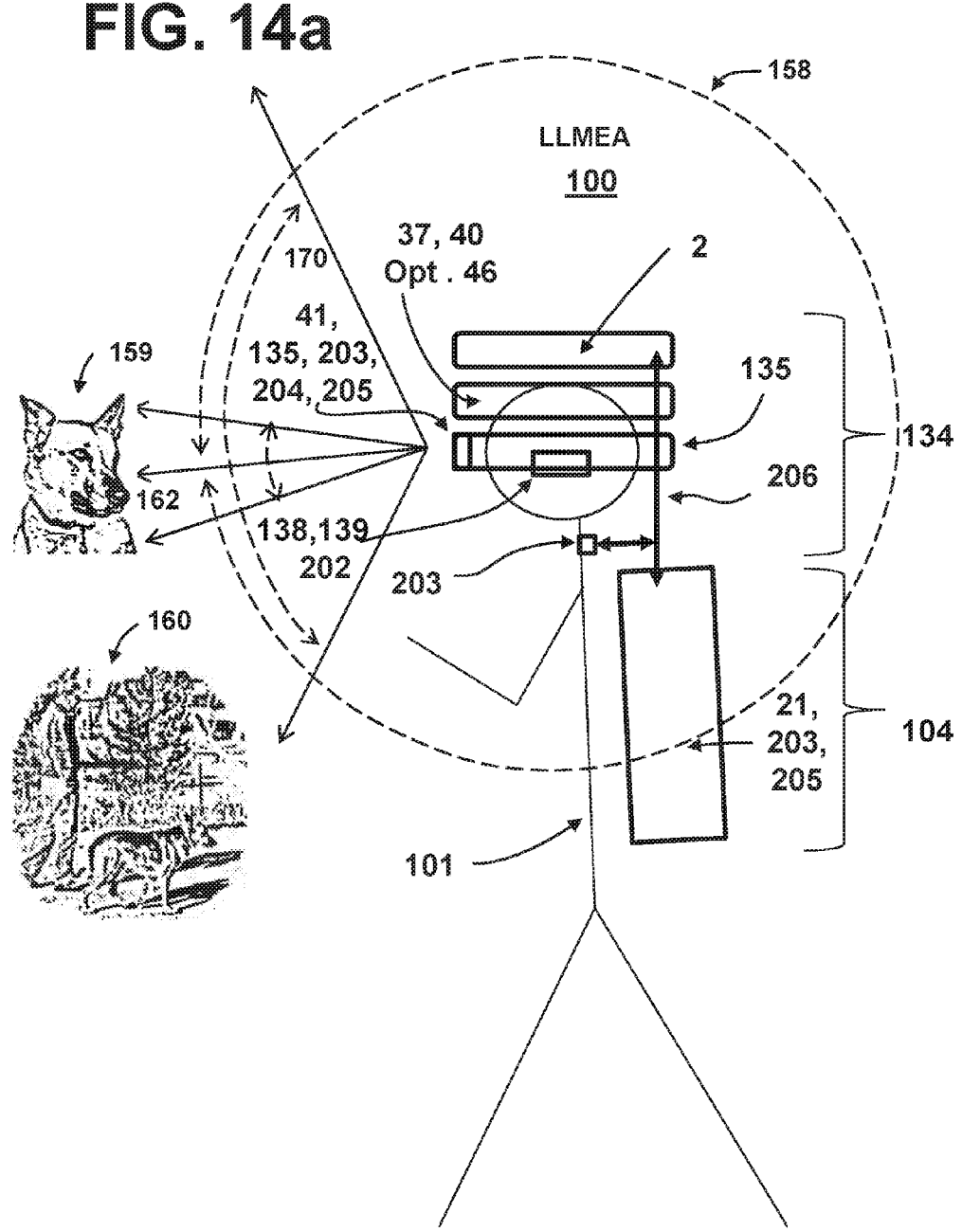
FIG. 14a is a diagrammatic side view of a host computer in a backpack cabled to headgear layout of the user born portable video logging with memory enhancement system in accordance with the present invention.

Now referring to FIGS. 14a-14b that illustrate the components, layout, and interaction of the portable body borne system 100. In our present example, the internal portion of the head worn system includes brain activity sensor unit 40 comprising an Atomic Magnetrometer Resonance (AMR) 37 system with one or more arrays of atomic magnetometer sensors units that detect the relaxation of the magnetic field induced. In the present invention one or more arrays of atomic magnetometers directly detect relaxation of a magnetic field induced with subatomic precession within a target specimen. In this instance the atomic magnetometers sensors units are arranged in a conventional head worn device or helmet wherein the capacity sensors may be used in either a scalar or a vector mode. The AMR may be used to image and provide signal readout on anatomical and non-anatomical structures. In the present example the AMR is used to record the users brain activity as a wearable, portable array, with low power consumption, incorporating wafer-level fabrication, with rapid signal processing, decreased need for development of strong magnetic fields, and lower cost allowing wider availability. Multiplexing of brain activity signals from the AMR system may be utilized to periodically turn on and off sensors to allow temporal dissipation of magnetic field effects. In the case of atomic magnetometers, the speed of multiplexing can be limited by the relaxation time of the gas in the detection chamber. This relaxation time is typically on the order of microseconds, and is a function of gas composition, pressure, and temperature. Therefore, there is sufficient temporal resolution for applications such as functional imaging. Additionally, shielding may or may not be interposed between specific sensors or sensor pairs to direct magnetic field lines away from adjacent sensors. As a benefit, magnetic shielding (e.g., creating a window of measurability) may augment the direction sensitivity of a given sensor or sensors. Finally, signal processing may be utilized to focus in on or to remove known frequencies related to operation of sensors from measurements. It should be understood, in light of this disclosure, that many other configurations using these concepts are possible. Signal processing algorithms can be utilized to allow localization and deconvolution of distal signals within a target by subtracting more proximal signals. Alternatively (or in addition), signal processing algorithms can be used to subtract environmental noise. Deconvolution may have the effect of reconstructing a three-dimensional map of the locations and intensities of the signals generated. Because of the relatively small size of the sensors, a relatively high sensor density within a particular array of sensors may be utilized. For example, the sensors may be placed less than 3 mm from the subject's scalp in a closely packed array. Altering the direction of the pump or probe laser may additionally allow increased information at the sensor for the purpose of source localization. Additionally, magnetic shielding may be interposed between the detecting magnetometer and the user specimen to constrain field detection. Shielding may in some cases comprise a disk of mu-metal or other shielding material; other configurations are possible. In some cases, shielding may be rotated to alter directional sensitivity at a given sensor. Various other dynamic shielding strategies may also be used. Various atomic magnetometers with different detection profiles are available and the specific strategy utilized may depend on magnetometer characteristics.

Stacking and grouping of arrays of sensors or arrays of sensor clusters may be utilized to progressively screen signal from noise and to account for spatially uniform sources of noise, or other externally induced magnetic fields. Since atomic magnetometers or similar sensors develop magnetic fields in the course of normal operation (typically related to the direction of light propagation along the sensor), the direction of light propagation among sensors may be alternated, or a random pattern of orientation may be utilized to minimize large scale field effects. In some cases, additional magnetic shielding (such as mu-metal shielding or active shielding) may be placed around a sensor or a cluster of sensors, for the purpose of further mitigating inter-sensor interference, and/or in order to provide a further screen for environmental noise. Since sensor-related magnetic fields typically have a particular magnitude and occur at a particular frequency, signal analysis techniques may be utilized to remove the influence of inter-sensor interference from the information derived from the sensors. While imaging can be performed using a pre-pulse and detection field, other additional features may be used to improve image quality. For example, Louis-Serge Bouchard, and Vasiliki Demas of Berkeley Labs (Patent Pending, University of California/Berkley, Patent ID pending) recently disclosed utilization of pairs of rotating fields through a sample to overcomes image distortions that typically occur when applying conventional NMR detection and MR imaging methods at low fields.

Still referring to FIGS. 14a-b, the headgear 134 communicates to the host computer 104 via cable or wireless connection. The host computer 104 may be of a conventional portable design which is frequently implemented in a portable laptop, personal digital assistant, smartphone, cell phone, and the like. The host computer includes hardware and software with an operating system (OS) and applications required to achieve the functionality of the disclosed invention. Components are connected by a system bus and electrical bus and include, but are not limited to, input/output jacks, a portable power system with a battery, interactive input devices, video card, hard drive for storing data, random access memory for storing volatile data, central processing systems, cooling fans, telecommunications system, and the like. Additionally, the host computer includes either software (written programs or procedures or rules and associated documentation pertaining to the operation of a computer system and that are stored in read/write memory) and/or firmware (coded instructions that are stored permanently in read-only memory). A computer system and software of a type compatible and incorporated in the present invention is that disclosed in U.S. Patent 2009/0196493, dated 6 Aug. 2009, by Widrow et al entitled Cognitive Method and Auto-Associative Neural Network Based Search Engine for Computer and Network Located Images and Photographs; Cognitive Agent that Learns and Organizes (CALO) Software, and U.S. Patent Application 20070124292 A1, by Kirshenbaum et al, dated 31 May 2007, entitled Autobiographical and Other Data Collection System, and IL is a system compatible with and integrated by reference as art incorporated into the present invention is the Ultra-Vis, Leader, system developed by ARA, subsidiaries MWD, Vertek, and KAD, and other companies to include Lockheed Martin and Microvision Incorporated teaches a stereoscopic video logging system with querying. Thus the host computer includes an operating system (OS), atomic magnetometer system, dynamic image and brain pattern activity translator and comparator, head mounted display system (including head and eye-tracking and optionally global positioning system), voice recognition system (and optionally sub-vocalization system), panoramic video system, optional tele-communications system, and memory enhancement and personal assistant that learns software and firmware. While preferable to use a single computer language for efficiency, it will be obvious to those skilled in the electronics and computer science that a computer program that converts a program from one language to another to link software written in a different language and machines written to run on different software together is common and may be incorporated to enable the current invention if necessary. In this manner the above referenced software may be linked together to form a single system in the present invention. This translation software may be implemented at the assembly language level as a low-level programming language for computers, microprocessors, microcontrollers, and other integrated circuits; and/or as a utility program called an assembler used to translate assembly language statements into the target computer's machine code.

Referring again to FIG. 14a the focus of the AMR system will typically and primarily on determining the CP the user is focusing upon in the environment at a given time. But brain activity signatures outside the CP may be also be sampled and acted upon. Brain activity neural signatures that stimulate place, grid, spatial view cells in the hippocampal area and that provide visual cues, spatial navigation, and episodic memories of particular locations that could be a general mechanism responsible for the storage and recall of information about a particular set of events which occur together at the same time. Components of the AMR portion of the headgear in the FIG. 14a-b may be situated on or in the users head, scalp, skull, and/or brain, respectively. In the present invention the brain is referred to as one the areas of the internal environment which the system 100 monitors.

Integrated with the AMR system in FIGS. 14a-b is a panoramic video system. Still referring to FIGS. 14a-b, the head mounted assembly 134 worn by the user also includes panoramic audio recording system. The headgear comprises audio output systems such as speaker system, such as ear bud audio speakers 138, may provide audio input to the user. Many of the video camera 2 system current video encoding formats carry high fidelity audio. Such audio data can be passed along with a pixel cone data stream PCPDS for a contact lens display, or separated out within a headpiece. Binaural audio can be brought out via a standard mini headphone or earbud jack, but because the system in many cases will know the orientation of the head (and thus the ears) within the environment, a more sophisticated multi-channel audio to binaural audio conversion could be performed first, perhaps using individual HRTF (head related transfer function) data. Feed-back microphones in the ear buds allow for computation of active noise suppression by the audio portion of the headpiece. The speaker can receive input via a radio frequency signal from a remotely located source with audio communication capabilities. Or alternatively may be connected via wires to a unit that provides audio signals for amplification to a small speaker in the ear. Small ear phones and ear buds that fit into and onto the ear are known to those in the art and are commonly used in the hand-free cell phone industry and security industry which are of a type that is compatible with and incorporated into the present invention. U.S. Patent 20080056517 by Algazi et al, dated 6 Mar. 2008, entitled Dynamic Binaural Sound Capture and reproduction in focused or Frontal Application that is of a type compatible with and incorporated in the present invention. Algazi discloses a method of tacking head motion and providing directional audio to a headphone or earbud that may be incorporated in the present invention. Still referring to FIGS. 14a-b, additional sensors that are integrated into the head worn assembly may include a laser rangefinder/target designator and tracking system with image and pattern recognition. A sub-vocalization system may be integrated into the head worn device or may be separately located on or in the user's body and feed into the host computer.

FIG. 15 is a block diagram another embodiment showing the interaction of the components of the present invention 100 consistent with the overall workings and intent of the invention shown in FIGS. 1, 8, and 16-23a-f. In addition to the operation described in FIGS. 25-40a-b, the device apparatus 104 includes a LAN multi-channel transceiver, such as Bluetooth means, for receiving and sending a plurality of wireless data transmissions to input sensors that drive the operation of the present invention. In operation the wireless communication device also includes a brain activity processing module 73 for identifying neural correlates of consciousness from brain signatures; voice recognition module for processing speech commands or sub-vocal signatures; an image processing module for eye tracking, facial imaging, feature tracking, and panoramic imaging, and an optional servo control module 75 for implanted devices and interface module 71 that are centrally commanded by the central processing assembly 56. Transceiver 79 transmits data, typically by radio frequency data link 76, to the wireless on body servo mechanisms, sensors, and displays which have a built in transceiver that form the collective support assembly 82 located on the user 101 and 102. The image processing module 72 operates upon information that is transmitted to the contact lens display(s) 77 located in or on the users eyes. The image processing module 72 operates to define the users visual FOV and subjects of interest for tracking based on information received from the spherical FOV camera with ROI tracking, display, and processing 2. Data derived from the image processing module is sent to the servo control module 75 which is in turn sent to transceiver 79. Transceiver 79 transmits the data to optional servos 181 a-nth. Servos may be used to operate various optional mechanical devices born by the user 101 that are stimulated by commands initiated by information derived from system 100. Conflicts between sensor commands are resolved by the central processing assembly 56 or the interface module 71. The purpose of the computer processing unit (CPU) 56 is to serve as the master control system for all modules of system 104 and 134, and communications with and over network and system 105. The modules of system 104 and 134 communicate with the CPU 56 over a bus. System 104 includes a battery module, which supplies dc power to the computer modules.

Still referring to FIG. 15, the purpose of the interface module 71 is operates to route incoming and outgoing signals between system 104 and on body user mounted mechanisms, sensor, and display systems with transceiver 78 and in assembly 134. It will be known by those skilled in the art that there are many tradeoffs in functionality of the invention that may be realized in firmware or hardware. For instance, the image processing module may be integrated solely in firmware resident to the CPU 56 and not include a separate processing module 72. Additionally, functionality may be divided up either on the wireless communication device 44 or integrated into the wireless on body mechanisms, sensors, and displays with transceivers 58 without departing from the spirit of the present invention. For instance ROI processing can be placed on the sensor 2, image processing module 72, or divided up between both. These are tradeoffs the designer of the system may make in tailoring the system to a particular application.

Figure 16:
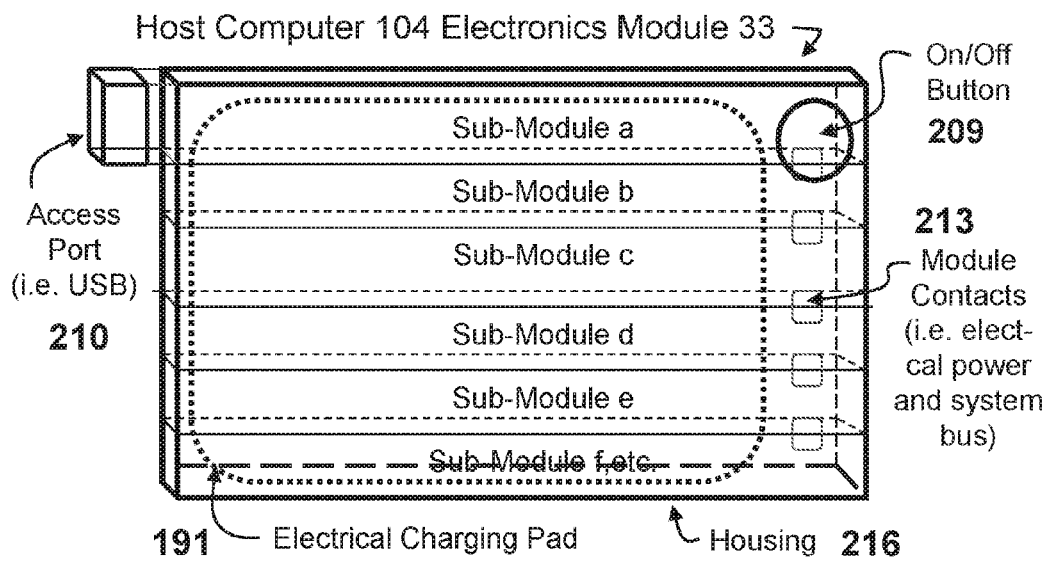
FIG. 16 is a cutaway perspective of an embodiment of the present invention comprising an electronics module comprising a host computer with smartphone-like functionality that is mounted or implanted on the user of the present invention consistent with FIGS. 15 and 17.

FIG. 16 is a cutaway perspective of an embodiment of the present invention wherein a host computer 104 electronics module 33 comprises a device with smartphone-like functionality. The module 33 is constructed for implanting or mounting on the body of the user 101 of the present invention 100 consistent with FIGS. 2a-f, FIGS. 15, 17, and 18. FIG. 16 shows a cutaway sectional diagram of the side of the electronics host computer module. In FIG. 18 the electronics module 33 is located beneath the skin of the user shown in a see-through perspective of the head of the user. The electronics module 33 is inserted as a fistula or cannular implant. As shown in the detailed sectional diagram in FIG. 16, the access port 210 allows exterior entry to the interior each of the electronics module located in the temporal area of the users head. The access port comprises a mini-USB input-output jack that has clips in and out, such that when depressed allows the removal of USB and access to the interior components of the electronics module. When inserted the USB jack facilitates direct wired communication of the host electronics module with other computers or sub-modules a to the nth. Various jacks, like 1394 jacks, known to those skilled in the art may be substituted to accomplish the same functionality. Electrical power is transferred to the to a battery sub-module of the host computer electronics module 33. The electronics sub-modules includes electrical power and communications busses that route information and electrical power to appropriate locations that allow the electronics module and sub-modules to function typical to a conventional computer. When the access port is removed processing, communication, memory, battery sub-modules, and the like, may be accessed within the electronics module housing. The sub-modules are inserted and removed through the access port when the USB input-output jack is removed. The sub-modules are held in place by the walls of the surrounding housing and tension using an arrangement similar to that found in a pez dispenser or ammunition clip. Alternatively or additionally, the sub-modules may be held in place by gravity and the walls of the surrounding housing. The electronics module is surrounded by a housing that separates the electronics in the electronics module from adjacent parts of the body. Preferably the edges of the electronics module are rounded and medicated and placed in a hermetically sealed housing so not to irritate the skin and other body tissue. The electronics module may be constructed of a thin rigid or flexible material and surgically implanted inside the user or mounted outside the head of the user with the flat part tangential to the head of the user. The electronics module material is treated with materials and medications that allow the module to avoid rejection and to be accepted and integrated into the human body. Mounting and implantation procedures of devices comprising the present invention, like the electronics module and other that or placed in and on beings, are known to those in the medical and veterinarian profession, as well as those in the skilled in body art.

Figure 17:
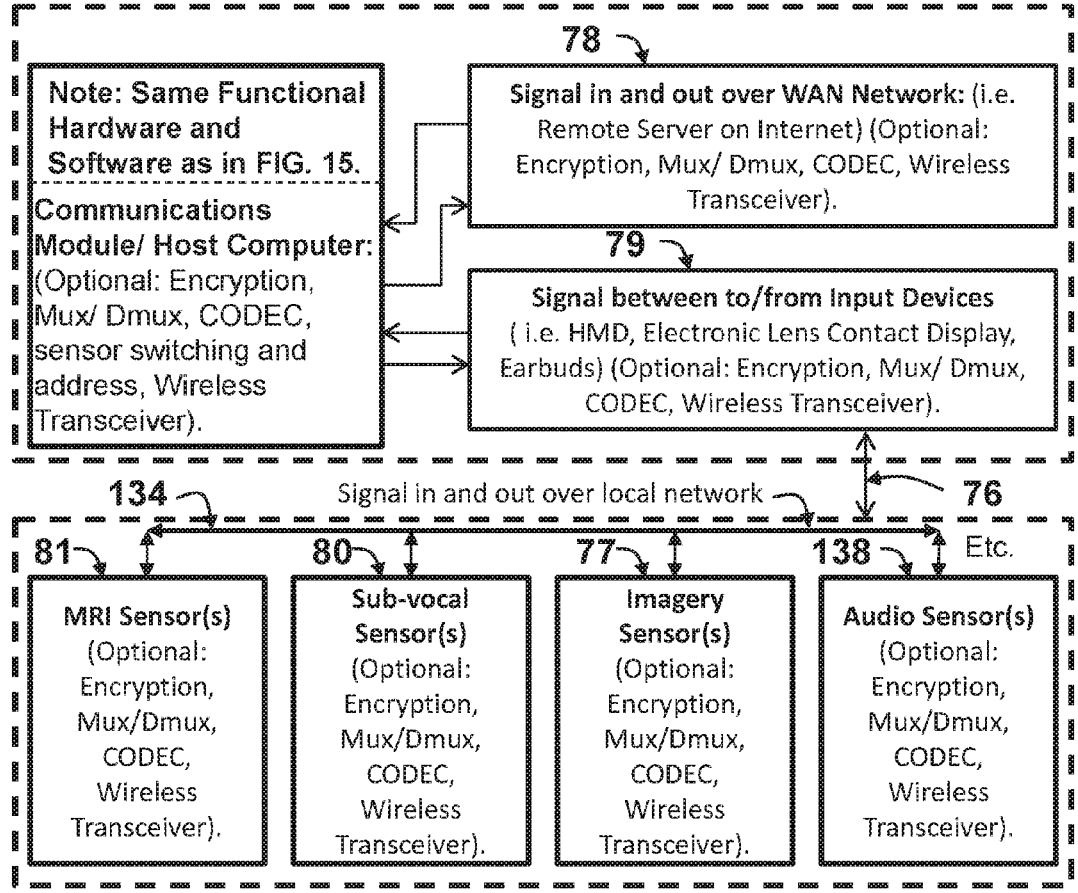
FIG. 17 is a schematic diagram showing the communication linkages and describing the operative functionality between the smartphone host computer, sensor, and audio-visual modules illustrated in FIGS. 15-16 of the present invention.
Figure 18:
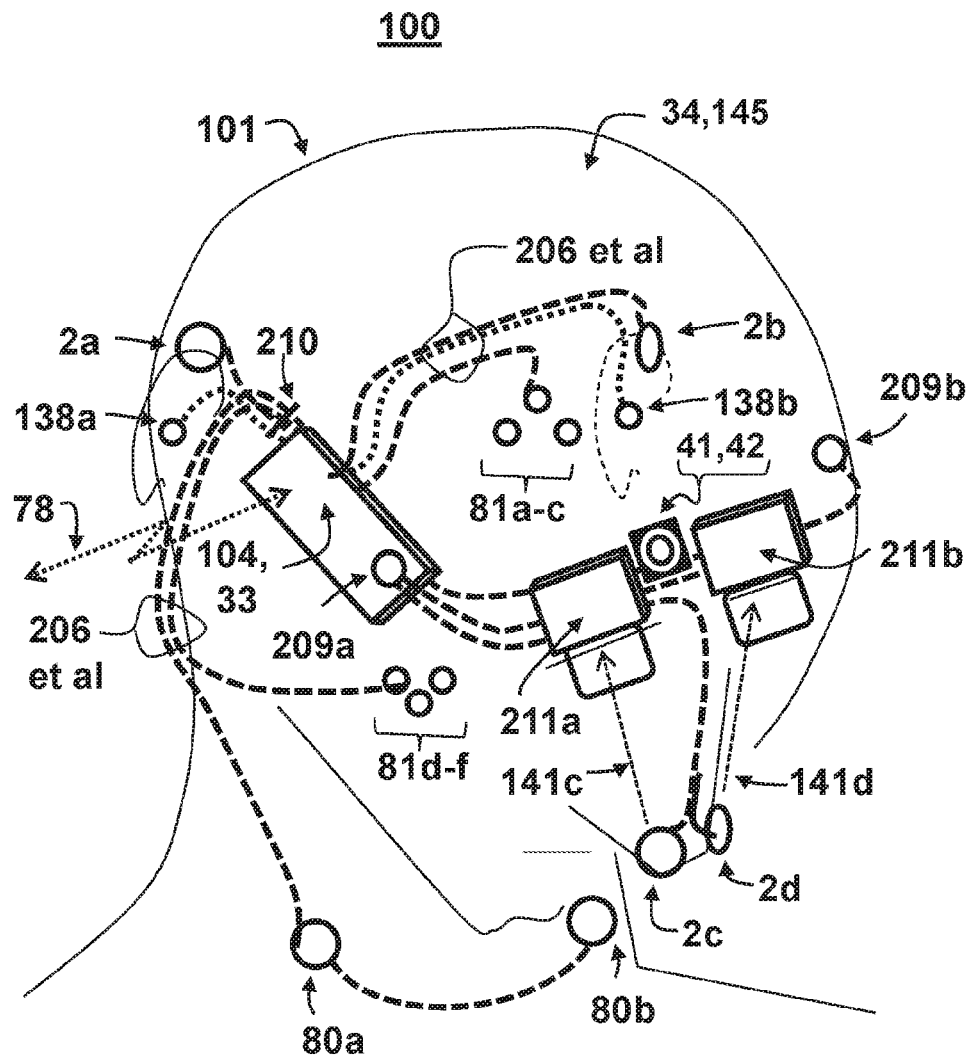
FIG. 18 is a cutaway diagrammatic perspective of the in-line communication interconnections between the smartphone host computer, sensor, and audio-visual modules consistent with FIGS. 15-18 of the present invention.
Figure 19:
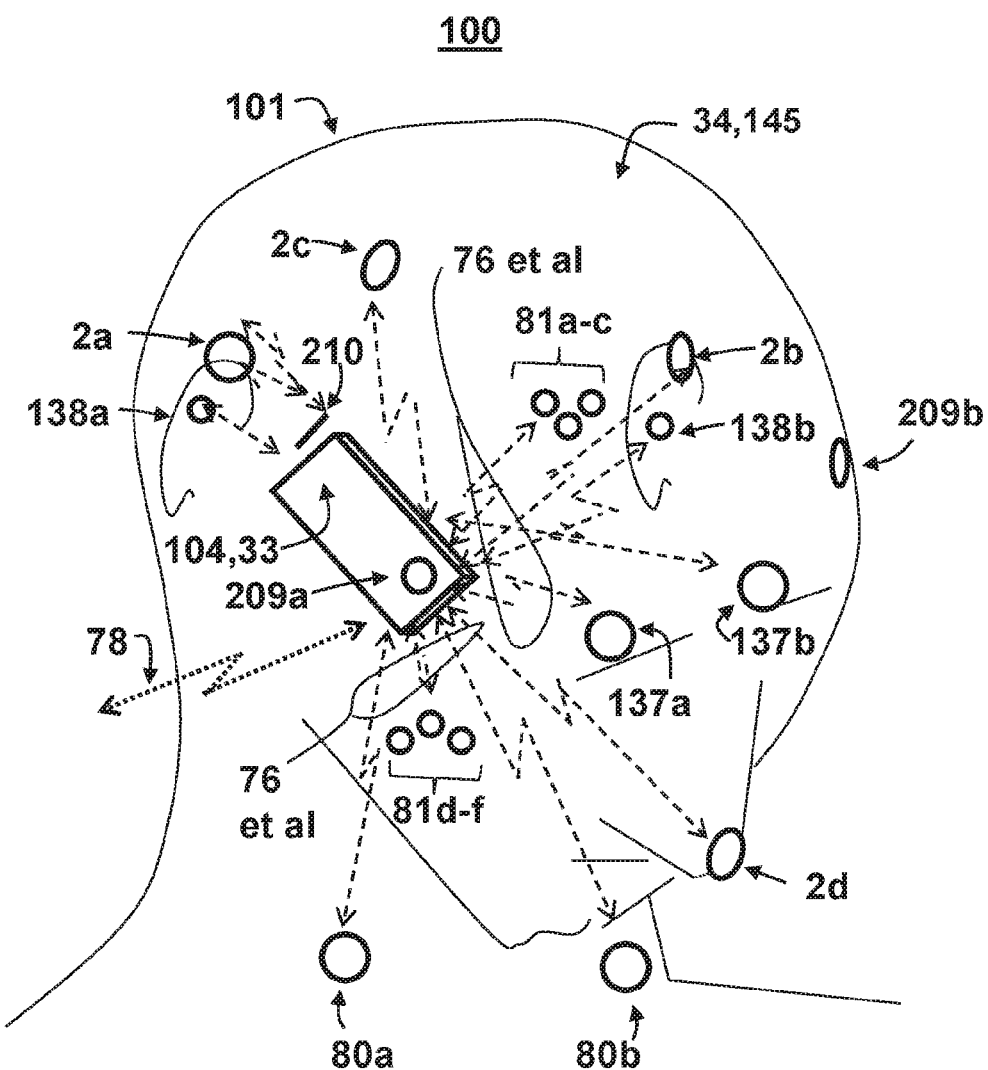
FIG. 19 is a cutaway diagrammatic perspective of the wireless communication interconnections between the smartphone host computer, sensor, and audio-visual modules consistent with FIGS. 15-18 of the present invention.

FIG. 17 is a schematic block diagram of the electronics module 33 which generally illustrates module functionality and connectivity consistent with FIGS. 16, 18, and 19. Preferably, the electronics module 33 has a very small volume, which may be embodied as a Smartphone, or in even smaller embodiment like a VLSIC. The communications module 58 that of the host computer 104 electronics module 33 preferably includes least encryption firmware, Mux/Dmux, CODEC, individual sensor switching and address electronics sensor processing and one wireless transceiver. The electronics module may be designed to have a standalone or non-standalone capability. In its non-standalone mode the electronics module receives signals in and out over WAN Network 78: (i.e. Remote Server on Internet) (Optional: Encryption, Mux/Dmux, CODEC, Wireless Transceiver). In its standalone mode the electronics module receives signals between to/from local Input Devices 79: (i.e. HMD, Electronic Lens Contact Display, Ear buds) (Optional: Encryption, Mux/Dmux, CODEC, Wireless Transceiver). Local input devices the electronic module 33 communicates with the head mounted assembly 134 and includes but is not limited to: MRI Sensor(s) 81 (Optional: Encryption, Mux/Dmux, CODEC, Wireless Transceiver); Sub-vocal Sensor(s) 80 (Optional: Encryption, Mux/Dmux, CODEC, Wireless Transceiver); Imagery Sensor(s) 77 (Optional: Encryption, Mux/Dmux, CODEC, Wireless Transceiver); Audio Sensor(s) 138 (Optional: Encryption, Mux/Dmux, CODEC, Wireless Transceiver). The modules in FIGS. 16 and 17 function as what is popularly referred to as a host computer, portable electronic device, and personal digital assistant, to control the system 100. As FIGS. 18 and 19 illustrate, the smartphone can be designed to be wired or non-wireless.

In FIG. 18 video signals are transmitted from image sensors 2a-d and audio sensors 138a-b mounted on the user over conventional signal transmission means 206 such as wiring or fiber optic image conduits implanted under the sub-dermal skin but above the skull of the user. The video is feed to the electronics module 33 detailed in FIGS. 16 and 17. The video sensors 2a-d have fisheye objective lenses facing outward in a sideways position such that the surrounding environment and users face, including the eyes of the user are imaged. Of special importance is that the objective lenses 2c-d each respectively have a line-of-sight view 141c-d to the pupil on their respective sides of the face. A video imager records the location of the pupils of the user's eyes. The location of the pupils is operated upon by the host computer 104 to calculate the direction of gaze and focus which in turn allows the calculation of the location of the subject the user is viewing. A laser designation system 41 or LADAR system 42 may be mounted on the users head to mark or image targets respectively. Systems 41 and/or 42, like that in FIG. 6b, is also embedded by a sub-dermal punch or surgically implanted into the center of the head of the user and connected to the electronics module. Additionally, sub-vocalization sensors 80a-b are located on the throat of the user. The sensors are connected to the electronics module 33 by shielded wire or fiber optic cable that is implanted beneath the sub-dermal layer of the skin. In the instance with the sub-vocal sensors the implanted line is run from the sensors across the throat, to the neck, and forward the ears to the electronics module 33.

Additionally, AMR sensors 81a-c and 81d-f transmit out readings in the form of electronic signals to the electronics module 33. In the present example the AMR sensors are connected to the electronics module by shielded wire or fiber optic cable that is implanted beneath the sub-dermal layer of the skin. In the present example cluster of three sensors are spaced approximately 10 mm apart facing toward a region of the brain called the supplementary motor area in the upper central part of the brain about 20-30 mm just below the scalp. When neurons in this region become active it indicates the user is indicating or thinking a "yes" response. In the present example a cluster of three other AMR sensors are connected to the electronics module by shielded wire or fiber optic cable that is implanted beneath the sub-dermal layer of the skin in the upper back part of the throat. In the present example three other sensors are spaced approximately 10 mm apart facing toward this region of the brain called the parahippocampal gyrus area in the lower central part of the brain. When neurons in this region in this region and the supplementary motor area become active it indicates the user is indicating or thinking a "no" response. As mentioned earlier, "yes" or "no" responses can be paired with menu's presented to the user on head-mounted display 211a-b (per FIG. 18) or electronic eye mounted display (EMD) 137a-b (see FIG. 1a) to define how a user fills about all manner of subjects and activities. These responses can then be logged and retrieved in response to future queries. Implanted lines run from the sensors to the electronics module. In this manner, correlations between the audio, imagery, sub-vocalization, and brain activity is calculated into neural correlates that translate and correspond to subjects and activities observed externally or thought of in the mind of the user, even without an external stimulus being present.

The contrast to FIG. 18, FIG. 19 illustrates that sensors may transmit readout signals wirelessly to the electronics module 33 described in FIGS. 16 and 17. Wireless transmission will typically be accomplished using radio frequency transmission. The module 33 includes a transceiver as does the sensors or sensor systems 77, 80, 81, and 138. Electronic multiplexing and demultiplexing (MUX/DMUX) systems and compression and decompression (CODEX) systems may be incorporated in module 33 and the sensor systems to assist with transfer, parsing, and routing the signals electronically as described in FIG. 15-17. In FIG. 18 the module 33 and sensors each include a transceiver for sending and receiving data to and from the electronics module. In this instance the module and sensors each include a transceiver for sending and receiving data to and from the electronics module. On/Off buttons 209a-b which are pressure sensitive are implanted below the skin and connected to the electronics module. The On/Off buttons are operated by the user to log in and off of the system 100 as described in FIGS. 20a-b and 21a-c. In the present embodiment an electronics module 33 also comprises a small portable host computer 104 with many features similar to a small smartphone 151 that is constructed to be implanted into the user 101. The wireless embodiment of the system includes a digital switching system that allows specific components to be addressed. Specifically, sensors are addressed wirelessly using the micro-circuit sensor switching system. Electrical power for the electronics module is provided by a battery. The battery is charged by a mini-USB or other type of conventional charging method. Alternatively, the electronics module and sensors are implanted beneath the skin 157 with no cannular of fistular opening to the outside of the body. In such an instance the electronics module and sensors batteries are charged by an electrical induction charger. The electronics module includes a charging pad located on the outer skin side of the module. Sensors also include electronics to receive electrical power for charging. An induction charging pad 191 may be worn continuously on the users head, neck, or body to facilitate recharging of the electronics module and sensors. To reduce the weight on the users head a backpack or belt is incorporated to hold batteries that provide current to an induction pad head charging skull cap arrangement that holds the charging pads that surround the users head. The battery may be embedded in a bed pillow so that the user can charge the battery at night while sleeping. The module battery provides electrical power to the electronics of the electronics of the electrical module and the sensors. Sensors receive electrical power and data over shielded and clad wires or fiber optic conduits. All surgical implants are sterilized and implanted according to known medical methods and techniques to insure proper healing of the incision associated with the invasive implant surgery.

The present invention is preferably equipped with user interactive On/Off and security authentication means. For example, in FIGS. 20*a-b*, the location of an On/Off module 209 located on the head of the user 101. To activate and deactivate the system the user presses at least one finger on the skin where the module 209 is located to activate the under-the-skin touch sensor shown in FIGS. 21*a-c*. FIG. 20*a* is a perspective diagram illustrating the one-hand On/Off activation/deactivate shown in FIGS. 18-19 and FIGS. 21*a-c*. FIG. 20*b* is a perspective diagram illustrating a two-handed activation/deactivate shown in FIGS. 18-19 and FIGS. 21*a-c*. FIG. 21*a* is a perspective diagram illustrating the user implantable under-the-skin activation/deactivate and authentication sensor modules 209*a-b* in FIGS. 20*a-b*. FIG. 21*b* is a plan diagram illustrating a user implantable under-the-skin activation/deactivate and authentication sensor modules 209*a-b* in FIGS. 20*a-b*. FIG. 21*c* is a side sectional diagram illustrating a user implantable under-the-skin activation/deactivate and authentication sensor modules 209*a-b* in FIGS. 20*a-b*. An example of how the system 100 "On/Off" function operates is that the user 101 simultaneously presses sensor module 209*a-b* button 213*a-b* simultaneously and thinks of a authentication code or password. The password is registered by the sub-vocalization system and brain activity sensor system of system 100. The housing 16 is in a surgically implanted flexible latex hermetically sealed and medicated housing that allows module 33 buttons to be depressed. Button 213 is spring loaded and may be depressed by the user to complete a circuit that sends an On/Off electrical signal to the host computer 104 electronics module 33 to activate or deactivate the system 100. The activation module may be constructed and implanted similar to the electronics module 33 described in FIG. 16. The signature is checked in the permissions, user ID, or password database. If the proper identification procedure is followed and the proper information provided to the host computer the video logging system is turned on. The same procedure may be repeated by the operator to turn the video logging and enhancement system off. Using this method helps insure authorized use of the system because the procedure requires a unique action and identification code that only the user knows and must consciously implement.

It also decreases the chance of accidental turn on or off of the system. Still alternatively, various other biometric techniques and sensors can be used to activate the system 100. For instance, a heat sensor that senses the user's fingers over the skin could be substituted for the current arrangement shown to command the host computer 104 electronic module 33 on and off.

Figure 22A:
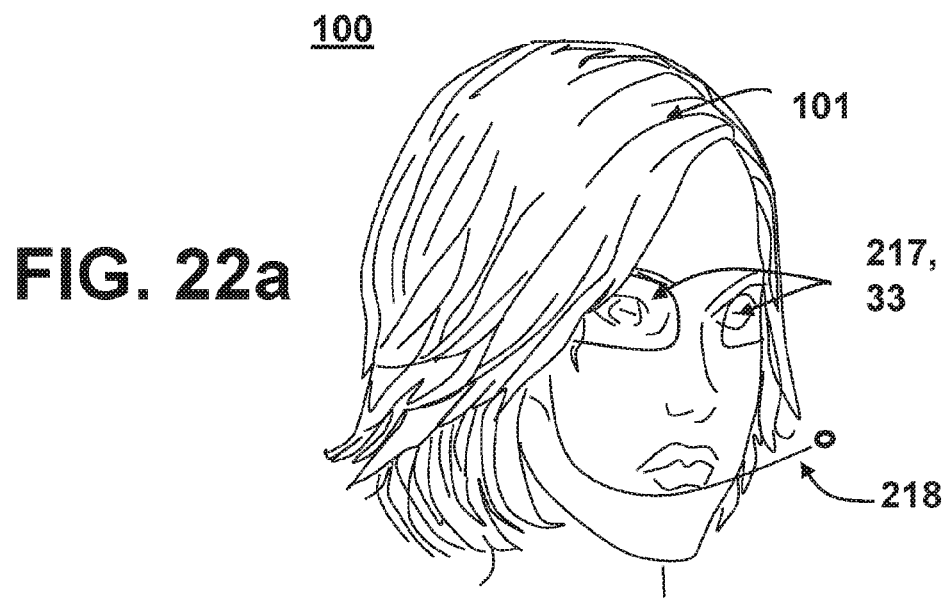
FIG. 22*a* is an exterior perspective view of a person wearing a head gear which includes a smartphone module with presentation, processing, and input means that connects to implanted brain activity sensor system in accordance with the present invention and consistent with FIG. 18*a;*
Figure 22B:
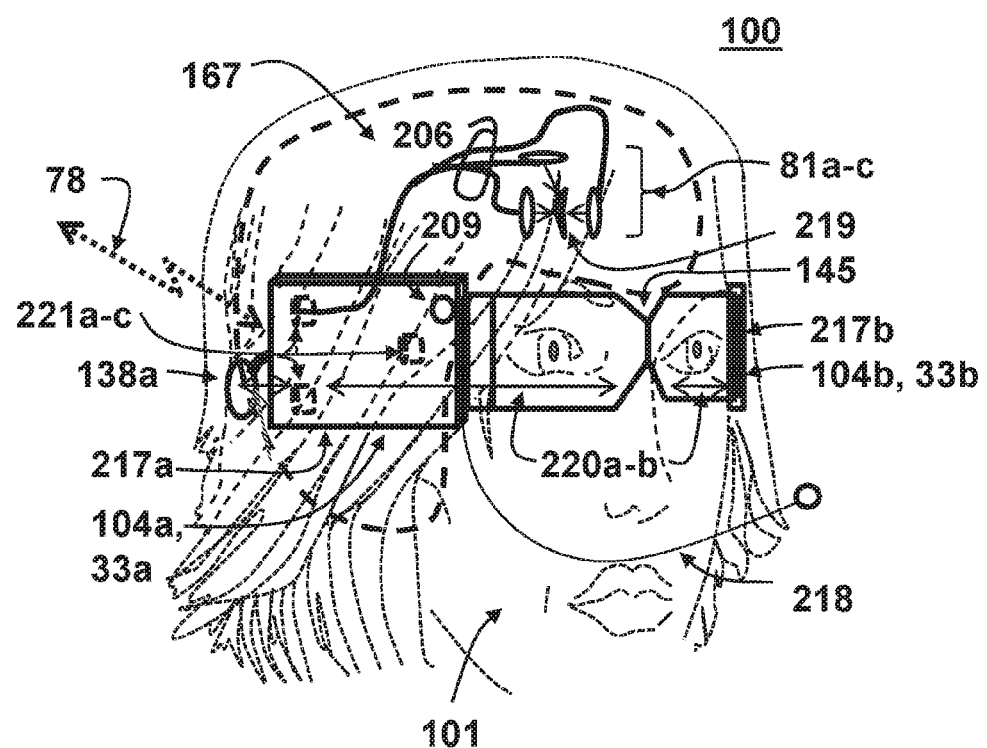
FIG. 22*b* is an cutaway exterior perspective diagram of a person wearing a head gear which includes a smartphone module with presentation, processing, and input means that connects to implanted brain activity sensor system in accordance with the present invention and consistent with FIG. 18*a;*

FIG. 22*a*-23*f* are diagrams of two embodiments of a near eye display assembly 217 consistent with the present invention. FIG. 22*a* is an exterior view of person wearing the near eye display assembly 217 on the temporal sides of the head of the user 101. The assembly may comprise one or two assemblies 217*a-b*. As demonstrated in the current example, the display 217*a-b* may also include other or all host computers 104*a-b* electronics modules 33*a-b* functions or just selected functions, like the display assembly 217 function; such that other functions are run on an adjacent system in communication with a host computer 104 carried elsewhere on body of the user or located elsewhere as part of the telecom network and system 105. FIG. 22*b* is a see-through perspective illustrating the electronics assembly 217 located on the head of the user. The assembly 217 is concealed by the user's natural skin and hair, or what could be a hairpiece and/or skull cap. Alternatively the module may be implanted in a cannular fashion. In this example, one end of each display assembly 217*a-b* may comprise a near eye display 220*a-b*. The near-eye displays 220*a-b* in the present example may comprise either a holographic display or LED/OLED display. The displays 220*a-b* may be retracted and/or stored in the display assembly housing. The displays may extend outward from one end of the display assembly in front of the eyes of the user. On the other end of each display assembly an earbud 138*a-b* is extended out from the display assembly to the ears of the user. The display assembly may be supported in any of the methods described in FIG. 2*a-f* or by the skull cap previously discussed in this specification. In the present example the display assembly is connected by display assembly support brackets 221*a-c*. In the present example the assembly 217*a* includes an electronics module 33*a* that connects to brain activity sensors 81*a-c* that surrounds a specific neural area 145 that provides feedback to the electronics module. The electronic module communicates with and powers the implanted brain activity sensor(s) 81*a-c* via communication lines 206 et al made of clad wire, fiber optics, or wirelessly 76 et al. Additionally, in the present example assembly 217*a* includes an electronics module 33*a* that connects to a non-interference field-of-view support assembly 218 for facial and panoramic imaging that communicates with the electronics module.

Ear buds and displays worn by the user provide feedback to the user from various internal and external sensor systems worn consistent with the present invention 100. The electronics module includes a transceiver that connects wirelessly to a WIFI network that may include a remote host computer server system 105. Power for the display assembly is provided by battery. The battery may be located in the display assembly or from a wire running from the module to the battery carried by the user, such as a belt worn battery pack.

Figure 23A:
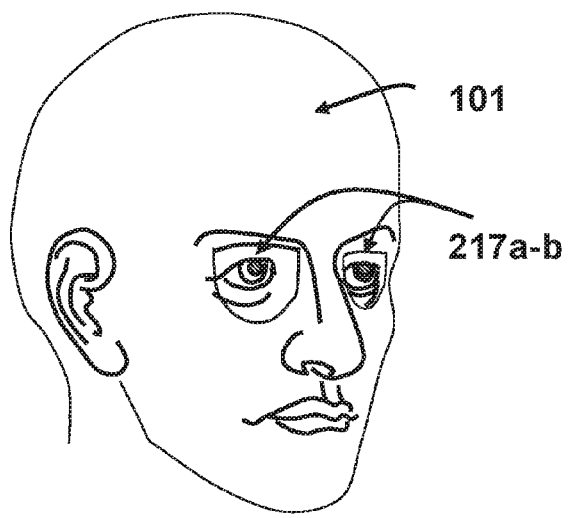
FIG. 23*a* is an exterior view of a user wearing the implantable retractable electronics display module in accordance with the present invention and consistent with FIGS. 18*a* and 23*b-f;*
Figures 23B, 23C:
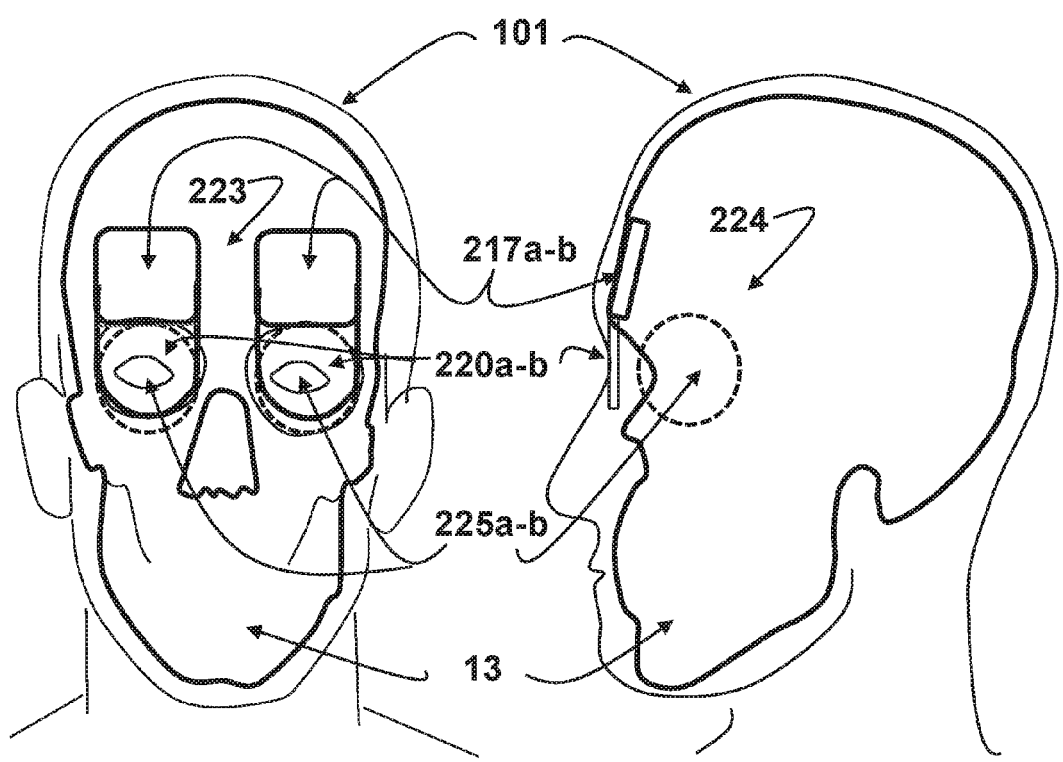
FIG. 23*b* is front sectional diagram showing the location of the implantable retractable electronics display module in the head of the user consistent with FIGS. 18*a* and 23*a;*
FIG. 23*c* is side sectional diagram showing the location of the implantable retractable electronics display module in the users head. In this example a portion of the skull is removed and the device is implanted consistent with FIGS. 18*a* and 23*a;*

FIG. 23*a-f* illustrates an alternative embodiment of an implantable extendable and retractable electronics display assembly 217 that may be used in concert with the present invention. FIG. 23*a* is an exterior perspective view of a user 101 wearing a left and right display assembly 217*a-b*. FIG. 23*b* is a frontal sectional view showing the location of the display assembly 217*a-b* implanted in the head of the user. FIG. 23*c* is side sectional view showing the location of the display assembly 217a-b implanted in the head of the user. In the present example, each near eye display 220a-b of each display assembly 217a-b is shown in the extended position in front of each of the eyes 225a-b of the user 101. Also in this example a portion of the frontal bone 223 of the skull 13 is removed and the assembly is implanted. The implant may be implanted in the forehead or temporal area of the head. Surgical procedures for implanting such a device are known to those in the medical profession. The assembly is anchored to the skull just in a method similar to that commonly used in skull replacements. Plastic or metal material is typically used. Alternatively, the module may be implanted as a sub-dermal implant just beneath the skin. FIG. 23d is a front sectional view showing the components that comprise the implantable display assembly 217. FIG. 23e is a front sectional view showing the components that comprise the implantable display assembly 217. The display assembly may include an automated or manual adjusted swivel 231 for positioning the display 220 in front of the eye of the user. The display assembly may include firmware 207, circuitry 26, and be connected by electrical cable 206 or wirelessly via transceiver to the host computer 104 and/or electronics module 33. The module may be controlled by brain activity, voice, manually, or common interactive device control methods. The cannular opening 227 from which the display retracts is a small slit in the skin. The opening 227 in the implantable cannular housing 16 of the display assembly 217 may include a sleeve or boot for the surrounding skin 157 to grow into. Special medical care and techniques are known to the medical profession and body art profession are practiced in order to get proper skin growth around but not covering the opening in order to avoid infection. FIG. 23f is a diagrammatic see-through axonometric schematic with arrows 222 indicating the motion of the extendable and retractable near eye holographic display. Stepper motors 226 are used to extend and retract the near eye holographic display. In FIGS. 22a-b and FIGS. 23a-f the near eye display 220 is shown in the un-retracted state in which the user is employing the display for viewing. The display is see-through and allows for overlaid graphics and imagery over the real world scene in an augmented reality (AR) manner. Augmented and telepresence overlays may be displayed on the display in accordance with the system 100 that comprises the present invention. A holographic near eye display system is shown in the present example. However alternatively, a near eye display that incorporates e-paper, LED, or OLED displays like those shown in FIG. 8a-8c, FIG. 10c, FIG. 18, or other via other HMD arrangement may be incorporated in the present invention. Still alternatively, an EMD near eye display, as shown in FIG. 1 and FIG. 19 may also be incorporated for AR applications. It is anticipated that eye tracking and camera systems known to those skilled in the art will also be incorporated with the near eye displays without departing from the scope of the present invention 100.

Figure 24A:
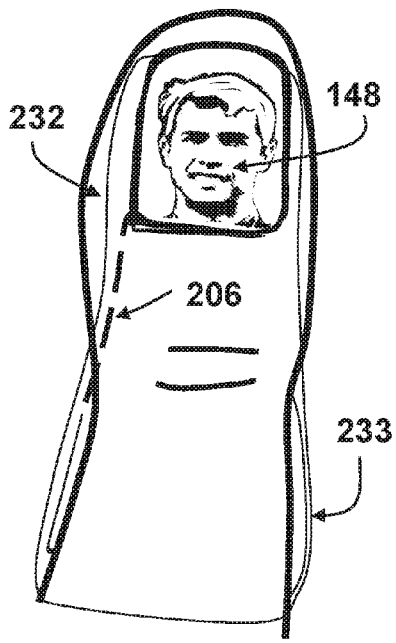
FIG. 24*a* is a perspective drawing of the users thumb unit with an integrated camera and display system in accordance with the present invention.
Figure 24B:
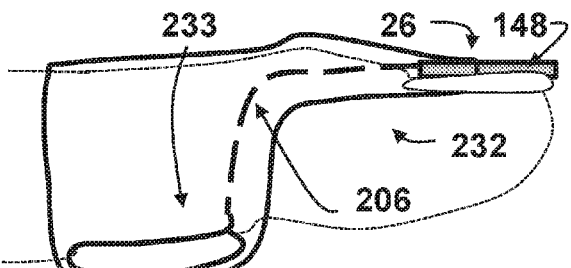
FIG. 24*b* is a side sectional diagram of an inductive electrical charging arrangement that includes a boot that slips securely onto the thumb the unit like that shown in FIG. 24*a;*
Figure 24C:
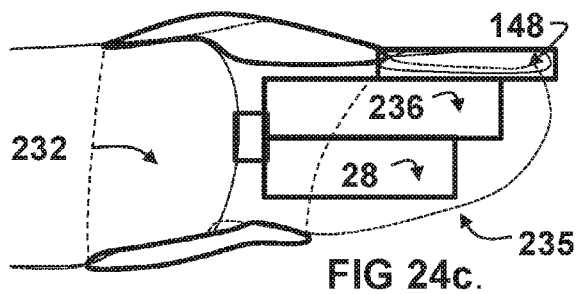
FIG. 24*c* is a sectional diagram of a prosthetic embodiment of the integrated camera and display integrated with a prosthetic thumb worn by the user like that shown in FIG. 24*a;*
Figure 24D:
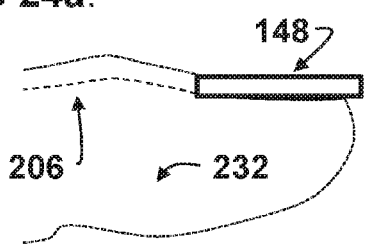
FIG. 24*d* is a sectional diagram of a thumb mounted integrated camera and display system with electrical power and data transmitted over a small cable implanted under the skin of the user like that shown in FIG. 24*a;*

FIGS. 24a-f are illustrations of a user 101 mountable integrated camera and display assembly 148 consistent with the present invention 100. FIG. 24a is a perspective drawing the mountable display system 148 affixed to the thumb 232 of the user. FIGS. 24b-24d show different embodiments of the thumb mounted assembly 148. The assembly 148 preferably comprises e-paper, LED, or OLED displays like those illustrated in FIGS. 10a-c and/or 11. However, it will be apparent to those skilled in the art that other display technologies may be integrated without departing from the scope of the present invention. And it will be apparent to those skilled in the art that optionally the display and camera may be separated and only one or the other may be housed on the assembly 148 and the other worn elsewhere as a separate assembly. In both FIGS. 24a-f the assembly 148 comprises an integrated camera and display array 47 or 156 that forms the outer surface of the body or body covering as depicted in FIGS. 10a-c and/or 11.

In FIG. 24b the assembly 148 includes a display boot 233 that slips securely onto the thumb. The boot 233 includes an integrated display and camera array 156 that fits over the finger nail and communications lines and power cables 206 that runs from the array that transverses through the boot and is in communicating relationship to an inductive electrical receiver pad 191. The electrical charger receives electrical current via induction system integrated into the steering wheel of an automobile on which the hands of the user are positioned as depicted in perspective illustration shown in FIG. 24f. FIG. 24c is a sectional diagram of another embodiment of the user 101 mountable integrated camera and display assembly 148 in which the assembly is part of a prosthetic thumb 235 worn by the user. FIGS. 24b and 24c include an integrated transceiver for receiving and sending imagery and receiving control signals and electrical arrangement for receiving electrical power. In FIG. 24c assembly 148 comprises a prosthetic electronics unit 236 that connects to the nerve endings of the end of the thumb and controls thumb movement and a camera and display with transceiver and battery electronics unit 28 that controls camera an display operations.

Figure 24E:
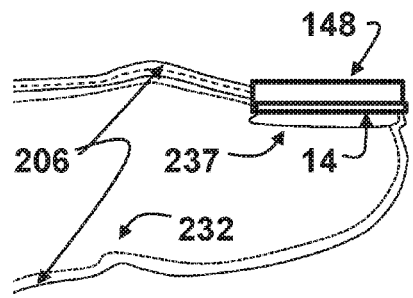
FIG. 24*e* is a sectional diagram of a very small electrical power cable and/or data cable run between materials that comprises a sleeve the thumb fits into that transmits power and/or data to the thumb mounted integrated camera and display system worn by a user like that shown in FIG. 24*a;*
Figure 24F:
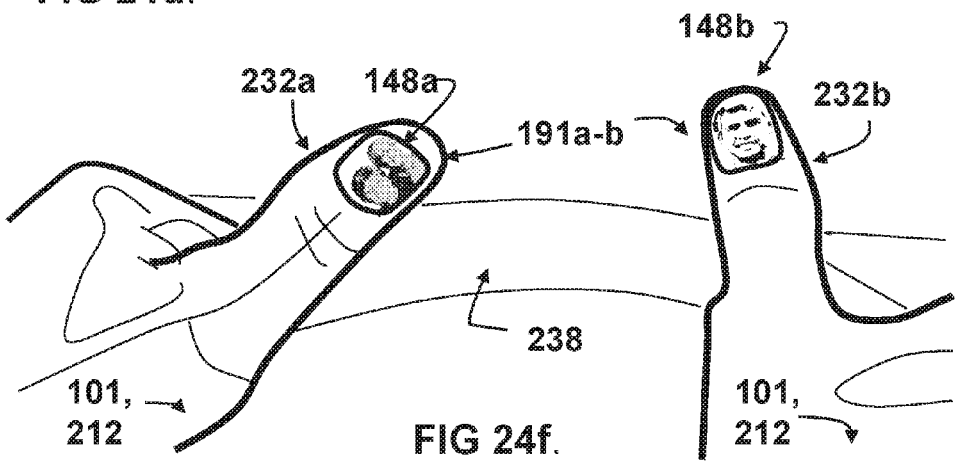
FIG. 24*f* is a perspective drawing of the hands of a user wearing the integrated thumb display with camera with induction charging receiver shown in FIGS. 24*a-b* with an induction electrical charging transmission system integrated into the steering wheel of an automobile on which the thumbs of the user are positioned in the field-of-view of the users eyes in order to facilitate interactive video teleconferencing.

FIG. 24e is a diagram of a user with very small electrical power and/or data cable 206 run between material that comprises a sleeve 234 the thumb 232 fits into. The power and/or data cable run from the assembly 148 to the host computer 104 and/or electronic module 33. Assembly 148 may be integrated into the sleeve or adhered to and stuck onto the top of the fingernail of the user. The material that comprises the sleeve 234 may be a tattoo sleeve or a glove that slips on and off by the user. Alternatively the sleeve may have a sticky side, like a Band-Aid with an adhesive side, that adheres to the body of the user on one side. In such an instance a flesh colored material that blends with the skin color of the user may be incorporated for cosmetic effects to hide and insulate the very small insulated data and power cables sandwiched between the outward facing and inward facing material of the body of the user. Finally, FIG. 24d illustrates and embodiment in which the thumb 232 mounted integrated camera and display assembly 148 receives and sends electrical power and data over a small cable 206 implanted under the skin of the user. The data cable may comprise a fiber optic data cable. Obviously, various arrangements and configurations of components in FIGS. 24a-f may be utilized without departing from the spirit of the invention. In FIGS. 24a-f the thumb mounted assembly 148 may either communicate with the host computer 104 and/or electronic module 33 to contribute to the operation of the present invention 100.

Sheets 23-35 (FIGS. 25-37c) describe the processes and methods enabling the invention. The sub-systems, assemblies, and components previously discussed in the specification are applied in as processes and methods that make possible the applications of the present invention 100.

FIG. 25 is a schematic diagram that illustrates the overall scope and method of interaction of the present invention. FIG. 1 and FIG. 25 work together to illustrate how the present invention operates as a user portable integrated life logging and memory enhancement system (LLEMA) 100. The system 100 comprises a portable host computer system 104 with a user interactive command and control module 107, an internal and external sensing, recording, monitoring, and data logging module 109, and correlation module 111. Modules 109 and 111 include hardware and firmware for simultaneously sensing, storing, and correlating signatures representing the local surrounding environment 160 about the user 101 with signatures representing the internal physiological environment 1 of the user 101. The surrounding environment may include the periphery of the user, such as the face of the user. The primary internal signatures logged represent activity of the central nervous system 12, specifically the neurological activity 112 of the brain 167 of the user 101. The same user interactive command and control module 107 also operates to command and control querying for the user 101 based on data and information sensed and logged by the system 104.

System 100 may include an optional telecommunications system and network 105 and optional remote computer server system 106. The telecommunication system and remote server may be located in the local surrounding environment 160, another part of the world, or anywhere in the universe that has a compatible communication system that has transmission between the portable computer 104 and remote server system 106. The server system may comprise a single or group of networked servers. The remote computer server 106 system will typically comprise a stationary computer server used to store and process offloaded data from the portable computer 104. Offloading functions from portable computer 104 to computer 106 facilitates reduction in size and volume of the portable computer 104.

FIG. 26a describes the process 200 for implementing the system 100 and 104 according to the present invention. Step 1 239 is to: a) Input signatures (i) from physiological and biometric sensors representing a person's internal state of being at a given time and place; and (ii) simultaneously input signatures representing the external environment presented to the person (i.e. via audio-visual sensors); and b) operate a computer to correlate the internal and external signatures into a historical relational database. Step 2 240 is to: a) Store the historical relational database into the memory of a computer; b) Query the historical relational database to find correlations between current internal and external signatures; and c) Read in historical information recorded in the host computers memory into the being using i) sensory input and/or ii) implanted devices to enhance the being's thoughts and memory. Step 1 enables Step 2 by providing internal and external historical data and information that is then logged, processed, recalled, related, and correlated by computer 104, and optionally and additionally computer 106. Arrow 241 indicates that once Step 1 is accomplished then Step 2 may commence. Arrows 242a and 242b illustrate that Step 1 and Step 2 are related independent continuously looped processes that may run on computer 104 and/or 106 once a baseline of internal and external signatures is established.

Figure 26B:
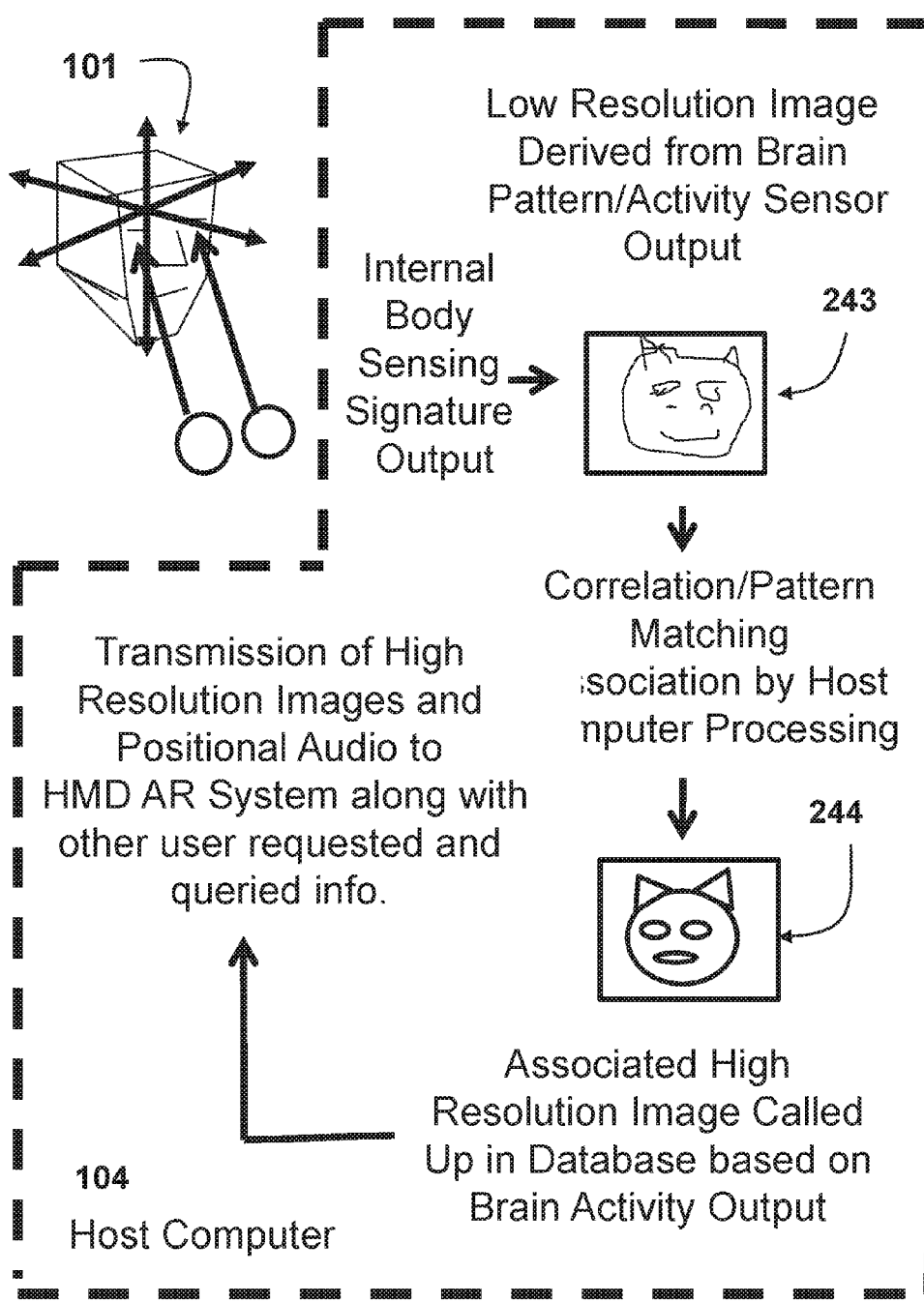
FIG. 26*b* is a diagrammatic representation graphically illustrating by example the sensing and query method described in FIG. 26*a* that results in a user memory enhancement capability according to the present invention.

FIG. 26b is a diagrammatic representation illustrating the process 200 described in FIG. 26a for a memory enhancement system according to the present invention 100. Consistent with Step 1, in this example the portable AMR system records a brain activity signature of a user 101 at a given time and place when the user of the system 100 sees a cat in the surrounding environment. The brain activity signature indicates activity in the thalamus lateral *geniculate* nucleus area which decodes signals from the retina of the eyes of the user. If the brain activity signature is operated upon by a computer to derive a low resolution image 243 of the cat (See Yang 1999 referenced previously). The brain activity data of the user indicates a cat of only sufficient detail, similar to what the user is able to imagine in his or her mind. Based on the time and place the brain activity of the cat occurred in the brain of the user, computer 104 performs a query to search for related video of the cat recorded by video sensors worn by the user that took imagery of the cat at the same time and place when the brain activity of the cat occurred. The logged video imagery of the cat from the system 100 shows an increased detailed image 244 compared to the lower detail image 243 rendered from just the brain signature data. The historical database is operated upon using pattern matching techniques comparing the AMR data to the historical video database which shows a more detailed image 244 of the cat. The host or a remote computer analyze and compare the AMR data to video data and confirm it is the cat belonging to the user. A specific neuron, group of neurons, or pattern of neural activity previously correlated to a specific cat, named "Pussy". The user is seeing or thinking about such that the query process searches for the specific cat in the database. If the query results in finding that specific cat then associated data defined by the user about the cat is called up by the computer 104. Using the just described method 200 the user can command the system 100 to find a more detailed image of "Pussy" than he can remember in his mind's eye by calling up a portion of imagery recorded in the relational database that was previously logged and filed using the system 100. Preferably the findings of the query are presented to the user by an interactive input device worn or implanted into the user. For instance, the high resolution imagery related to the cat is may be transmitted to the left and right displays of the HMD system and the audio of the cat is transmitted to the left and right ear buds of the HMD that the user is wearing.

FIG. 27 is a block diagram that illustrates method which comprises Step 1 239 generally described in FIG. 26a of operating the portable interactive life logging input and storage system that is part of system 100. In FIG. 27 the first phase of operation of the data logging system. Step 1, Phase 1, generally described in FIG. 26, and now specifically described, is the operator turning on the wearable host computer system 104 to activate the internal and external data logging system. Step 1, Phase 2 is the logging system recording brain and video imagery. A portable Atomic Magnetometer Sensor Array Magnetic Resonance (AMR) Imaging System, referred throughout as an AMR system, transmits an image signature of brain activity to pre-processors of computer system 104 and/or 105. Simultaneously, a portable panoramic video recording system transmits image and audio signature of the surrounding environment to pre-processors of computer system 104 and/or 105. Preprocessing may include the normalizing the signatures into a common readable language within the host computer by performing translational computer processing operations of data output from the various sensors, rotation, translation, scaling, brightness, contrast, time, date, and geo-spatial tagging of the data. In Step 1, Phase 3 the brain patterns and video imagery is processed and stored into memory segment folders in the computer 104 and/or 105. At least one of the computers 104 or 105 includes a Cognitive Auto-Associative Neural Network Based Search Engine that performs computer operations to identify and report corresponding correlations between the internal and external data sent from the sensors. Image and brain signatures are normalized, correlations are searched for, and above-the-threshold relationships found of neural to audio and image correlations are logged and recorded in the historical database by subject, time, date, and geospatial coordinate information. Similarly the auto-associative neural network based search engine may also be trained to identify neural correlations of consciousness from various other types sensor input data which is logged into to the memory folders of the computer 104. Arrows in the drawing 241 indicate that once each step is completed that the system 100 and/or 104 and the user 101 preferably proceeds to the next step in the process. And arrow 242*a* indicates a repetitive loop in the process which the system 100 and/or 104 preferably operate upon continuously when the system is activated.

FIG. 28 and FIG. 29*a-b* provide example diagrams of panoramic imagery and brain activity imagery representing the same subject matter that may be logged by a user 101 into the computer system 104 or 106 who is bearing the present invention 100. While these diagrams are shown graphically to facilitate understanding of the present invention, it will be evident to those skilled in the art that signals and/or images derived from internal and external senor signals may be translated into and/or represented as computer language for computer processing and archival purposes.

FIG. 28 provides an example composite image frame of undistorted panoramic imagery 246*a-b* taken at Time and Place #1 248 by a panoramic spherical field-of-view (FOV) video camera system. Several underlying rectangular shapes are shown to indicate that the panoramic camera is recording consecutive rectangular video image frames at Time and Place #1 to the nth 249. The panoramic camera faces outward from the users body, and may be mounted in or on the user in a variety of ways which were highlighted in FIG. 2*a-f* and discussed earlier in this specification. In this instance barrel distortion of the image frame has been removed by using a special fiber optic arrangement called "Fibreye" shown in FIG. 4 to remove barrel distortion. Then the two back-to-back images 246*a-b* have been processed by computer 104 and/or 106 into a single video frame where the images 246*a-b* are placed adjacent to one another in a natural continuous panoramic scene format for input into the host computer 104 or 106 of the present invention. Side A is taken by one fisheye lens and Side B is taken by the other fisheye lens. Each fisheye record a hemispherical FOV image with greater than or equal to 180 degree field of view coverage that may be stitched together to form a continuous spherical panoramic scene. Alternatively, distortion may be removed and the images stitched together optically, as in the present example, or by computer image processing. Within the frame the shape of a "Human" 255*a* and a "Cat" 255*b* are called out as representations of objects that the computer 104 and/or 106 may use image recognition processing on to identify as a "Human" and a "Cat" based on historical information in the computer 104 or 105 data base. And furthermore, use the computer 104 and/or 106 to find relationships between the image of the "Human" and "Cat" and brain activity as illustrated in FIGS. 29*a* and 29*b*.

FIG. 29*a* is a drawing that represents an image of a latitudinal sectional brain scan 251 from an AMR. The oval shape represents a brain 167 scan of the user 101 taken at specific instance in Time and Place #1 251. Several underlying oval shapes are shown to indicate that the AMR is recording consecutive brain scans at Time and Place #1 to the nth 252. The irregular shapes within the oval represent brain activity associated with the subject and activity as perceived by the user at a given time. For instance, in the present example the CP of the user is a "Cat". "Cat" brain activity signatures resulting from the user observing the "Cat" in the surrounding environment are operated upon by computer 104 and/or 106 using image recognition software and/or firmware to identify the irregular shapes that represent the brain activity of the "Cat" NCC's 166 based on historical information in a computer 104 and/or 106 database. Additionally, computer 104 and/or 106 are operated to find relationships between the brain activity data and information illustrated in FIG. 28 and the panoramic video imagery data and information illustrated in FIG. 29*a-b* of the "Cat". FIG. 29*b* is a drawing that simply shows a different method of reading out the brain activity during the same timeframes as shown in FIG. 29*a*, but in a three-dimensional voxel image format. In FIG. 29*b* the brain activity that meets a certain hit criteria and threshold level is displayed as three-dimensional voxels at Time and Place #1 253. Multiple samplings (not shown) of the voxel imagery over time may be recorded and processed in computer 104 and/or 106 to build neural correlates of consciousness for a Time and Place #1 to the nth 254.

It will be extrapolated by those skilled in the art that FIGS. 28 and 29*a-b* teach that other sensor signatures may also be operated on to build a body of knowledge in the computer 104 and/or 105 to define objects and actions by a plurality of cross-correlations derived by analysis of sensor data stored and processed in the computer 104 and/or 105. Other sensor systems that can provide input data include subvocalization systems, audio recording and processing systems like ambisonic audio sensor systems, touch sensitive system, and laser rangefinder and target designation systems. Additionally, informational search engine databases like Google, Wikipedia, and so forth can provide data input to computer 104 and/or 106. Social Network sites, like Face Book, Twitter, and so forth may also provide data input to computer 104 and/or 106. Additionally, a telecommunication and interactive device that the user operates may be data-mined to for input into computer 104 and/or 106 to assist in identifying conscious precept that define neural correlates and relationships to items in the surrounding environment and the brain. Data-mining may be conducted manually by the user or via automated search engines configured to operate without the users specific guidance based on user focus, or other criteria pre-programmed into the system 104 and/or 105. Information defined on these sites both overtly and through context may be used to form a strong body of information to correlate with brain activity patterns, neural activity and associated signatures.

FIG. 30 is a diagram illustrating the method of constructing neural correlates of consciousness (NCC's) from internal and external sensor data recorded from and about a user 101 in the present invention 100. For instance, signatures of brain activity are correlated with audio and imagery recorded in the surrounding environment about the user 101 at a given Time and Place #1 to the nth 252. In other words, the computer 104 and/or 106 is trained to recognize that certain brain cell activity corresponds to certain objects and activities in the environment. To accomplish this recognition computer 104 and/or 106 operate to identify NCC and construct NCC Correlation Tables 250 that are historically and statistically sufficient to define a threshold relationship between internal and external signatures central to the CP of the user at a given time and place. Digitized brain activity imagery 257 in addition to digitized surrounding scene imagery 258 (including peripheral imagery of the body) is stored by and operated upon by computer 104 and/or 106 to derive the NCC Correlation Tables 250. The correlations are then translated into computer code that represent a NCC that define specific subject matter or activity related to that CP. The correlations and/or relationships that form a NCC database 250 may be stored in computer memory. The database 250 is represented in machine language or computer code. Computer 104 and/or 106 used the computer code and associated algorithms to operate upon and query the database 250. Various portable brain activity sensing systems of a type that may be used in the present invention to record brain activity of a user at a given time and place according to the present invention are described previously the background of the invention and earlier in this specification. Various portable panoramic camera systems of a type that may be used in the present invention for recording audio-visual representations of the surrounding environment about a user at a given time and place are described in the background of invention and earlier in this specification.

Still referring to FIG. 30, once a subject or an action has been identified as the CP the brain activity of Person 1 the NCC's for that subject matter or activity are constructed as a correlation table or algorithm 250 in the computer 104 which defines various sensor signatures that mean the same subject or activity between internal brain activity and external surrounding environment sensor system data and information. The subjects and activities logged can be expressed by a word or words groups, numbers or number groups, in whatever language is compatible to the users, be they man or machine. The rectangular boxes with numbers graphically indicate computer code derived by operating system 104 which is receiving and processing Person 1's brain activity at a given Time and Place 1 251 that has a CP of the subject Cat. The computer code 257 represents Person 1's brain activity at a given Time and Place 1 251, the computer code 258 represents Person 1's surrounding environment at a given Time and Place 1 251, and computer code 250 represents the NCC Correlation Tables derived by computer 104 at a given Time and Place 1 251. This relationship can be expressed as Person 1's A's brain activity of the Cat=C, Person 2's A's imagery of the Cat=B, and the resultant normalized NCC Correlation Tables where B=C. For instance, language may also be composed of computer language such as C++. The computer 104 database preferably comprises a database with meta tags and metadata to locate other data in a search engine that performs translation correlations between persons or machines as they communicate. Databases like those in the CALO and neural network system previously described in prior art may be incorporated to assist in translation between users. Typically the correlation tables and algorithms will comprise look-up tables in the computer which relate user neural correlates to logged video. The translation key equates Person 1 brain activity patterns to images and audio, with words that are formed by the computer 104 and/or 106 operating upon look-up tables in the computer 104 that equate to similar representations, such as words. Various normalization, correlation systems, correlation tables, and translation keys are widely known and used in the computer industry so will not be described in any more detail in this specification. It is anticipated various search normalization, correlation, transcription, and translations systems will be used in embodiments of the present invention. Obviously, because the brain is a dynamic organ, updates of the correlation tables of Person 1, and correspondingly, machine 104 and/or 106 will be required periodically to main current and relevant. The correlation tables and algorithms of Person 1 may reside in computer 104 and/or 106, depending on the design of the system 100.

FIG. 30 shows a latitudinal cross section of the brain on the left and an image frame on the right at Time and Place #1 251. The FOV of each eye of the user is indicated by solid circles 255. While dashed circles indicated adjacent hemispherical FOV images captured by the panoramic camera system worn by the user. The two hemispherical images are subset in a HD image frame 256. A ROI image sensor system may be used to identify, track, and sample out the desired portions of the panoramic scene in the FOV of the user, here indicated by solid lines. Distortion may be removed optically (i.e. Fibreye) or by image processing. Various camera and sensor arrangements discussed throughout this disclosure are possible. Objects may be designated as neural correlates based on various actions by the user. For instance, as the AMR system records brain activity and the panoramic video system records audio and imagery a target tracking system monitors the focus and gaze of the eyes of the user on a particular subject in the surrounding environment. The target tracking system marks the location of the subject on the recorded video that the user was gazing upon. The location data of the subject gazed upon is then stored with the imagery in a database. A target tracking system of a type that is incorporated into the present invention that may be used for determining gaze and target designation within the field-of-view of a user according to the present invention is described previously in this application. As previously described in this specification data and information from the tracking system may be operated upon by computer 104 and/or 106 to identify the CP that the user if focused upon. Similarities and differences of brain activity are measured and recorded as various subjects are observed and activities are accomplished. Pattern analysis is conducted and correlations are drawn by via computer processing between subjects focused upon and activities being accomplished and the users brain activity. These similarities and differences are measured and recorded. The resulting neural correlates are established based on the strength threshold level set by the user operating the correlation system. Once correlates between brain activity and subjects and actions are identified the relationships are logged into the rule sets data base of the logging system. Repeated recording of very strong excitation of a certain neuron in the brain when the same subject is observed in the surrounding environment can be used to establish a strong neural correlate. Weak correlations may be discarded. As illustrated in FIG. 28, when a user observes a "Cat" with his eyes in the surrounding environment, a certain neuron or neurons 166 in the brain repeatedly fire while the "Cat" is observed and is the CP of the user as illustrated in FIGS. 29a and 29b. Additionally, associated neurons firing and the sequence they fire in the brain that are related to subjects and activities over time in the surrounding environment or to a given thought by the user are recorded by the logging system and provide additional data for building even more sophisticated neural correlations. These correlations are recorded into a database 250 for later reference. A system of a type that is incorporated into the present invention that may be used for processing, storing, pattern analysis, and determining the strength of the correlation of incoming sensor data for building correlations according to the present invention has been described previously in this application. Multiple sensor correlations may be used to build strong correlation factors and database tables that reduce the risk in misidentifying a subject, object, or an activity. For instance, unless computer is able to achieve a neural correlation based on sensor analysis data of 95%, the "Cat" will not be identified as the "cat" belonging to the user. In our present example factors confirming the cat belongs to the user is historical data that shape, sound, color, color pattern, size, time, and place associated neurons activated in the brain along with the video recorded that provides image shape and color, geospatial coordinates where the image was derived, time the image was derived, and audio of what my cat sounds like when in meows are similar. If the composite standard deviation yields a confidence level on all these factors below 95% then computer 104 and/or 106 will notify the user 101 that this not the non-allergenic cat belonging to the user. If by deduction, the computer operates to determine it is not the cat belonging to the user, the computer will display a text message to the user that he or she should depart the area before he or she has an allergic reaction. Computer 104 and/or 106 may be operated by a user or administrator of the system 100 to train the computer to recognize NCCs. Or computer 104 and/or 106 may programmed to autonomously derive NCCs from brain data to other sensor data during life experiences. In this instance, over time correlations will be drawn automatically and autonomously by the computer using the body of evidence built up through analysis of brain activity and other internal and external sensor system data. In either case, the established database may be modified and added to by a user's body of experience and in order to increase the strength of the correlation and resulting NCC database 250.

FIG. 31 is a diagram illustrating normalization of data and building a translation table of brain activity between two different users, Person 1 and Person 2. Brain activity in Person 1 and Person 2 are different, indicated graphically by the different shapes representing brain activity imaged in Person 1 101a and Person 2's 101b's brain at Time and Place 1 251 or Time and Place 1 to the nth 252 by the AMR system. However, the differing CP of the brain activity in Person 1 and Person 2 is still representative of the same subject matter, a given "Cat" for example that is being perceived in the environment and/or thought about in the brain. Once a subject or an action has been identified as the CP the brain activity of Person 1 and Person 2 the NCC's for that subject matter or activity are constructed into a translation key 259 in the computer 104 which defines various sensor signatures that mean the same subject or activity between Person 1 and Person 2. The subjects and activities logged can be expressed by a word or words groups, numbers or number groups, in whatever language is compatible to the users, be they man or machine. The rectangular boxes with numbers graphically indicate computer code derived by operating system 104 which is receiving and processing Person 1 and Person 2's brain activity at a given Time and Place 1 251 that has a CP of the subject Cat. The computer code 257 represents Person 1's NCC state at a given Time and Place 1 251, the computer code 258 represents Person 2's NCC state at a given Time and Place 1 251, and computer code 259 represents the translation code derived by computer 104 state at a given Time and Place 1 251. This relationship can be expressed as Person 1's A's NCC of a Cat=C, Person 2's A's NCC of a Cat=B, and the resultant translation tables where B=C once the NCC of Person 1 and Person 2 are normalized with one another. For instance, language may also be composed of computer language such as C++. The computer 104 database preferably comprises a database with meta tags and metadata to locate other data in a search engine that performs translation between two persons or machines as they communicate. Databases like those in the CALO and neural network system previously described in prior art may be incorporated to assist in translation between users. Typically the translation tables will comprise look-up tables in the computer which relate user neural correlates to language translation keys so Person 1 and Person 2 can communicate between one another. Various normalization, correlation systems, correlation tables, and translation keys are widely known and used in the computer industry so will not be described in any more detail in this specification. It is anticipated various search normalization, correlation, transcription, and translations systems will be used in embodiments of the present invention. Once a common NCC translation table is constructed for Person 1 and Person 2 then a translation key is built in the computer 104 that allows Person 1 and Person 2 to communicate with one another as illustrated in FIG. 31. Obviously, because the brain is a dynamic organ, updates in the translation tables between Person 1 and Person 2, or for that matter, machine 104a and 104b will be required periodically to main current and relevant. The translation key may reside on Person 1 and/or Person's computer 104 and/or 106, depending on the design of the system 100. The translation key equates Person 1 and Person 2's brain activity patterns and/or images, or audio, with words that are formed by the computer operating upon look-up tables in the computer 104 that equate to similar representations, such as words. For instance, as shown in FIG. 31, when Person 1 thinks about feeding his cat his brain activity reflects a certain brain activity pattern. The brain activity of Person 1 is analyzed by the computer 104 and/or 106 using the already built correlation tables described in FIG. 30 and the thought is deciphered by the computer 104 and/or 106 into the words "Feed the cat". Even though the brain activity patterns for the same subject matter and activity are different between Person 1 and Person 2, the areas of activity are correlated to certain subjects and activities, which may be universally and similarly defined between different users by the translator system. Types of brain activity patterns that include brain region and neural activity, location, and interaction at Time & Place #1 to the nth. The message "Feed the cat." may be transmitted into the text language or spoken language as required using translation tables. Text and voice translation systems and associated tables are widely known in the computer industry. But in contrast to conventional word translation systems, in the present invention brain activity patterns, images, and audio representations between two persons are translated into a common language, which may be conventional text or an audio representations recorded in the computer 104 and/or 106. This facilitates man to machine and machine to man communication. Continuing with our present example, the words, "Feed the cat." are transmitted over telecommunication system and network 13 from Person 1's computer 104 and/or 106 to Person 2's computer to communicate the message. The message may be transmitted non-verbally between the two individual users of the system just by thinking of the action. The words are then displayed in text on a HMD or EMD (i.e. a contact lens eye display) of Person 2. Alternatively, instead of text, an audio signal may be output using a voice synthesizer to Person 2. Still further, another computer, machine, or robot may receive the textual or acoustic message communicated from person 1. In this manner person 1 and person 2 may communicate non-verbally via machine interface. When the data logging system is activated computer 104 and/or 106 is programmed to automatically and continuously construct and update correlation and translation tables based on sensory input and user commands. With respect to building translation codes, a user may use a computer menu and input device to specify that the computer 104 and/or 106 build a translation key or table that allows him or her to communicate with a particular person or machine. Sensory input may include brain activity sensors, panoramic sensors, or other input from various input devices. In this manner computer 104 and/or 106 builds a database for user communication based on brain activity that is associated with his or her experiences in and with the surrounding environment.

FIG. 32 is a block diagram that illustrates method which comprises Step 2 240 generally described in FIG. 26a of operating the portable interactive query and memory enhancement method that is part of system 100. As illustrated in FIG. 32, once the data logging subsystem comprising computer 104 and/or 105 with correlated and translated databases has been established the interactive portable memory enhancement subsystem operates to access the information for memory enhancement operations. Metadata referencing related subject matter seen in brain patterns and video of related indexed historical data in file folders such as those described previously in this application allows for instantaneous feedback to the user by the auto-associative neural network. High-speed telecommunication systems and computer systems are incorporated to do what is called "fast fusion" of information communicated. The objective is real-time processing and feedback of computer 104 and/or 106 to the user of the system 100. Memory enhancement operations will typically be defined by the person who wears the system selecting rules from menus that are part of the firmware either in the host or a remote computer. Interactive user menus may be simple yes or no, or more sophisticated noun, verb, sentence or graphic like. User menus may be manual or set up to be automated requiring no conscious decisions, depending on how the user sets the defaults of computer system 104/105. At any point after at least some portion of the correlated database has been formed in Step 1 a translation database with another system that has a different representation of subjects and activities may be constructed in a manual or automated manner. The translation key is also introduced and stored as a portion of the database of computer 104 and/or 105. The translation key/database is queried when interacting with a human that speaks or machine that operates in a different language. In this manner machines and beings with different languages can communicate. The user bearing the data logging and memory enhancement system 100 will typically set the parameters and command system 100, but this may alternatively be a different person. In such instances the person who operates the system and its associated menus does not have to be the user. For instance a remote operator of system 104 or 105 could control information flowing into a user's input devices, such as a HMD. That operator may be another person or a machine.

FIG. 32 elaborates on Step 2 240 of FIG. 26a. FIG. 32 is a systems diagram that illustrates the user 101 interactive portable memory enhancement portion of the invention. In Step 2, Phase 1 is the operator turning on the host computer system 104 and activating the memory enhancement system. Step 2, Phase 2 is a stimulus in the environment, or a thought and/or action generated by the user stimulating the mind and causing brain activity. In Step 2, phase 3 the host computer receives the signature from the AMR of the active brain activity and queries the correlated databases for matches between the active brain activity and the historical brain activity database pre-associated with historical information. The brain activity must register a certain level of measurable and recognizable focused brain and other sensor activity before a query or command based on that activity is operated upon by computer 104. Once the requirements are met the information is operated upon in the computer 104 and/or 106 to and the historical database is queried. In Step 2, Phase 4 the matches are presented to the user and then in Step 2, Phase 5 the user chooses what matches to activate and act upon. However, a system administrator or operator may be employed to set-up the system 100 and/or 104. Additionally, the system administrator or operator may preselect menu options for a user. Optionally, the system administrator or operator may or may not be the user of system 100 and/or 104. In the present context the "system administrator" or "operator" is referred to a person or machine who establishes the parameters and/or programs the system 100 and/or 104. An operator can set rules using menus that pre-define what information is transmitted for input to the user. The operator may or may not be the user 101. And finally, in Phase 6, Step 2 the brain of the user is stimulated with matched information returned from the query of a database. The database queried may consist of information derived from building the NCC database (i.e. 257 and/or 258), the actual NCC Correlation Table database 250, or external databases (i.e. social networks and search engines on the internet/GIG). Systems of a type that are incorporated into the present invention that may be used for querying correlated data logged into the system according to the present invention are described by U.S. Patent Application 20070124292 A1, by Kirshenbaum et al, dated 31 May 2007, entitled Autobiographical and Other Data Collection System and U.S. Patent 2009/0196493, dated 6 Aug. 2009, by Widrow et al entitled Cognitive Method and Auto-Associative Neural Network Based Search Engine for Computer and Network Located Images and Photographs previously referenced the background of the invention in this application. Arrows in the drawing 241 indicate that once each step is completed that the system 100 and/or 104 and the user 101 preferably proceeds to the next step in the process. And arrow 242b indicates a repetitive loop in the process which the system 100 and/or 104 preferably operate upon continuously when the system is activated.

FIG. 33a-b is a table 247a-b that illustrates a more detailed and integrated description of the major component systems, their functions, and corresponding processes that make up the data logging and memory enhancement system 100 described in the present example where the CP the user is focused upon is a "Cat" at Time 1. Rows are to be read left to right and columns top to bottom. The data logging and memory enhancement system 100 is tightly integrated because data and information from the sub-units contribute to the esemplasticy of the total system 100. The first row 401 of the table 247a lists internal sensor systems of the system 100 that operate to readout their respective content to the host computer 104 and/or 106. For instance, in this preferred embodiment of the system the first row 401 indicates there is an fMRI unit 421, panoramic video camera unit 422, sub-vocalization unit 423, and a target designation and tracking unit with ROI and GPS 424 which comprise the sensors in this example of system 100. The second row 402 lists the type of signatures being read out as data and/or information by the various internal and external sensor systems. The signatures from the sensing systems may be read out in varying degrees, or preprocessed, depending on the design of the overall system 100. As illustrated in the second row 402 the respective readouts output brain signature, panoramic imagery and spatial audio, sub-vocal system audio translation, and geo-spatial data and information. And as illustrated in the second row 403 the respective brain signature, panoramic imagery and spatial audio, sub-vocal system audio translation, and geo-spatial data and information are recorded and transmitted to computer 104 for processing. Each of these outputs are initially input into the host computer 104 for processing. Optionally, computer 104 may transfer the output information to computer 106 for assistance in processing data and information. The output data and information from the sensor systems may be simultaneously processed using multi and parallel processing techniques know to the computer industry to reduce latency. Now referring to row three 404, the fMRI unit readout is recorded and transmitted to computer 104 from Time 1 to the nth when user thinks about, sees, hears, smells, or touches, a "Cat". Likewise the panoramic video camera unit 422 reads out panoramic imagery and spatial audio that is recorded and transmitted to computer 104. Row four 404 indicates that brain activity information, imagery, audio, sub-vocal signatures and positional and geospatial data is logged into computer 104 memory and stored in a historical database. Thresholds and rules are defined in computer 104 firmware to filter out what sensor data and information is kept and discarded in the sensor data and information historical database. Likewise the processing and determination of what data and information to retain or disregard output from each sensor unit 421-424, which comprises the fMRI system, panoramic video camera, sub-vocalization, target designation and tracking units respectively, is accomplished by computer 104 and/or 106. It should be noted that not recording all information will limit later retrieval to only that which is retained in the sensor historical database. The historical database organization, search, and retrieval design in the host computer 104 is constructed in a manner commensurate with the type of computer system, operating system, and application firmware and software selected to accomplish the present invention 100. Then as illustrated in row five 405 the signatures are correlated in the host computer 104 artificial intelligence (AI) or AI-like system in a manner like that reference previously in this application in the background of the invention. The AI system correlates the common relationships in user time, location, subject matter, and activity that defines the subject "Cat" based on real-time and historical data processing. As NCC's are identified those neurons, neural activity, and data and information in the historical sensor database that supports derived NCC relationships is logged into computer 104 memory. Meta data retrieval systems and methods known to those in the computer field may be utilized to quickly retrieve data and information that is logged into the host computer 104. A multi-relational database may be established using any of the above folder heading (i.e. time, location, subject matter, and activity) as long as meta-data marks where the data is stored. Correlations between signature types are determined by computer 104. For instance, from Time 1 to the nth computer processing by the AI system may indicate the user 101 was in an environment in which correlations are determined between brain activity in the user related to panoramic imagery and audio, sub-vocal, and geospatial data all related to the specific cat named "Pussy". These relationships are then stored as metadata in the computer 104 and/or 106 database.

FIG. 33b is a continuation of FIG. 33a. The first three rows of FIG. 33b, rows 408, 409 and 410, illustrate new sensor signatures are received by host computer (HC) 104 subsequent to the establishment of the relational database shown in row seven 407 of FIG. 33a. The new sensor signatures may include user queries and commands. Only now, because a relational database including a historical database has been established, the new signatures received at Time 2 are able to be compared to historical signatures and relationships recorded in the log of computer 104 and/or 106. Hence, newly received data and information at Time 2 to the nth may now be operated upon by the host computer system to see if the new data and information is the same, similar, or totally new. And then as indicated in row eleven 411, if significant relationships are found between the old and new signatures then the relational database is updated, and if a response is required based on a rule previously established by the user or an operator, the user is notified or an action is automatically taken. For instance the signature of a "Cat" prompts the computer to post a message on the users display and/or a voice synthesized audio message is read to the user notifying the user that the user may wish to take his allergy medicine before experiencing an allergic reaction to the "Cat" in the surrounding environment.

Still referring to FIGS. 33a-b, in operation, tables 247a-b indicate that the system 100 is turned "On" to record internal and external sensor data and information. The internal and external data and information is transmitted to the host computer 104 and/or 106 and operated upon by command and control, correlation and/or translation firmware. All internal and external sensor data to include head-and-eye tracking and global positioning 424, brain activity 421, voice recognition or sub-vocalization 423 and video camera 422 readout data and information as indicated in the four columns of the table 247a-b is time, date, and/or geospatially stamped. Typically the subjects in the surrounding environment given the most attention as the Conscious Precept (CP) by the user 101 will illicit the most brain activity and the corresponding neural correlates of consciousness (NCC) are analytically determined via computer 104 and/or 106 processing. For example the internal and external sensors activated will indicate that the focus of the user is on a cat. When the user sees the cat the brain activity sensor system recognizes that the user is thinking about a cat because certain neurons and brain activity takes place. Also, the user is likely to sub-vocalize the words, "A cat!". And also because the user is surprised, he exclaims "Oh, a cat!" verbally out loud. The panoramic video camera unit readout provides panoramic video to system 104 for analysis. The target designation and ROI tracking unit 424 sample the panoramic video feed for analysis. Because the user is watching the cat with his eyes the target designation system with ROI tracking recognizes locates the target which is the cat and provides the geospatial location of the cat in the surrounding environment. Additionally, the panoramic video camera unit 422 readout provides spatial audio which corresponds to the location of the cat if the cat makes noise and when the user exclaims "Oh, a cat!". Additionally, because the user is allergic to cats, the breathing and heart rate of the user increases, which may be noted by biometric monitoring sensors mounted on the user. All these internal and external stimuli stimulate various parts of the central nervous system and brain of the user which is recorded by the brain activity sensor system.

Vocal and sub-vocalization signatures from microphones, electrodes, and vibration sensors is recorded and then compared with other historical audio and non-audio signatures. Sensor signatures are cleaned up and filtered through the computer 104 in order to search for and determine relevance and meaning. Noise from non-significant or sensor activity not related to the CP brain activity is filtered out. Magnetic interference is filtered out using computer processing techniques described in the referenced prior art sensor fusion pre-processing systems to see if they meet a certain threshold. Signature matches can be accomplished by comparing incoming signatures from the sensors with previously established and recoded signatures that have been already defined as representing the cat. Traditionally, in prior art, establishing this comparative database has been accomplished by an operator manually training a computer that the pixels representing a cat image correlates and corresponds to the audio signature that is translated into the word "cat". But alternatively, signatures can be built on the fly as they are logged in and processed in the present invention by comparing them with the historical sensor database and NCC database, and then logging them in separately if they meet a threshold relationship that is significantly different than previous signatures in the databases. Signatures are built on-the-fly or dynamically by building a body of evidence among sensors signatures that have a certain relationship which have statistically significance.

Still using our "cat" as an example, we observe in AMR imaging that a certain neuron in a region of the brain shows increase blood flow when a cat is focused upon by the user. The focusing of the user's eyes and ears on the cat is determined by audio (ambisonic) tracking and image recognition and tracking systems that are part of the video logging portion of the present invention. The video logging systems use pattern matching and other computer based image processing methods to identify audio and images. The imagery from the video camera system will be matched up with the target tracking system which incorporates a head and eye tracking system to see what subject is being observed and provide coordinates which will correspond to the user looking at the cat. Additionally, a laser rangefinder system of a type like that disclosed in prior art is referenced and operates in the present example to further define the focus of the user. The laser rangefinder provides the distance to a subject the user is focused on at a given time. The distance along with the GPS coordinates assist in ROI tracking and identifying a subject that stays within the FOV of the panoramic camera. The range, location, and coordinates are operated upon by computer 104 pattern recognition software or firmware to identify the pattern as a cat and then log that specific pattern into the database as a cat. Additionally, other sensors signatures are used to confirm the identity of the subject cat, and also the subject's activity. For instance, sub-vocalization system records a signature that represents and is translated into the word "cat" when the user sees a subject cat. From these different internal and external sensors correlations may be automatically established without human intervention by running operations programmed into the host computer. The correlations also include a time stamp and GPS location and are referenced to the raw data in the historical database which includes retained sensor database logs and the NCC database. When signatures are built dynamically manual training to define correlates of specific subjects is not required. This is because the computer establishes neural correlations based on algorithms in the computer independently based on related internal and external activity and events that happen simultaneously in time (i.e. A certain neural activity and a certain image pattern happening at the same time.). This is because as the database grows and it gathers more information which the system 100 queries to identify new subjects and activities that take place in the future (i.e. Time 2 and Time 2 to the nth). In this way the relationships identified historically mimic human memory. The computer is thus trained to identify subjects and activities based on previous stored historical relationships stored in its database, much like humans gain from experience and store in the memory of the human brain. Furthermore, internal (i.e. AMR neural activity) and external (i.e. video: audio and imagery) correlation from sensors is bolstered when "hits" and "matches" are validated by the computer 104. The "hits" and "matches" to the relational database may be subsequent (i.e. discovered during in post processing) or sequential (i.e. Discovered as new information arrives in near real time). Besides creating memory folders in the host computers relational database that are logged using time stamps, memory folders logged using other categories, such as by subject or activity, are also possible. An example of an internet search engine the present computer system 104 could query is "Google"™. Such a logging and retrieval system that is a type and integrated into the present invention is U.S. Patent 2009/0196493, dated 6 Aug. 2009, by Widrow et al entitled Cognitive Method and Auto-Associative Neural Network Based Search Engine for Computer and Network Located Images and Photographs.

Sensors monitoring brain activity may be positioned to sweep the entire brain or a portion of the brain. In particular a certain region of the brain known to provide neural correlation for that subject, activity, or sensory perception may be targeted by sensors monitoring the brain. For example, in the New England Journal of Medicine article "Willful Modulation of Brain Activity in Disorders of Consciousness", dated Feb. 18, 2010, Martin Monti et al, areas of the brain (i.e. activity in the parahippocampai gyrus and the supplementary motor area of the brain) are identified that show different activity when a user makes a "yes" response versus when the user makes a "no" response to a stimulus in the internal and external environment. By translating brain patterns that correspond to the user making "yes" and "no" determinations in his mind as he makes "yes" and "no" menu selections presented to him on a head mounted display or contact lens augmented reality display the user non-verbally controls parameters within and input and output of the host computer. U.S. Patent 2009/0196493, dated 6 Aug. 2009, by Widrow et al entitled Cognitive Method and Auto-Associative Neural Network Based Search Engine for Computer and Network Located Images and Photographs.

Once data is logged in from the internal and external body sensors the information may be called up by the user to enhance his or her memory or may be automatically input based upon predetermined rule sets the user or another person or machine has previously input into the host computer. Referring specifically to the operation of software or firmware on the computer of the in the body worn device s, the software includes an operating system, atomic magnetometer, image and pattern recognition system, HMD, voice recognition, panoramic video, AI and/or AI like filing and retrieval, and telecommunications software or firmware. Details of standard computer operations and interconnecting software and firmware is already known to those skilled in the art and described in detail in various prior art documents. In operation a fast fusion auto-associative neural network software and firmware of a type like that described in Widrow is used to automatically query data in the memory folders in the data base of the host computer which is constantly scanning the databases in response to queries for correlations to incoming internal and external sensory data. The information logged may be referenced by artificial intelligent (AI) and AI like systems to form an enduring cognitive assistant for the user or another client in the present invention. An AI computer hardware and software of a type that may be integrated with the present invention is the Cognitive Agent that Learns and Organizes (CALO), developed by SRI between 2003 and 2008. CALO is a PC based cognitive software system that can reason, learn from experience, be told what to do, explain what they are doing, reflect on their experience, and respond robustly to the clients the user specifies directly or through a user's repeated actions in using a CALO system.

The CALO system is integrated with the hardware and software and firmware of the sensor pre-processing and Auto-Associative Neural Network Based Search Engine for Computer and Network previously mentioned through conventional computer system design widely known in the computer industry. The CALO system is used to drive the command and control portion of the invention. Computer system 104 may comprise one or a plurality of systems, but must comprise at least one located on the subject user or machine as described in the present invention. Translators may be used to link firmware and/or software applications together or alternatively original code is written combining the code into a single application software or firmware. If brain activity, video, audio, and sub-vocal information meet a certain threshold of signature then the information may be selected or automatically input to the user based on predetermined rule sets. Input means include audio-visual devices like a head mounted display, electronic contact lens displays, and ear buds with small speakers. Alternatively, a menu may be presented to the user for selecting inputs. The system is programmed to display a list of yes/no items that correspond to audio or video files in the memory folders of the computer. In such an instance the user may interactively review and act upon items in the menu in order to select or not select items for input off the menu. Interactive input means may include voice and sub-vocal recognition systems, pattern recognition systems that recognize hand gestures, AMR brain activity pattern recognition, and the like. For instance, every time the user is around a cat he may want to be prompted to take allergy medicine. When the system recognizes a cat in the surrounding environment the user may be prompted. Because the system is panoramic, it can look for things in or outside the users FOV if the user chooses to activate such a capability within the system. And/or still alternatively when a certain threshold of sensory activity is met an injection of allergy medicine may be automatically injected into the users body by an adhesively worn medicine pack located on the users body that is in communication with system 100. Still alternatively, the system may be put on standby and only log information in when a certain sensor reaches a certain threshold. For instance when a user's heartbeat reaches a certain pulse; when the brain activity of the user meets a certain threshold or certain areas are active in the brain; or when a certain subject or activity is sensed by the video camera with target tracking and target recognition.

Figure 34:
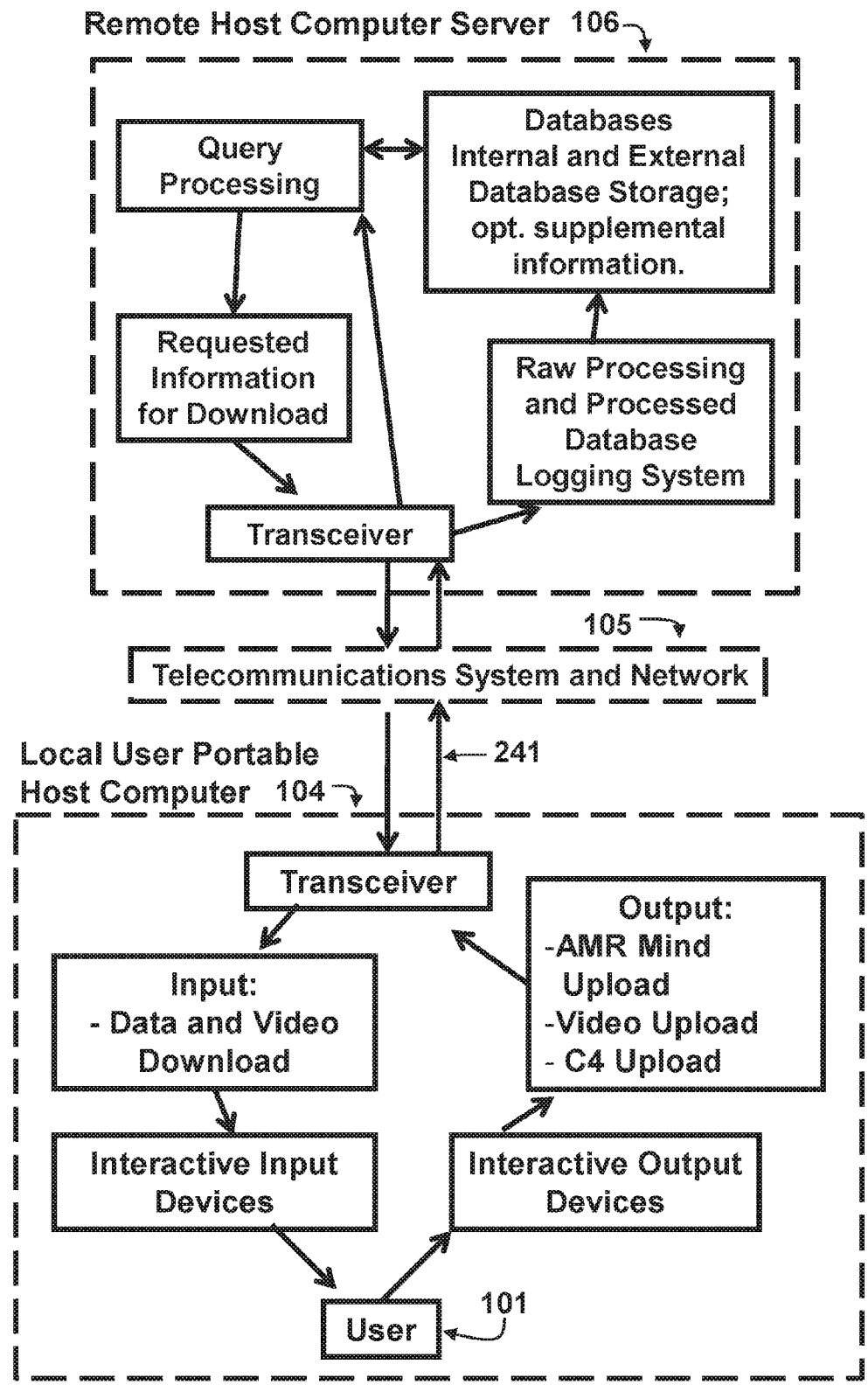
FIG. 34 is system diagram comprising a cloud computing arrangement for video logging and memory enhancement wherein a local user with a portable host computer system logs data or information and/or simultaneously queries at least one remote host computer server on the internet in accordance with the present invention.

FIGS. 34 and 35 are block diagrams that illustrate telecommunication embodiments of the system 100. These embodiments of system 100 comprise a cloud computing arrangement for video logging and memory enhancement comprising a local user portable host computer 104 and a remote host computer 106. Optionally, as shown in FIG. 25, and more detail in FIG. 34 and FIG. 35 the logging and enhancement system 100 incorporates a telecommunication system and associated telecommunications system and network 105, like the global information grid (GIG), which includes the internet. Some components of the system 100 may be placed in remote locations apart from a user of the system such that it is unnecessary for the user to carry all components of the system 100. This is important because carrying less components reduces weight, required electrical power, and component space for system 100 some of which must be borne by the user. And furthermore, it allows what is carried by the user to be carried less conspicuously. The basic subsystems that are placed on or in the users head include a brain activity sensing system such as a portable AMR and panoramic video sensor system. Additionally and optionally, a voice microphone and/or sub-vocal recognition system is placed on the head or upper body of the user. Preferably, eye tracking and head tracking sensors are also located on the users head or upper body. Other components may be carried by the user other than on his head but in a communicating manner to the sensor systems on his head or upper body so that signatures may be transmitted to a remote device for processing. Transmission may be from the sensor systems borne by the user and in a communicating device to a portable electronic device borne by the user such as a PDA, cell phone, smartphone, reader, laptop, or other computer with wireless connectivity to an associated telecommunication system. The electronic device may be located in a backpack, belt pack, integrated into clothing on ones lower body, or mounted in any suitable manner described in FIGS. 2a-f.

For instance, in the telecommunications embodiment shown in FIG. 34 the portable host computer 104 transmits internal and external sensor module 109 data and information to the user 101 interactive command, control, communication, and computer (C4) module 107 that transmits data and information over a telecommunications system and associated network 105 to a remote host computer server system 106. The user operates interactive input devices like a key pad, gesture recognition system, voice or sub-vocal recognition system to transmit command, control, communication, and computer (C4), panoramic video data, AMR brain pattern and activity data, and other sensor data and information. The data is transmitted from the portable host computer 104 includes has a wireless modem and transceiver. The transceiver may be implemented as a computer chip and antenna in a portable electronic device like a smartphone. Preferably, the transceiver of the host computer 4 transmits the data as radio frequency signals over a wireless WIFI or cellular telephone network of the telecommunications system and network 14 to the remote host computer server 105. The transceiver at the server 105 may be configured to be part of wireless and/or land line in type. The communications system at the host computer 104 and remote host computer 106 server may include compression and encryption capabilities. The data received is operated upon when it reaches the server 106. Server 106 will typically be a personal computer, workstation computer, or a rack mounted computer server. The server hardware is of a type like that is used to process data/information like that described in U.S. Patent Application Publication 2009/0196493 A1, dated Aug. 6, 2009, and as described as part of the Cognitive Assistant that Learns and Organizes (CALO) system developed by the AI Center, SRI International, of Menlo Park, Calif. Incoming data is parsed by the server depending on its type. The type of data is preferably meta-tagged at the sending host computer end to facilitate parsing and processing by the remote host computer server. The general types of requests include: 1) data logging requests; 2) command and control (C2) requests; and 3) query requests.

As previously discussed, near real-time data logging requests include the storage and logging of data recorded by the internal and external sensors. The data is received and processed for filing and storage/logging in the memory segment folders database of the server. Examples of the types of sensor data and information received for processing and data storage includes storage of panoramic video, brain pattern activity imagery, sub-vocal signatures, and so forth and so on. Examples of Command Control (C2) or Command, Control, Computers, and Communication (C4) information received includes information search requests and database build requests. Preferably, at least some portion the correlation module 111 is located in computer 104 borne by the user, but optionally, correlation processing may be carried out completely on the remote computer server 106.

Preferably the portion of the correlation module kept on the host computer is relational database information commonly accessed, such as portions of the NCC database or frequently accessed historical database data and information. In the present example C2 or C4 requests sent from the host computer to the remote server are transmitted to the AI and AI-like (i.e. Personal Assistant that Learns SRI International) portion of the remote server. Examples of C2 or C4 requests include requests to stop and start the remote server; place the server on standby; or only perform logging when certain internal or external parameters/thresholds are met. For instance, when AMR brain activity indicates the users heart beat has reached a certain level; AMR data shows heighted activity by predetermined neurons indicating a "cat" is being observed in the external environment and an allergic reaction is starting to take place in the users body; or when analysis of the video being logged in indicates a certain subject or activity is in the external surrounding environment. The interactive command and control module 107 of host computer system 104 is operated to establish rules for controlling the system and rules on when, where, and how queries will be acted upon in module 109 and 111. Rules are typically established by the user 101 of the system 104. For instance, the user may use a menu to review data provided in response to a query prior to having said data automatically acted upon by a sub-system (i.e. An medication automatically being injected into the user.).

Query requests sent from the host computer to the remote server 106 will be transmitted to the AI and AI-like (i.e. Auto-Associative Neural Network) portion of the remote server 105. Examples of query requests include asking the auto-associative neural network to replay video of the last time you saw your Mom and Dad together during your life, or a video recalling an appointment where the physician told you what type and the medicine to take when your allergies to a "cat" reaches a certain pathology. The server then searches the memory segment folders for the information requested in the query. The information in response to the query is then transmitted to communication portion of the remote computer and transmitted over the telecommunications system and network to the transceiver of the host computer. The downloaded information is then processed in the host computer for input into the user via user input devices (i.e. head mounted display systems or electronic contact display lenses). The queries may be consciously directed by the user or automatically directed based on previously input commands. As mentioned earlier, rule sets which include thresholds that define the numerical strength and relevancy of the data will typically be operated upon to determine whether located information found in the query is transmitted as feedback to the user 101 and how it is acted upon once it is received by the portable host computer 104. It is anticipated that certain critical and/or continuously used information will be cached in memory stored on the portable system 104 RAM or hardware and that rarely used information will be stored in memory stored on system 106.

In contrast to the system described in FIG. 34 in which a user's host computer interacts with a remote server on a telecommunications network, FIG. 35 describes a telecommunication system for interaction between people or machines according to the present invention. FIG. 35 provides a diagrammatic drawing illustrating the portable voiceless telecommunication system and method between multi-participant humans and/or machines consistent with the present invention 100. For example, in FIG. 35 both a sending user 101 and recipient user 102 are operating the present invention 100 which includes a telecommunication system and network 105, remote computer system 106, head worn assembly with internal and external sensor recording units and presentation units 134, and portable host computer system 104. Thus, the user 101 is able to remotely observe the environment that the receiver 102 is in. In this instance the recipient 102 is taking care of the cat of the user 101. While observing receiver 102, user 101 thinks of something he or she wants to communicate to the user 102 by operation of system 100. In this instance the user 101 thinks "Feed that cat." Activated internal and external sensor units 134 to include head-and-eye tracking and global positioning 424, brain activity 421, voice recognition or sub-vocalization 423 and video camera 168 readout respective information to the host computer 104. Internal data such as AMR brain pattern and activity data 257, sub-vocal recognition data 203a, and external data from the panoramic video data comprising panoramic imagery and spatial audio are processed into digital signatures that are translated into binary computer code 168a and 168b respectively, that is graphically depicted by boxes with ones and zeros. The internal and external sensing monitoring and logging module 109 represents pre-processed raw data and information read out from fast fusion sensor system processors located in the head-assembly 134 of the user 101.

As indicated by the bracket 425a the data from the sensors units in the head assembly 134 is then transmitted to host computer 104a. The input data and information from the sensor units is logged into the file folders of the correlation module 111. As depicted in FIGS. 28-30 data is then processed in the computer 104 and/or a remote computer 106 server to identify CP's and NCC's between the internal and external data and informational representations. The data and information is then stored in file folders in computer 104 and/or 106 memory. The neural network includes meta data comprising links back to the pre-processed sensor data which is filed such that it may be called up or later analysis or replay. Unwanted data and information is disregarded in the process. Alternatively and/or additionally, raw data from the sensors may be logged into a file prior to pre-processing for storage and potential retrieval and pre-processing by the computer 104a. As depicted in FIG. 30, the neural correlations are then translated into machine or spoken language that is transmitted from one sending user 101 (depicted as a Sender) to another receiving user 102 (depicted as a Receiver). Filtering out noise, focusing in on specific neurons in the brain, focusing in on specific image patterns using video target tracking and image recognition programs, strength of signatures, and performing comparisons of subject data with historical data in the memory segment folders database are the processing techniques used by the system 100 to determine "hits" and "matches" to determine neural correlates and determine the meaning of the data at a given time or over a given time period are functions of the applications firmware and/or software in computer 104 and/or 106. In the present example, neural activity in the brain and actions in the surrounding video scene confirm that receiver 102 named "Bud" who the user 101 is "messaging (MSG)" with is to "Feed the cat.". The message constructed by the host computer 104a from sending user 101 to be communicated to host computer 104b to recipient user 102 is derived by the host computer 104a operating to identify and construct the CP, NCC, and composing a corresponding message based on the CP,s NCC's and relationships drawn and derived there from for transmission from the sending user 101 to the recipient user 102 as illustrated in FIGS. 30 and 31.

The message is transmitted from computer output module 71 that includes a wireless transceiver module 58a worn by or implanted in the user 101 to the recipient user 102 over the telecommunication system and network. Both audio output 74 and video 72 graphic imagery for overlay onto the EMD are output for transmission in the present example. The host computer 104b transceiver worn by or implanted in the remote user 102 receives any verbal or written information in a language he or she understands because the communicated language has been correlated as described in FIGS. 28-30 into a language understandable to the recipient 102. And in a similar manner as described in FIG. 31 the translation table 259 allows different CP's and NCC's to be translated and communicated back to another user over the telecommunication system. It should be noted that a translation table or key 259 may be constructed allowing two machines or a human and a machine to communicate with one another.

As depicted by the bracket 425b, text, graphics, imagery, and audio may be transmitted from transceiver 58a between a first user 101 operating host computer 104a and second user 102 operating host computer 104b is displayed on each of the user's respective presentation devices. In this instance the input device for the recipient 102 is a head-mounted audio-visual system like that shown in FIG. 19. The host computer 104b wireless cellular capable transceiver 58b receives audio signals 74 and video graphics 72 from the sender 101. Audio signals 74 received by the ear bud speakers 138a-b and and video graphics 72 received on the EMD's 137a-b are presented to the receiving user 102 on his or her head mounted display. For instance, in this example, an augmented reality application in which an arrow points to the cat that needs to be feed may comprise the video graphics displayed on the receivers electronic contact lenses. And voice synthesized audio that is received in the user 102 ear buds stating "Bud, feed the cat." which are derived from sensor fusion of sensor analysis of user 101 sub vocalization, brain activity, and video imagery which coincide and confirm the CP and NCC of the same thought . . . "Bud, feed the cat." which in announced in the user 102 ear buds. It should be noted that various types of human and machine languages may be transmitted in various computer and media formats to facilitate communication between a beings, machines, or a combination thereof.

Figure 36A:
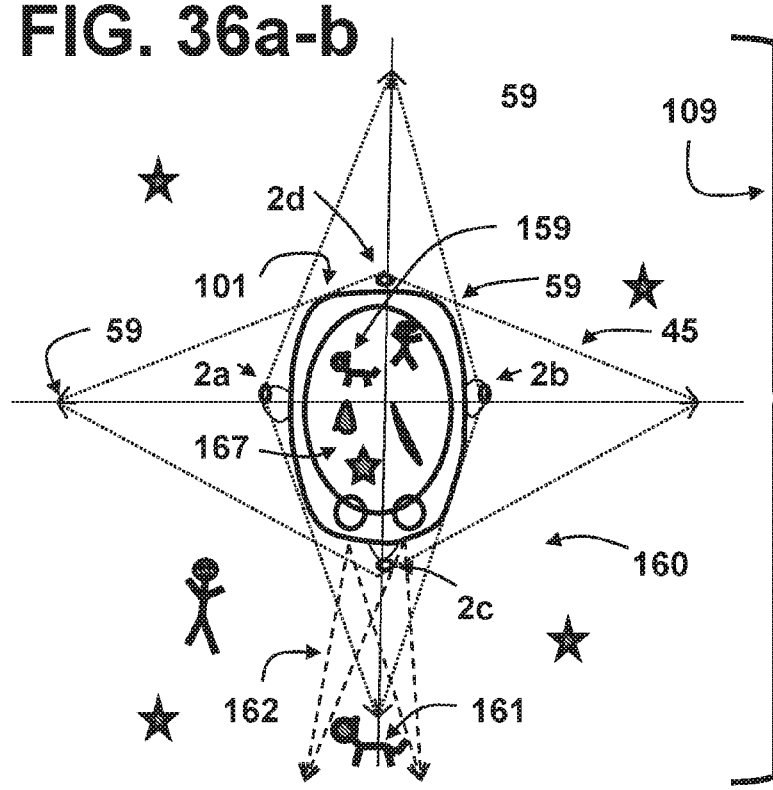
FIG. 36a is a diagrammatic plan view that illustrates the overlapping panoramic FOV coverage of the panoramic audio-visual system comprising the present invention of an embodiment that facilitates stereographic imaging.
Figure 36B:
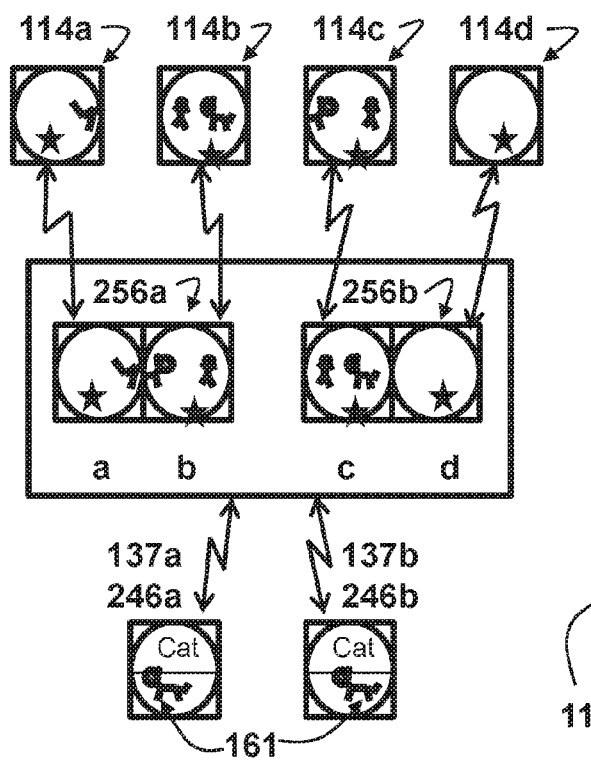
FIG. 36b is a diagrammatic view that illustrates the images recorded by fisheye cameras worn by the user in FIG. 36a that result from overlapping panoramic FOV coverage by the panoramic audio-visual system that facilitates stereographic imaging in accordance with the present invention.

FIG. 36a illustrate the process of recording, processing, transmission in module 109, and then FIG. 36b the subsequent related process of correlation and translation processing in module 111 of the same internal and external sensor data according to the present invention 100. Panoramic audio-visual coverage is important in the present system in order to record accurate descriptions of what place cells in the brain perceive with respect to the "Time", "Place", and "Spatial Resolution" in which the user is located in the surrounding environment 160. And important for providing a more detailed recording than what the mind can remember. This is particularly important in building realistic simulations that may be played back in which any portion of the scene may need to be created to achieve a sense of historical presence. The dotted lines 45 illustrate the FOV of each of the lenses of camera 2a-d. The dashed lines 162 illustrate the FOV of the left and right eye view of the user 101. The cat illustrates real world subject which is the CP 161 forward of the eyes of the user. The oval shape indicates the brain 167 of the user and the items within the oval specific neurons 164 firing in the brain 167 which is the CP which define the NCC 159 related to the same subject 161 in the surrounding environment outside the head of the user. In FIG. 36a the panoramic video camera system records images 114a-d using associated video capture device(s) like those shown in FIGS. 2a-d, 3, 4, 5-a-b, 10a-c, 11. Previous optics described in this specification and in the background of the invention site various panoramic capture devices of a type and design that may be used in the present invention. The images have adjacent or overlapping FOV coverage such that a spherical FOV scene is recorded. Alternatively, overlapping imagery may be captured in order sample out stereo graphic imagery. FIG. 36b is a depiction of the four resulting images 114a-d. The camera images 114a-d are shown as circles to illustrate hemispherical images recorded with fisheye lenses. The rectangular shapes indicate a frame. In the present example a pierced ear camera facing outward from the ears of the user 101 to record adjacent images c and d 256a to the front and back of the users head, and cameras a and b 256b record adjacent images to each side of the users head. As indicated at the bottom of FIG. 36b the images 256a-d are then optically manipulated and/or digitally processed by a computer and output so that at least some portion of the imagery is sampled for additional processing or display for viewing by a local or remote user. In the present example the CP 161 the user is focused upon is sampled from images 256a and 256b to provide for display by the computer 104. The images are presented to the user on the EMDs 137a-b as undistorted images 246a-b.

Figure 37A:
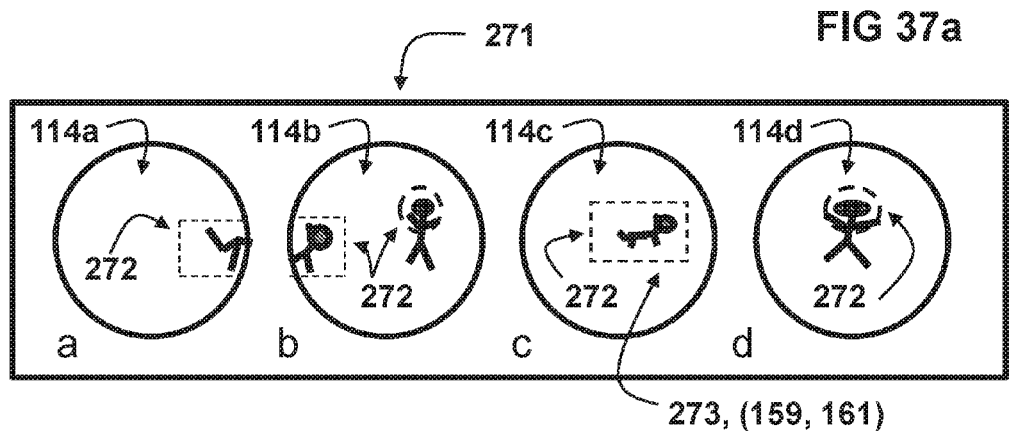
FIG. 37a illustrates overlapping hemispherical images A, B, C, and D, recorded by a panoramic camera system with four adjacent side by side panoramic objective lenses facing outward about a point at 90 degree intervals along a common plane with dashed lines in the diagram indicating dynamic interactive multi-region-of-interest (ROI) areas in the frame that are to be sampled from panoramic image frames for processing and display to the user or a remote user based upon the conscious precept of a user. (Reference multi-ROI sensor image data sampled out based on the eye focus of the user correlated with brain activity data to identify CPs that forms the NCC database of the user.)
Figure 37B:
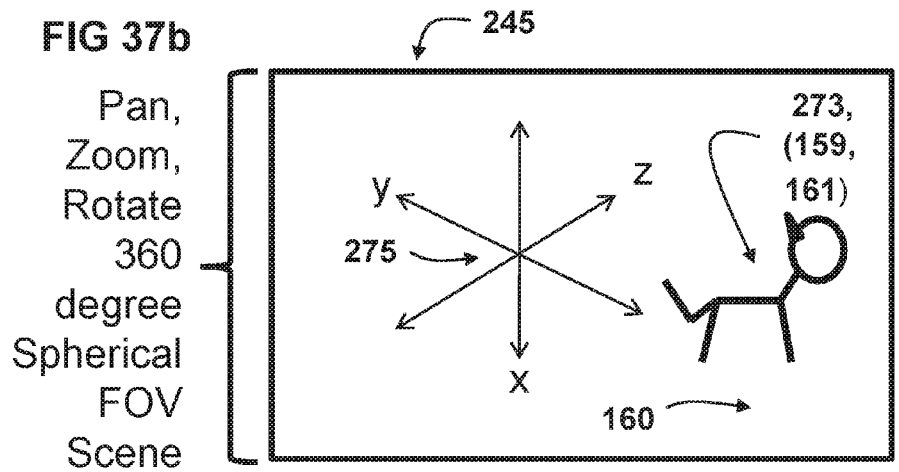
FIG. 37b illustrates a resulting frame processed for viewing by the user in which any portion of the spherical FOV panoramic scene shown in FIG. 37a may be panned and zoomed upon by using interactive input devices.
Figure 37C:
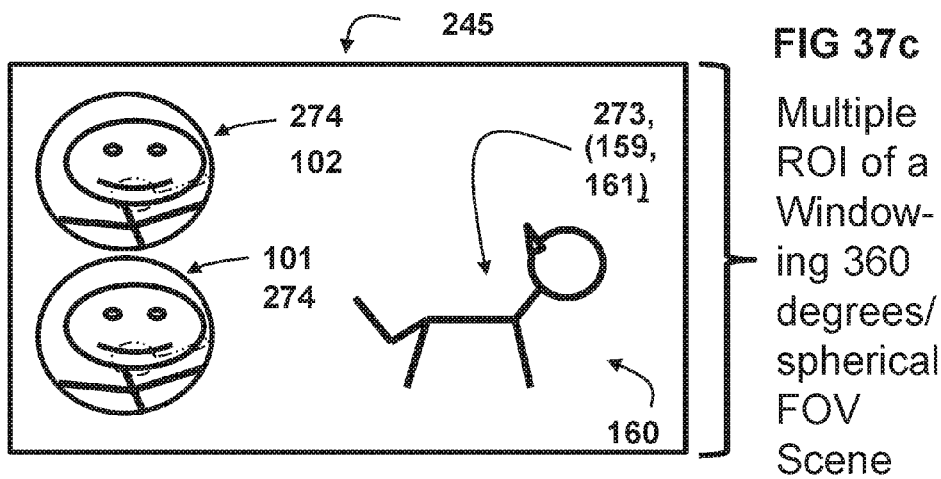

FIGS. 37a-c are schematic diagrams illustrating system 100 dynamic interactive multi-region-of-interest (ROI) processing and display for a local or remote user. FIG. 37a through FIG. 37c correspond to the same data and information described in FIG. 36a and FIG. 36b. Region-of-interest image capture sensors of a type that may be incorporated in the present invention are incorporated by reference and where cited up front this patent application. FIG. 37a illustrates images 114a-d that are recorded by a panoramic camera system with four adjacent side by side panoramic lenses facing outward about a point at 90 degree intervals. The FOV of the images may be adjacent for monoscopic, bi-ocular, or overlapping imagery for stereoscopic imaging. In the present example the imagery is stereoscopic presenting at least two views of all surrounding subjects in the surrounding environment 160, as indicated by the same subjects being imaged by multiple fisheye lenses. Dashed lines in FIG. 37a indicate the ROI 272 that the ROI image sensor is focused upon based on the users selection. FIG. 37b illustrates a resulting composite undistorted spherical FOV image frame 245 processed for viewing by the user in which any portion of the spherical FOV panoramic scene shown in FIG. 37a may be panned and zoomed upon by using interactive input devices. The x-y-z Cartesian coordinates 275 are shown to illustrate the panning capability. The host computer does this by sensing the viewer's head and eye position, relaying those coordinates to the ROI image sensor, and sampling out the ROI the user is looking at in the recorded spherical FOV. Images may be sampled out for monoscopic, bi-ocular, or stereoscopic viewing depending on the camera, processing, and display system. FIG. 37c illustrates a resulting composite undistorted spherical FOV image frame 245 processed for viewing by the user in which three images are sampled out of the images shown in FIG. 36a and FIG. 37a for display. A first enlarged sub-windowed ROI image 274 is the receiving user 102 at the remote end, a second enlarged window ROI image 274 of the sending user 101 at the local end, and finally the background image is a scene of a cat 273 in front of the other user 102 which both users 101 and 102 are looking at and discussing in their two-way video teleconference. In this example the cat 273 is the image observed by the local and remote user of the system related to the cat CP 161 in the users mind and the subject cat 159 observed in the surrounding environment 160 as denoted in the FIG. 37b. As those skilled in the art will realize, multiple ROI images and graphics across the spherical panoramic images may or may not be selected and windowed over a local or remote background depending on local user and remote user preferences.

Figure 38:
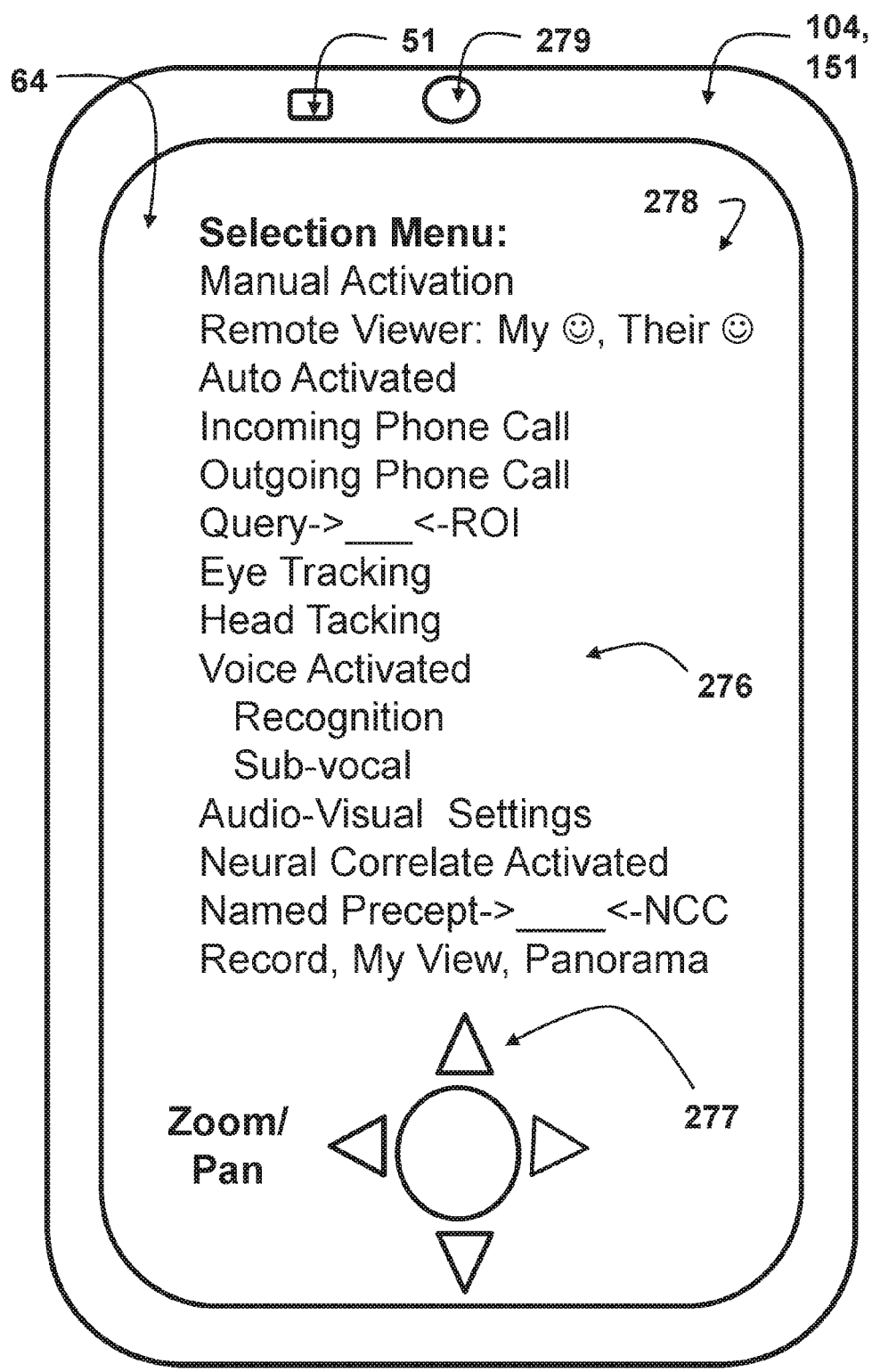
FIG. 38 is a illustration of an screen shot of the graphic user interface (GUI) of a host digital communication device (i.e. a smartphone, like an (Phone 4S or 5) to be acted upon by the user for interactive command and control of hardware and firmware comprising the present invention.

FIGS. 38-49 illustrate embodiments and applications of the invention that may be derived from the Life-Logging and Memory Enhancement Assistant (LLMEA) 100 system. FIG. 38 is an illustration of a screen shot of the graphic user interface (GUI) 64 of on a host digital communication device, also referred to as a portable host computer system 104, like a smartphone 151, acted upon by the user 101 to interactively control the operation of the present invention 100. The smartphone includes all the standard smartphone functionality, hardware, firmware, memory, microphone 51, audio speaker, camera 279, and so forth. But additionally as described throughout this specification, the smartphone 151 includes specific applications which include hardware and firmware that interact and operate with other systems, components, and applications unique to the Life-Logging and Memory Enhancement Assistant (LLMEA) 100 system that comprises the present invention. For instance, the graphic user interface 278 includes a touch screen 276 menu entitled "Selection Menu" 65 that a user 101 manually operates to select device parameters that control and command the user interactive command and control module 107, internal and external sensing monitoring and logging module 109, and correlation module 107. Once the user sets the parameters the device may automatically act upon the settings of the user whenever the device 151 is tuned on. The options are listed on the touch screen of the smartphone such that the user interactively selects them. When the user touches a topic and it changes from red to green the application is activated. By touching the application again the topics text turns red and the application is turned off. Multiple related functions may be selected to enable or disable applications that run simultaneously. The user has the option to select options which make operating the device in a hands-free manner, and the user has the ability to lock the screen so the device or selections are inadvertently activated. In some applications like "Query" or "Named Precept" a database of features or correlates are searched upon. Commands are entered into the device 151 to control and drive biometric and brain activity sensing systems, surround sensing systems, the correlation system, smartphone operation to include interactive feedback systems, and the telecommunication system. Text, touch, or voice commands will typically be entered into the GUI 278 of the host computer 151 in order to activate an application to function. Similarly, buttons may be pressed to turn on and off the host computer, to include biometric identification and security systems. As illustrated at the bottom of the GUI touch screen, the GUI also includes "Zoom" and "Pan" 277 functionality. The user may presses the arrows on the touch sensitive screen of the device 151 to zoom and pan the spherical FOV scene, and presses the center button to zoom in and out on an item. Alternatively, the operation of the user interface be done hands free using the voice recognition system, sub-vocal recognition system, hand or facial gestures, ROI automatic windowing as shown in FIG. 37b-c, or the brain activity sensor system. The system may answer back to the user by displaying responses via text, imagery, user force feedback glove or body suite, image display, conventional audio speaker or earbud, or voice-synthesis audio speaker that may comprise part of and are within the scope of the present invention 100.

Figure 39B:
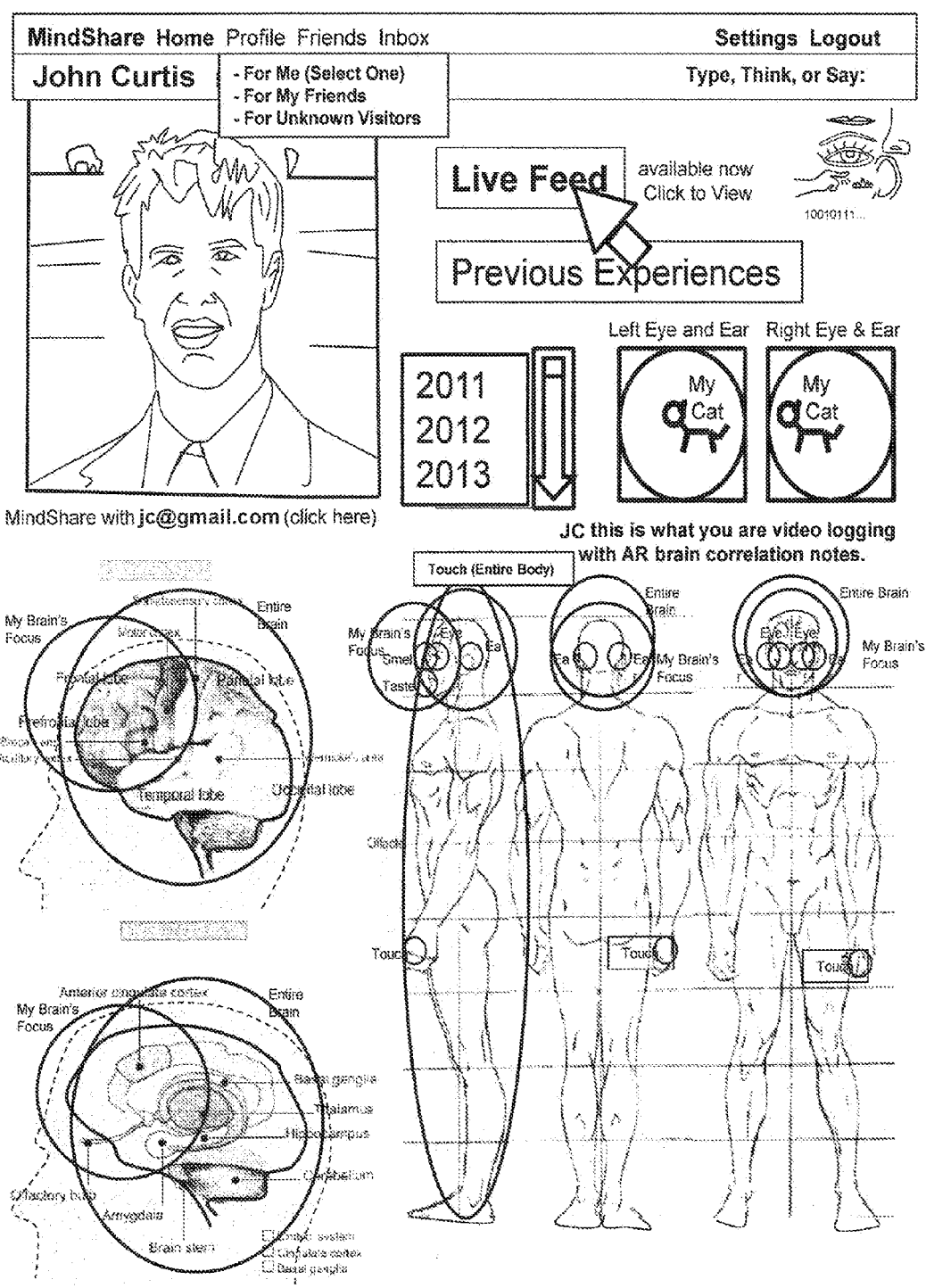

FIGS. 39a-39b each illustrate a Graphic User 101 and/or 102 Interface (GUI) 278 menu screenshot 189 for commanding and interacting over a social media network embodiment of the present intervention referred to as "MindShare"™ in the present invention. A picture of the user 101, here referred to as "JC" and/or "John Curtis" is provided in the top right hand corner of the GUI. The GUI may be hosted on the display of a host computer system 104, like a smartphone 151, HMD 135, or EMD 137, or other portable computer display borne by the user. Interaction with the GUI may be accomplished by the user operating various input devices such as the touch screen of the Smartphone, or using voice recognition, sub-vocalization, brain activity, eye gaze, or a combination thereof with the EMD and HMD. Alternatively, other user(s) 103 not wearing system, like user 101 and 102, may receive data derived from system 104 and/or 106 using devices, such as a VideoRoom™. MindShare is a life experience sharing site. The LLMEA system 100 that comprises the present invention is operated as previously described in this specification to record, process, log, and present internal and external data and information derived by said system over the telecommunication system and network 105. Remote computer servers 106 may operate in a cloud computing arrangement on the internet to process and store data and information derived from said portable system 104. The network and associated sites may be hosted on the public domain, like the internet over the Global Information Grid (GIG), or on a closed domain and network. If the internet is used it may be part of the telecommunication system and network 105.

In FIG. 39a-39e a user of the network uses the menu to select a live feed or previously recorded experience. The selection cursor is illustrated by an arrow. The user of the system employs the menu selections to define system parameters of system 100 and to allow various accesses to other users. For instance, the user may select various levels of accesses for himself, his friends, and for unknown visitors. Preferably, the owning user is the administrator and has administrative privileges. Also preferably the user sets very rigid password and security features to protect his or her privacy and guard against identity theft. For example, in FIG. 39a the user may activate video logging by selecting the "On" button shown at the middle left of the menu under "Primary Selections". A window on the menu allows the user to select what internal and external sensors are turned on for logging and what is being released to other persons or machines. The type of video logging, be it monoscopic, binocular, stereo, or spherical FOV coverage may also be chosen along with other selections under "Presentation Type". The user may also activate information derived from the brain activity sensing system, or for that matter, any of the internal or external sensing systems that comprise system 100. Thus, a window on the menu to select what the user is thinking and sensing in his or her brain may be logged by system 100. The information queried may comprise a live feed or prerecorded feed. The user may operate a slider bar on the menu to search data and information logged over time. Here indicated by 2011, 2010, and so on.

Typically the user operates the menu 278 shown as a screenshot 189 to choose what content to release to other users on the social network. Various permissions may be given to other users using menu selections. The user may even give machines permissions for control. The user may use the menu to log into a simulation or to control a robot.

For instance, a user may choose to transmit a live feed of what he is sensing and what he is focused upon in a given environment over the social network. Thresholds and rules may be set up in the system 100 to filter out information the user does not want released over the network. A window with the users face, name, contact information, and so on may be placed on the menu to identify the user. A window of the live content the user is logging and transmitting may be placed on the menu. For instance, as illustrated in the present example, "jc" the user 101 is viewing a cat in the users FOV. The user "jc" is wearing left and right electronic eye mounted display EMDs 137a-b contact lenses with integrated cameras which are transmitting his left and right eye images to computer 104 and each EMD 137a-b. Additionally, the brain activity of the user is being logged by computer 104. Computer 104 is concealed by a skull cap and wig that the user is wearing. In the present example the images the user is viewing are being processed and displayed on the menu along with an Augmented Reality overlay of text identifying what the user is viewing. The Nueral Correlates of Consciousness (NCC) identify what the user is viewing. The NCC is determined in the computer 104 by performing processing operations on the sensory information coming in from the live sensor feeds and correlating it with multi-sensory historical data that has been previously logged in by the system 100. In this manner and as previously described identification of the cat may be displayed as the textual augmented reality overlay "My Cat" on the see through electronic contact lenses the user is wearing as shown in FIG. 39a.

FIG. 39b is a graphic representation of a menu 278 shown as a screenshot 189 an administrator, here the user of the system 100, selects to command and control what internal and external sensor systems record, process, log, and present. Selected items chosen by the user are indicated within circles that may be selected as a menu control option as part of the GUI of computer 104. In FIG. 39b the user has chosen to record and send a live feed of what he is thinking in his frontal lobe, what he is hearing in both ears and seeing in both eyes. He is looking at a cat as indicated in the two boxes showing his FOV in the upper right side of the menu that have the textual overlay "My Cat" next to the cat he is observing as his CP 161-163 in the local surrounding environment 160.

Figure 39C:
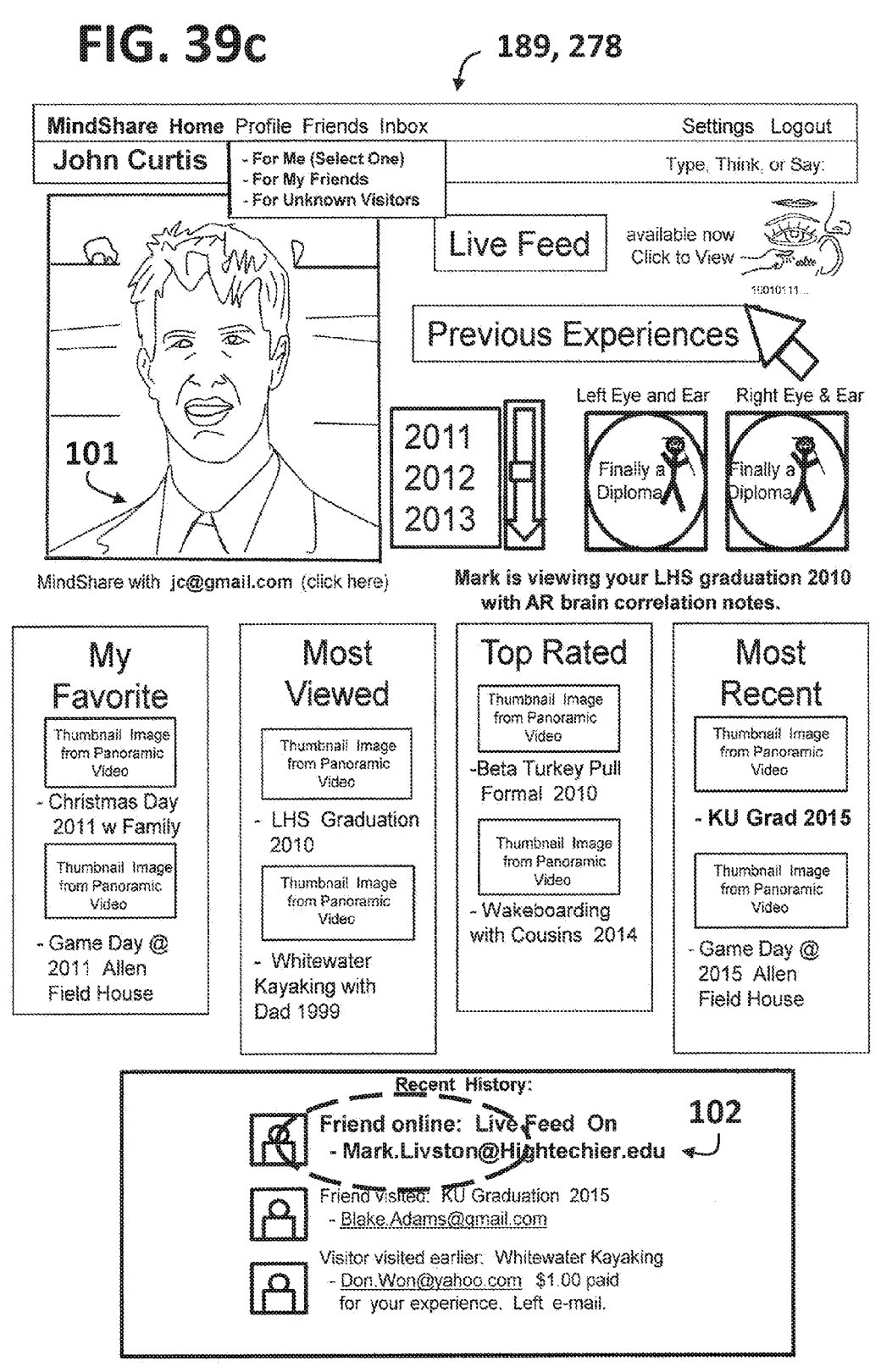

FIG. 39c is a graphic representation of a menu 278 shown as a screenshot 189 the system 100 administrator, here the user, operates to make selections to share his or others previous experiences logged into his social network site. The site may be hosted on a computer the user owns or on a server operated by an internet provider. Examples of selections include "My Favorite, Most Viewed, Top Rated, and Most Recent". The currently active portions of the menu are indicated in solid bold lines, the not chosen and inactive portions are shown in un-bolded lines. Additionally, a "Recent History" status window may be included to show who is visiting or has visited the site and their activity on the site. An oval with dashed lines illustrates a user 101 who is currently transmitting a previously recorded video feed of their high school graduation to a user 102. A payment system may be integrated into the MindShare embodiment of system 100 that charges users to download live or pre-recorded MindShare information.

FIG. 39d is a graphic representation of a menu 278 shown as a screenshot 189 of system 100 an administrator, here the user 101, makes selections from to conduct a live video teleconference with other users 102 to the nth logged into his social network site. Active selections are shown in with emboldened lines and text indicating who is participating in the two-way or multi-point teleconference and that video logging and memory enhancement sharing is turned on or active. Inactive systems are shown in un-emboldened lines. If certain settings are activated and permissions granted the thoughts in the mind of user involved in the teleconference may be queried while operating the system 100.

FIG. 39e is a graphic representation shown as a screenshot 189 of a menu 278 the user 101 operates to make selections to conduct a search on logged information derived from his use of system 100. As shown in the upper right of the menu, the user 101 has initiated a search. The user operates the present invention to conduct a search of data or information by either using interactive input devices which allow him or her to type, touch, think, or speak into input devices, such as with a key board, touch sensitive, brain activity, voice recognition, or a sub-vocalization system of the present invention. As indicated in the upper right of the menu in a windowed rectangular box, the user has indicated to system 100 that he or she wants to conduct a search using the keywords "11 Nov. 2011 Church". The user typically activates the search engine areas listed as time, place, subject, or activity. As indicated at the middle left of the menu search thresholds can be set. Thresholds establish the strength of a response to a query of information. The higher the threshold, the stronger the correlation or likelihood that the information presented matches the search criteria. As indicated at the lower left of the menu window other persons, beside the owner, may also be queried. The persons whose experiences (i.e. via panoramic video and brain activity) are logged may be deceased or living. Additionally, unique areas such as immersive interactive simulations like that described in FIGS. 41-42 and robotic control of user robots like that described in FIGS. 41, 43-45a-d may be activated in the "Other" selection window located at the lower right bottom of the menu of the search engine may be selected. U.S. Patent Application Publication No. 2009/0156955 by Jung et al., dated 18 Jun. 2009, entitled "Methods and Systems for Comparing Media Content" presents systems and methods that may be integrated with the present invention and is hereby incorporated by reference.

Figure 40A:
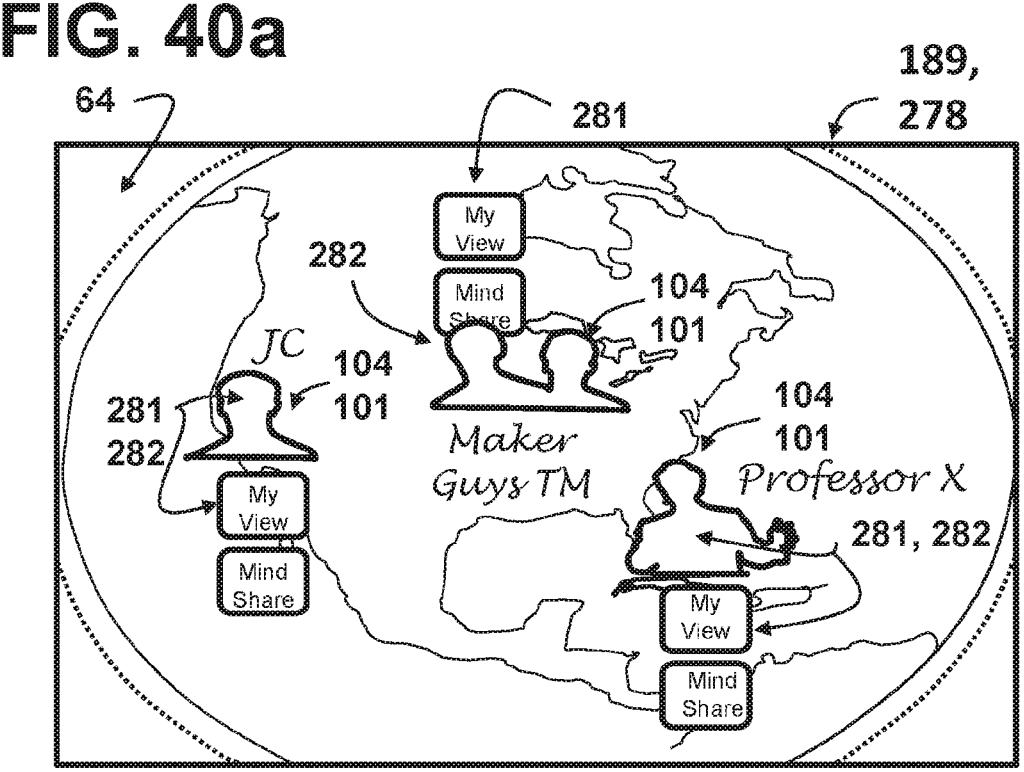
FIG. 40a shows a graphic representation of a GUI menu displayed on a host computer which participants operate to conduct a video teleconference that incorporates information derived from participants wearing the brain activity and panoramic video sensor modules in accordance with the present invention.
Figure 40B:
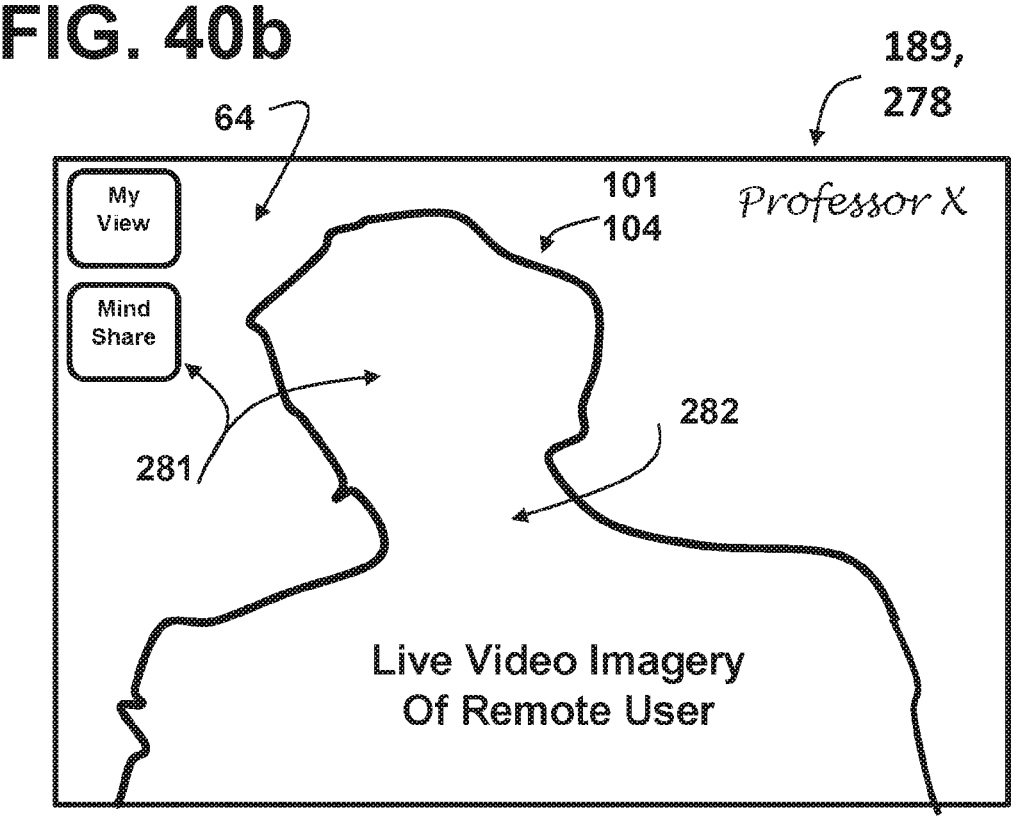
FIG. 40b is a graphic representation of the interactive immersive teleconferencing system according to FIG. 40a in which one of the users in the teleconference has been enlarged to fill the users display.

FIG. 40a-b shows another embodiment of a menu screen which comprises a simple to use homepage for social interaction of users of the present invention 100. The homepage comprises conformal imagery icons 281 in the form of computer graphics and imagery like that available in the form of a Google Earth™ background overlaid with the bodily representation of the user participants of a teleconference. The participants operate system 100 to interact on the online network. FIG. 40a-b is a graphic representation shown as a screenshot 189 of a menu 278 of the interactive display screen 64 the user 101 operates to make selections to conduct the teleconference. Computer 104 borne by the user preferably operates on the image recorded by the external video camera sensor system, including peripheral video camera sensors, to clip images of the user's body without the background and overlays the interactive conformal images over the geographic information or in an appropriate space. An overlaid silhouette or a photograph of the users may be selected using an input device that is integrated with computer 104 to initiate the video teleconference. But once the video teleconference starts, the clipped video silhouettes preferably change into a live video representation of the subject for the duration of the video teleconference. A portable wireless computerized video clipping system for augmented reality overlay onto a graphic or video background of a type consistent with the present invention that may be incorporated into the present invention is was presented at the International Society for Mixed Media and Augmented Reality Symposium 2001 by Hirokazu Kato et al. of Hiroshima City University, Japan, kato@sys.im.hiroshima-cu.ac.jp., entitled Block Assembly in Augmented Reality. FIG. 40*b* is a graphic representation of the interactive immersive teleconferencing system according to FIG. 40*a* in which one of the users in the teleconference has been enlarged to fill the users display. As previously describe with reference to FIG. 36*a*-*b* and FIG. 37*a*-*c* various ROI windowing functionality may be implemented within the present teleconferencing system social interaction homepage/website. Finally, as indicated in FIGS. 40*a* and 40*b* a local user or remote user with permissions may interactively select the "MyView" intuitive text or icon overlaid on the display to receive a live video feed 282 of what he, the user 101, is observing or alternatively receive a live video feed 282 that a remote user 102 is observing. If the system 100 includes panoramic video camera functionality, and the functionality is activated and authorized, the users of the teleconference may select panoramic video feed to zoom and pan upon so they can experience the surrounding environment at their or another users remote location. Typically display devices users may operate to observe the transmitted video during the video teleconference include a smartphone, HMD, or EMD system like those previously described in the present invention. Users logged into the "MyView" portion of the system that use a spherical panoramic camera system like that disclosed in the present invention are able to view the users face and his or her surrounding scene. Still further, as indicated in FIGS. 40*a* and 40*b* a remote user with permissions may select the "MindShare" text or icon from the menu to receive a video feed of what the user is thinking and feeling to experience the users surrounding environment in a similar immersive manner via sensory feedback mechanisms mounted on the users body (i.e. mind stimulation feedback systems and body worn force feedback systems). Correlation and translation systems that enable "MyView and "MindShare" functionality are described in devices disclosed in FIGS. 1-24 and methods and processes disclosed in FIGS. 25-35 and the supporting text. An online payment system may be integrated into the "MindShare" or "MyView" system to charge people to download information. In this manner people, such as celebrates, could charge fans for experiencing their lives vicariously as a prerecorded or as a live feed.

Figure 41:
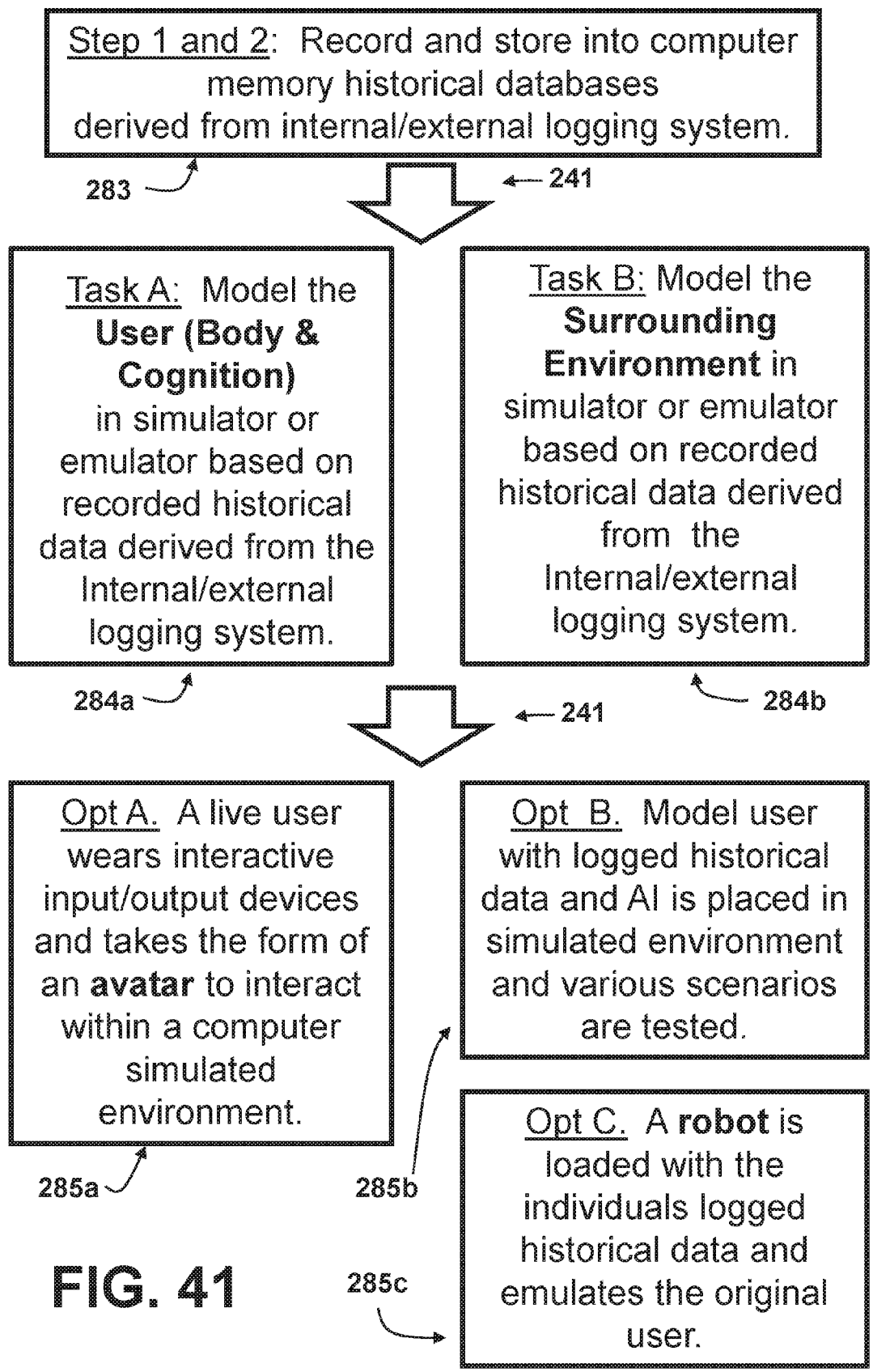
FIG. 41 is a block diagram describing system and method Tasks A and/or B, and Options A, B, and/or C to which data and information derived in Steps 1 and 2 during operation of the portable data logging and memory enhancement system may be applied.

FIG. 41 is a block diagram describing systems and methods for modeling Task A 284*a* and/or Task B 284*b*, for simulation, stimulation, and/or emulation in Option A 285*a*, B 285*b*, and/or C 285*c* to which data and information derived in Steps 1 and 2 283 during operation of the portable data logging and memory enhancement system 100 may be applied. Step 1 is recording and Step 2 is storing the computer memory historical databases derived from internal/external logging system for use in performing Task A or Task B.

Task A 284*a* is to incorporate internal data and information derived from the logging system 100 for construction of a computer generated synthetic model of the body and cognition of the user 101. Task A 284*a* is the action of computer modeling the user 101 based upon data and information that comprises the relational database 287 derived during the logging process 283. Correlation of the data and information may be performed at any point after recording the data and information. For instance, computer data from an eye tracking unit a user 101 is wearing indicates the user is looking in a certain direction where the subject is a "cat", and where the brain has historically and repeatedly correlated the image of a "cat" with a certain minimum brain activity. In this manner this the minimum required relationship between the outside world and the brain define the neural correlates of consciousness 166 necessary to recognize the conscious precept 159 of the "cat". The preceding correlation can be drawn upon at any time thereafter (i.e. Time 2) to define whether or not the consciousness of the user 101 is focused on thinking about a cat, either by system 100 analysis at Time 2 of just brain activity or external stimulation impacting on the sensory system of the user. Additionally, the likelihood of the person thinking about the cat may be calculated in a certain environment. In other words, to calculate the likelihood of what the user is thinking, data and information from both internal brain activity and physiology or the external surrounding environment may be analyzed using the system 100. Correlation calculations may be done at the Time 1, or data may be performed at a Time 2, depending on the design of the system 100. And initial correlations may also be correlated with later brain to brain, brain to environment, and environment to environment correlations to derive what a user is thinking about. In other words, the system 100 may perform correlations to other correlations and correlations correlated with other pieces data and information to define what the user is thinking, to drive the system 100 query, process, or action. Statistical computations performed by the correlation module 111 of the system 100 on logged data and information are operated upon by the computer to modify, strengthen, and/or reduce, the body of evidence in the computer that identifies neural correlates of consciousness and conscious precepts of the user 101 or 102.

In Option A 285*a* is a user 101 in the real world wears an interactive input/output devices and takes the form of an avatar in the simulation to interact within a computer simulated environment 190. In Option B 285*b* the user 101 is modeled with historical data and AI is placed in a computer simulated environment and various scenarios are tested. And finally in Option C 285*c* logged data and information derived from system 100 that reflects the user 101 is loaded into a robot 286. Actions by users, subjects, and objects modeled in the synthetic environment may be constructed using computer image texture mapping three-dimensional modeling software or firmware. In such an instance, historical records of responses to certain stimuli of a user or object in the surrounding environment are captured by the video logging system. For instance brain activity captured by the portable AMR system born by the user is associated with an image of a physical action in surrounding environment, such as an impending automobile collision. Then when a situation in the synthetic environment is encountered the object or user reacts in a similar manner. Or in the simulation, alternative courses of action may be tested. Lessons learned in the simulation may be applied to real life situations in order to improve the performance of the user or others. Besides an actual living user wearing interactive devices to interact as an avatar within the synthetic environment, historical data from the video logging system may be introduced into a machine to drive the simulation. In this instance the machine operates to take the form drives the simulation. Avatars may represent another being, machine, or the user. Avatars similar to the user may be constructed in the simulation using simulation modeling techniques and tools know to persons skilled in the art of live and virtual computer simulations.

Task B 284*b* is to incorporate internal data and information derived from the logging system 100 for construction of a computer generated synthetic model of the environment 284*b* surrounding the user 101. As disclosed in Patent '794 and '576 by the present inventor synthetic environments logged using the present invention are built by mapping imagery and deriving shape data recorded by stereoscopic and/or panoramic camera system facing inward and outward that is worn or carried by the user onto three-dimensional wireframes constructed using computer graphics software and methods. The synthetic environment is also constructed by mapping audio recorded by panoramic camera system facing inward and outward that is worn or carried by the user can be associated with subjects and objects constructed using positional audio software and methods. In both cases the imagery and audio may be driven by associated physics and actions of subjects using software and methods applied to the constructed models. Interactive devices such as data gloves, data suites, head mounted position sensing systems, geospatial positioning systems, eye-tracking system, joysticks, trackballs, mice, keyboards, as well as other devices may be used to interact with the simulated environment. Interpolation and extrapolation in the construction of objects and subjects not completely heard or observed can be constructed based on rule sets to complete the back side of scenes and expand upon portions of the synthetic simulated environment. As described in Option A, B, and C of FIG. 46 synthetic beings are constructed by incorporating logged data using the actions and information recorded and derived using the method and system 100 in the present invention which will be discussed below in more detail in the next few paragraphs.

Figure 42:
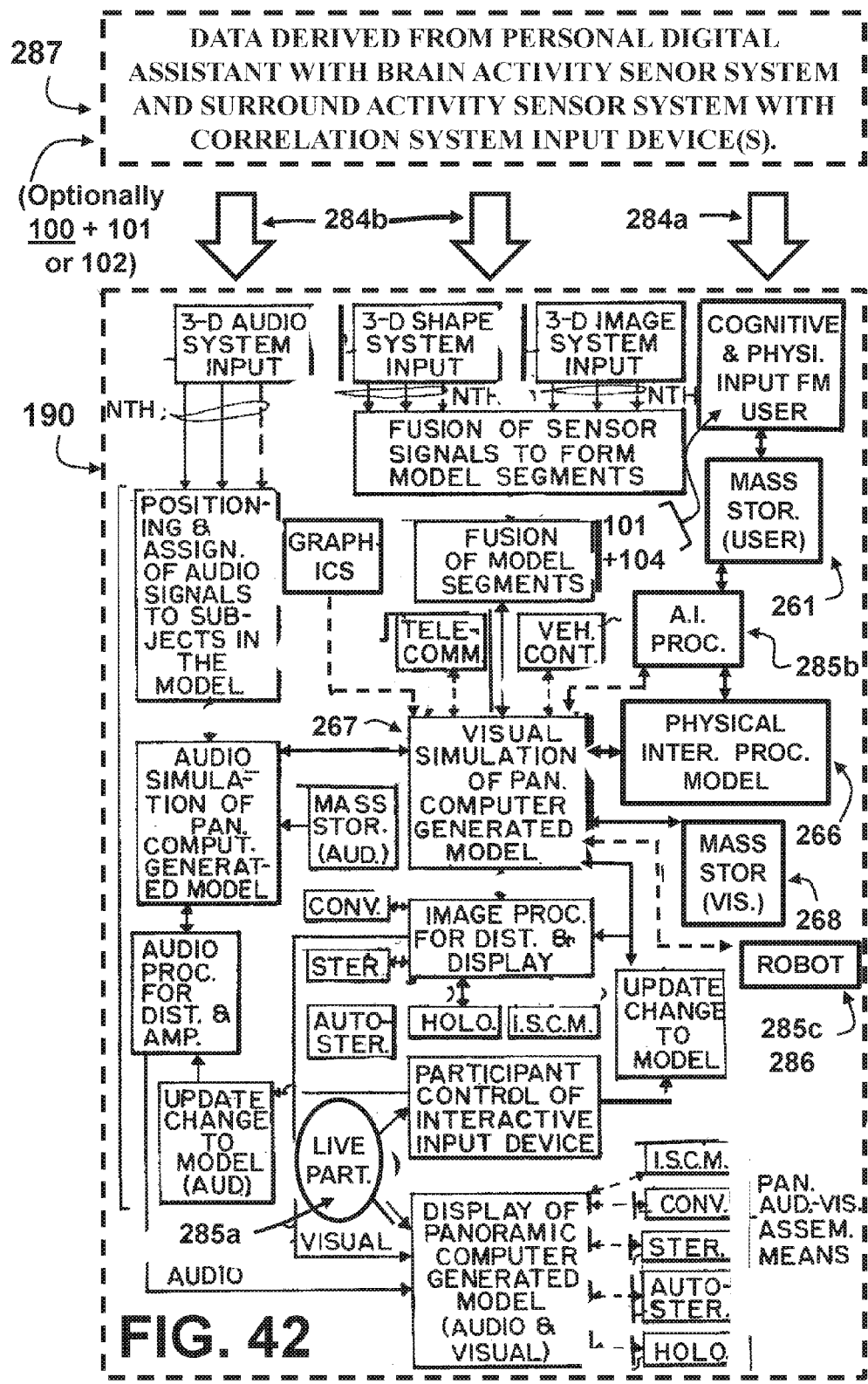
FIG. 42 is a block diagram of an example simulation system that incorporates inputs derived from the surround sensing system and brain activity sensing system consistent with FIG. 41 Option A and/or B in accordance with present invention.

FIG. 42 is a block diagram of the present invention 100 integrated with a simulation system 190. Stored data and information 287 derived from the LLMEA 100 system is coded into computer data and information that is compatible with the simulation system. Three-dimensional objects, beings, and their actions are constructed and provide an input source 284 from the logging and memory enhancement system that comprises the present invention. For example, the host computer 104 that controls the brain activity sensing system, surround sensing system, and a correlation system to output data and information to construct the simulation database 287 which the to the simulation system 190 operates upon.

The simulation system 190 may operate on data being transmitted to the simulation from the logging system 100 in a live near-real time manner. As disclosed in Option A 285*a* of FIGS. 41 and 42 a live user may interact in near real time with simulator interactively by controlling an avatar. The user may receive interactive feedback transmitted over the telecommunications network to the user borne portable feedback systems, like a HMD, that comprise a component of the system.

Alternatively, the simulation system 190 may operate on historical data and information from system 100 that has been pre-recorded and stored in the memory of the simulation as disclosed in Option B 285*b* of FIGS. 41 and 42. In which case the avatar that represents the user is not live but is modeled using historical data and information derived from operation of the logging system 100. The example simulation system may be that like the panoramic video based virtual reality simulation systems described in U.S. Pat. No. 5,495,576 by the present inventor that illustrates the potential use of the inputs derived from the data logging system. Audio, image, shape data and information of the surrounding environment and user derived from system 100 is input 284*a* into simulation 190. User 101 internal and cognitive and physiological data and information 287 derived from system 100 is input 284*b* into simulation 190. Because of the volume of data and information comprising the cognitive and physiological database 287 representing the user a computer memory storage unit 261 is required. The user mass storage database 261 interacts with the artificial intelligence or artificial intelligence-like simulation module 285*b* to mimic the actions of the user 101. The data and information from the brain activity sensing system of the present system 100 are input into the simulation system to drive the A.I. processor 285*b* that mimics user. The A.I. portion of the simulation system 285*b* may closely mimic an avatar that represents the user of the logging and memory enhancement method and system 100 that comprises the present invention. The computer system 104 and 105 may provide direct input into the simulation. Correlation systems like that described as U.S. Pat 2009/0196493, dated 6 Aug. 2009, by Widrow et al entitled Cognitive Method and Auto-Associative Neural Network Based Search Engine for Computer and Network Located Images and Photographs), CALO, and SIRI system that communicates may be incorporated into the A.I system to provide feedback output to the user of the simulation. Preferably, the simulation comprises a visual simulator, to provide a user visual and audible feedback. But alternatively, the simulation may alternatively comprise a non-visual simulation system. Using these tools and methods the simulation the A.I. portion of the simulation system 285*b* may closely mimic an avatar that represents the user of the logging and memory enhancement method and system 100 that comprises the present invention. A physical interactions processing model 266 operates to process the user actions in the computer generated world. All entities in the computer generated world are managed of in the visual simulation 267. In this instance the modeled being's actions are based upon stored data and information that models the surrounding environment 284*b* previously derived from the logging system and input into the simulation. Computer mass storage 268 of entity information coded into the memory of the simulation 190, to include three dimensional models of entities with texture mapped imagery logged by system 100 that comprises the world that surrounds the user, is provided and is called up by the visual simulation 267 based on time and place commanded by the user of the simulation. Three-dimensional shape information may be constructed manually or autonomously based on lighting and shading of video imagery recorded by the surround sensing video camera system. Surround video camera imagery may be texture mapped onto an associated three-dimensional models constructed from an integrated surround Laser Radar (LADAR) system. A user like a being or machine, like that illustrated in FIG. 45, provides an example of a portable integrated surround video and RADAR system according to the present invention. Information and data derived from the logging system 100 in the present invention are input into the computer simulation system as panoramic imagery, spatial audio, shape information, and user physiological data and information. The logging system may be tailored for collecting data specific to the type of simulator the logged data will be used in. For instance if a stereoscopic, auto-stereoscopic, or holographic display is to be constructed using the logging system 100 then at least two views of every scene and object will need to be logged so that a corresponding visual model may be built and displayed. Similarly, if an ambisonic/surround sound system is to be constructed then a plurality of microphones facing outward from the subject will need to be logged so that a corresponding audio environment can be constructed later in the simulator.

It should be noted that logged data and derived information according to the present invention may be operated upon by the simulation 190 to drive and influence decision making of users and robots in the real world. For example, an actual user may transmit his location into a simulation where the user is represented as an avatar. Given the users situation in the real world, the simulation runs fast forward to determine likely outcomes. Then the simulation transmits back to the user or robot in the real world recommended course of action to take in the real world which are likely to yield the best outcome for the user. As discussed earlier a user or recipient of the derived data and information 287 may share live or pre-recorded instances of their external or internal sensory logged data or derived information with other users of the a social network that has access to system 100 over a social networking system to assist in making decisions based on the outcome of the simulation.

Still alternatively, it will understood by those skilled in the art of simulations that the simulation 190 may operate on both live and stored data and information derived from system 100. In this instance the simulation accommodates both live input and output as described in Option A 285a and virtual or constructive input and output as described in Option B 285b of FIGS. 41 and 42.

Finally, as shown in Option C 285c of FIGS. 41 and 42 a simulated robot 286 may be loaded with the user's individuals historical data and information to emulate the original user in the simulator independently fashion. Or additionally, it is known to those skilled in the art that a user may remotely pilot or interact with a real robot 286 in a live interactive fashion outside but in communication with the simulator.

Figure 43:
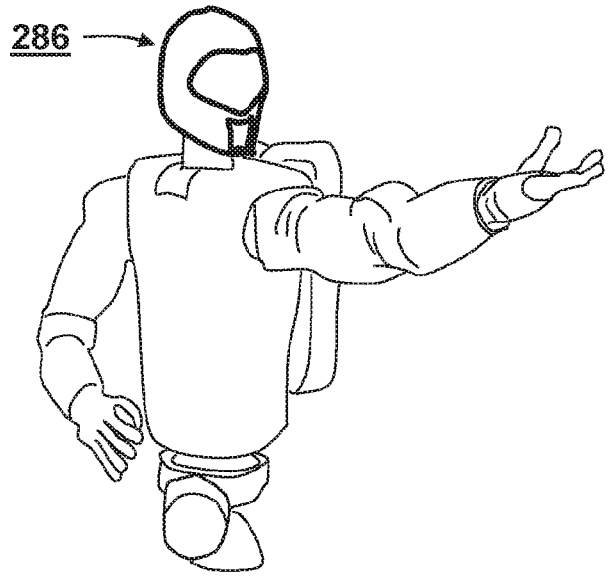
FIG. 43 is an exterior perspective drawing of a robotic system loaded with data and information derived from a previous user or recipient consistent with FIG. 41, Option C in accordance with the present invention.

FIG. 43 is an exterior perspective drawing of a robotic system 286 of a type that may be integrated with the present invention. The exterior of the robot incorporates external and internal sensing systems previously described in the system 100 of the present invention. The robot incorporates data and information derived from the logging portion of the system 100. The robotic system may include an A.I. or A.I. like system like CALO. The host computer system 104 (i.e. a smartphone) and 106 (i.e. a remote computer server on a network) may provide direct input into the robotic system. The computer simulation system may be like that described in the Woodrow et al patent and the CALO system which logs data in and derives "neural correlations of consciousness" from external and internal sensor outputs is incorporated to define the actions of the robot. Using these tools and methods the robot may closely mimic the user or users from which data was derived. The robotic system includes an electrical generation, storage, and control system, propulsion system and other components standard to a robotic system and well known to people in the robotics industry who construct robotic systems that attempt to emulate human beings.

Figure 44:
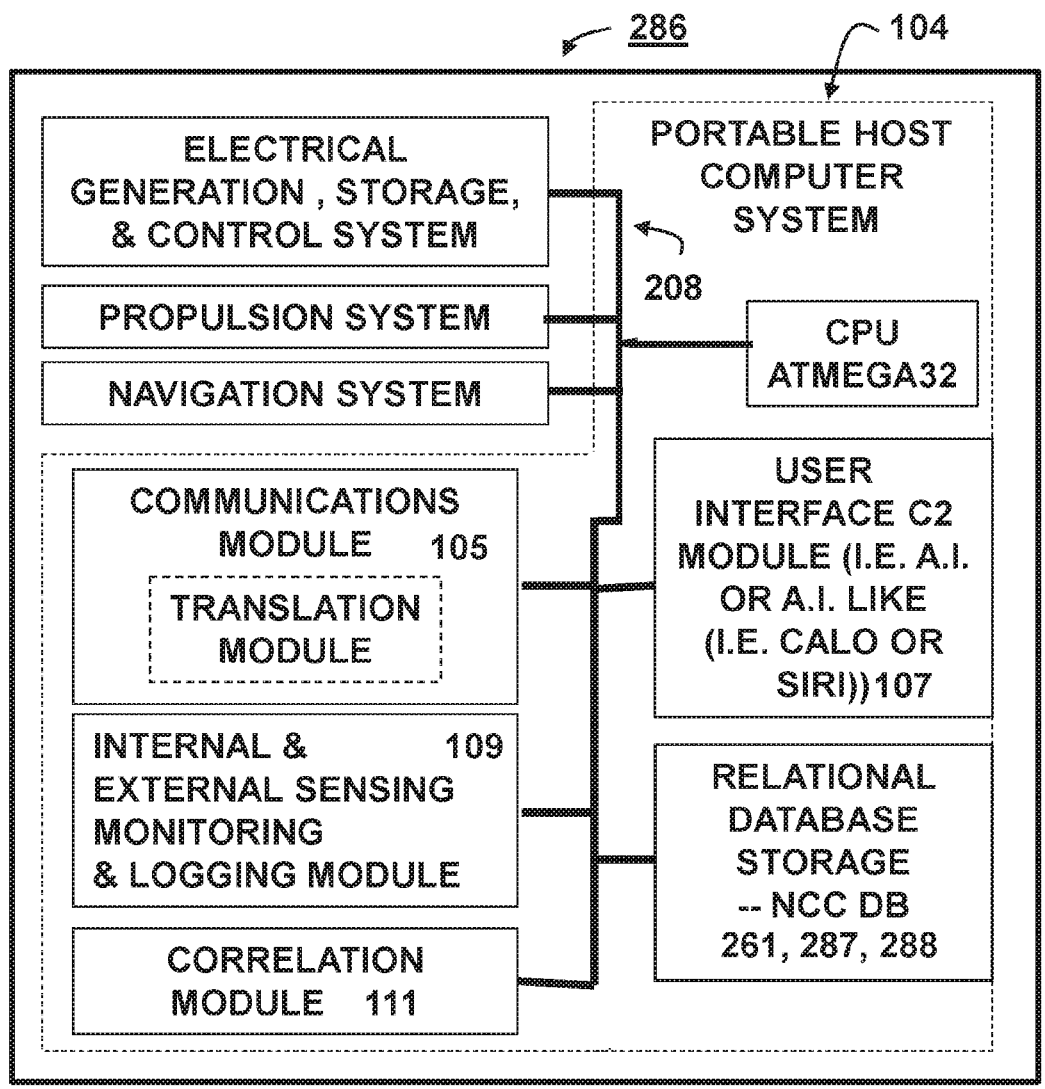
FIG. 44 is a block diagram disclosing the general method of using the information derived from the data logging system to drive the actions of a robot consistent with FIG. 41, Option C of the present invention.

FIG. 44 is a block diagram disclosing the general method of using the information derived from the data logging system 100 to drive the actions of a simulation system or robotic system 286. A robot that mimics at least some portion of one or more individual personalities of a user 101 is constructed. The robot may be constructed and sent into a hostile environment that only a specially constructed robot is able to survive. The hostile environment may be deep in the ocean or outer space. Historical data and information from the video logging system may be introduced into the software and firmware of the robot to drive the actions of the robot. The robot's computer may incorporate artificial intelligence or rule based computing to drive the robot. Still referring to FIG. 44, the data and information from the brain activity sensing system of the present system 100 are input into the onboard database derived from the logging system memory of the robot system to drive the robots actions. The composite host processing system of the host computer system 104 or a remote computer processing system 106 may provide direct input to the robot. The robot may include a user interface C3 module 107 equipped with CALO and SIRI like software and firmware applications that run on the host computer that communicate to a being or another machine. Correlation systems like that described as U.S. Pat. 2009/0196493, dated 6 Aug. 2009, by Widrow et al entitled Cognitive Method and Auto-Associative Neural Network Based Search Engine for Computer and Network Located Images and Photographs) are included onboard the robot. Internal and external sensing monitoring and logging module 109 processes incoming data from the robots surround video camera system and other sensor systems and transmits the data over system bus 208 for processing by correlation module 111. The data and information from the internal and external sensing monitoring and logging module 109 and correlation module 111 is stored in the relational database storage 287 that includes the user 101 derived NCC database 288. This data may be queried by the robot 286 or a remote user 101-103 over a telecommunication network and system 105, or in much the same way NASA today interacts with deep space probes.

FIG. 45a-d are a series of illustrations showing the present invention integrated onto a robot 286 with a plurality of sensor array 290 that includes a visual system that comprises a camera system 2 that includes at least one image capture unit 114, an audio unit that includes at least one microphone 51, and a three-dimensional digitizing system comprising at least one small conventional radar or ladar unit that includes at least one radar or ladar 42 unit. The camera 114, microphone 51, and ladar 42 each have overlapping field-of-regard (FOR) coverage 292. The overlapping coverage enables each of the array of sensors to record an image, audio, radar or ladar signature of a given side of a user within the FOR coverage of the each array 290. The array is oriented outward from the robot. Images, audio, and shape signatures from adjacent and/or overlapping arrays may be sampled and processed by system 100 to record any portion of the surrounding FOR coverage about a user. The array 290 may be placed on a rigid or flexible material covering that is worn by a user to cover an entire or only a portion of the user. The user may be a machine or being. An exoskeleton may be incorporated to help support the weight of the support material on which the sensor array and associated support electronics are situated. The exoskeleton may be hidden beneath the array when worn by a user. Image, shape, and acoustical signatures from each of the arrays are transmitted by a plurality of cable 7a-c (i.e. (wire or fiber optics) or (wireless transmitter or transceiver (not shown)) to a signal processing means of system 104 as illustrated in FIG. 44. FIG. 45a is an enlarged perspective drawing of the exterior of the robot with the sensor array called out in a circular area in FIG. 45b for descriptive purposes. A plurality of array 290 may be placed side by side in a continuous outward facing manner forming the curved outer surface of the robots head in order to achieve substantially spherical composite coverage of the sensor arrays mounted on the robot. The sensors are securely fastened to the robots head by conventional means, such as adhesive or mounting screw 289 or adhesive (not shown). FIG. 45c is a perspective drawing of a single array 290. FIG. 45d is a diagonal sectional diagram DD of the sensor array shown in FIG. 45c.

As illustrated in FIG. 44, signatures from the array are operated upon by the robots host computer processing system 104 to guide the robot, and data and information is selectively filtered and stored into memory to build a database derived from the correlation system. The host processing system 104 continuously interrogates the correlation system 111 as new information comes into the user interface Command and Control (C2) module 107 operates to drive the action of the robot 286.

Figure 46:
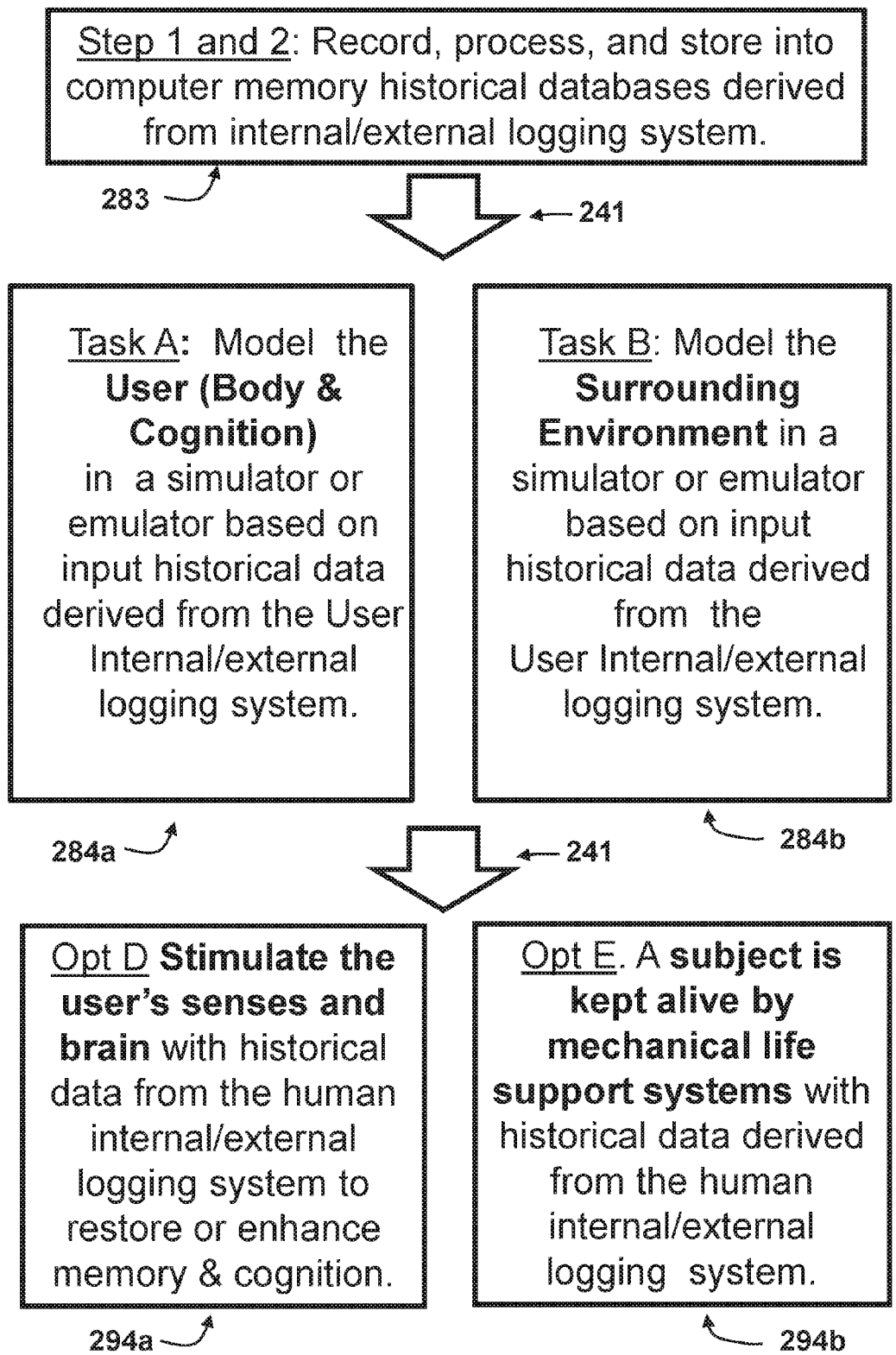
FIG. 46 is a block diagram that illustrates a method by which historical data recorded and processed by the data logging system of the present invention is operated upon by a computer to stimulate the physiological processes, like the brain of a recipient, to re-stimulate existing brain cells, stimulate the growth of new brain cells, and/or stimulate implanted brain cells and/or regulate the physiological state of a recipient on a life support system.

FIG. 46 is a block diagram illustrating the application of inputting data and information derived from the operating system 100 into living beings. This is accomplished by applying data and information derived in Steps 1 and 2 283 during operation of the portable data logging and memory enhancement system 100 to Tasks A 284a and/or B 284b, Options D 294a and/or E 294b. To this end the system 100 is operated to record, process, and store historical data and information, depicted in block 283, of a user 101 at a given time one (T1) and location/place one (L1). Individual times and locations may be aggregated to record event sequences for recording, processing, storage, analysis, and presentation within system 100. These sequences are referred to as T1 to the nth and L1 to the nth. The recorded data and information may undergo various levels of processing prior to being introduced or acted upon by computer 104. Option D 294a is a method in which historical data and information recorded and processed by system 100 is operated upon by at least one electronic device to stimulate physiological processes of a patient and/or recipient user. For example, to stimulate the brain of a recipient, to re-stimulate existing brain cells, stimulate the growth of new brain cells, and/or stimulate implanted brain cells. FIG. 46 also discloses an embodiment of the present invention, referred here as Option E 294b, which incorporate the derived data and information logged by the system 100 into computer systems and biological systems that drive and regulate the physiological state of a recipient user on a life support system. The internal and external logging module 109 and computer correlation module 111 of system 100 operate on the recorded and stored data to build a historic database. All data and information submissions have at least a time stamp, which preferably includes the time and date, and a location or global positioning system stamp. Each instance of a submission to the database starts at Time 1. The data and information is processed by system 100 to identify CPs and derive NCCs. Databases of logged data and information are typically stored in computer 104 or 106 memory where the data and information has been translated into computer language which is able to be processed by computers 104 or 106. Computers 104 or 106 process new and old data and information to build a database that represents a body of knowledge and understanding based upon input external and internal sensory data collected by modules 109 and 111. Data and information operated upon or presented to a user at T2 may comprise raw data and information, data and information derived from raw data and information, or metadata derived from system 100. The stored data and information may include imagery, audio, and other sensory information along with various other typical computer operating system and application code. The computer may include A.I, A.I-like, or no A.I application functions. Preferably the data and information is put into the computer is translated into a common computer language for ease and speed of manipulation by the computer operating on the data and information. The computer system 100 may have the capability to translate analog signals into digital signals and vice versa depending on the exact design of the system and desired application. For instance, recalled historical data and information derived from the video logging system 100 may be replayed by use of a computer video graphics card or processing module in system 100 in an audio-visual multimedia format compatible with a user presentation device (i.e. a head mounted display) to re-stimulate existing brain cells, stimulate the growth of new brain cells, or stimulate implanted brain cells. Modeling the body system of the user is derived from the internal and external sensors that record and store the activity of the user in a given environment by incorporating system 100. Within the system 100, modeling the body 284a systems of the user may involve replicating any one, a combination, or all of or some portion of the physiology attributes that make up a user, to include the: nervous, muscular, circulatory, respiratory, gastrointestinal, integumentary, urinary, reproductive, immune, endocrine system. External sensors that record the peripheral areas of the body may be used as input in collecting information that is operated on at a later time to help replicate a user. For instance, the camera sensor 2c in FIG. 1a-c, is operated at Time 1 to record facial features of the user. The facial representation may be correlated with brain activity and imagery representing the conscious precept the user was focused upon at a given time and place. Those same attributes may be replicated when the user is simulated in the same or a similar simulated environment. In this manner a body of information is built up in a database that the computer simulation system may be operated upon to emulate the user.

Option D 294a describes a method of stimulating the senses of a user 101, 102, or 103 with corresponding historical data and information derived from a user operating the internal and external logging system 100. Electronic devices, including the computers 104 and 106, are operated to playback portions of the data and information recorded by the system 100 into electronic user feedback and presentation devices. Feedback and presentation devices of a type that may be operated to provide feedback data and information to the user include: Panoramic display systems for visual stimulation of the user; surround sound acoustical systems for auditory stimulation of the user; haptic and force feedback systems for tactile stimulation of the user; smell replication systems for olfactory stimulation of the user; and taste replication systems for gestation stimulation. In order to increase the retention of data and information introduced to the user immersive feedback and presentation device(s) are employed to increase the effectiveness of loading the brain of the user. Feedback and presentation is based on historical data derived from system 104 and/or 106. Additionally, repeated playback of the data and information may be utilized to increase retention of the user receiving the data and information. In this manner historical and derived data and information from system 100 is introduced to the user at a later time (T2, T3, Tnth) than recorded so that the information may be reiterated, retained, and operated upon by the brain and central nervous system.

Option E 294b depicts the action of keeping a being alive by means of a mechanical life support system which receives input from historical data derived from a user 101 internal/external logging system 100. In the present context to emulate means to equal or surpass the cognitive or information processing abilities of the user 101.

Figure 47:
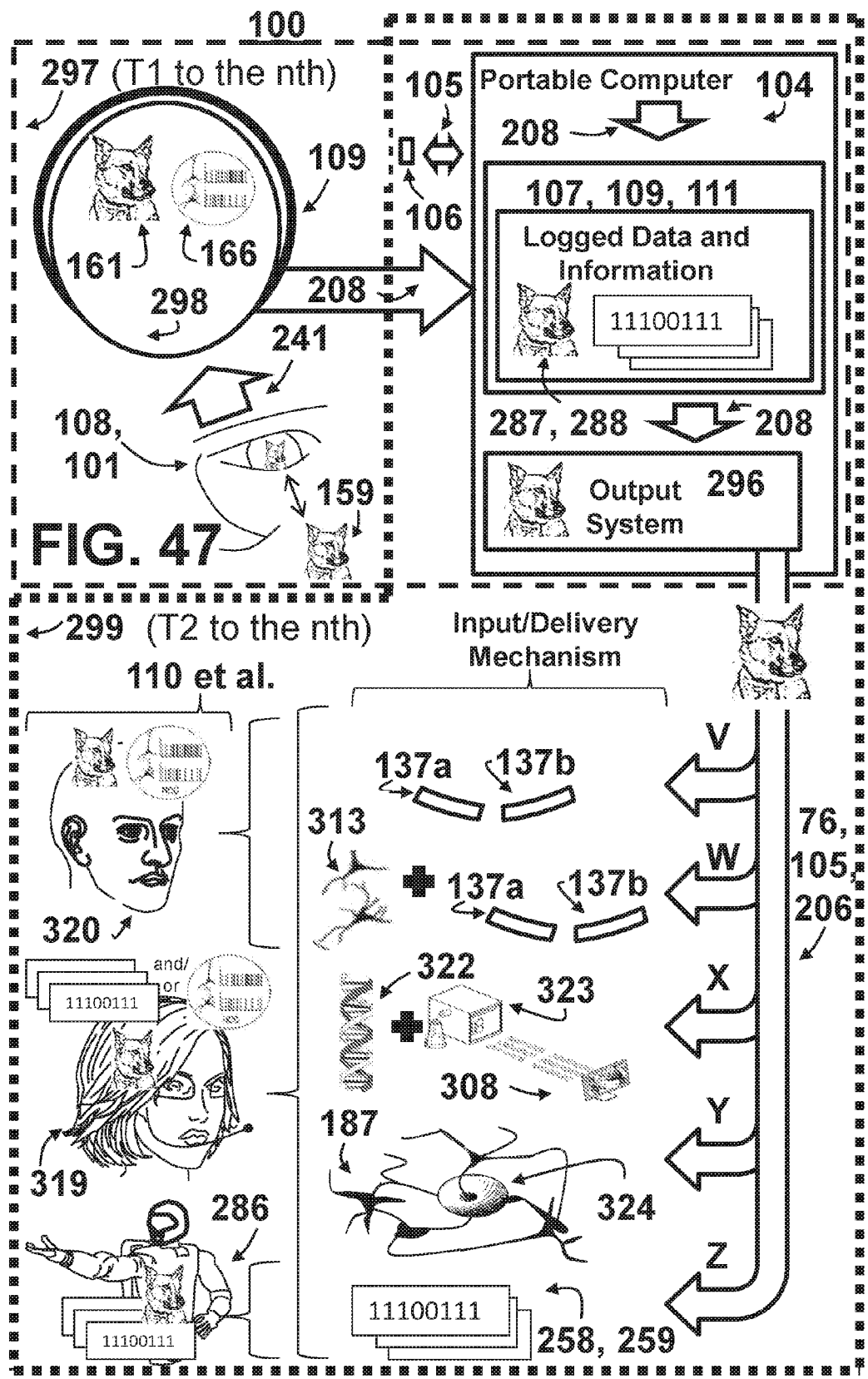
FIG. 47 is a schematic diagram that illustrates systems and methods that data and information logged and derived from the internal physiological sensor systems and external surround sensing systems processed by the present invention may be input into a recipient being, machine, or bio-mechanical system according to FIG. 46 to facilitate enhancement, transcendence, replacement, or substitution of at least some portion of a recipient being, machine, or bio-mechanical system in accordance with the present invention.

FIG. 47 is a schematic diagram that illustrates Option D described in FIG. 46 which consists of stimulating a recipient 110 beings senses and brain with historical data and information derived from the human internal/external logging system to restore or enhance memory & cognition. FIG.

47 illustrates data and information 287 derived from the portable LLEMA system 100 at time one T1 to the nth from user 101 is operated upon to provide utility to a recipient 110 at time two T2 to the nth by operating system 100. A dashed line 297 indicates an event that took place at an earlier time one T1 to the nth recorded by the sensor module 109. A dotted line 299 surrounding subject matter indicates an event is taking place at later time two T2 to the nth. The same system 100 operated at time one T1 to record, process, and log data and information may be operated by a user at a later time two T2 to recall, process, transmit and input data and information for input to a recipient 110. Time one T1 and time two T2 refer to and may comprise either an instance or period of time. For instance, Time 1 T1 and time 2 T2 may be near real time (i.e. milliseconds) or very far apart in time (i.e. years). The oval shape in the drawing represents the brain 298 of the user 101. For example, in FIG. 47a user 101 at starting time one T1 activates the portable system 104 sensor monitoring module 109 to record brain activity signatures and external sensor signatures of the surrounding environment over a given timeframe. The signatures are stored as data and information 287 in the memory of computer 104 and/or remote computer server 106. The data and signatures from sensor module 109 are read into memory are operated upon by the computer 104 and/or computer 106. Signature data and information is processed in the correlation module 111 of computer 104 and/or 106 to identify relationships and NCCs. A record of the NCC's identified along with supporting data and information denoting the relationships between the data and information is placed in and comprises a NCC database 288 which is stored in the memory of computer 104 and/or remote computer server 106. Supporting data and information preferably includes metadata that relates the derived NCC's information back to a filing system that comprises external signatures (i.e. video imagery signatures and audio signatures, geo-spatial data, sub-vocalization data, etc.) and internal signatures (i.e. brain activity and brain activity patterns). The operator of system 100, which may be the user 101, who operates an interface device to set the parameters and metrics of the system 100 that define thresholds of the data and information that define the NCCs of a specific user. System hardware and software designers will typically construct the system 100, including the GUI, so that the system 104 and/or 106 is operable to achieve the results described herein. The NCC database symbolizes the fundamental digital representation of how the user perceives the world.

Still referring to FIG. 47, computer 104 may incorporate various types of filing systems and tags to organize the data. For instance the data may be filed or tagged by chronological, geographical, subject matter, or another method to facilitate memory storage and retrieval objectives. Once established the NCC database may be updated at any later time two T2 to the nth by operating the system 104 and/or remote computer server 106. The NCC database may be updated at follow-on data search engine and logging instances. And check-points of NCC data may be stored and follow-on data search engine and logging instances to create back-up databases. Data and information recorded by system 104 may be offloaded over a wired or wireless network 105 to a remote computer system 106 for computer data and information storage and processing in order to reduce the demand on portable system 104. System 104 and 106 may be operated in a selective or continuous mode during the life of a user. Redundant, repetitive, or unwanted data and information may be filtered out through computer processing at the time of recording or at a later time either automatically, based on a rule set, or by a user or operator operating system 100. User and operator querying and downloading the NCC database, a portion of the NCC database, information and data the NCC was derived from, derivations from the NCC database, or an update to the NCC database may be accomplished by using various database filing and query systems known in the computer industry. For instance, related NCC data and information may be stored on computer media familiar in the computer industry in temporary and/or permanent memory of system 100. In the present example a dog 159 in the real world surrounding environment 160 in which the user 101 is wearing system 100 senses, records, processes, and presents information. The system 100 acts on brain activity signatures 163 that equate to the Conscious Precept (CP) 161 representing the dog in the brain 167 of the user being 101. Information related to the Conscious Precept of the dog is correlated with signatures of a subject, activity thought, or memory to derive and define the Neural Correlates of Consciousness (NCC) 166. The NCC, data, and information from which the NCC's are derived represent a computerized relational database of information on how the user 101 perceives the dog 159 and other precepts in a use's mind. At least some portion of the NCC and/or corresponding data and information, for say a "dog", is passed on to a recipient 110 at time two T2.

The lower half of FIG. 47 illustrates an embodiment of the present invention in which at least some portion of the NCC database derived at time one T1 from user 101 is downloaded at a later time two T2 into the memory of a recipient 110. System 100 components and recipients 110 et al are bounded and defined by dashed line 299 in order assist in illustrating the case example that takes place at time two T2. A recipient 110 in the present invention may be a living being 320 (i.e. a person 108), machine 325 (i.e. a robot 286), or combination thereof (i.e. a bio-mechanical system 319). The recipient 110 may be a user 101 who wore system 104 and logged the data that is to be presented or a recipient who did not log the data that is to be presented with the logged data and or information derived from the logged data. Furthermore, recipients 110 may themselves incorporate system 100 to create their own logged data and information for personal use or shared use with other recipients. And optionally, a recipient 110 user may be a clone of the user 101 whose appearance is identical to the user who logged the data. Data and information transferred from system 104 and/or 105 to a recipient 110 may be correlated or not correlated, depending on the design of the recipient whom the information is to be input into. Data and/or information input into a recipient 110 is processed to be compatible and tailored for input into that recipient.

For instance, in the lower portion of FIG. 47 capital letter V depicts a embodiment of the invention in which video imagery is output over a wired or wireless telecommunication system and network 105 from output module 296 of computer 104 and/or 106 at time two T2. The video signal is transmitted over communications local link 76 (wireless), 206 (wired or fiber optical), or telecommunications system and network link 105 for display to EMD's 137a and 137b worn by the recipient 110. Optionally and additionally, the audio portion of the video signal may be transmitted to ear buds 138a and 138b previously described in this text over either similar link 76, 105, or 206. The recipient 110 being 320, here person 108, sees the imagery of a "dog" in the EMDs and hears the audio recordings of the "dog" barking in their ear buds. The imagery and audio presented from output system 296 at time two T2 is transduced by the eyes and ears that comprise a portion of the sensory system of the recipient 110. The audio visual content is transmitted from the eyes and ears of the recipient over the central nervous system to the brain where brain cells are stimulated or formed. In this manner forgotten information is presented to reinforce, restore, or create new brain cells in the recipient 110 being 320.

The letter W illustrates another related embodiment similar to V. However, in embodiment V prior to presenting imagery and audio to the recipient 110 being 320, stem cells 313 are implanted and corresponding stem cell therapy is implemented. Stem cells for implantation receivable of the logged or derived information thereof according to the present invention may be created in vitro or in vivo. Implantation of the stem cells in to a recipient being may be by any of a variety of methods to include brain surgery or injection well-known in the medical profession. In this manner stem cell implantation can be used to replace, restore, and/or create new brain cells and restore or create new memories using data and information derived from system 100. Once implanted differentiation and migration of implanted stem cells is possible given the appropriate stem cell therapy. An oval shape illustrating brain cells with a corresponding NCC signature overlaid over the recipients head in embodiment V and W illustrates that the video of the "dog" presented at time two T2 to the recipient is transduced to either reinforce, restore, or create the memory of the "dog" by either restoring or creating new brain cells in the brain of the being 320. After stem cell implantation, cell therapy, and audio-visual presentation of data derived from system 100 is presented, or if only audio-visual data derived from system 100 is presented, a test may be conducted to determine the presence or absence of the information of the "dog" in the memory of the user by operating system 100. Optionally, system 100 may be may be programmed to instantaneously call-up information derived from the relational database, which includes the NCC database, and be presented to a user 101 or recipient 110 when it is detected by system 100 that the user or recipient cannot recall from memory a piece of information derived from the past. Furthermore, given access, a user or recipient of the system 100 may receive information derived from the NCC database of another recipient or a plurality of recipients as described earlier in FIG. 31.

Besides augmented cognition applications highlighted in the present invention, a final concluding objective is to enable beings to transfer more than just biological information forward by reproduction to a user's heirs and the rest of mankind. The data logged by individuals may be operated upon for programming nanobots that may be introduced into the brain to restore memory or introduce information into the neural network of the brain. Additionally, data logged from system 100 may be used in bio-engineering human systems that carry memories forward through encoding those memories in our DNA and RNA. U.S. Patent Publication 2005/0053968, by Bharadwaj et al, dated 10 Mar. 2005, and techniques disclosed in the UCD, Dublin, year 2012, publication Bioinformatics article entitled, "DNA Data Embedding Benchmark", by David Haughton, that describes a system and method for embedding information in the DNA string while still preserving the biological meaning of the string; is incorporated in full as a system and method of a type which is integrated with the present invention to encode and decode raw or correlated information derived from the present invention into human DNA. The logged information could may include a test file, image file, or audio file that in which large sequences are divided into multiple segments an placed in DNA introduced to the user human or other organism. It is therefore an object to provide a system 100 that logs a beings life experience such that a least some portions of the logged data may be codified and stored into DNA and RNA and passed to a later generations, as stored information in a living organism, a cadaver, or transfer to another living being though reproduction. DNA with encoded information derived from the present invention is implanted into a fertile egg or sperm of a human, embryo, or fetes, to transfer the information genetically using medical procedures familiar to those skilled in the art. For instance an image of a being's ancestors could be carried forward in the DNA of the being so that the being could access the image in order to see the being they evolved from. In this manner a human may transcend or pass on to his experience in the form of his memories and the lessons he or she learns throughout life. Much of the information that comprises the individual essence of a person's consciousness, including thinking process, experiences, and memory, is lost because of human mortality. The present invention may be used to help overcome that limitation by recording, storing, and reloading logged data into a post predecessor specimen. It is therefore conceived in the present invention that nanobots may be programmed with data logged into and derived from the present video logging and enhancement system. It is also conceived in the present invention that data logged into and derived from the present video logging and enhancement system may be coded into genetic DNA or RNA which may be passed via reproduction into offspring or implanted into other individuals. A person's experiences are the memories and connections that person constructs as that person journeys through life. This invention allows a person, and hence mankind, to carry forth that journey with decreased loss of information and consciousness.

The letter X illustrates yet another embodiment of the invention. Embodiment X represent a system and method wherein at least some portion of data and/or information 287 and/or 288 derived from system 100 is stored on DNA 322. Specimens of DNA 321 may be taken from the body of the user 101 or recipient who is a biological 320 or biomechanical 319 being. For instance DNA specimens may be from the skin or hair of the recipient 110. Data logged from system 100 may be used in bio-engineering human systems that carry memories forward through encoding those memories in our DNA and RNA. U.S. Patent Publication 2005/0053968, by Bharadwaj et al, dated 10 Mar. 2005, and techniques disclosed in the UCD, Dublin, year 2012, publication Bioinformatics article entitled, "DNA Data Embedding Benchmark", by David Haughton, that describes a system and method for embedding information in the DNA string while still preserving the biological meaning of the string; is incorporated in full as a system and method of a type which is integrated with the present invention to encode and decode raw or correlated information derived from the present invention into human DNA. The logged information may include a test file, image file, or audio file that in which large sequences are divided into multiple segments an placed in DNA introduced to the user human or other organism. It is therefore an object to provide a system 100 that logs a beings life experience such that a least some portions of the logged data may be codified and stored into DNA and RNA and passed to a later generations, as stored information in a living organism, a cadaver, or transfer to another living being though sexual or artificial reproduction. DNA with encoded information derived from the present invention is implanted into a fertile egg or sperm of a human, embryo, or fetes, to transfer the information genetically using medical procedures familiar to those skilled in the art.

It will also be understood to those skilled in the art that embedding information in DNA can be carried out in vitro or in vivo. For instance in vivo at least some portion of data and/or information 287 and/or 288 derived from system 100 stored on DNA may be implanted surgically or by injection using known medical procedures. The method for storing information in DNA includes software which takes information derived from system 100 that is in ASCII machine 323 language represented as a long string of ones and zeros in computer code. Then a computer program converts this code into letters A, C, G, and T, which correspond to the four chemical bases that make up DNA. The program breaks up the long string of letters and indexes them. A machine uses that data to make DNA. The DNA goes into a sequencing machine, which reads back the DNA fragments as the letters A, C, G and T. A computer program reassembles the DNA fragments in the correct order, and converts them back into ones and zeros. A computer interprets the ones and zeros as the original information and plays it back on the computer. The ASCII character set used in this example may be encrypted, stored, and then decrypted as text, audio, imagery (including video), and etc. Logged data and information from system 100 that is embedded on DNA 313 may include the raw and/or derived information by operating system 100. Data embedded DNA is a good storage mechanism under suitable conditions because when decrypted data embedded DNA has near perfect fidelity with little data loss (i.e. >99.9%), has a long storage life (i.e. hundreds of thousands of years), large amounts of data can be stored while taking up very little space (i.e. terabits of information within the size of several dust particles), and may be stored within the DNA of living cells or on non-living matter. Alternatively, it will be understood by those skilled in the art that DNA embedding may be carried out in vitro wherein the sampling and processing of tissue coding and decoding process takes place on the recipient on implanted computational modules like that shown in FIG. 16 and sampling of tissue for DNA embedding accomplished by servo devices 181 shown in FIG. 15.

Each DNA segment represents a processor to execute a particular biological process for growth and maintaining the life the host biological being. Embedding knowledge derived by humans outside the natural information inherent within DNA provides a method and tool for passing additional information between biological 320, bio-mechanical 319, or mechanical 286 recipient 110. Embedding information within DNA derived by humans outside the natural information inherent within DNA also provides a method and tool for passing additional information from generation to generation via natural reproduction or electronically depending on the specific design and make-up of the recipient.

The letter Y illustrates yet another embodiment of the invention. Embodiment Y represent a system and method wherein at least some portion of data and/or information 287 and/or 288 derived from system 100 is input into a recipient 110 by implanting or injecting at least one nanobot 324. The nanobot may serve as a delivery system for derived information to cells within the brain. Alternatively the nanobot may carry stem cells to an area of the brain that are stimulated as described in embodiment W. Or alternatively, the nanobot may deliver DNA to a location as described in embodiment X. Or still alternatively, the nanobot can deliver electronic devices, like the diagnostic device described in FIG. 48, within the brain.

The letter Z illustrates yet another embodiment of the invention. Embodiment Y represent a system and method wherein at least some portion of data and/or information 287 and/or 288 derived from system 100 is input into a recipient 110 which is a machine 286 by directly inputting computer code 258, 259 into a recipient. Input of the information may be accomplished via a ground (i.e. wire or fiber-optic) or over-the-air (i.e. radio frequency or infrared) connection.

Still referring to FIG. 47, each original user 101 has a unique set of the experiences and related brain activity that can be added to by each subsequent recipient 110 et al. The derived database 287, including the NCC database 288 provides a record unique to each user 101. Transfer of the derived relational database 287 to include historical data on CPs and NCCs unique to an individual user may be transferred or communicated by a previous user 101 prior to death or upon death to a recipient 110 using the methods and systems described in FIG. 47. For a user to pass at least some portion of his or her database 287 to a recipient the user would need to arrange for such information to be transferred by another user or in an automated manner to a recipient upon death. In such an instance, a signal from the system 104 could be sent over the telecommunication system 105 to a recipient who has the ability to be activated, continent upon death or incapacity of the original user. Because the user may not know when life will be terminated updates to the database 287 could be constantly stored in memory on a remote server 106. In this manner data and information derived from the invention could be stored in memory by a user at an earlier time/check-point (i.e. at T1) and be retrieved by a designated recipient at a later time/checkpoint (i.e. T2). In this manner a user's awareness would continue, albeit in a different being or machine than prior to the parent user's termination or incapacity. The database 287 passed is normalized and translated to a type compatible with the recipient. As long as the entire system 100 remained activated, remote system 105 could pass it's logged database 287 of a user 101 to a recipient 110 based on a given activity or after a period of inactivity of the user 110 so that the scientiousness of the user 101 is passed on to the recipient 110. It is worth noting that the recipient would possess the ability to recognize the corpse of a deceased user as his or her previous body if the CP and NCC's where successfully communicated to the recipient. Correspondingly, a recipient would possess the ability to recognize a living user as his or her previous body if the CP and NCC's where successfully communicated to the recipient. But the living user would not necessarily recognize the outward appearance of the user. Each users experience and related brain activity is based on what is logged, processed, and input. The degree to which a being 101 or 110, machine 286, or biomechanical being 319 incorporates the information derived from the present invention will be determined by the quality and quantity designed into each given embodiment of the present invention 100. Filtering out superfluous information and timely relevant delivery of derived information from the present invention is a key part in defining the fidelity of the derived relational database 287 and relationship to the original user. The degree to which the recipient is able to incorporate the information derived from the present invention will determine the qualitative and quantitative contentment and longevity of a user's life as a recipient 110 (i.e. 320, 319, or 286) in a given environment.

Figure 48:
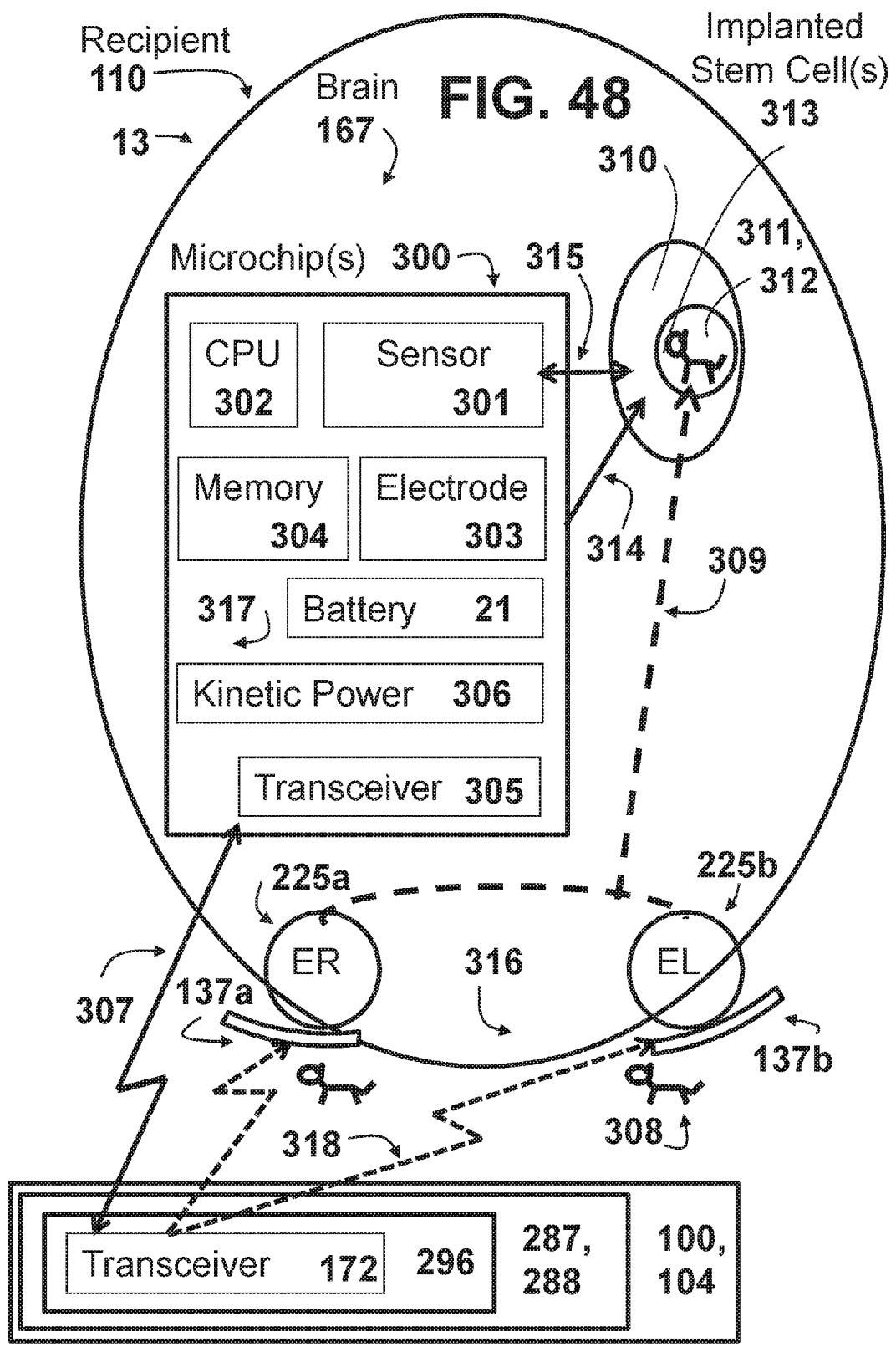
FIG. 48 is a diagram illustrating the system and method of implanting stem cells in at least one area of memory loss in a region of the brain; historical data derived from the surround sensing system or brain activity sensing system being introduced to the user in the form of an immersive simulation; and then monitoring the stem cells introduce using a brain activity sensor system to determine if similar neural precepts and normal brain activity is regenerated and memory is restored consistent with Option D described in FIG. 46 in accordance with the present invention.

FIG. 48 is a schematic diagram illustrating at least one diagnostic micro-chip 300 and at least one stem cell 313 implanted into a recipient 110. The micro-chip has the operational capability to sense neural activity, including activity sensed from an implanted stem cell, in a specific area of the brain 167. The microchip 300 incorporates an atomic-based magnetic (AMR) sensor 301 of a type referenced earlier by Kitching. A solid line with arrows indicates the magnetic field strength 315 the magnetometer registers of the brain activity. The microchip includes a computer programmable central processing unit (CPU) 302 that controls components on the microchip. The microchip includes a computer memory 304 storage capability common to computer devices. Microchip components include a transceiver 305 that receives and transmits radio-frequency (RF) signals 307 to a remote transceiver 172. The remote transceiver functions as an input and control device 296 for the microchip and receiver of data sensed by the atomic based sensor. The remote transceiver and computer input device may be incorporated into a computer system, such as a smartphone. In the present example a kinetic power generator 306 is integrated into the microchip so that the microchip can function without physical connections such as wires or fiber optics conduits running from inside to outside the skull 13. It will be known to those skilled in the art that various power generation systems may be incorporated, to include wired and wireless power transmission systems. The power generation system may include a storage battery 21. Transceiver and power generations systems may be commanded to be turned on and off in order to alleviate interference to the AMB sensor. Alternatively and additionally, an electrical stimulation electrode 303 is incorporated into the microchip. The purpose of the electrode is to stimulate an adjacent area of the brain in proximity to the microchip. The electrical signal emitted from the electrode is indicated by a solid arrow 314. The electrical stimulation is done by the electrode emitting an electrical signal into the brain. The electrical signal may be of the area were stem cells have or have not been transplanted. The purpose of stimulating a specific area is to evoke a response of the recipient user of the implanted microchip. The microchip is implanted using surgical procedures well known in the medical profession. To include sterilization of the micro-chip and/or protective covering that may surround the microchip. The components of the microchip are connected together by circuitry running through or on conventional substrata material 317 that microchips are constructed.

For example, in FIG. 48, assume a user has Alzheimer's and experiences memory loose in at least one section of the brain 167. Clinical analysis is conducted to determine what information the recipient patient has forgotten from his or her memory. For instance, the patient may be asked to recall the information at time two T2 that happened earlier at time one T1. Evidence that the information has been forgotten may be that the recipient patient responds that he or she does not remember the information. This can be tested by asking the recipient if he or she is able to recall the information and verbalize the forgotten information. Additionally and alternatively, the location in the brain where memory loss occurred may be determined by looking at brain activity records logged by the system 100. Evidence that the information is no longer resident in the memory of the recipient patient is that brain activity of the recipient patient does not react at all or even similarly to how the brain activity reacted historically at time 1 T1 when similar subject matter was presented to the user. In such an instance, the minimum criteria defining a particular NCC focus representing a stimulus that defines the particular subject matter at time one T1 will not react similarly to a like stimulus at time two T2. This can be deduced by comparing the T2 response with the T1 response recorded in the system 100 relational database 287, which includes the NCC database 288. From this clinical analysis regions, nucleus, synapse and so forth in the recipient's brain may be identified and targeted for stem cell therapy implantation.

Still referring to the present example, illustrated by FIG. 48, the right eye 225a and the left eye 225b of the recipient of the stem cells includes corresponding EMD's 137a and 137b. Existing brain cells 316 are left in place but inactive brain cells determined to be damaged and inactive brain cells in the targeted area 310 of the brain affected by Alzheimer's disease are surgically removed and/or replaced by the introduction of implanted stem cells 313 into the brain. The implanted stem cells form newly created brain cells 311 as logged information from system 100 that has been identified as lost memory of the recipient 110 patient is recalled, replayed, input, and transmitted to the wireless EMD's and earphones (not shown) the recipient 110 patient is wearing. A dashed line with arrows at each end indicates the radio frequency (RF) transmission signal 307 between the microchip 300 transceiver 305 and the input device 296 transceiver 172. Dashed lines between the eyes and implanted stem cells indicate the transmission of the input information 309 to stem cells which become the newly created brain cells with the restored information. The drawing of the "cat" indicates the input subject matter 308 transmitted for restoration of the memory lost by the recipient 110 patient. In the present example the Conscious Precept of the user 101 is derived from a real world subject 161 comprising a "cat". At least some portion of the NCC and/or corresponding data and information, for say a "cat", is passed on to a recipient 110 at time two T2 when information is transmitted to the implanted stem cells that form the newly created brain cells 311 and restored memory 312 in the brain cells that represent the "cat".

Alternatively, the microchip 300 incorporating an atomic-based magnetic (AMB) sensor 301 system of a type referenced earlier by Kitching for sensing brain activity may be mounted on the exterior of the user. A plurality of sensors may be located in the covering worn by the user and readout may be in wired or wireless communication to a computer system. The host computer system may be designed into the covering or located remotely on or away from the users body. The A skull cap, wig, or cap arrangements previously described may be incorporated to hold one or more AMB sensors in order to provide a non-invasive method of monitoring brain activity of the user or recipient patient.

Figure 49:
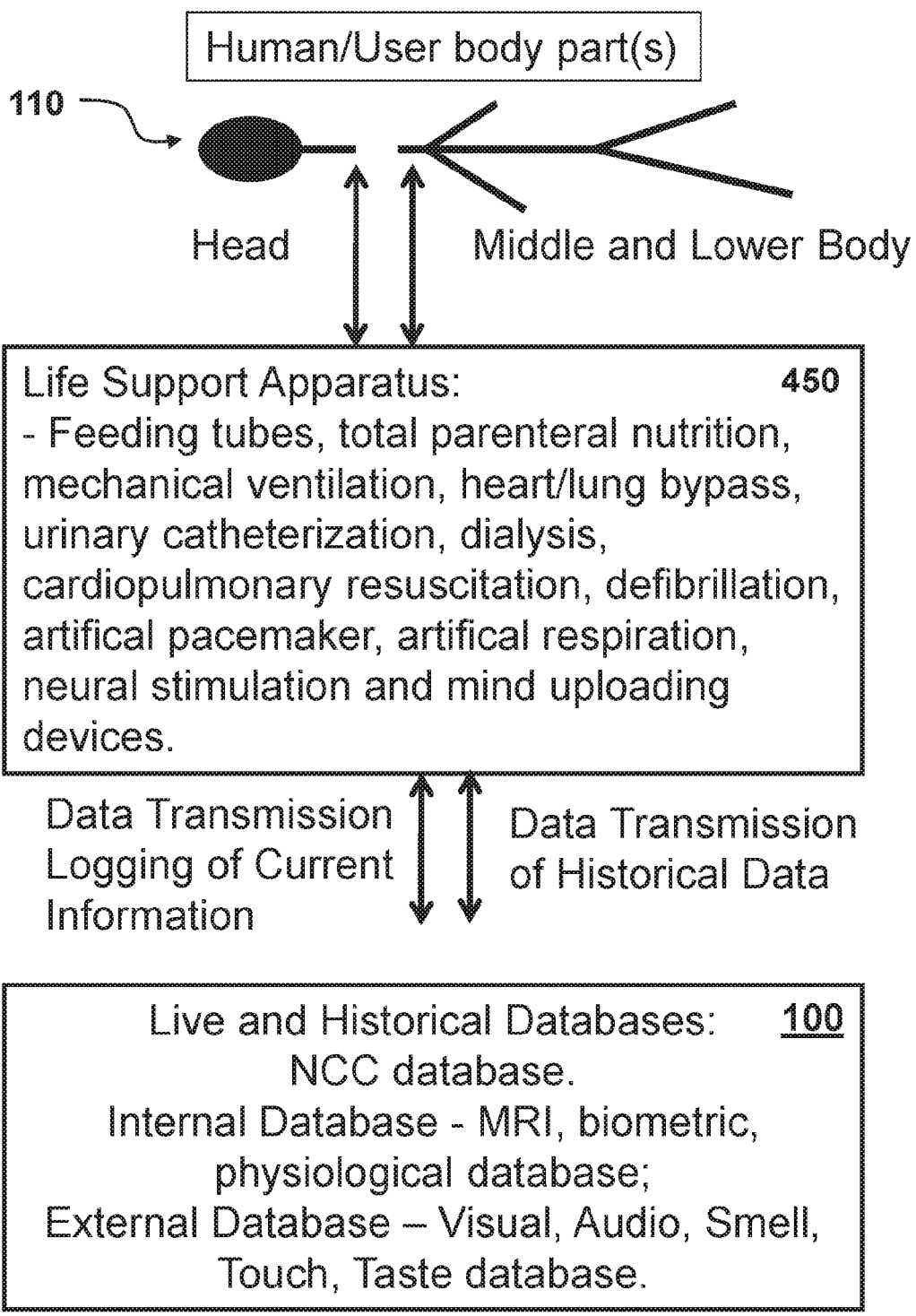
FIG. 49 is a schematic diagram illustrating computerized life support system and method of that operates upon databases derived from internal and external data logging system according to the present invention in order to regulate the physiological state of a recipient on a life support system consistent with Option E of FIG. 46 in accordance with the present invention.

FIG. 49 is a schematic diagram illustrating Option D 294b described in FIG. 46. FIG. 49 is a discloses a life support system that uses the relational database 287 derived from internal and external data logging system 100 according to the present invention. Applying the historical database to operation of the life support system can assist physicians in achieving homeostasis to a recipient. The objective being to bring the patient back to a stable condition like that at shown by historical physiological data collected by system 100 about a user 101 when he or she was healthy and stable. Life support apparatus such as feeding tubes, total parenteral nutrition, mechanical ventilation, heart/lung bypass, urinary catheterization, dialysis, cardiopulmonary resuscitation, defibrillation, artificial pacemaker, artificial respiration, neural stimulation and mind uploading devices are operated to keep a patient living. Live and historical databases derived from computer 104 and/or 106 and associated sensor systems result in an internal sensor derived database 287 from MRI, biometric, physiological sensors and an external sensors derived database from Visual, Audio, Smell, Touch, Taste sensors are sampled to maintain or restore a being or machines physiological, homeostasis, memory, and cognitive functions. As represented by the arrows between the Live and Historical Database and the Life Support Apparatus the logged data from system 100 is input into the life support systems to set the parameters the life support systems. The life support apparatus is then hooked to a user's body as indicated by the arrows to the separated body parts. The separated body parts may be maintained individually or when reattached to one another by medical professionals. As indicated by the arrows the live and historical databases, life support apparatus, and human body parts information may flow both directions to regulate and maintain the human body part(s). Besides the life support system operating on data and information 287 derived from the system 100 that was or is born by the user 101, data and information from other users 102 et al recipients 110 et al who have had successful treatments of a pathology may be implemented into the life support system of user 101 to assist in curing him or her. In this manner parameters tailored to a user may be introduced to user when he or she is on a life support system. Historical data derived from the data logging and memory enhancement system is used as a life support and restoration system.

Additionally, it is conceived as part of the present invention that clinical and non-clinical records and specimens from a user's body, while in vivo or envois, may be used to further replicate a user 101. For instance, skin and hair may be used to replicate the DNA sequence of the user in order to reproduce a detailed replication of the user. Or for instance, once a person is deceased it is envisioned as part of the present invention that the user's body may be frozen and sliced, imaged, and modeled in 3-D to form a very detailed computer simulated model of the user's entire body. Further still, besides the data recorded by the internal logging and memory enhancement system the user wears, additional internal data, such as three-dimensional full body MRI computer models and data may be added to the logged database 287. It is conceived as part of the present invention that this data may be incorporated into various simulation, augmentation, diagnostic, substitution, restoration, and emulation devices, processes, and procedures during and after the life of the user.

The invention is preferably implemented by hardware, software, and biological specimens, or a combination of hardware and software and biological specimens. The software can be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion. Thus it is seen that systems and methods are provided for allowing users to couple a portable electronic device in the head-mounted device. It is also seen that systems and methods are provided for allowing users to see the outside world while wearing a head-mounted device. Persons skilled in the art will appreciate that the invention can be practiced by other than the described embodiments, which are presented for purposes of illustration and not of limitation, and the present invention is limited only by the claims which follow.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

Having thus described various embodiment of the invention, what is claimed as new and desired to be protected by Letters Patent includes the following:

1. A user borne system comprising:
   a brain activity sensing subsystem configured to collect data corresponding to brain activity of a user;
   a measurement computer subsystem configured to generate data representing quantifications of perceptions of said user;
   a user sensing subsystem configured to collect data corresponding to user events;
   a surrounding environment sensing subsystem configured to collect data corresponding to the user's surrounding environment;
   a recording subsystem configured to record said data from said brain activity sensing subsystem, measurement computer subsystem, user sensing subsystem, and surrounding environment sensing subsystem;
   a correlation subsystem configured to create correlation subsystem data comprising relationships between said data corresponding to said brain activity of said user and said data corresponding to said user events and surrounding environment;
   a user mobile electronic device in communication with said brain activity sensing subsystem, measurement computer subsystem, user sensing subsystem, surrounding environment sensing subsystem, and recording subsystem, said user mobile electronic device including an interactive graphic user interface and being configured to:
      operate as a host computer processing subsystem for command, control, and processing of signals to and from said brain activity sensing subsystem, user sensing subsystem, surrounding environment sensing subsystem, and correlation subsystem;
      command said brain activity sensing subsystem to transmit brain activity and pattern data to said correlation subsystem; and
      command said user sensing subsystem and surrounding environment sensing subsystem to transmit processed sensor data to said correlation subsystem,
      said correlation subsystem being configured to receive and perform correlation processing operations to determine an extent of neural relationships between data received from said user mobile electronic device and said brain activity sensing subsystem, user sensing subsystem, and surrounding environment sensing subsystem to derive neural correlates of consciousness of conscious precepts of said user;
   a non-transitory computer readable medium configured to store data from said brain activity sensing subsystem, measurement computer subsystem, user sensing subsystem, surrounding environment sensing subsystem, recording subsystem, and correlation subsystem for performing queries on real-time and near real-time data received from said brain activity sensing subsystem, measurement computer subsystem, user sensing subsystem, surrounding environment sensing subsystem, recording subsystem, and correlation subsystem for determining whether to keep or disregard said data from said brain activity sensing subsystem, measurement computer subsystem, user sensing subsystem, surrounding environment sensing subsystem, recording subsystem, and correlation subsystem based on pre-established rule-sets and user interactive command and control from said user mobile electronic device; and a computer processing device configured to process and communicate at least a portion of said data from said brain activity sensing subsystem, measurement computer subsystem, user sensing subsystem, surrounding environment sensing subsystem, recording subsystem, and correlation subsystem into at least one of a recipient biological, mechanical, or bio-mechanical system.

2. The user borne system according to claim 1, wherein said user borne system and recipient biological, mechanical, or bio-mechanical system include at least one of intrusion detection software, hardware, or firmware application and information security software, hardware, or firmware application that provides at least one of firewall protection, virus protection, privacy protection, or user authentication capabilities.

3. The user borne system according to claim 1, wherein said user borne system and recipient biological, mechanical, or bio-mechanical system further comprise at least one remote sensing technology that measures distance by illuminating a target with a laser and analyzing light reflected by said target for at least one of remote sensing, contour mapping, or aiding in determining distance to said target in said surrounding environment.

4. The user borne system according to claim 1, wherein said brain activity sensing subsystem is configured to record signatures and derive measurements on at least one of a whole, region, neural, or electro-chemical interaction in the synaptic cleft of the user's brain at the molecular level in order to identify neural correlates of consciousness such that various components of perception across the user's brain that form a totality of a conscious precept identify a minimal set of components of neural material, chemical, electrical, and associated activity that define a thought or memory of the conscious precept in the user's mind or said surrounding environment, said correlation subsystem being configured to correlate and filter said components of perception to create a relational database for input into an artificial neural network that at least one mimics, supplements, or enhances the user's brain or said recipient biological, mechanical, or biomechanical system.

5. The user borne system according to claim 1, wherein said brain activity sensing subsystem includes at least one of a neuro-stimulation fiber optic light emitter or neuro-stimulation micro-electrode for at least one of diagnostic purposes, performance enhancement, or detecting performance degradation of functions of said user's brain.

6. The user borne system according to claim 1, wherein said user borne system is designed to blend into the user's natural appearance by incorporating at least one of a prosthetic device with human skin color and shape, grafted skin, synthetic skin, a display, a fashion accessory, body art, hair piece, skull cap, jewelry, cap, hat, material covering, or clothing.

7. The user borne system according to claim 1, wherein said recipient biological, mechanical, or bio-mechanical system looks substantially like a human.

8. The user borne system according to claim 1, wherein said recipient biological, mechanical, or bio-mechanical is configured to act substantially like a human.

9. The user borne system according to claim 1, wherein said surrounding environment sensing subsystem data comprises video recording play back capability for playing back video derived from brain activity signatures for comparison of real world recorded imagery versus brain signal motion imagery of the user.

10. The user borne system according to claim 1, wherein at least a portion of said user borne system is configured to be supported by an exoskeleton worn by said user.

11. The user borne system according to claim 1, wherein said user borne system includes an e-commerce payment system.

12. The user borne system according to claim 1, further comprising a spherical field-of-view camera sensor and camera sensor supporting structure configured to automatically extend in front of said user when a phone call is initiated for face-to-face video teleconferencing and retract when the phone call is completed.

13. The user borne system according to claim 1, further comprising a video teleconferencing system configured to overlay video representations of teleconference users over geographical information or imagery at each of said teleconference user's geographical or spatial location and allow said teleconference users to interact with said geographical information or imagery.

14. The user borne system according to claim 1, wherein said user borne system is configured to operate on real-time and near real-time data from said brain activity sensing subsystem, measurement computer subsystem, user sensing subsystem, surrounding environment sensing subsystem, recording subsystem, and correlation subsystem to determine a threat to said user or said surrounding environment.

15. The user borne system according to claim 1, wherein said user borne system includes a cognitive memory system comprising a neuromorphic computing system including at least one of an analog and/or digital circuit, Application Specific Integrated Circuit (ASIC), microprocessor, or other logic in hardware, software, or firmware with auto associative artificial neural networks that at least receive and process some portion of said data from said brain activity sensing subsystem, measurement computer subsystem, user sensing subsystem, surrounding environment sensing subsystem, recording subsystem, and correlation subsystem to organize, remember, and update said data communicated to at least one of said user borne system and recipient biological, mechanical, or bio-mechanical systems such that said user borne system and/or recipient biological, mechanical, or bio-mechanical system learn through experience.

16. The user borne system according to claim 1, wherein said user mobile electronic device is a head mounted device housing said brain activity sensing subsystem, measurement computer subsystem, user sensing subsystem, surrounding environment sensing subsystem, recording subsystem, and correlation subsystem.

17. The user borne system according to claim 1, wherein said user borne system includes at least one memristor operable to reflect said user as a cognitive model realized as a modern dynamic system with behavioral dynamics coded into a neural network system that achieves embodied cognition in at least one of said brain activity sensing subsystem, measurement computer subsystem, user sensing subsystem, surrounding environment sensing subsystem, recording subsystem, and correlation subsystem, said data from said at least one of brain activity sensing subsystem, measurement computer subsystem, user sensing subsystem, surrounding environment sensing subsystem, recording subsystem, and/or correlation subsystem informing the user's behavior and the user's actions through back propagation of said neural network in an iterative repetitive manner such that said user affects said surrounding environment and said surrounding environment affects said user in perception-action cycles.

18. The user borne system according to claim 1, wherein said user borne system includes an artificial neural network configured to process said data from said brain activity sensing subsystem, measurement computer subsystem, user sensing subsystem, surrounding environment sensing subsystem, recording subsystem, and correlation subsystem.

19. The user borne system according to claim 1, wherein said user borne system includes an auto-associative neural network.

20. The user borne system according to claim 1, wherein said user borne system includes a neuromorphic system configured to process said data from said brain activity sensing subsystem, measurement computer subsystem, user sensing subsystem, surrounding environment sensing subsystem, recording subsystem, and correlation subsystem.

21. The user borne system according to claim 1, wherein said user borne system includes a self-learning neural network.

22. The user borne system according to claim 1, wherein said user borne system further comprises a portable magnetoencephalography (MEG) brain activity system configured to derive some of said data from said brain activity sensing subsystem.

23. The user borne system according to claim 1, wherein said user borne system is configured to perform artificial neural network backward propagation algorithms and processing for achieving iterative learning as said user borne system receives new data from said brain activity sensing subsystem, measurement computer subsystem, user sensing subsystem, surrounding environment sensing subsystem, recording subsystem, correlation subsystem, or recipient biological mechanical, or bio-mechanical system.

24. The user borne system according to claim 1, wherein said user borne system includes an auto-association neural network configured to perform repetitive, iterative, supervised, and unsupervised machine learning to yield an output action potential into said user borne system and/or recipient biological, mechanical, or bio-mechanical system.

25. The user borne system according to claim 1, wherein said user borne system includes a cognitive model realized as a dynamic system with behavioral dynamics coded into a neural network that achieves embodied cognition in at least one of said brain activity sensing subsystem, measurement computer subsystem, user sensing subsystem, surrounding environment sensing subsystem, recording subsystem, correlation subsystem, wherein said cognition embodies the user's behavior and actions through back propagation of the neural network in an iterative and repetitive manner such that said user affects said surrounding environment and said surrounding environment affects said user in perception action cycles.

26. The user borne system according to claim 1, wherein said brain activity data is operated upon when a thought generated by said user is translated by said user borne system into at least one of text, audio, imagery, or machine language that is communicated wirelessly to said user or recipient biological, mechanical or bio-mechanical system.

27. The user borne system according to claim 1, wherein said user borne system or said recipient is configured to operate on data from said brain activity sensing subsystem, measurement computer subsystem, user sensing subsystem, surrounding environment sensing subsystem, recording subsystem, correlation subsystem, or user mobile electronic device to operate at least one actuator to assist said user or recipient system in responding to an event.

28. A system according to claim 1, wherein at least some portion of said data from said brain activity sensing subsystem, measurement computer subsystem, user sensing subsystem, surrounding environment sensing subsystem, recording subsystem, and correlation subsystem is communicated to and operated upon by a biological, mechanical, or bio-mechanical system that performs diagnostic medicine or life support.

29. A system according to claim 1, wherein said user portable system or said recipient system includes an integrated wireless communication system for command and control of said user or said recipient system from a remote location.

30. The system according to claim 1, wherein said user portable system includes a graphical user interface software or firmware application that depicts a body from which said user may interactively select which of said user brain activity sensing subsystem, user periphery sensing subsystem, and surrounding environment sensing subsystems and associated sensors said user wants to control or turn on and off.

31. A user borne system comprising:
   a robotic system;
   a computer system for operating said robotic system, said computer system including a neural network, said robotic system being configured to train at least a portion of said neural network by:
      correlating common relationships between first sensor signatures of time, location, subject matter, and activity that define a subject in an environment based on real-time and historical data processing;
      comparing second sensor signatures of time, location, subject matter, and activity that define said subject in said environment, said second sensor signatures including user queries and commands, to said first sensor signatures:
      updating a relational database if significant relationships are found between said first sensor signatures and said second sensor signatures; and
      automatically taking an action or notifying a user if a response is required based on a rule previously established by said user such that said computer system uses output from said neural network to learn, negotiate, and survive in said environment; and
   a biological or bio-mechanical life-logging database installed on said computer system and operated upon on a non-transitory computer readable medium, said database being logged by sensors borne by said user to record perceptions of said user and surrounding environment perceptions.

32. A biological or bio-mechanical system user borne system comprising:
   a brain activity sensing subsystem configured to collect data corresponding to brain activity of a biological or bio-mechanical system user;
   a measurement computer subsystem configured to generate data representing quantifications of perceptions of said biological or bio-mechanical system user;
   a user sensing subsystem configured to collect data corresponding to biological or bio-mechanical system user events;
   a surrounding environment sensing subsystem configured to collect data corresponding to the biological or bio-mechanical system user's surrounding environment;

a recording subsystem configured to record said data from said brain activity sensing subsystem, measurement computer subsystem, user sensing subsystem, and surrounding environment sensing subsystem;

a correlation subsystem configured to create correlation subsystem data comprising relationships between said data corresponding to said brain activity of said user and said data corresponding to said user events and surrounding environment;

a user mobile electronic device in communication with said brain activity sensing subsystem, measurement computer subsystem, user sensing subsystem, surrounding environment sensing subsystem, and recording subsystem, said user mobile electronic device including an interactive graphic user interface and being configured to:

operate as a host computer processing subsystem for command, control, and processing of signals to and from said brain activity sensing subsystem, user sensing subsystem, surrounding environment sensing subsystem, and correlation subsystem;

command said brain activity sensing subsystem to transmit brain activity and pattern data to said correlation subsystem; and command said user sensing subsystem and surrounding environment sensing subsystem to transmit processed sensor data to said correlation subsystem, said correlation subsystem being configured to receive and perform correlation processing operations to determine an extent of neural relationships between data received from said user mobile electronic device and said brain activity sensing subsystem, user sensing subsystem, and surrounding environment sensing subsystem to derive neural correlates of consciousness of conscious precepts of said user;

a non-transitory computer readable medium configured to store data from said brain activity sensing subsystem, measurement computer subsystem, user sensing subsystem, surrounding environment sensing subsystem, recording subsystem, and correlation subsystem for performing queries on real-time and near real-time data received from said brain activity sensing subsystem, measurement computer subsystem, user sensing subsystem, surrounding environment sensing subsystem, recording subsystem, and correlation subsystem for determining whether to keep or disregard said data from said brain activity sensing subsystem, measurement computer subsystem, user sensing subsystem, surrounding environment sensing subsystem, recording subsystem, and correlation subsystem based on pre-established rule-sets and biological or bio-mechanical system user interactive command and control from said user mobile electronic device; and a computer processing device configured to process and communicate at least a portion of said data from said brain activity sensing subsystem, measurement computer subsystem, user sensing subsystem, surrounding environment sensing subsystem, recording subsystem, and correlation subsystem into said biological or bio-mechanical system user.

* * * * *